US011725138B2

(12) United States Patent
Kim et al.

(10) Patent No.: US 11,725,138 B2
(45) Date of Patent: Aug. 15, 2023

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Hyun Kim, Gyeonggi-do (KR); Ji-Won Um, Gyeonggi-do (KR); Kyoung-Jin Park, Gyeonggi-do (KR); Mi-Ja Lee, Gyeonggi-do (KR); Chi-Sik Kim, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 265 days.

(21) Appl. No.: 17/111,339

(22) Filed: Dec. 3, 2020

(65) Prior Publication Data

US 2021/0175433 A1 Jun. 10, 2021

(30) Foreign Application Priority Data

Dec. 6, 2019 (KR) ........................ 10-2019-0161950

(51) Int. Cl.

| | |
|---|---|
| ***H01L 51/00*** | (2006.01) |
| ***C07D 413/14*** | (2006.01) |
| ***C09K 11/06*** | (2006.01) |

(52) U.S. Cl.

CPC ............ *C09K 11/06* (2013.01); *C07D 413/14* (2013.01); *C09K 2211/1018* (2013.01)

(58) Field of Classification Search

None

See application file for complete search history.

(56) References Cited

FOREIGN PATENT DOCUMENTS

KR 101982792 B1 5/2019

*Primary Examiner* — Po-Chih Chen

(74) *Attorney, Agent, or Firm* — G. Creston Campbell

(57) ABSTRACT

The present disclosure relates to an organic electroluminescent compound and an organic electroluminescent device comprising the same. By comprising the organic electroluminescent compound according to the present disclosure, it is possible to provide an organic electroluminescent device having improved driving voltage, luminous efficiency, lifetime and/or power efficiency properties.

11 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent (EL) device is a self-light-emitting display device which has advantages in that it provides a wider viewing angle, a greater contrast ratio, and a faster response time. The first organic electroluminescent device was developed by Eastman Kodak in 1987, by using small aromatic diamine molecules and aluminum complexes as materials for forming a light-emitting layer (see Appl. Phys. Lett. 51, 913, 1987).

The most important factor determining luminous efficiency in the organic electroluminescent device is light-emitting materials. Until now, fluorescent materials have been widely used as light-emitting materials. However, in view of electroluminescent mechanisms, since phosphorescent light-emitting materials theoretically enhance luminous efficiency by four (4) times compared to fluorescent light-emitting materials, phosphorescent light-emitting materials have been widely researched. Iridium(III) complexes have been widely known as phosphorescent light-emitting materials, including bis(2-(2'-benzothienyl)-pyridinato-N,C -3') iridium(acetylacetonate) [(acac)Ir(btp)$_2$], tris(2-phenylpyridine)iridium [Ir(ppy)$_3$] and bis(4,6-difluorophenylpyridinato-N,C2)picolinate iridium (Firpic) as red-, green-, and blue-emitting materials, respectively.

In the prior art, 4,4'-N,N'-dicarbazol-biphenyl (CBP) is the most widely known phosphorescent host material. Recently, Pioneer (Japan) et al., developed a high performance organic electroluminescent device using bathocuproine (BCP) and aluminum(Ill) bis(2-methyl-8-quinolinate)(4-phenylphenolate) (BAlq), etc., as host materials, which were known as hole blocking materials.

Although these materials provide good luminous characteristics, they have the following disadvantages: (1) Due to their low glass transition temperature and poor thermal stability, their degradation may occur during a high-temperature deposition process in a vacuum, and the lifetime of the device decreases. (2) The power efficiency of the organic electroluminescent device is given by [(π/voltage)×current efficiency], and the power efficiency is inversely proportional to the voltage. Although the organic electroluminescent device comprising phosphorescent host materials provides current efficiency [cd/A] higher than one comprising fluorescent materials, a significantly high operating voltage is necessary. Thus, there is no merit in terms of power efficiency [Im/W]. (3) In addition, when these materials are used in an organic electroluminescent device, the operational lifetime of an organic electroluminescent device is short and luminous efficiency is still required to be improved.

In order to improve luminous efficiency, operating voltage and/or lifetime, various materials or concepts for an organic layer of an organic electroluminescent device have been proposed, but they have not been satisfactory in practical use. Korean Patent No. 1982792 discloses a group of organic electroluminescent compounds.

However, the aforementioned reference does not specifically disclose an organic electroluminescent compound described in the present disclosure. Further, there is a need to develop an organic electroluminescent compound having improved performance, when used alone or in combination with other host materials, compared to the organic electroluminescent compound disclosed in the aforementioned reference, for example, a light-emitting material with improved driving voltage, luminous efficiency, lifetime property, and/or power efficiency as compared to conventional light-emitting materials.

DISCLOSURE OF INVENTION

Technical Problem

The objective of the present disclosure is firstly, to provide an organic electroluminescent compound effective for producing an organic electroluminescent device having improved operating voltage, luminous efficiency, lifetime property and/or power efficiency, and secondly, to provide an organic electroluminescent device comprising the organic electroluminescent compound.

Solution to Problem

The present inventors found that the above objective can be achieved by an organic electroluminescent compound represented by the following formula 1.

(1)

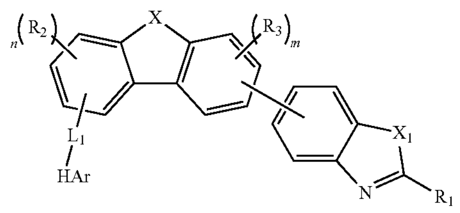

In formula 1,

X and $X_1$, each independently, represent O or S;

HAr represents a substituted or unsubstituted (3- to 30-membered)heteroaryl;

$L_1$ represents a single bond, a substituted or unsubstituted (C6-C30)arylene, or a substituted or unsubstituted (3- to 30-membered)heteroarylene;

$R_1$ represents a substituted or unsubstituted (C1-C30) alkyl, a substituted or unsubstituted (C6-C30)aryl, a substituted or unsubstituted (3- to 30-membered)heteroaryl, or a substituted or unsubstituted (C3-C30)cycloalkyl;

$R_2$ and $R_3$, each independently, represent hydrogen, deuterium, a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30)cycloalkyl, or may be linked to adjacent one(s) of $R_2$ and $R_3$ to form a ring(s); and n and m represent an integer of 1 to 3; in which if n and m, each independently, are an integer of 2 or more, each of $R_2$ or each of $R_3$ may be the same or different.

Advantageous Effects of Invention

By using the organic electroluminescent compound according to the present disclosure, it is possible to produce an organic electroluminescent device having improved operating voltage, luminous efficiency, lifetime properties, and/or power efficiency.

MODE FOR THE INVENTION

Hereinafter, the present disclosure will be described in detail. However, the following description is intended to explain the present disclosure, and is not meant in any way to restrict the scope of the present disclosure.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, an electron injection material, etc.

The term "a plurality of host materials" in the present disclosure means a host material(s) comprising a combination of at least two compounds, which may be comprised in any light-emitting layer constituting an organic electroluminescent device. It may mean both a material before being comprised in an organic electroluminescent device (for example, before vapor deposition) and a material after being comprised in an organic electroluminescent device (for example, after vapor deposition). For example, the plurality of host materials of the present disclosure may be a combination of two or more host materials, and may optionally further include a conventional material comprised in organic electroluminescent materials. The two or more compounds comprised in the plurality of host materials of the present disclosure may be included in one light-emitting layer or may be respectively included in different light-emitting layers. For example, the two or more host materials may be mixture-evaporated or co-evaporated, or individually deposited.

The organic electroluminescent material of the present disclosure may comprise at least one compound represented by formula 1. The compound represented by formula 1 may be comprised in a light-emitting layer, an electron transport layer, and/or an electron buffer layer, but is not limited thereto. When comprised in the light-emitting layer, the compound represented by formula 1 may be comprised as a host material. Herein, the host material may be a host material of a green or red light-emitting organic electroluminescent device. In addition, when comprised in the electron transport layer, the compound represented by formula 1 may be comprised as an electron transport material. Further, when comprised in the electron buffer layer, the compound represented by formula 1 may be comprised as an electron buffer material.

Herein, the term "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, tert-butyl, etc. The term "(C2-C30)alkenyl" is meant to be a linear or branched alkenyl having 2 to 30 carbon atoms constituting the chain, in which the number of carbon atoms is preferably 2 to 20, and more preferably 2 to 10. The above alkenyl may include vinyl, 1-propenyl, 2-propenyl, 1-butenyl, 2-butenyl, 3-butenyl, 2-methylbut-2-enyl, etc. The term "(C2-C30)alkynyl" is meant to be a linear or branched alkynyl having 2 to 30 carbon atoms constituting the chain, in which the number of carbon atoms is preferably 2 to 20, and more preferably 2 to 10. The above alkynyl may include ethynyl, 1-propynyl, 2-propynyl, 1-butynyl, 2-butynyl, 3-butynyl, 1-methylpent-2-ynyl, etc. The term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. The term "(3- to 7-membered)heterocycloalkyl" is meant to be a cycloalkyl having 3 to 7 ring backbone atoms, preferably 5 to 7 ring backbone atoms, and including at least one heteroatom selected from the group consisting of B, N, O, S, Si, and P, and preferably the group consisting of O, S, and N. The above heterocycloalkyl may include tetrahydrofuran, pyrrolidine, thiolan, tetrahydropyran, etc. The term "(C6-C30)aryl(ene)" is meant to be a monocyclic or fused ring radical derived from an aromatic hydrocarbon having 6 to 30 ring backbone carbon atoms, preferably 6 to 25 ring backbone carbon atoms, and more preferably 6 to 18 ring backbone carbon atoms. The above aryl or arylene may be partially saturated, and may comprise a spiro structure. The above aryl may include phenyl, biphenyl, terphenyl, naphthyl, binaphthyl, phenylnaphthyl, naphthylphenyl, phenylterphenyl, fluorenyl, phenylfluorenyl, diphenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, azulenyl, etc. More specifically, the aryl may include phenyl, 1-naphthyl, 2-naphthyl, 1-anthryl, 2-anthryl, 9-anthryl, benzanthryl, 1-phenanthryl, 2-phenanthryl, 3-phenanthryl, 4-phenanthryl, 9-phenanthryl, naphthacenyl, pyrenyl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 1-fluorenyl, 2-fluorenyl, 3-fluorenyl, 4-fluorenyl, 9-fluorenyl, benzofluorenyl, dibenzofluorenyl, 2-biphenylyl, 3-biphenylyl, 4-biphenylyl, o-terphenyl, m-terphenyl-4-yl, m-terphenyl-3-yl, m-terphenyl-2-yl, p-terphenyl-4-yl, p-terphenyl-3-yl, p-terphenyl -2-yl, m-quaterphenyl, 3-fluoranthenyl, 4-fluoranthenyl, 8-fluoranthenyl, 9-fluoranthenyl, benzofluoranthenyl, o-tolyl, m-tolyl, p-tolyl, 2,3-xylyl, 3,4-xylyl, 2,5-xylyl, mesityl, o-cumenyl, m-cumenyl, p-cumenyl, p-tert-butylphenyl, p-(2-phenylpropyl)phenyl, 4'-methylbiphenylyl, 4"-tert-butyl-p-terphenyl-4-yl, 9,9-dimethyl -1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, etc.

The term "(3- to 30-membered)heteroaryl(ene)" is an aryl(ene) having 3 to 30 ring backbone atoms, and including at least one, preferably 1 to 4 heteroatoms selected from the group consisting of B, N, O, S, Si, and P. The above heteroaryl(ene) may be a monocyclic ring, or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl such as benzofuranyl, benzothiophenyl, isobenzofuranyl, dibenzofuranyl,dibenzothiophenyl,benzimidazolyl,benzothiazolyl,benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, dihydroacidinyl, etc. More specifically, the heteroaryl may include 1-pyrrolyl, 2-pyrrolyl, 3-pyrrolyl, pyrazinyl, 2-pyridinyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolidinyl, 2-indolidinyl, 3-indolidinyl, 5-indolidinyl, 6-indolidinyl, 7-indolidinyl, 8-indolidinyl, 2-imidazopyridinyl, 3-imidazopyridinyl, 5-imidazopyridinyl, 6-imidazopyridinyl, 7-imidazopyridinyl, 8-imidazopyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-tert-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl, 4-tert-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, etc. "Halogen" includes F, Cl, Br, and I.

In addition, "ortho (o-)," "meta (m-)," and "para (p-)" are prefixes, which represent the relative positions of substituents, respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position. Para indicates that two substituents are at positions 1 and 4, and for example, when two substituents in a benzene derivative occupy positions 1 and 4, it is called a para position.

Herein, "substituted" in the expression "substituted or unsubstituted" means that a hydrogen atom in a certain functional group is replaced with another atom or another functional group, i.e., a substituent. In the present disclosure, the substituents of the substituted alkyl, the substituted aryl(ene), the substituted heteroaryl(ene), the substituted cycloalkyl, the substituted alkenyl, the substituted alkynyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, and the substituted alkylarylamino, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with a (C6-C30)aryl(s); a (C6-C30)aryl unsubstituted or substituted with a (3- to 30-membered) heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30) alkylamino; a mono- or di-(C6-C30)arylamino unsubstituted or substituted with a (C1-C30)alkyl(s); a (C1-C30)alkyl(C6-C30)arylamino; a (C1-C30)alkylcarbonyl; a (C1-C30) alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl. According to one embodiment of the present disclosure, the substituents, each independently, are at least one selected from the group consisting of a (C1-C20)alkyl; a (5- to 30-membered)heteroaryl unsubstituted or substituted with a (C6-C25)aryl(s); an unsubstituted (C6-C25)aryl; and a tri(C6-C25)arylsilyl. According to another embodiment of the present disclosure, the substituents, each independently, are at least one selected from the group consisting of a (C1-C10)alkyl; a (5- to 20-membered) heteroaryl unsubstituted or substituted with a (C6-C18) aryl(s); an unsubstituted (C6-C20)aryl; and a tri(C6-C18) arylsilyl. For example, the substituents, each independently, may be at least one selected from the group consisting of a methyl, a phenyl, a naphthyl, a biphenyl, a phenylfluorenyl, a pyridinyl unsubstituted or substituted with a phenyl(s), a carbazolyl substituted with a phenyl(s), and a triphenylsilyl.

In the formulas of the present disclosure, when adjacent substituents are linked to each other to form a ring, the ring may be a substituted or unsubstituted mono- or polycyclic (3- to 30-membered) alicyclic or aromatic ring, or the combination thereof; preferably, a substituted or unsubstituted mono- or polycyclic (3- to 26-membered) alicyclic or aromatic ring, or the combination thereof; and more preferably, an unsubstituted mono- or polycyclic (5- to 20-membered) aromatic ring. In addition, the ring may contain at least one heteroatom selected from N, O, and S. For example, the ring may be a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, a substituted or unsubstituted carbazole ring, etc.

Herein, the heteroaryl(ene) and the heterocycloalkyl, each independently, may contain at least one heteroatom selected from B, N, O, S, Si, and P. In addition, the heteratom may be bonded to at least one selected from the group consisting of hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30) arylamino, and a substituted or unsubstituted (C1-C30)alkyl (C6-C30)arylamino.

Hereinafter, the compound represented by formula 1 will be described in more detail.

In formula 1, X and $X_1$, each independently, represent O or S.

In formula 1, HAr represents a substituted or unsubstituted (3- to 30-membered)heteroaryl. According to one embodiment of the present disclosure, HAr represents a substituted or unsubstituted (5- to 30-membered)heteroaryl. According to another embodiment of the present disclosure, HAr represents a substituted or unsubstituted (5- to 25-membered)heteroaryl. Specifically, HAr may be any one selected from the following group 1.

[Group 1]

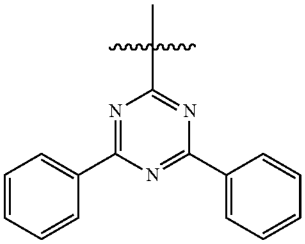

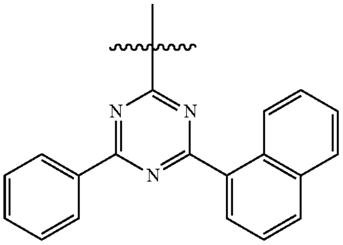

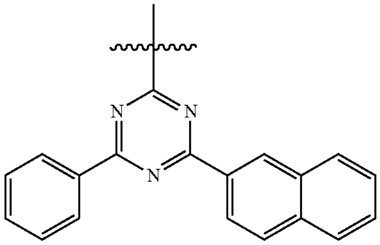

-continued

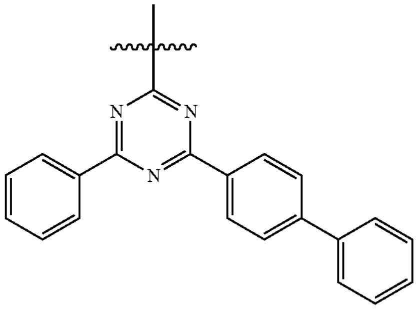

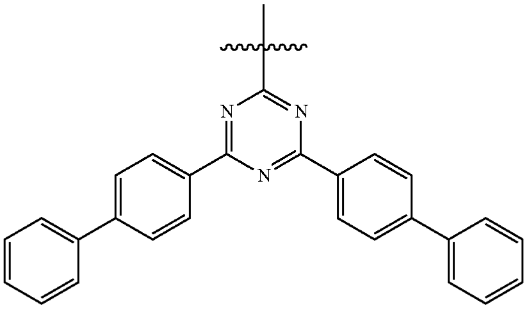

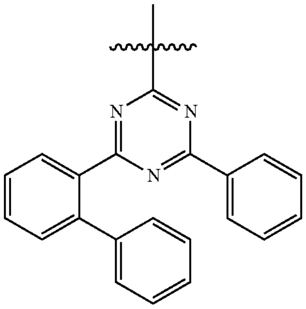

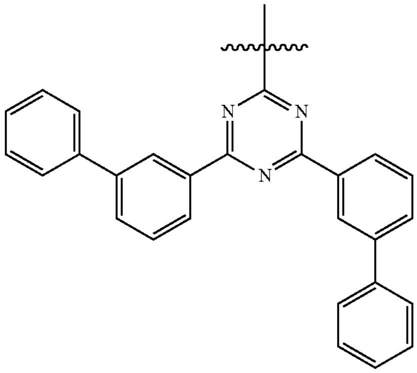

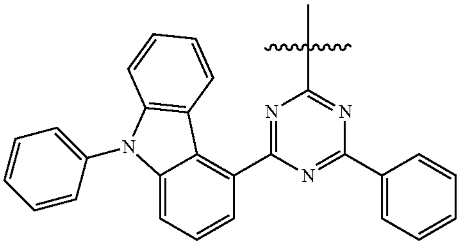

-continued
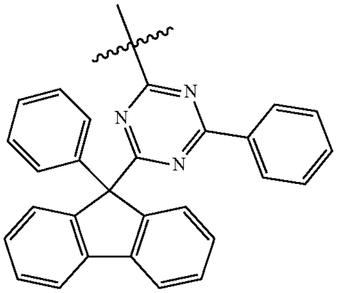
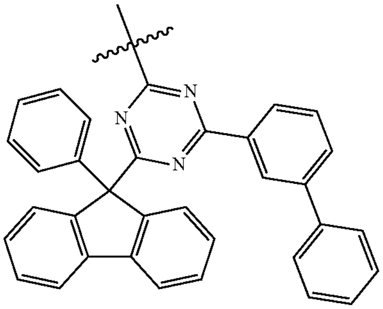
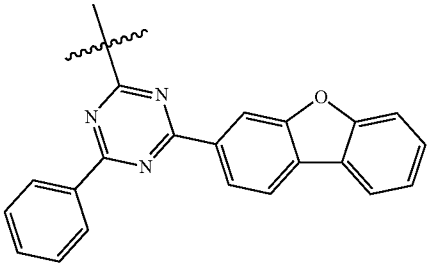
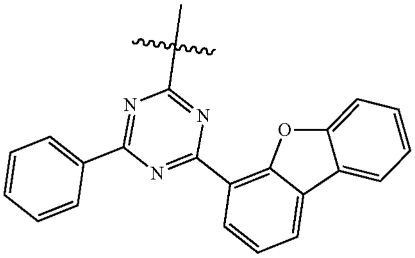
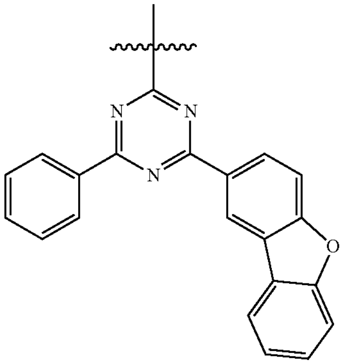
-continued
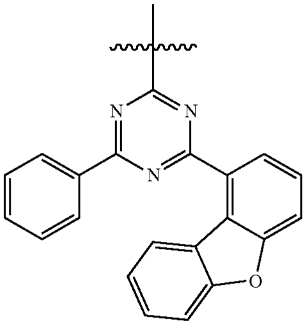
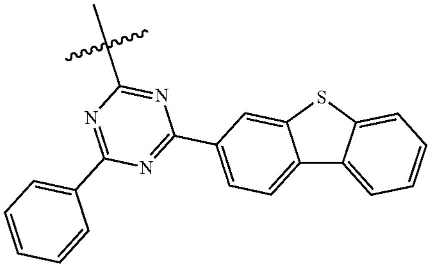
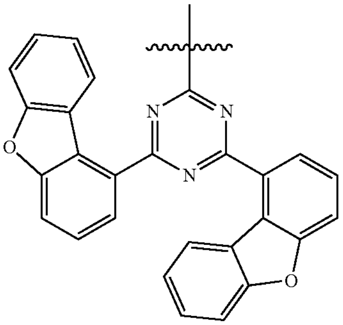
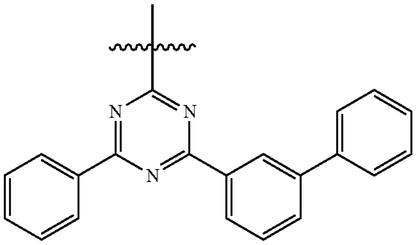
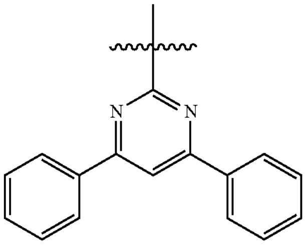
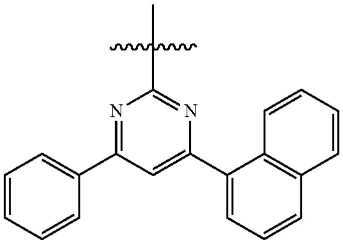

-continued
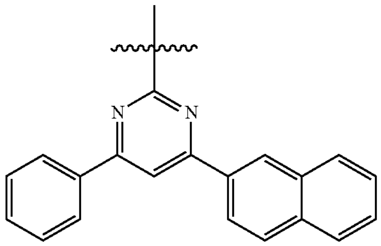
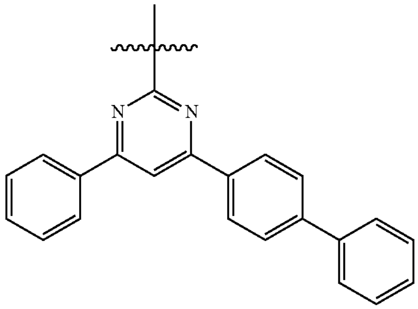
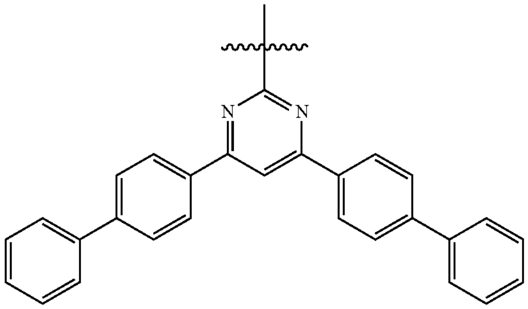
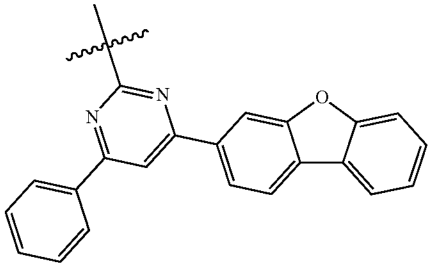
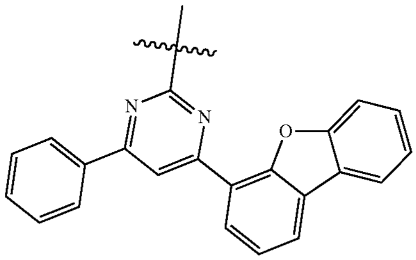
-continued
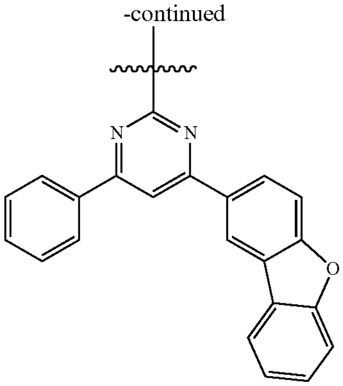
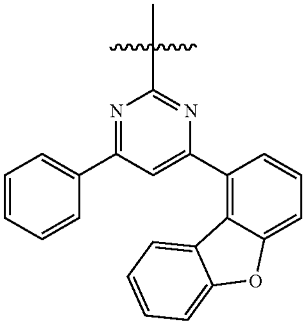
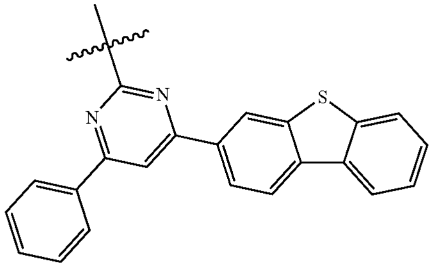
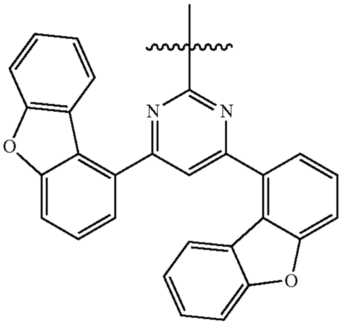
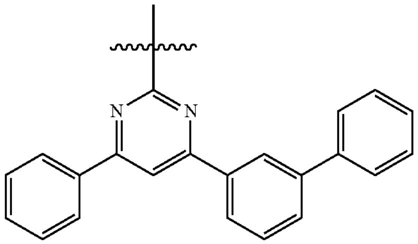

-continued
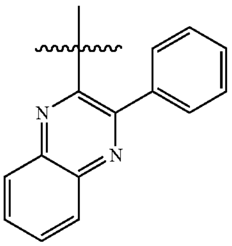
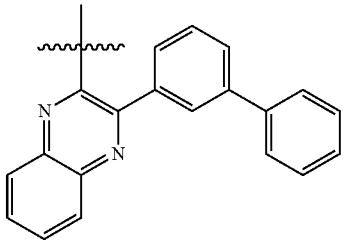
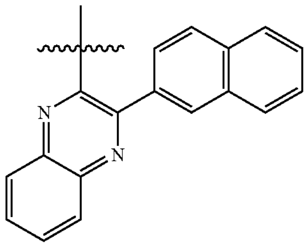
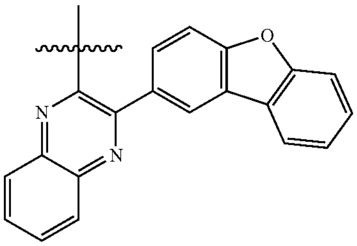
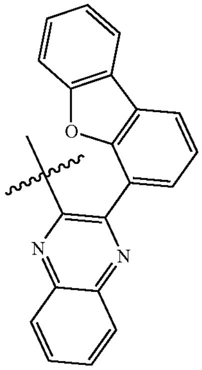
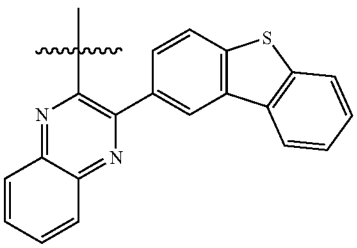
-continued
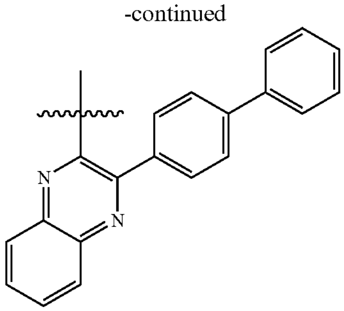
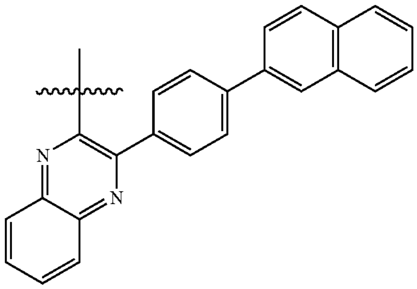
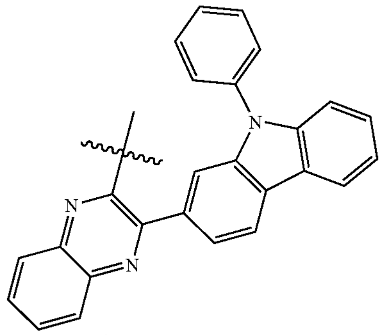
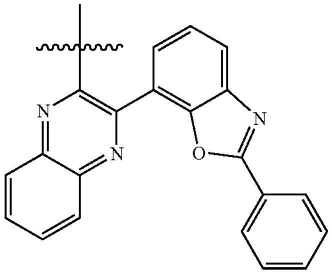
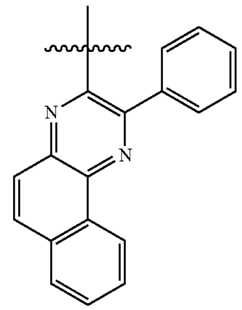
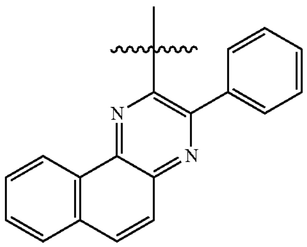

-continued
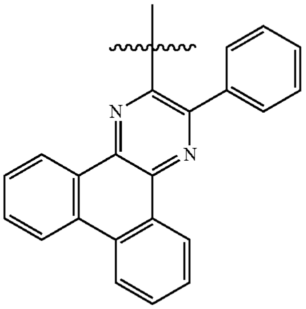
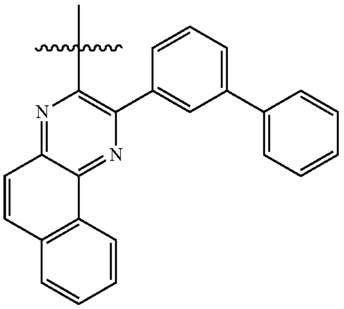
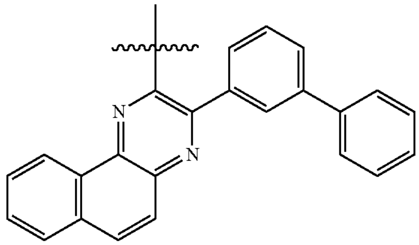
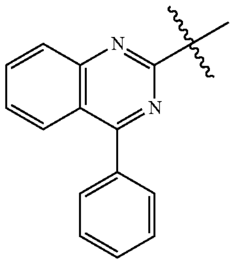
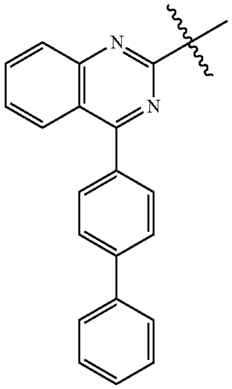
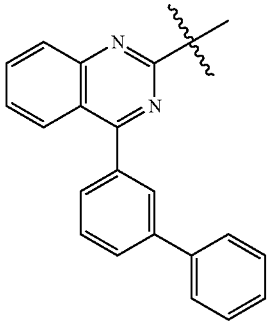
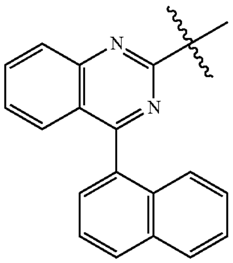
-continued
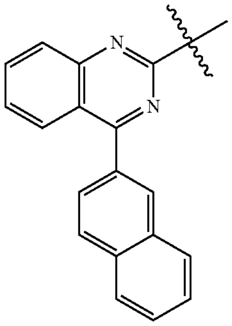
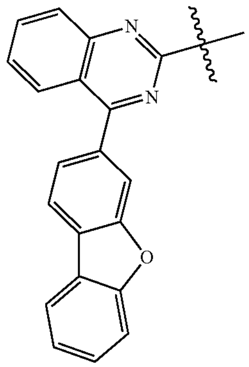
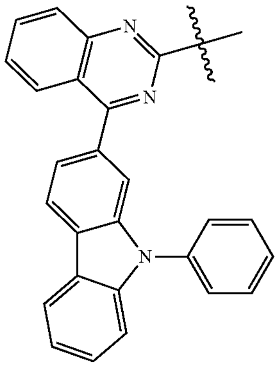
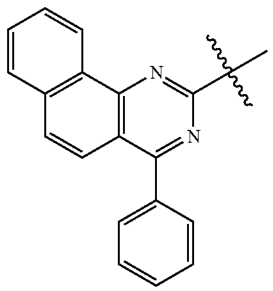
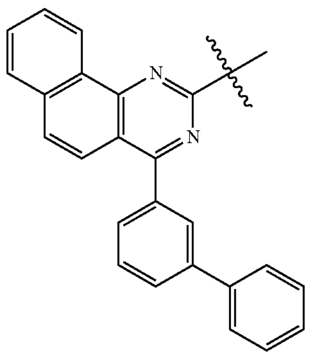
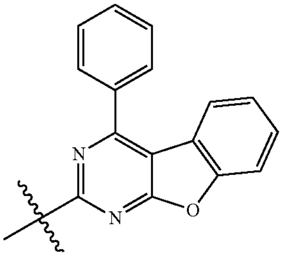
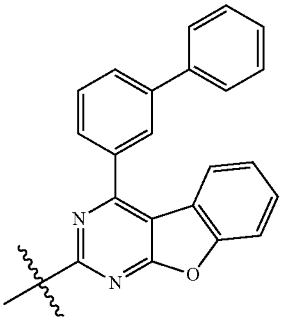

-continued
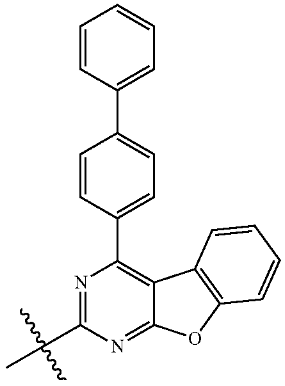
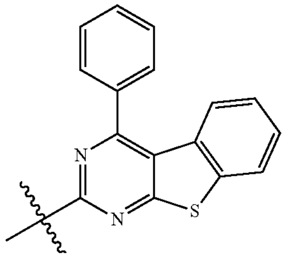
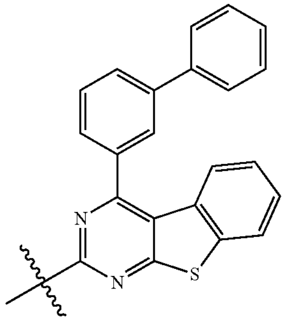
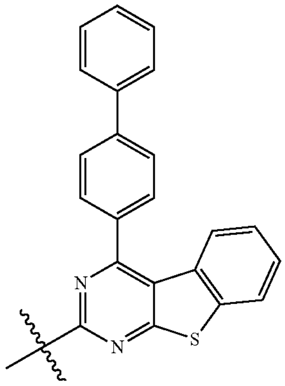
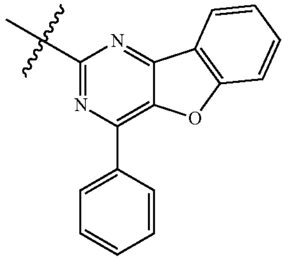
-continued
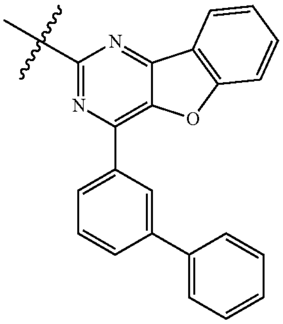
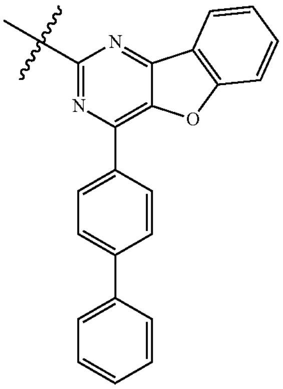
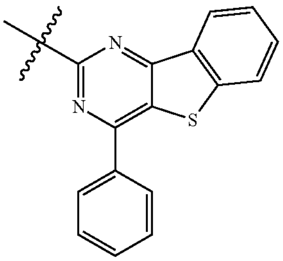
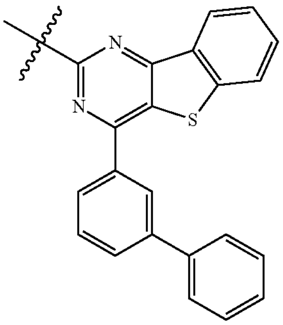
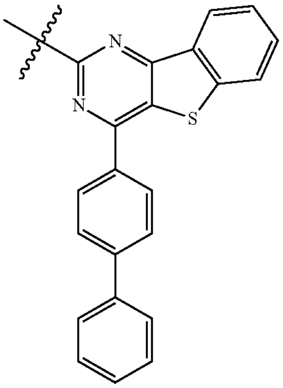

-continued

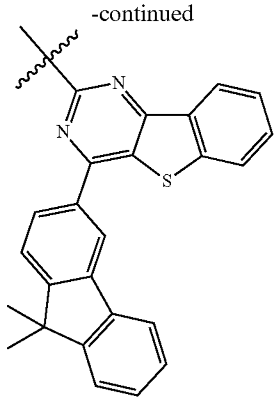

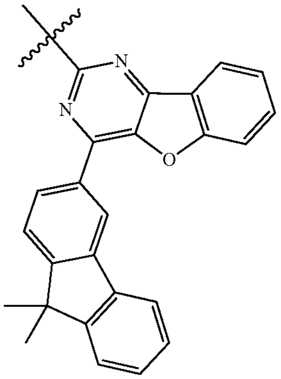

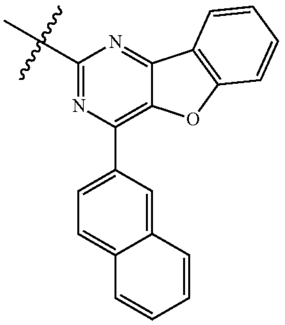 [SMILES: *c1nc(-c2ccc3ccccc3c2)c2oc3ccccc3c2n1]

In formula 1, $L_1$ represents a single bond, a substituted or unsubstituted (C6-C30)arylene, or a substituted or unsubstituted (3- to 30-membered)heteroarylene. According to one embodiment of the present disclosure, $L_1$ represents a single bond, or a substituted or unsubstituted (C6-C25) arylene. According to another embodiment of the present disclosure, $L_1$ represents a single bond, or an unsubstituted (C6-C18)arylene. For example, $L_1$ may represent a single bond, a phenylene, etc.

In formula 1, $R_1$ represents a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30)cycloalkyl. According to one embodiment of the present disclosure, $R_1$ represents a substituted or unsubstituted (C6-C25)aryl, or a substituted or unsubstituted (5- to 25-membered)heteroaryl. According to another embodiment of the present disclosure, $R_1$ represents a (C6-C18)aryl unsubstituted or substituted with a (C1-C6)alkyl(s), or a (5- to 20-membered) heteroaryl unsubstituted or substituted with a (C6-C18) aryl(s). For example, $R_1$ may represent a phenyl, a naphthyl, a biphenyl, a terphenyl, a phenylnaphthyl, a naphthylphenyl, a dimethylfluorenyl, a dibenzofuranyl unsubstituted or substituted with a phenyl(s), a dibenzothiophenyl unsubstituted or substituted with a phenyl(s), a pyridyl unsubstituted or substituted with a phenyl(s), etc.

In formula 1, $R_2$ and $R_3$, each independently, represent hydrogen, deuterium, a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30)cycloalkyl, or may be linked to adjacent one(s) of $R_2$ and $R_3$ to form a ring(s). The ring may be formed by linking at least two of adjacent $R_2$'s to each other and/or by linking at least two of adjacent $R_3$'s to each other. For example, $R_2$ and $R_3$ may represent hydrogen.

In formula 1, n and m represent an integer of 1 to 3; in which if n and m, each independently, are an integer of 2 or more, each of $R_2$ or each of $R_3$ may be the same or different. For example, each of n and m may represent an integer of 1.

The formula 1 may be represented by at least one of the following formulas 1-1 to 1-8.

(1-1)

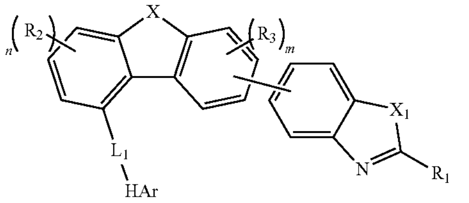

(1-2)

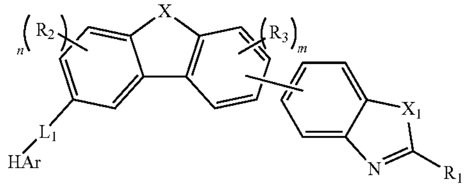

(1-3)

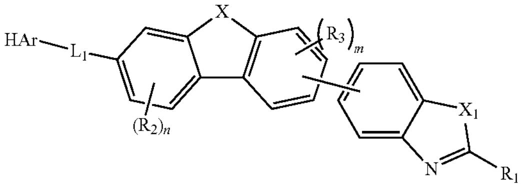

(1-4)

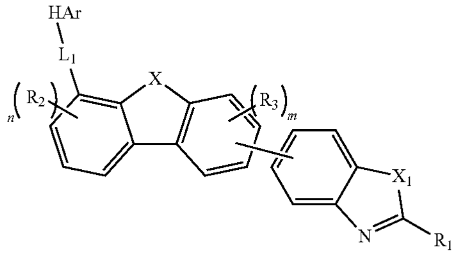

-continued
(1-5)
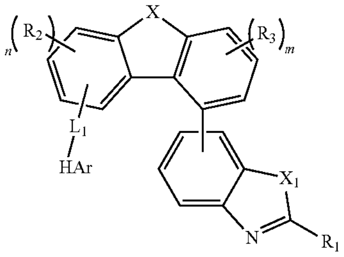
(1-6)
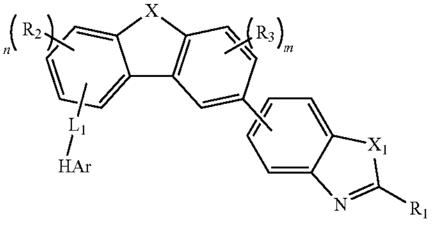
A-1
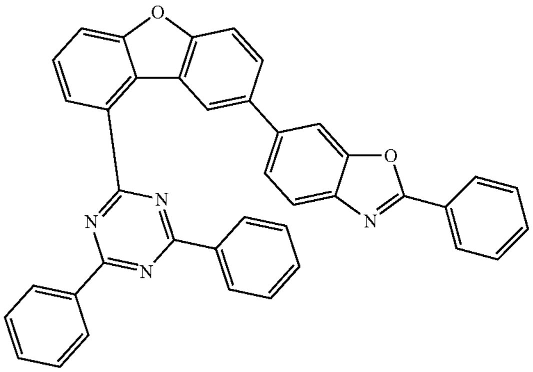
A-3
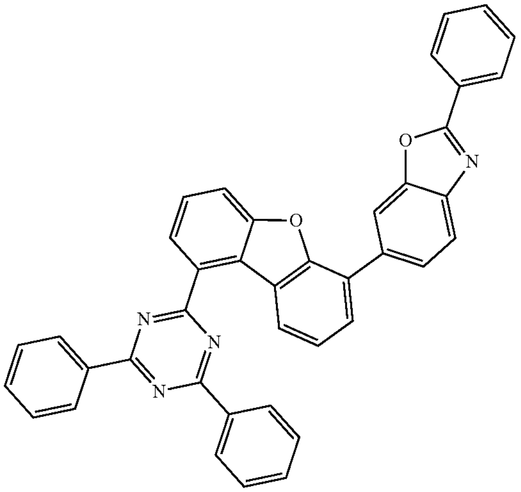
-continued
(1-7)
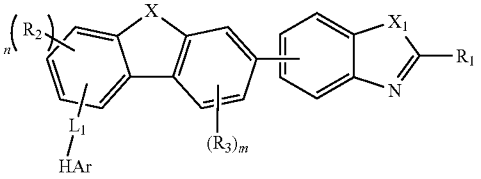
(1-8)
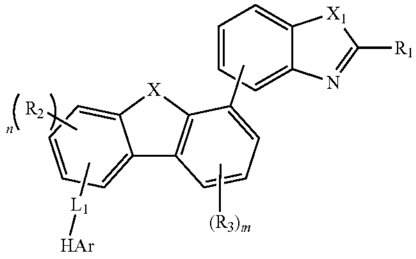
In formulas 1-1 to 1-8, X, $X_1$, HAr, $L_1$, $R_1$ to $R_3$, n, and mare as defined in formula 1.
The compound represented by formula 1 may be specifically exemplified by the following compounds, but is not limited thereto.
A-2
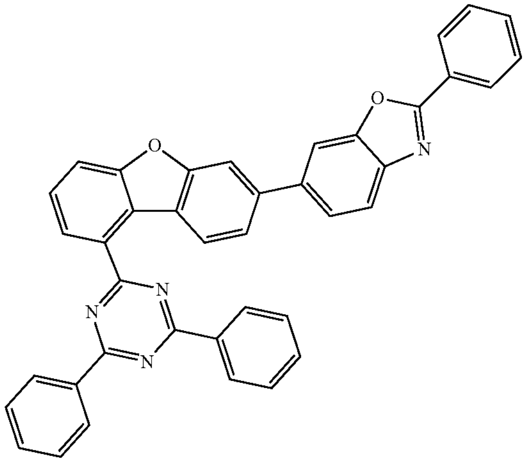
A-4
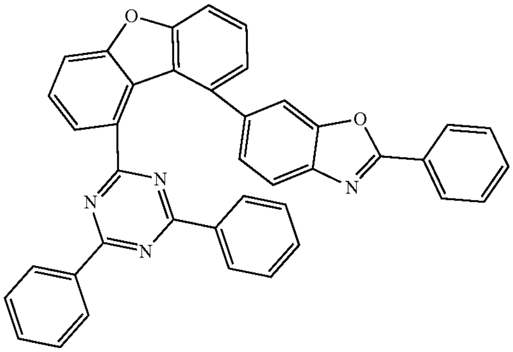

-continued
A-5
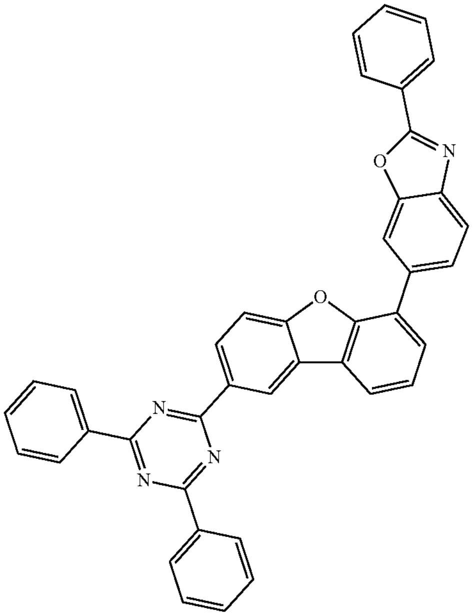
A-6
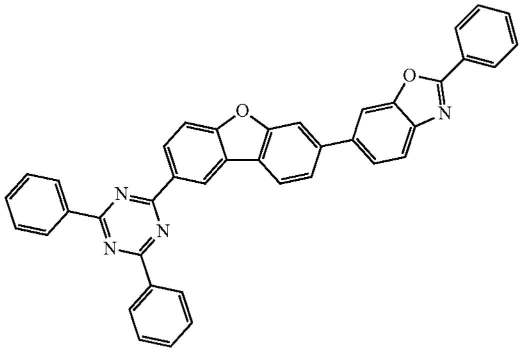
A-7
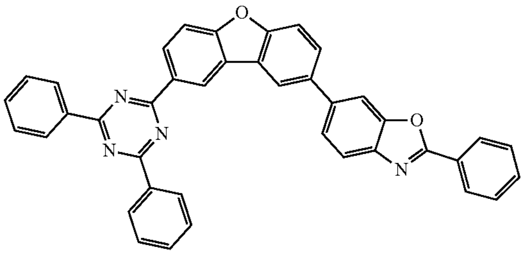
A-8
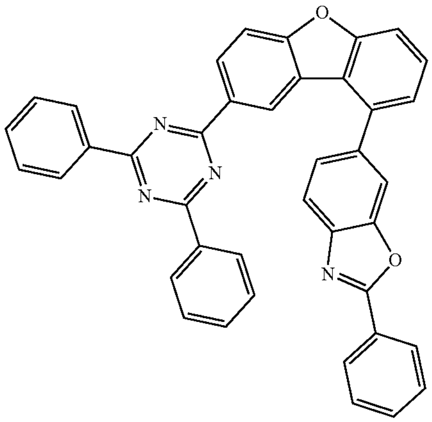
A-9
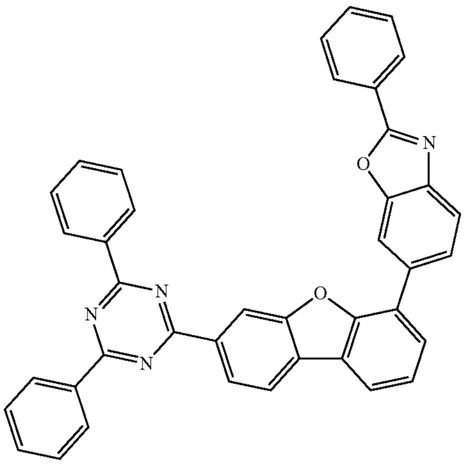
A-10
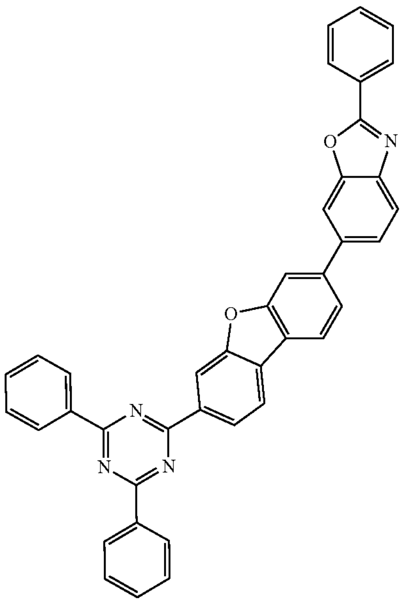

-continued
A-11
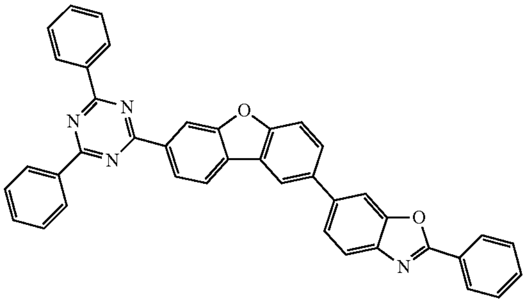
A-12
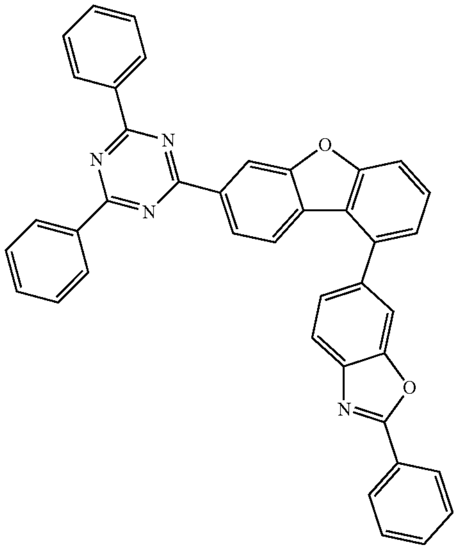
A-13
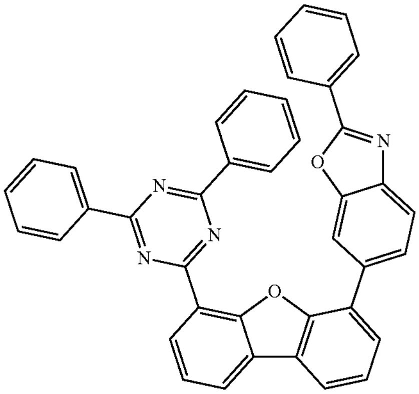
A-14
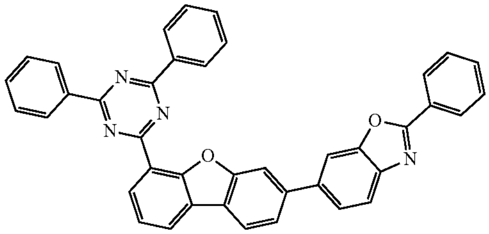
A-15
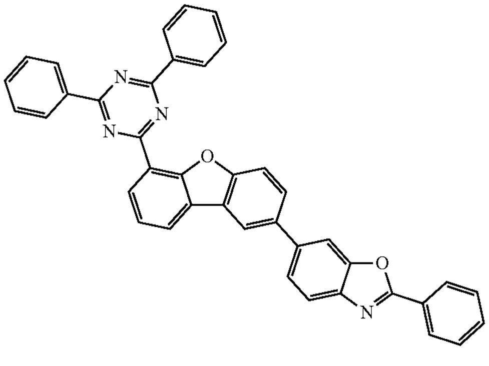
A-16
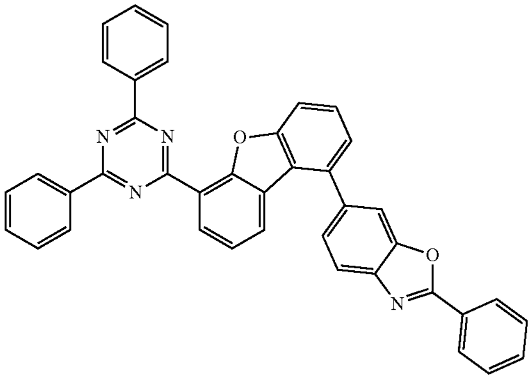

-continued
A-17
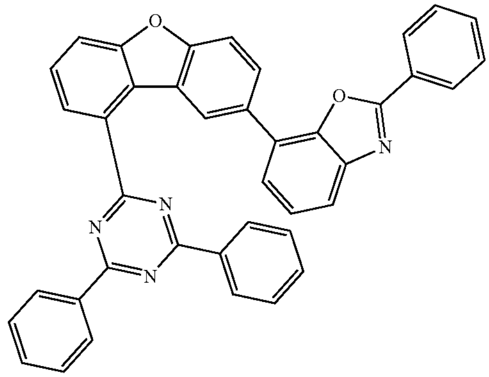
A-18
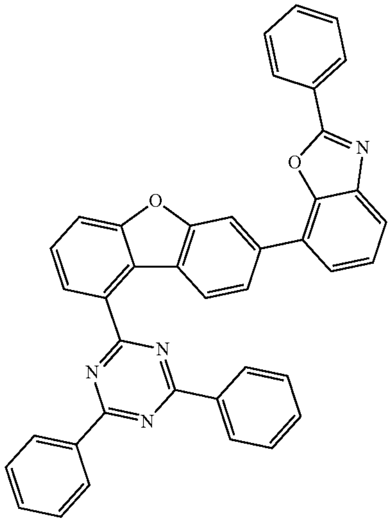
A-19
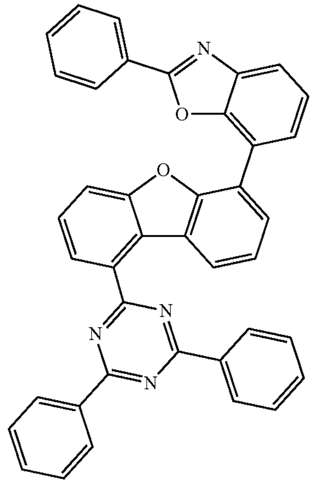
A-20
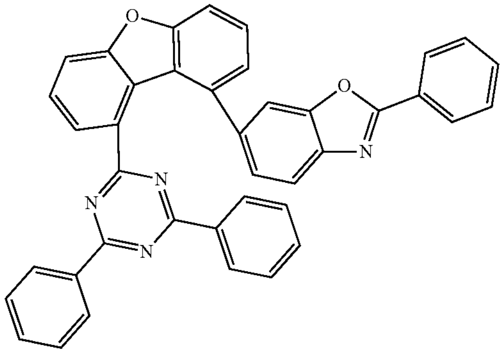
A-21
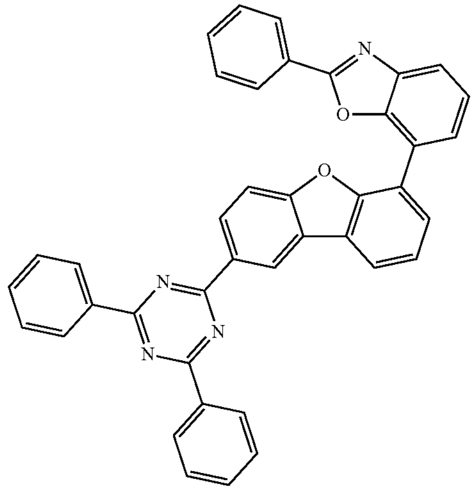
A-22
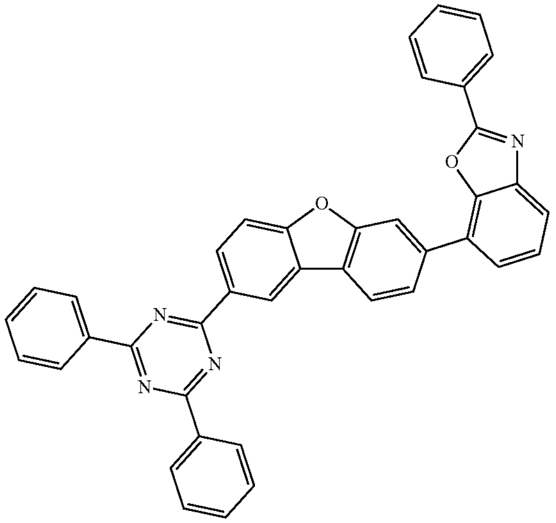

-continued
A-23
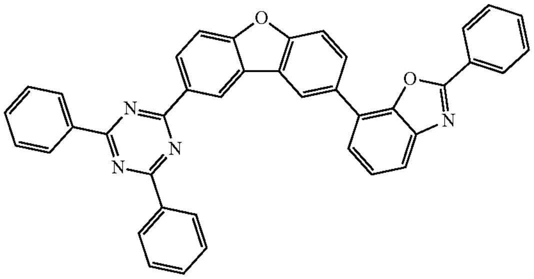
A-24
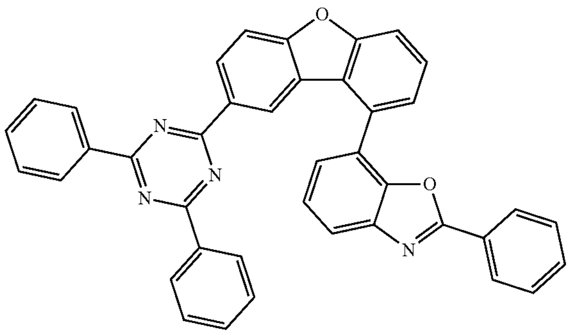
A-25
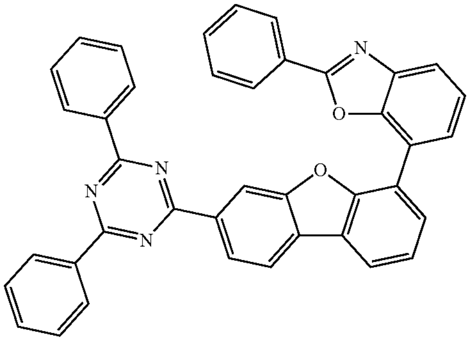
A-26
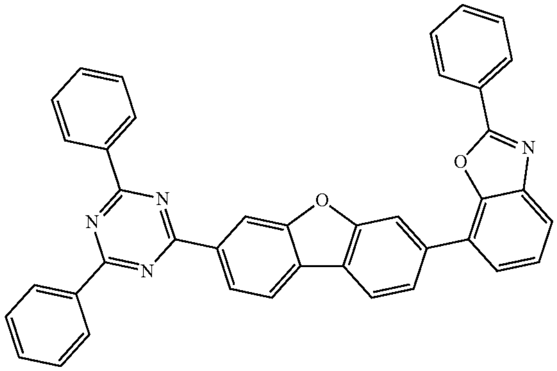
A-27
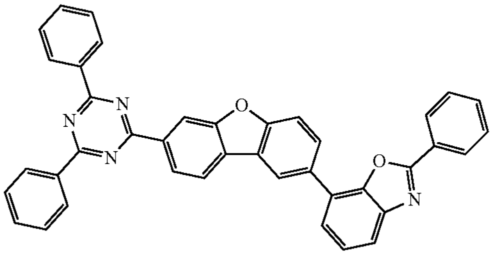
A-28
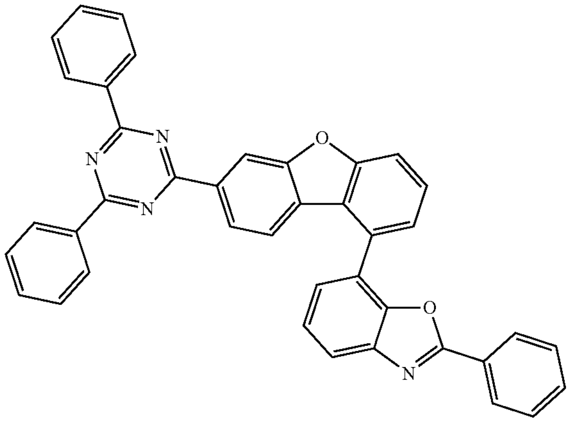
A-29
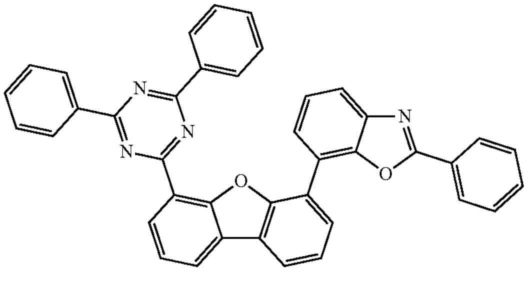
A-30
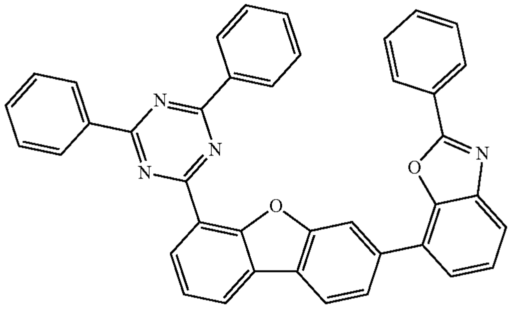

-continued
A-31
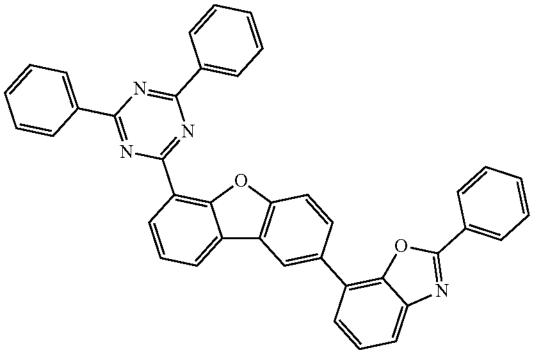
A-32
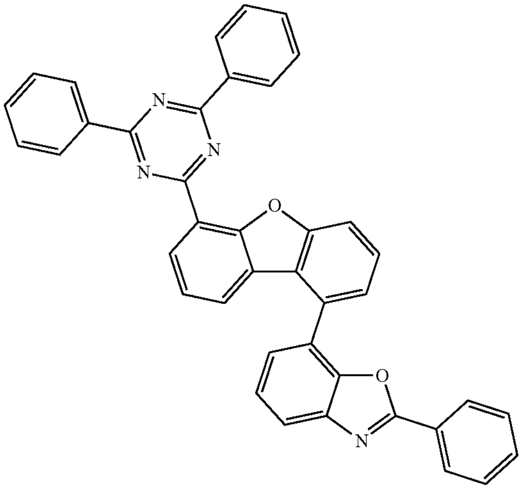
A-33
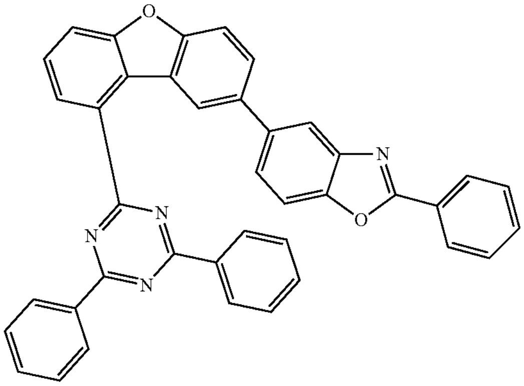
A-34
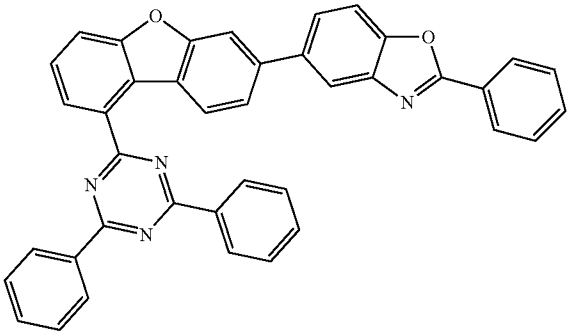
A-35
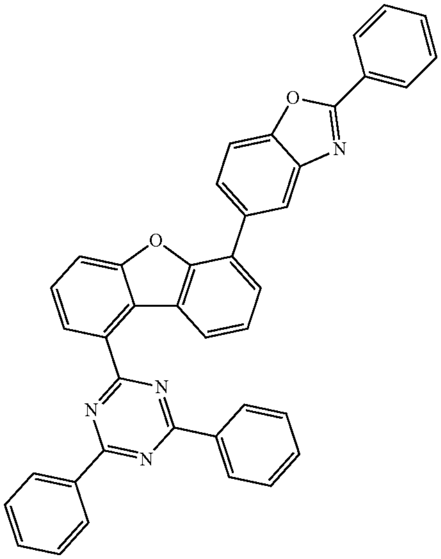
A-36
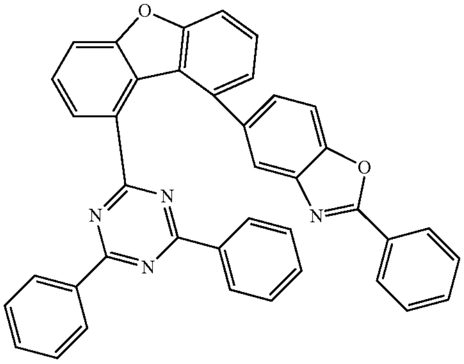

-continued
A-37
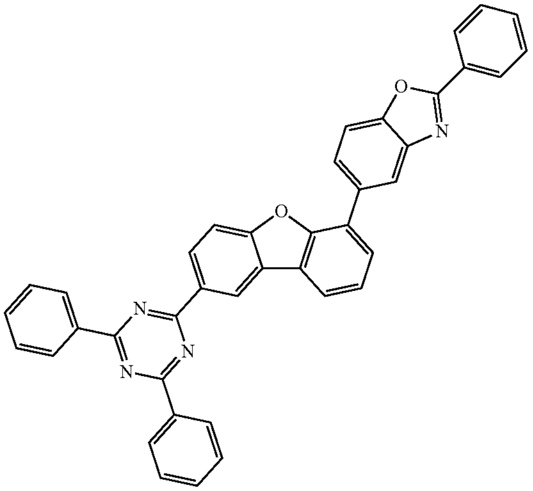
A-38
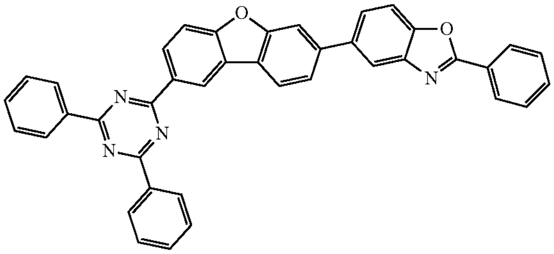
A-39
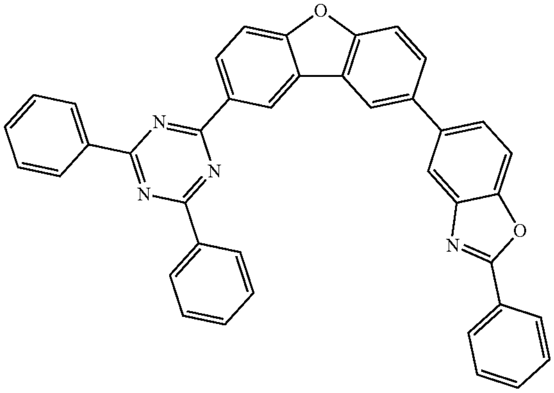
A-40
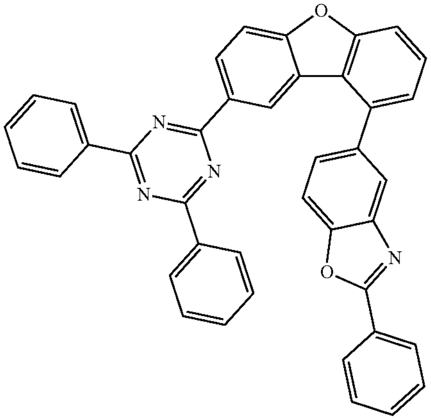
A-41
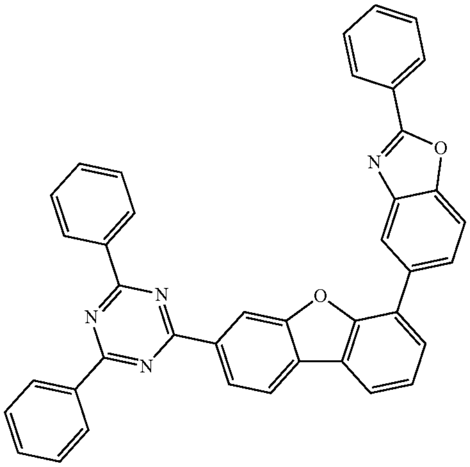
A-42
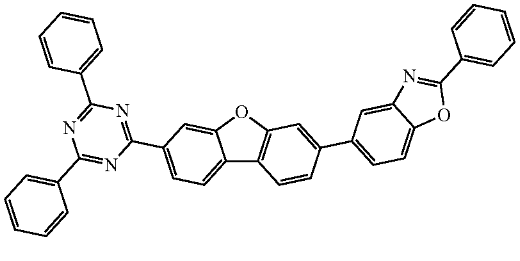

-continued
A-43
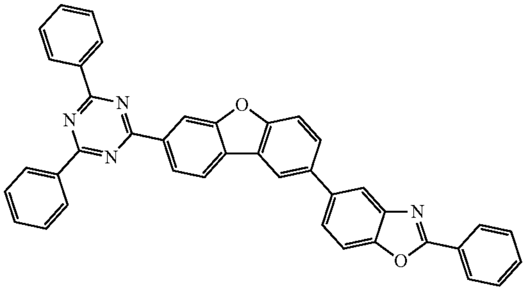
A-44
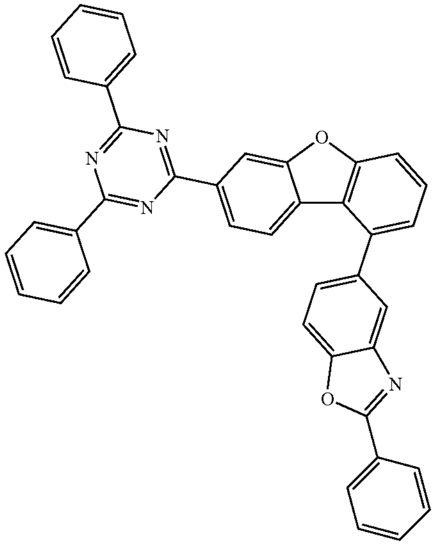
A-45
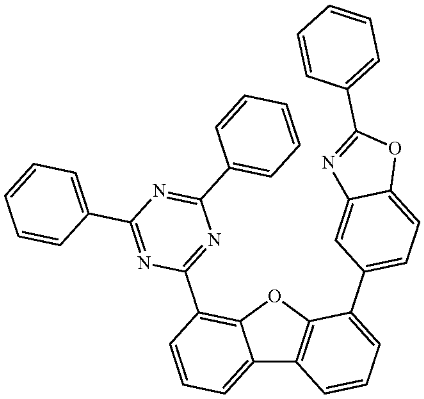
A-46
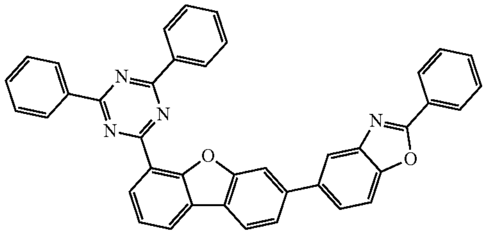
A-47
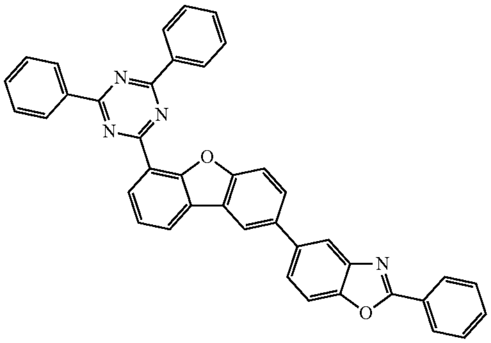
A-48
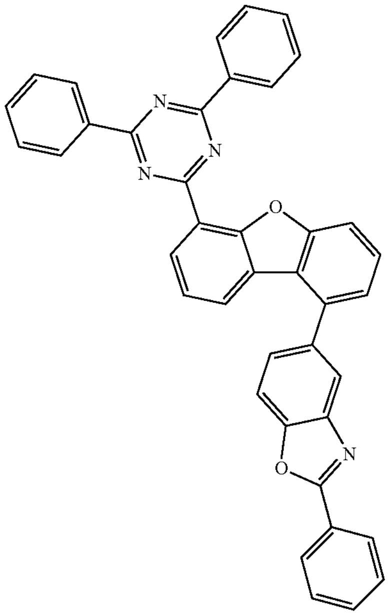

-continued
A-49
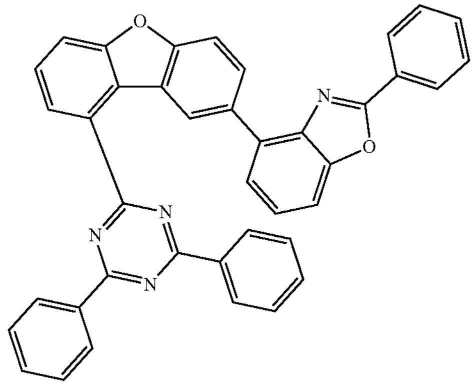
A-50
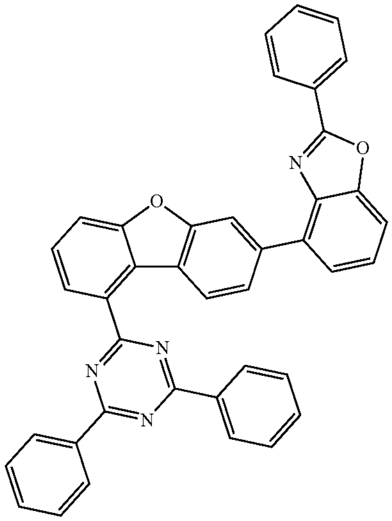
A-51
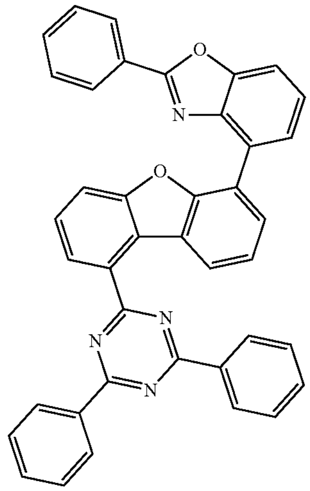
A-52
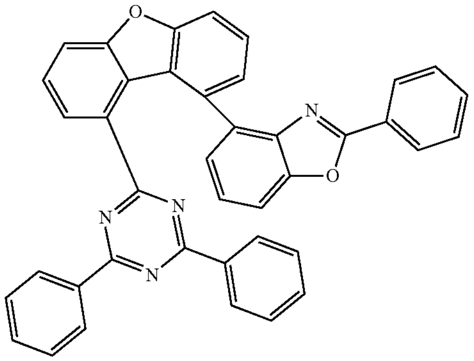
A-53
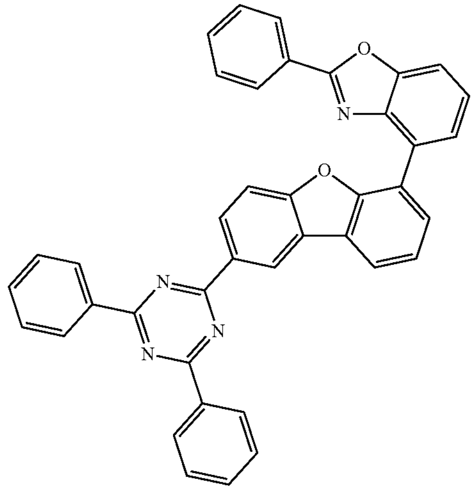
A-54
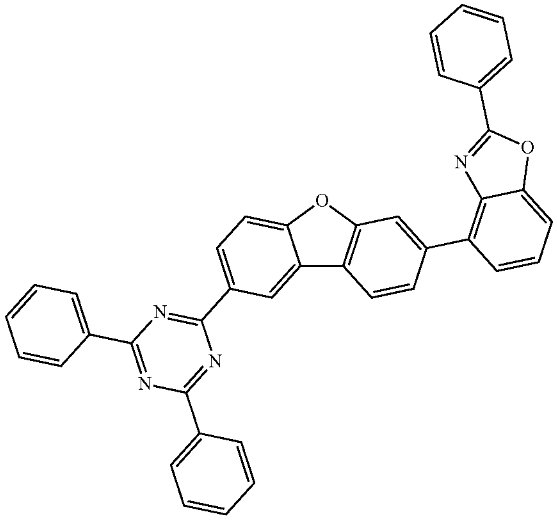

-continued
A-55
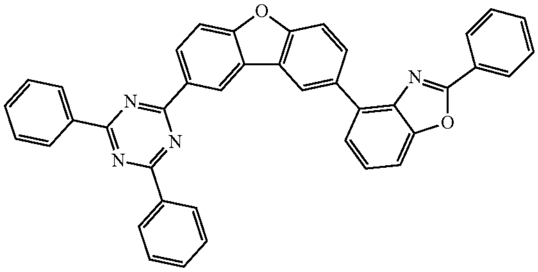
A-56
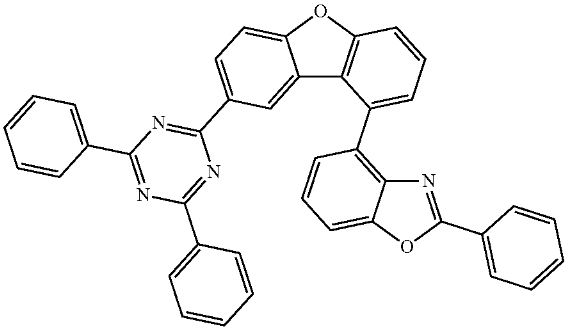
A-57
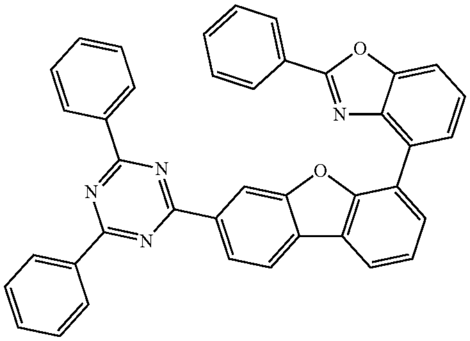
A-58
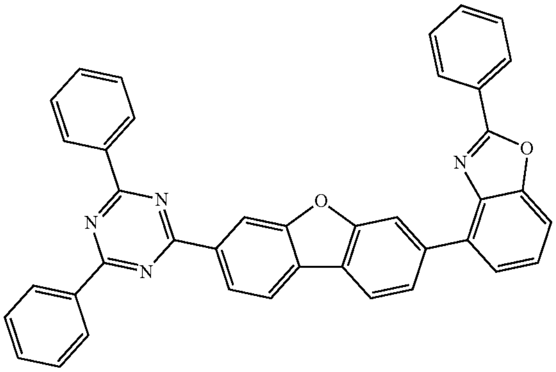
A-59
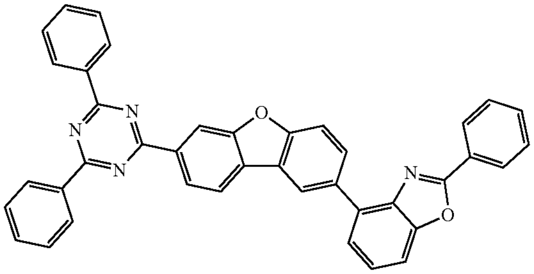
A-60
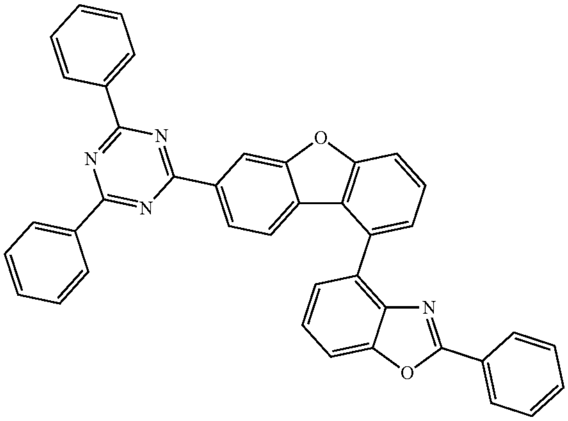
A-61
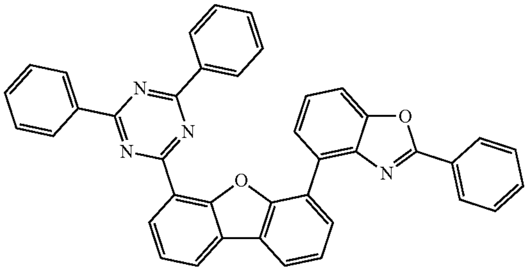
A-62
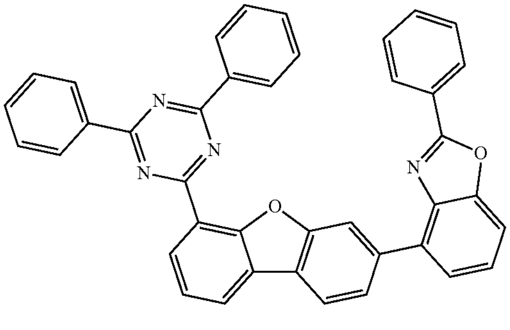

-continued
A-63
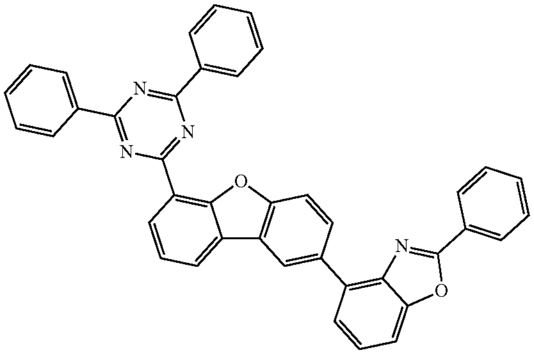
A-64
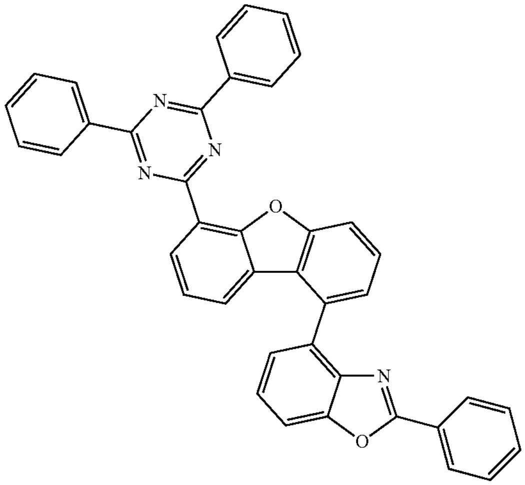
B-1
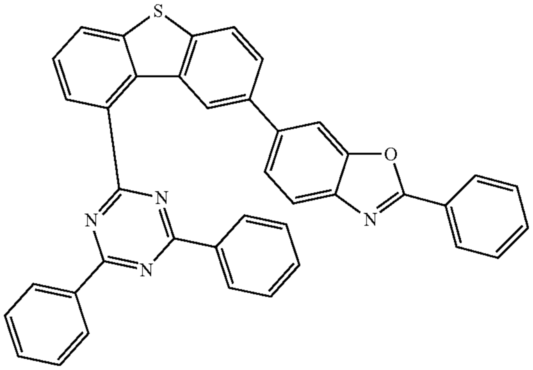
B-2
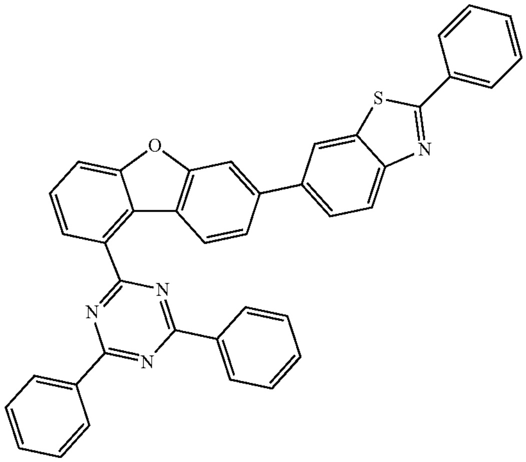
B-3
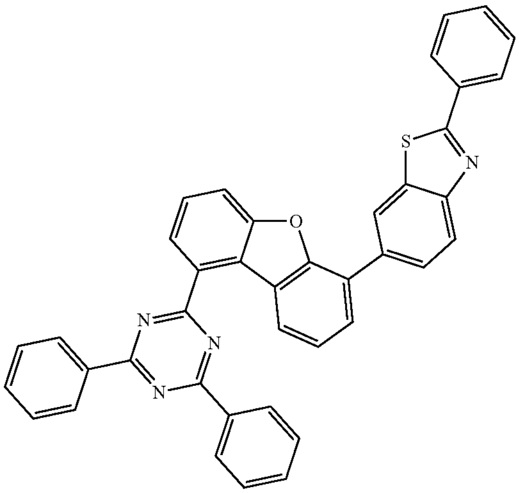
B-4
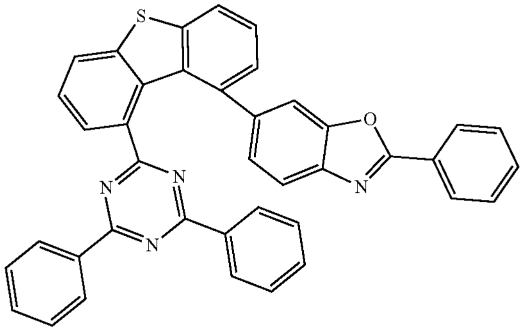

-continued
B-5
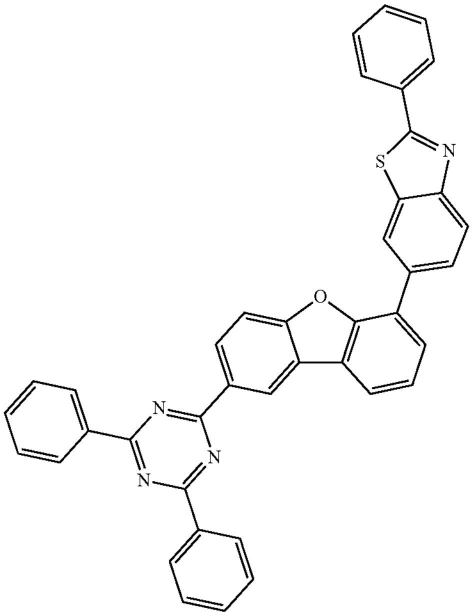
B-6
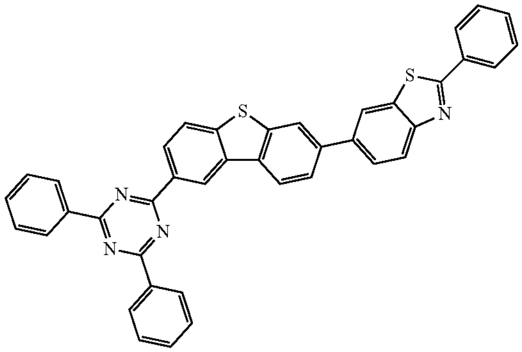
B-7
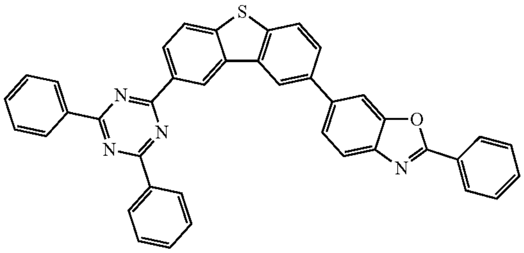
B-8
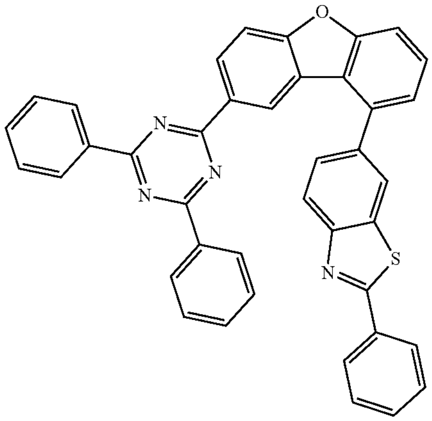
B-9
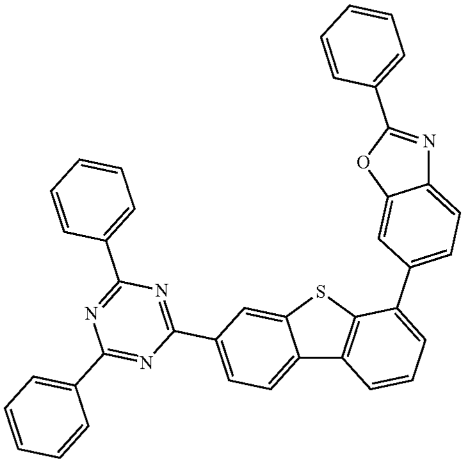
B-10
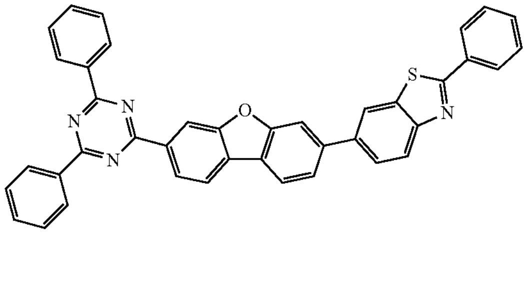

-continued
B-11
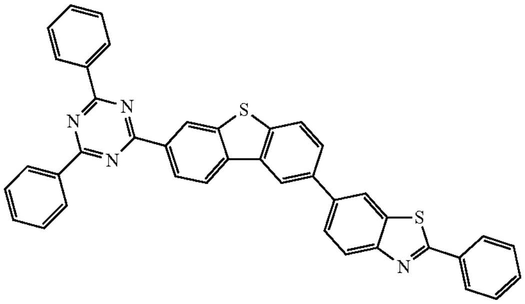
B-12
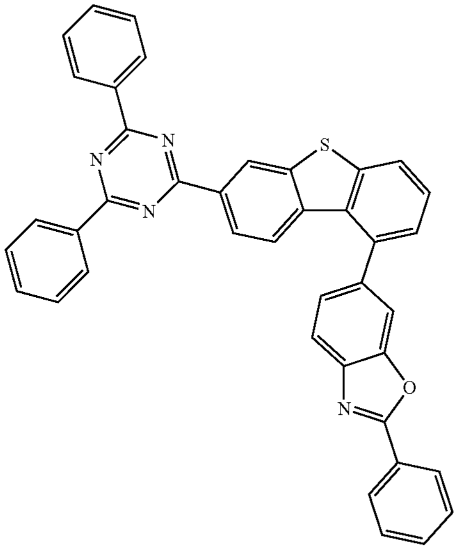
B-13
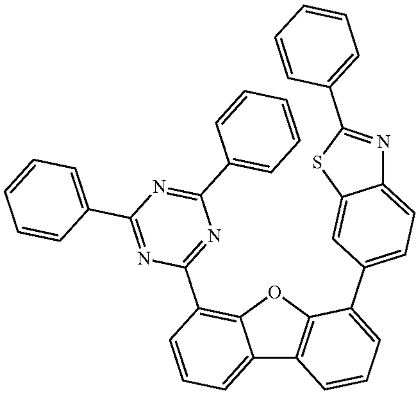
B-14
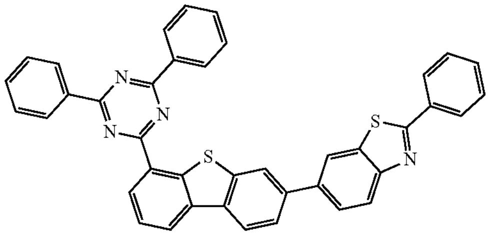
B-15
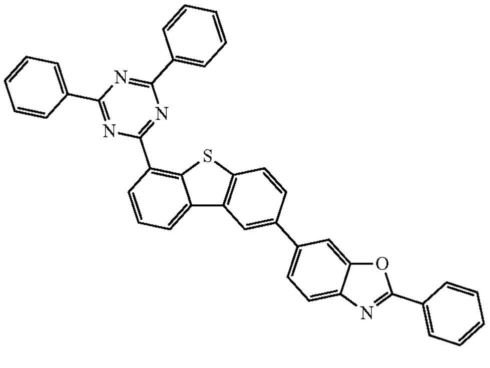
B-16
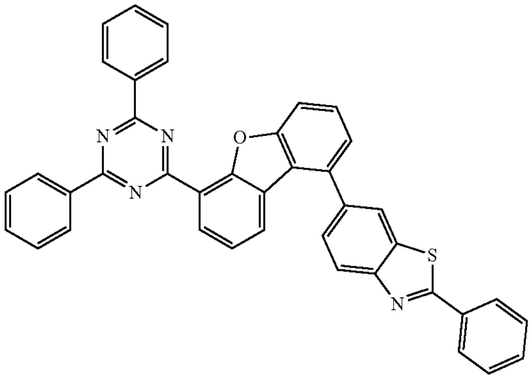

-continued
B-17
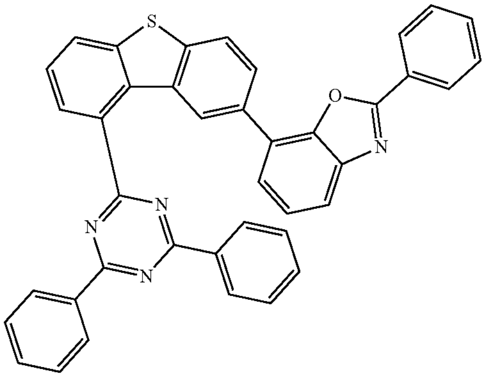
B-18
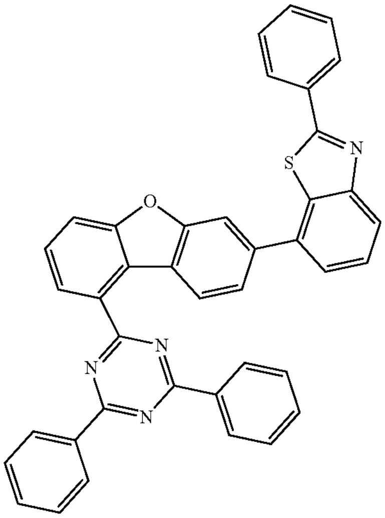
B-19
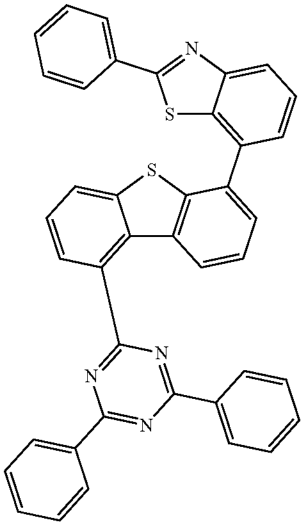
B-20
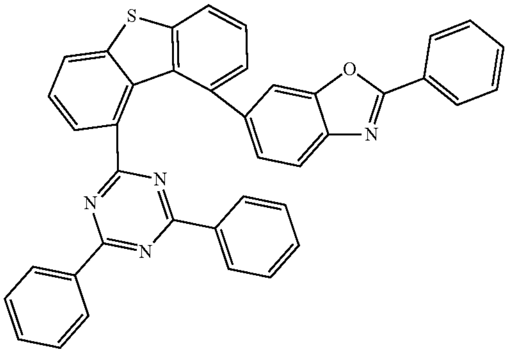
B-21
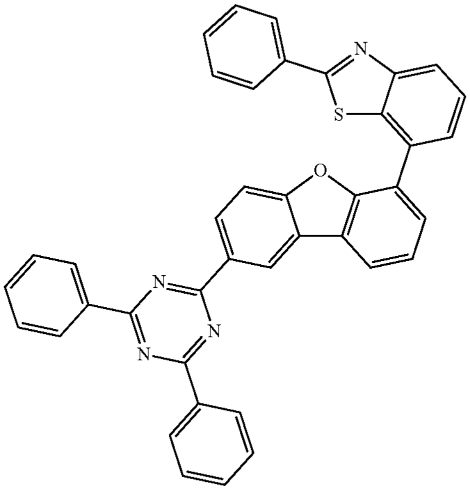
B-22
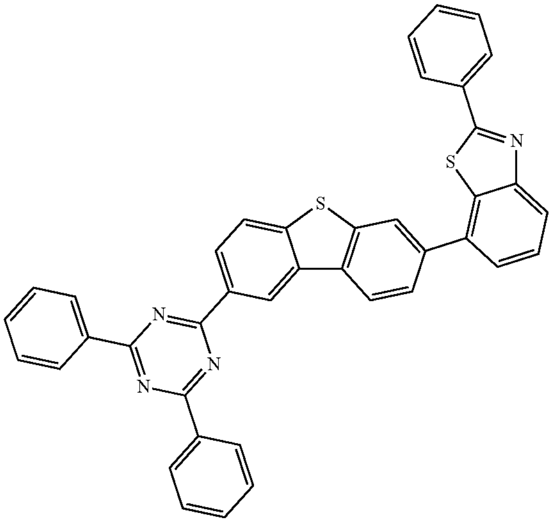

-continued
B-23
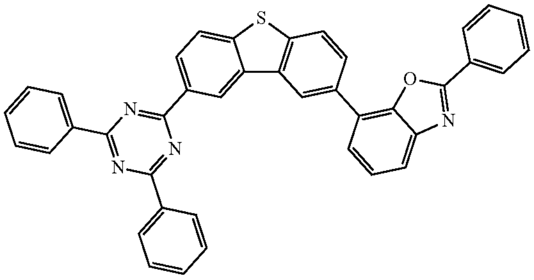
B-24
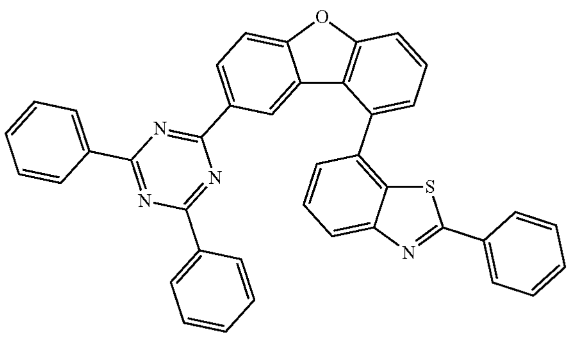
B-25
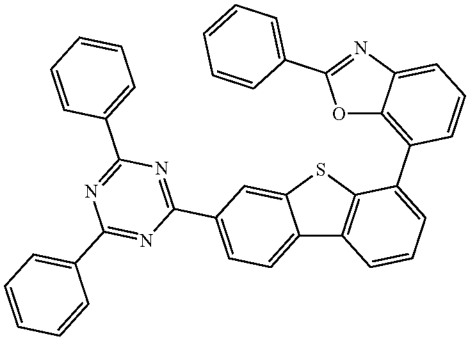
B-26
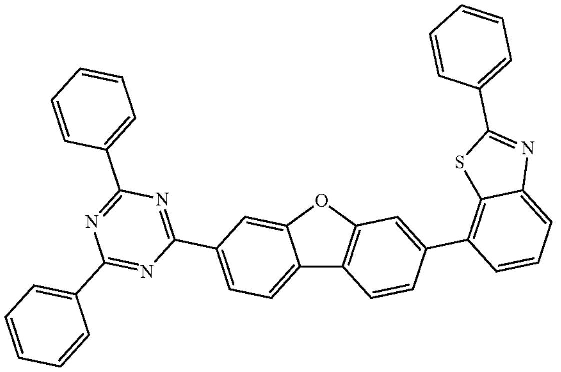
B-27
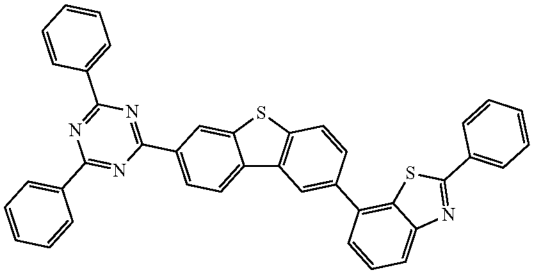
B-28
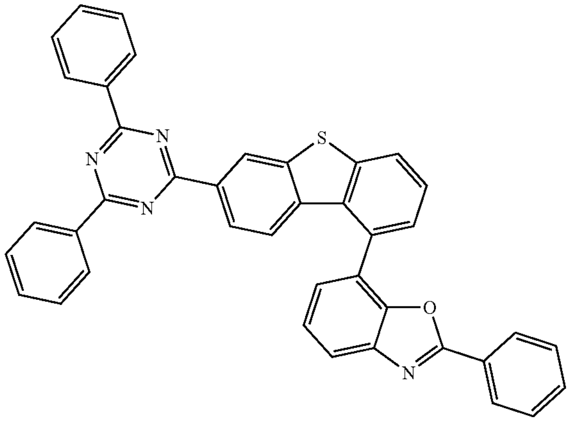
B-29
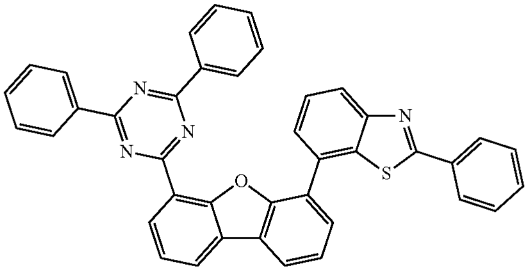
B-30
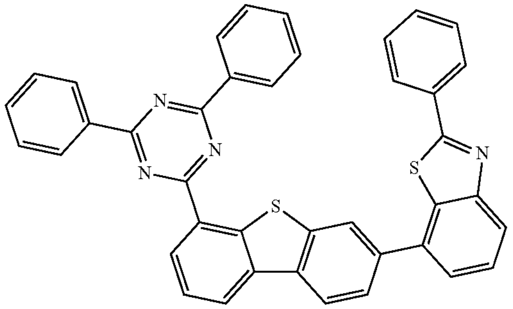

-continued
B-31
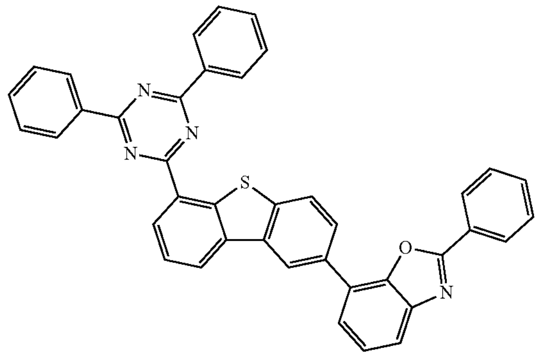
B-32
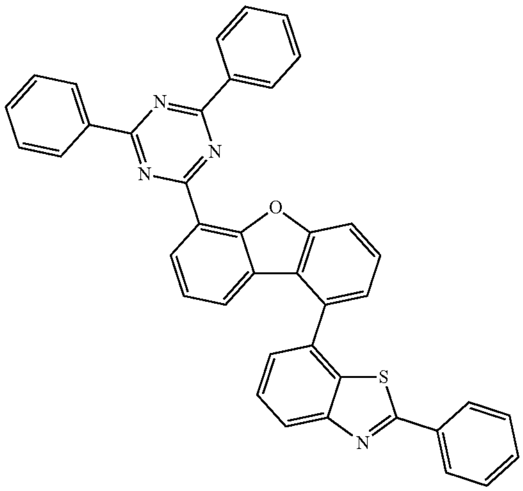
B-33
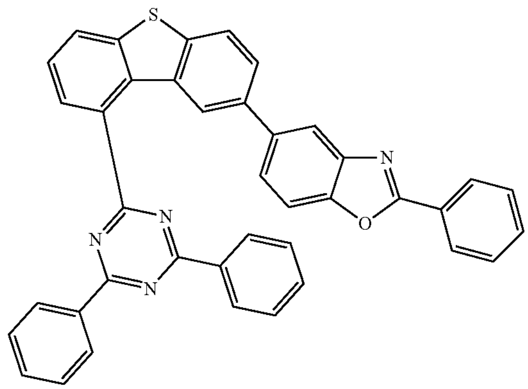
B-34
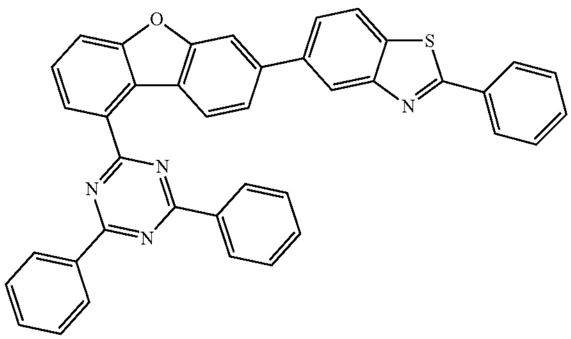
B-35
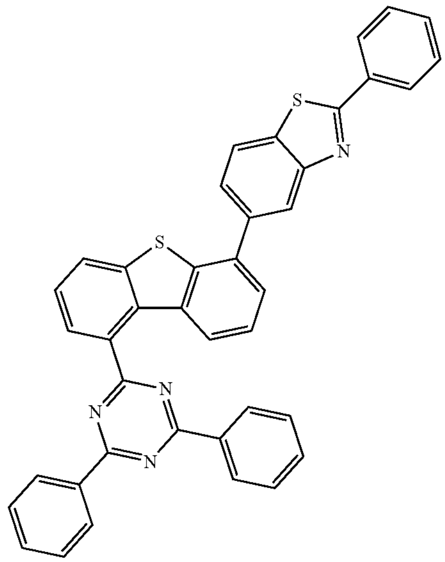
B-36
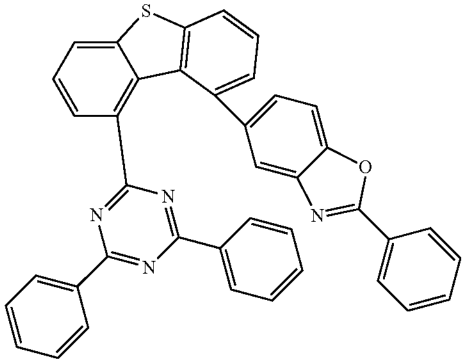

-continued
B-37
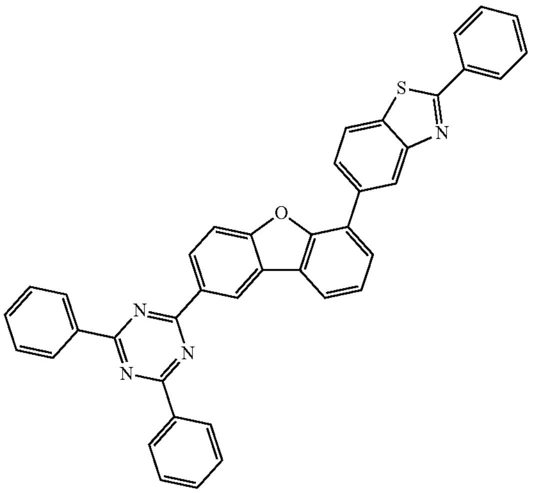
B-38
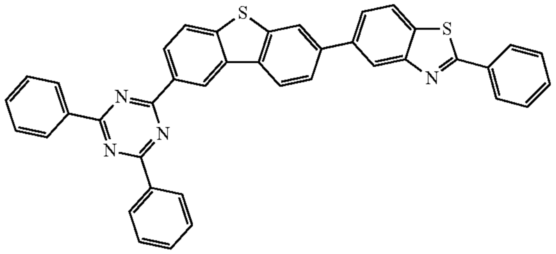
B-39
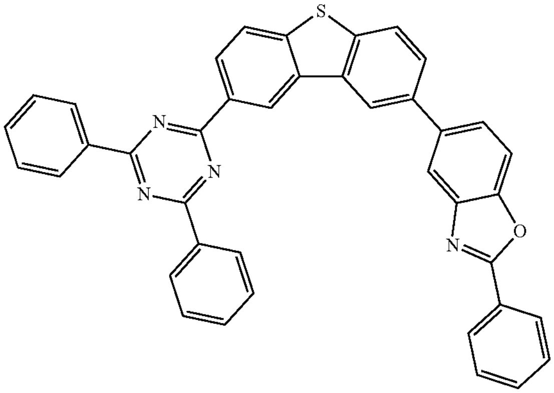
B-40
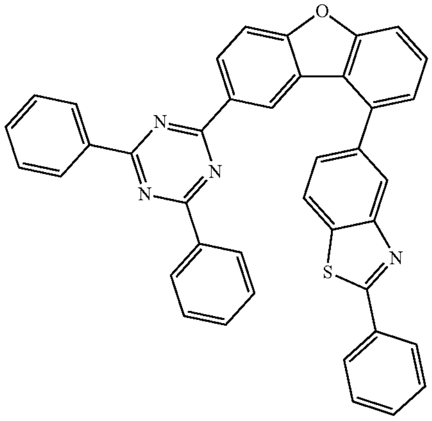
B-41
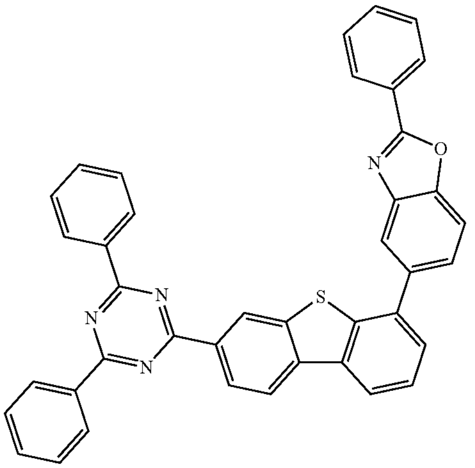
B-42
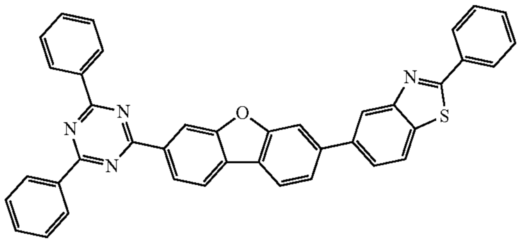

-continued
B-43
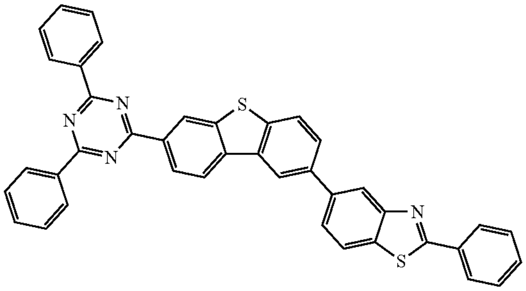
B-44
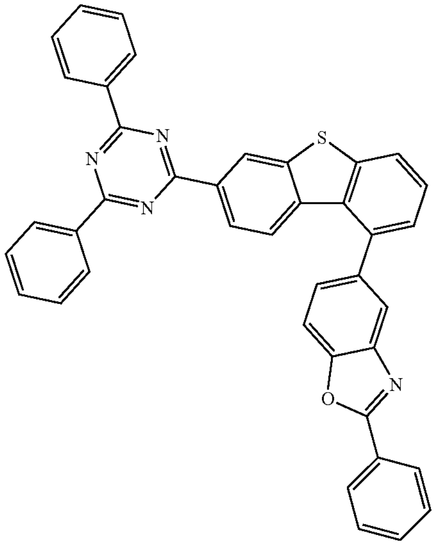
B-45
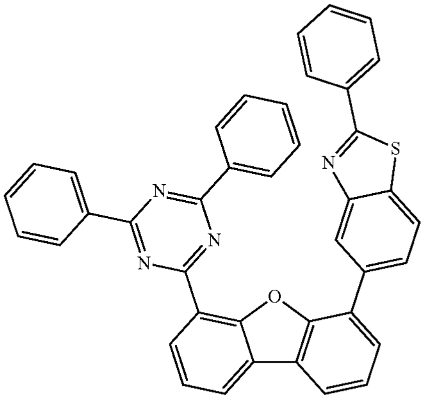
B-46
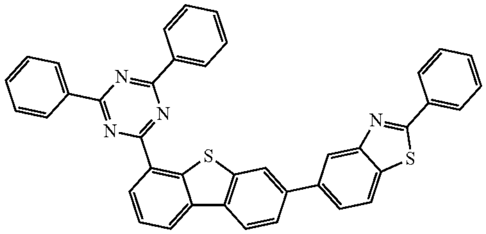
B-47
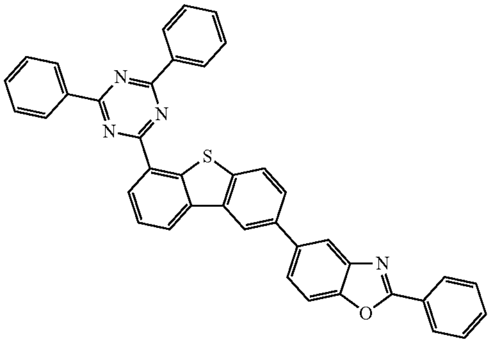
B-48
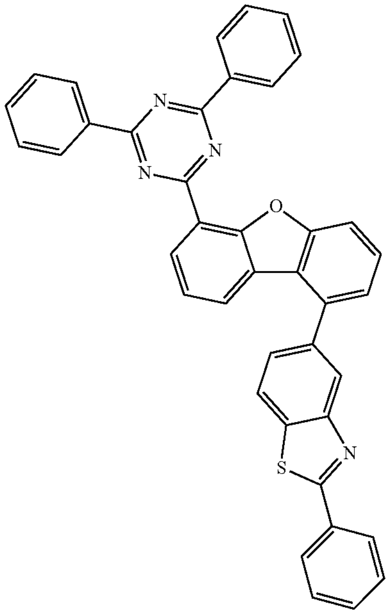

-continued
B-49
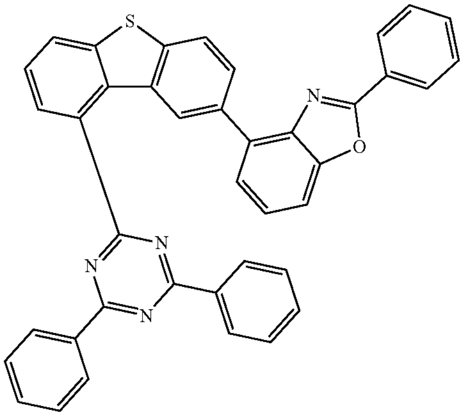
B-50
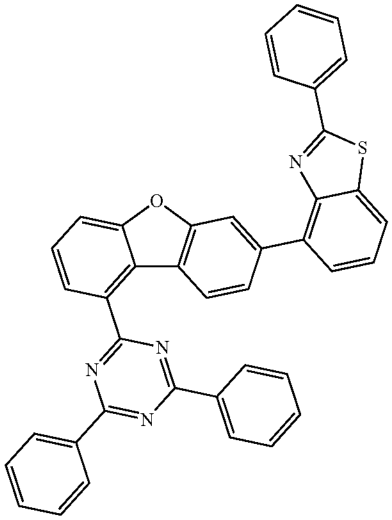
B-51
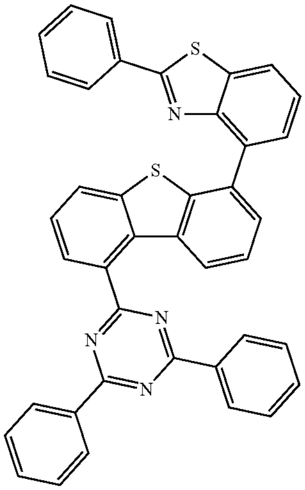
B-52
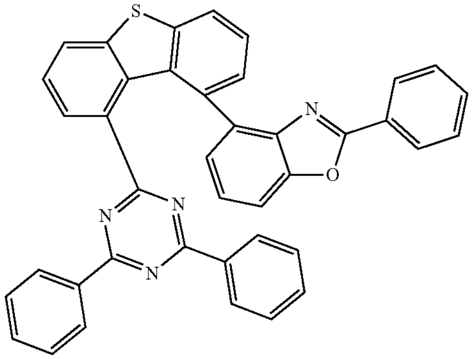
B-53
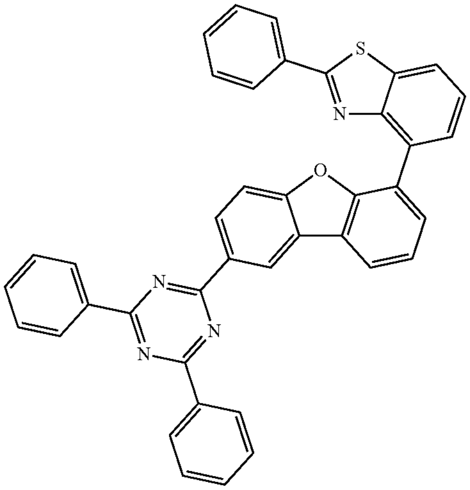
B-54
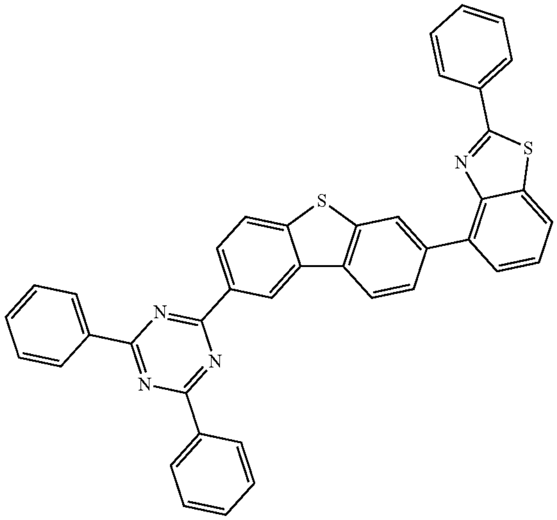

-continued
B-55
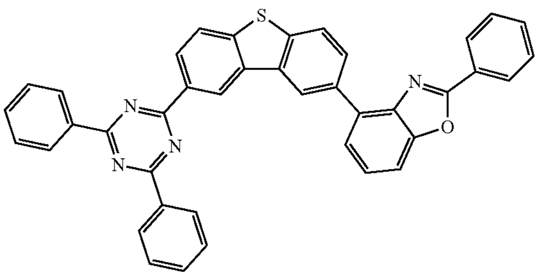
B-56
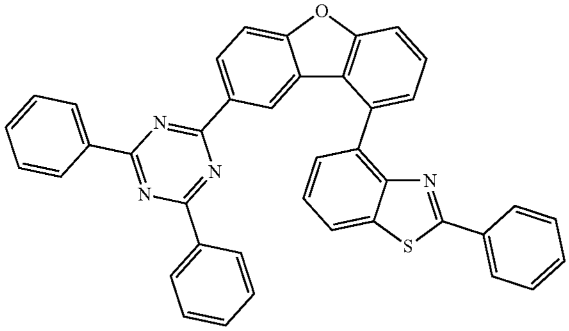
B-57
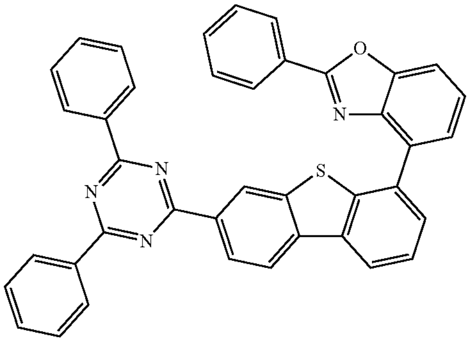
B-58
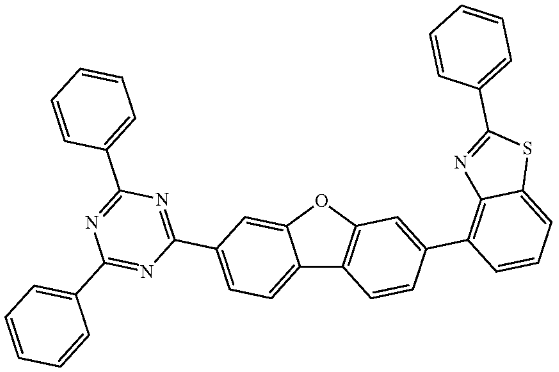
B-59
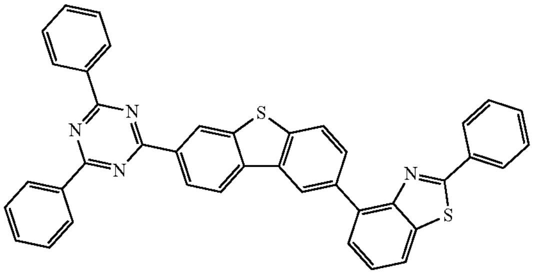
B-60
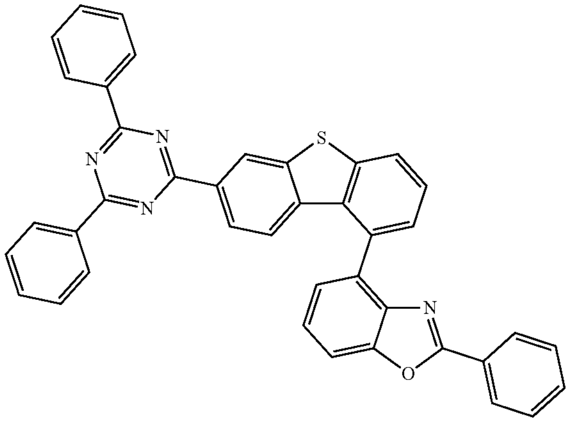
B-61
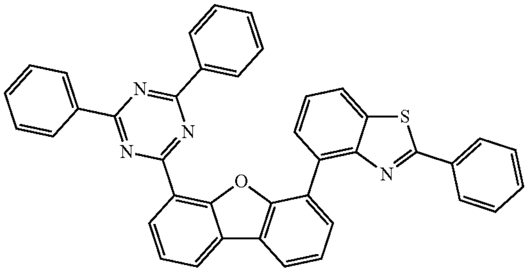
B-62
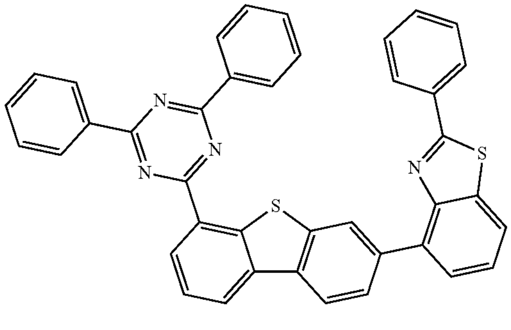

-continued
B-63
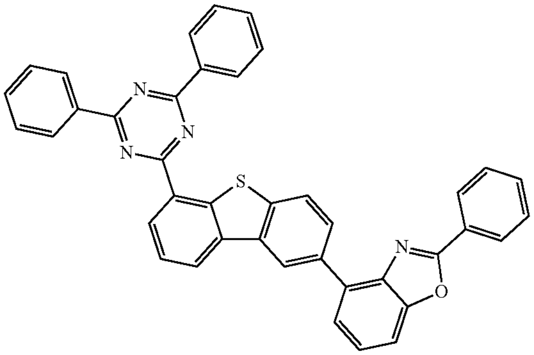
B-64
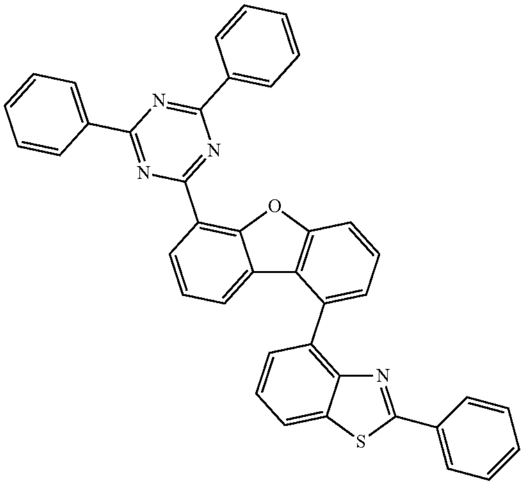
C-1
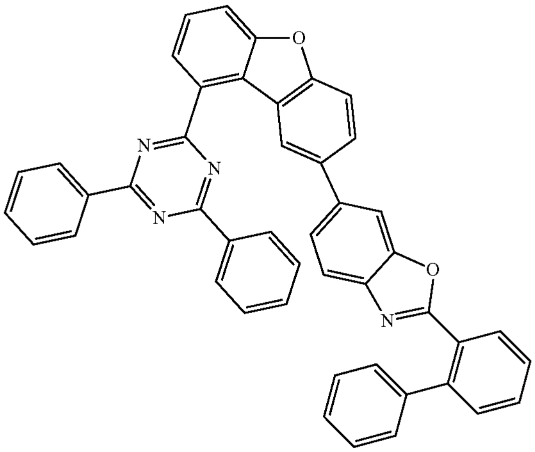
C-2
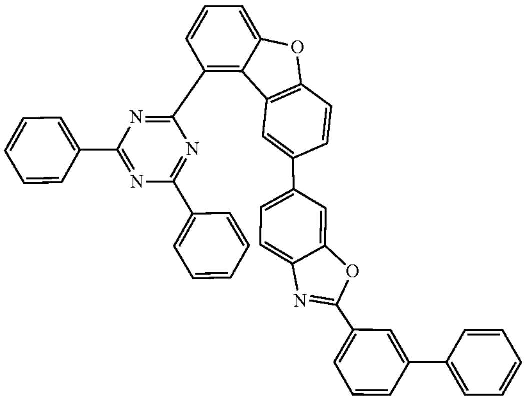
C-3
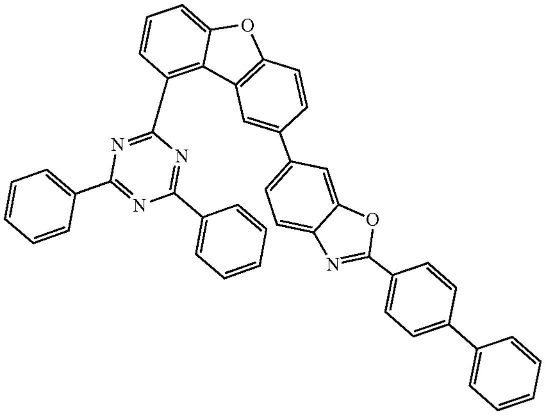
C-4
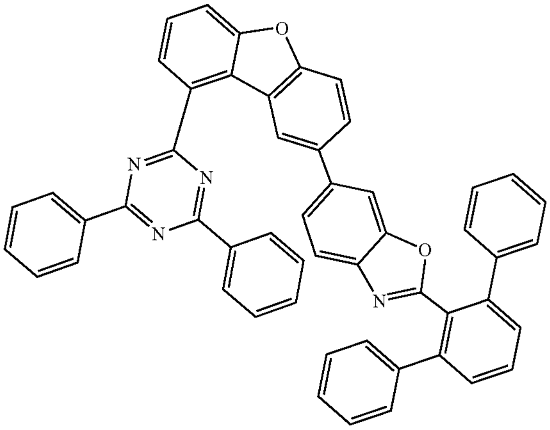

-continued
C-5
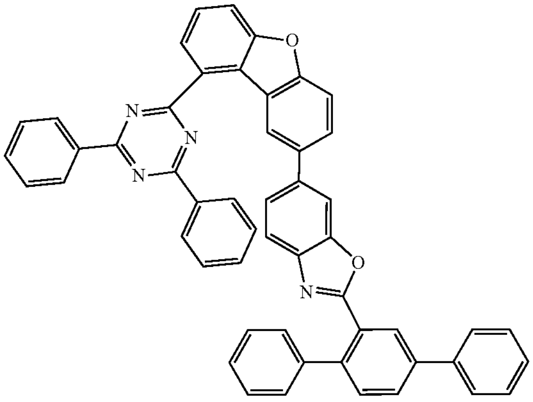
C-6
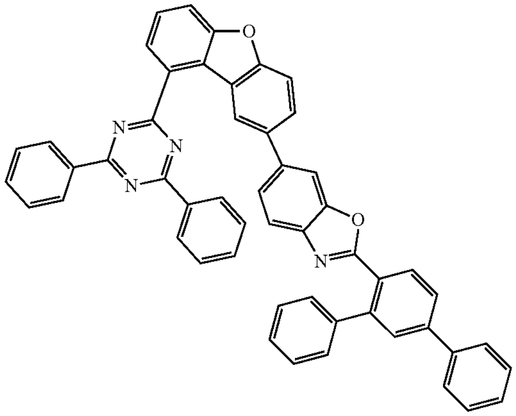
C-7
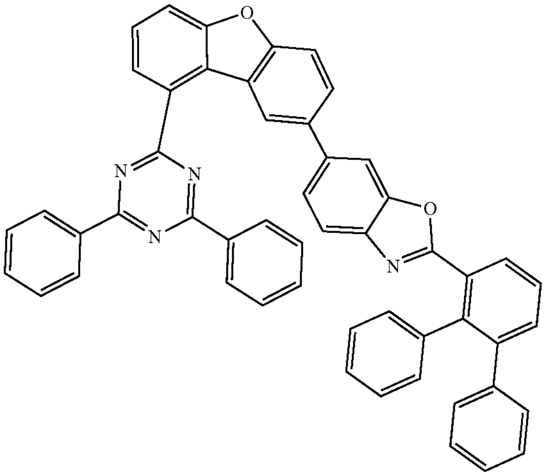
C-8
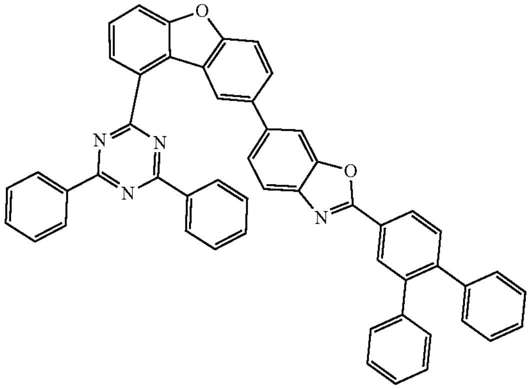
C-9
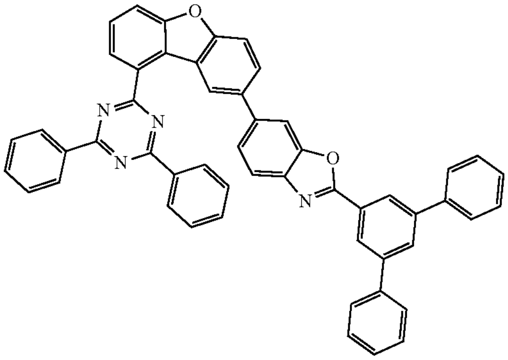
C-10
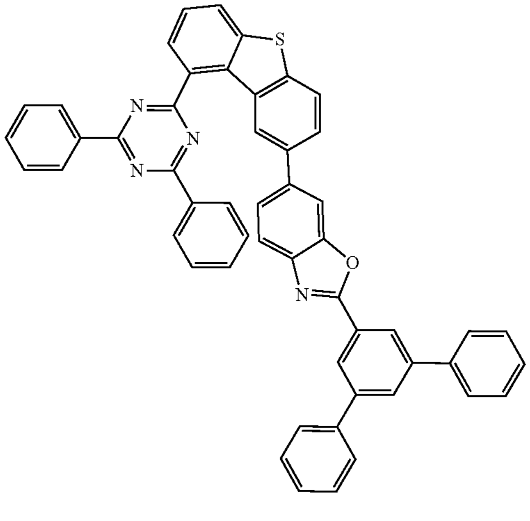

-continued
C-11
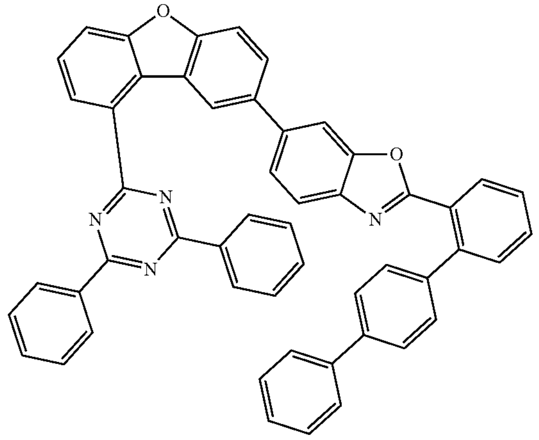
C-12
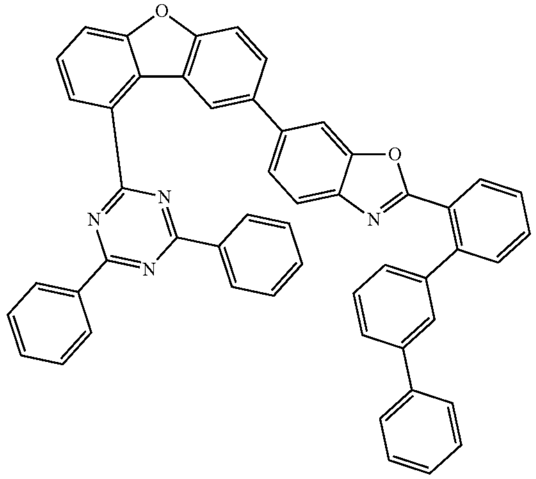
C-13
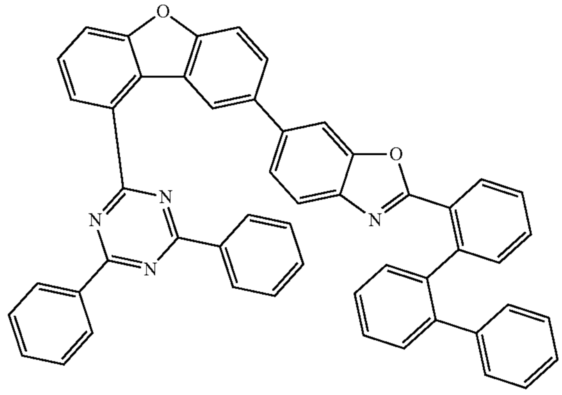
C-14
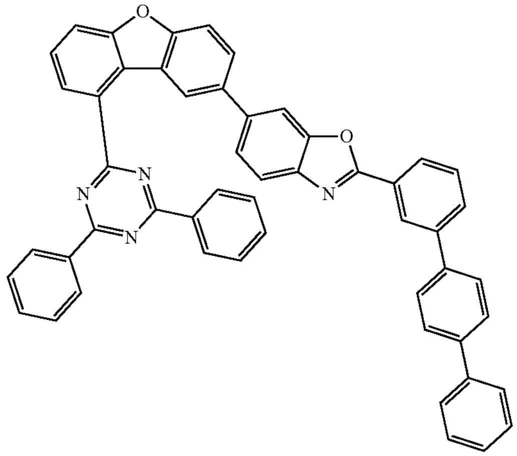
C-15
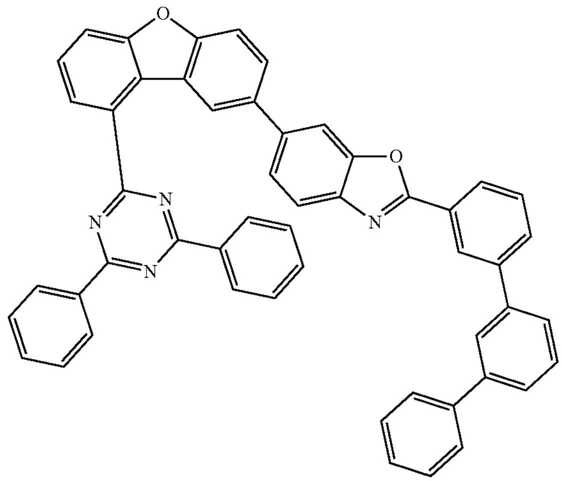
C-16
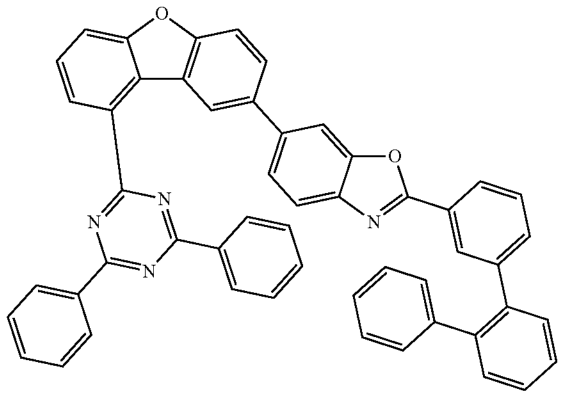

-continued
C-17
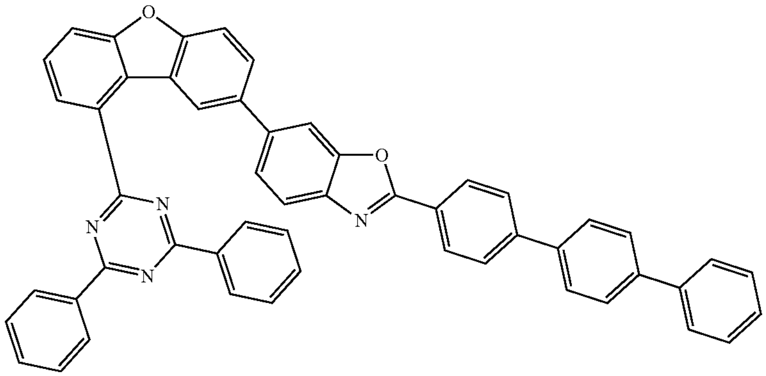
C-18
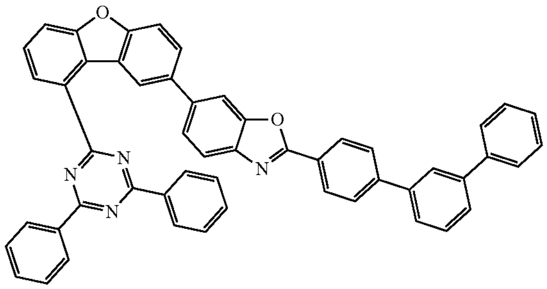
C-19
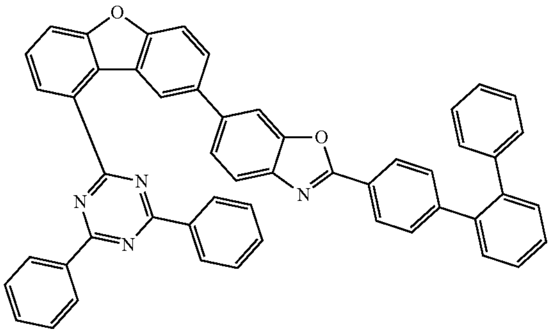
C-20
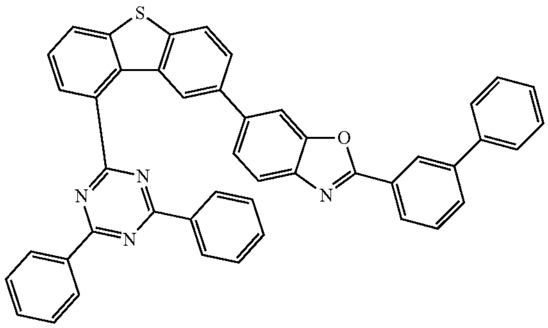
C-21
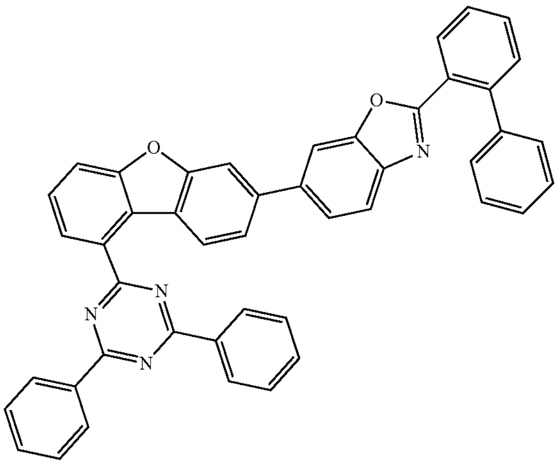

-continued
C-22
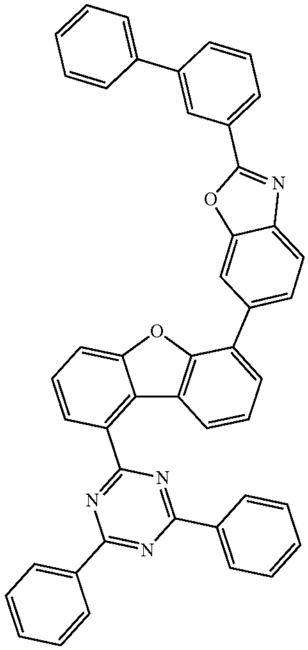
C-23
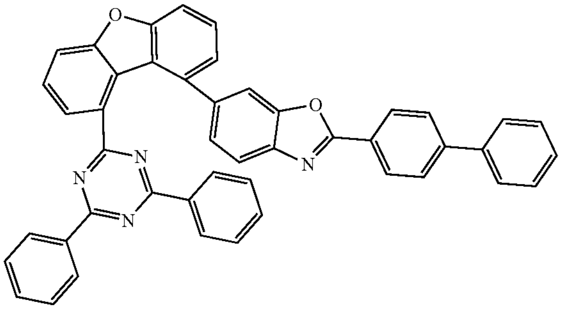
C-24
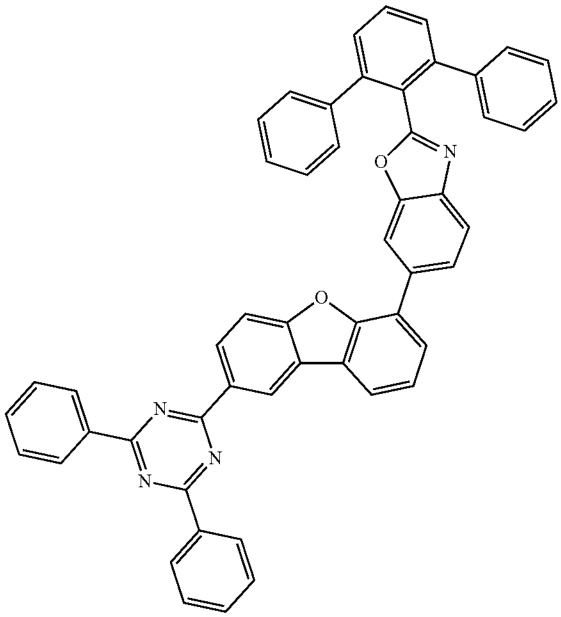
C-25
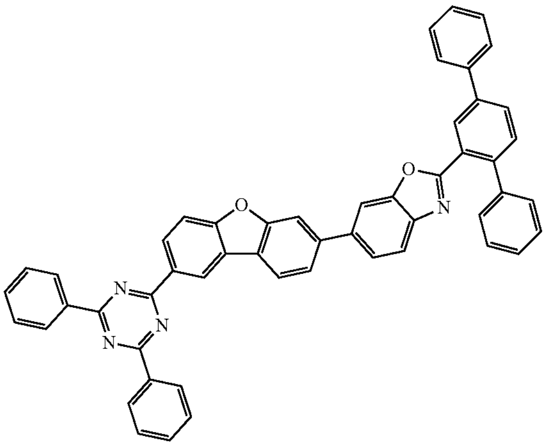
C-26
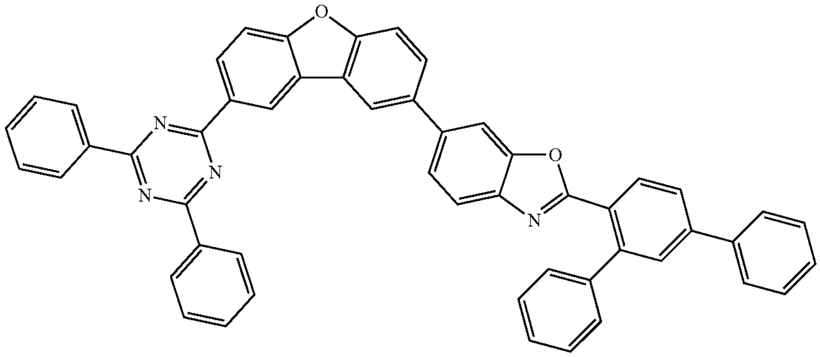

-continued
C-27
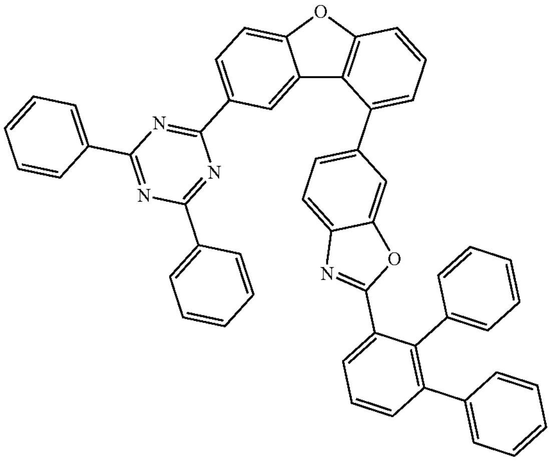
C-28
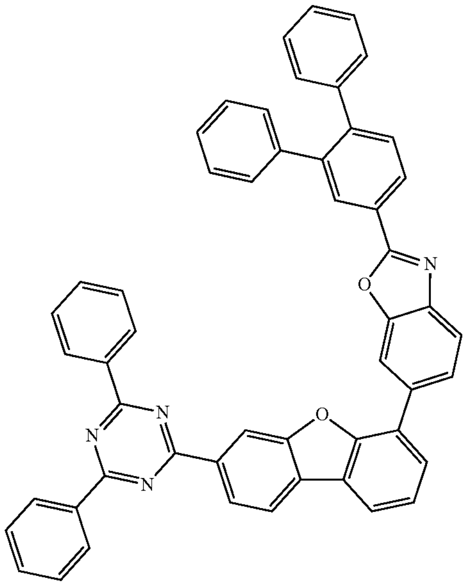
C-29
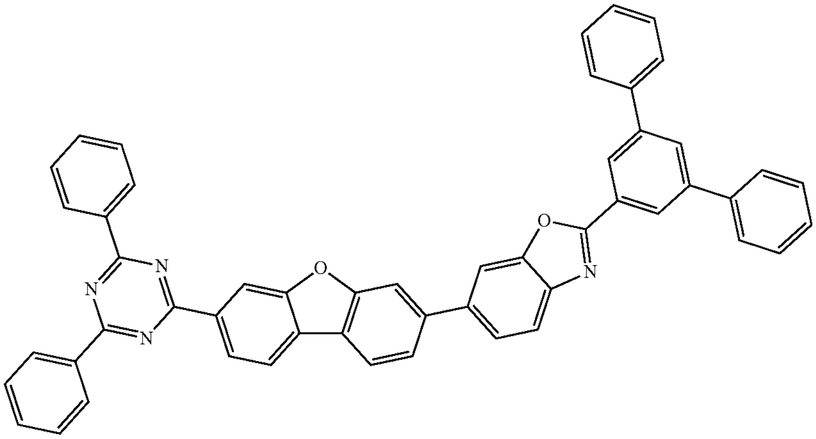
C-30
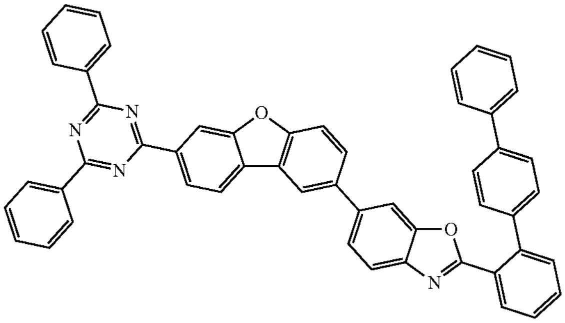
C-31
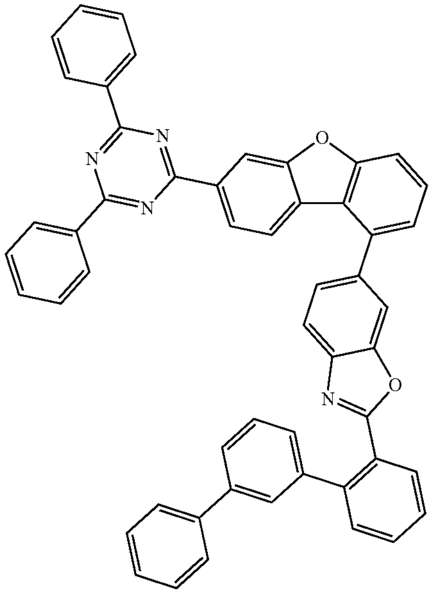

-continued
C-32
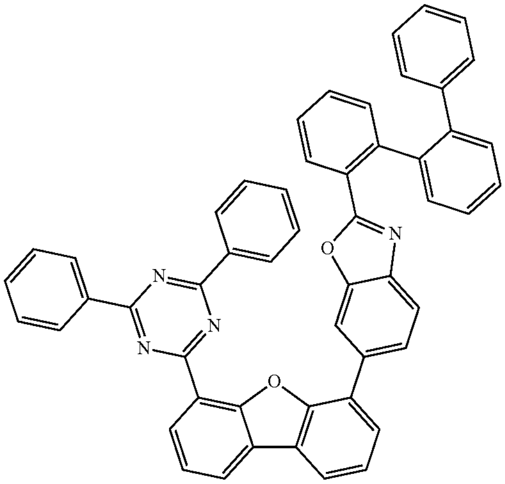
C-33
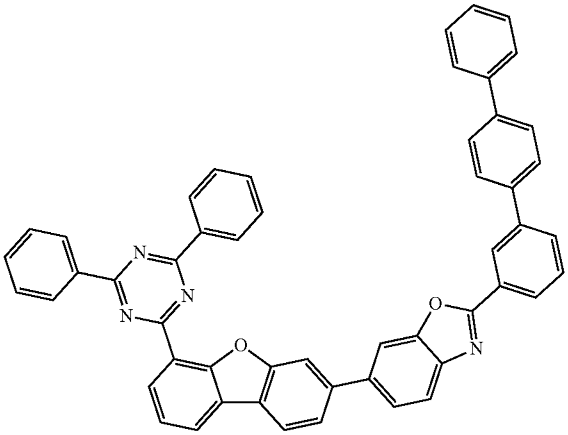
C-34
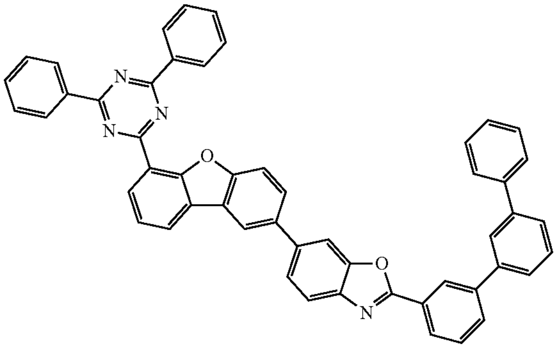
C-35
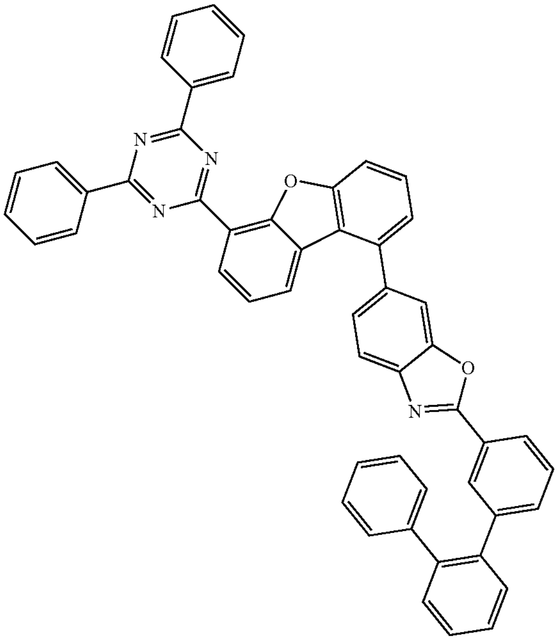

-continued
C-36
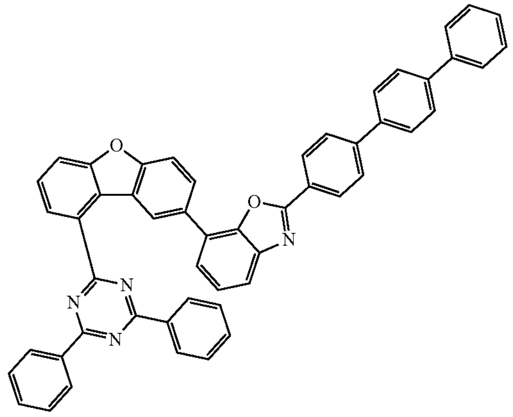
C-37
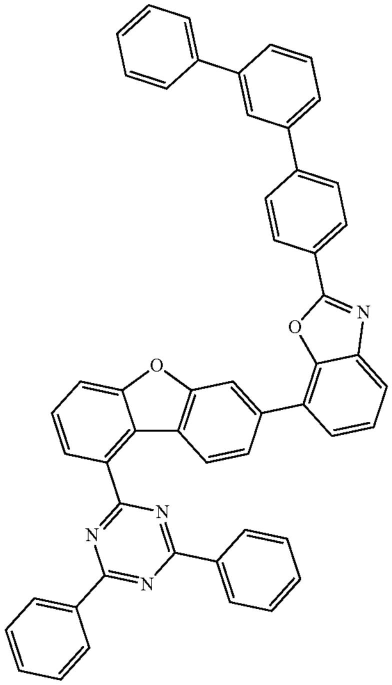
C-38
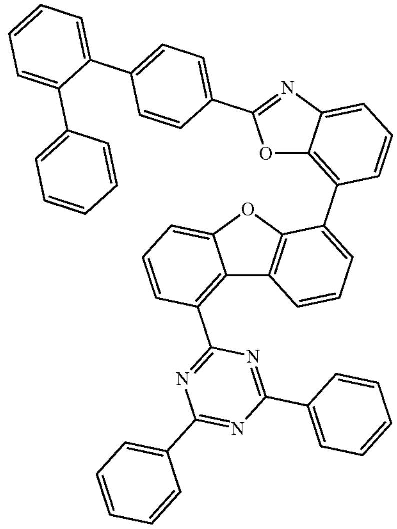
C-39
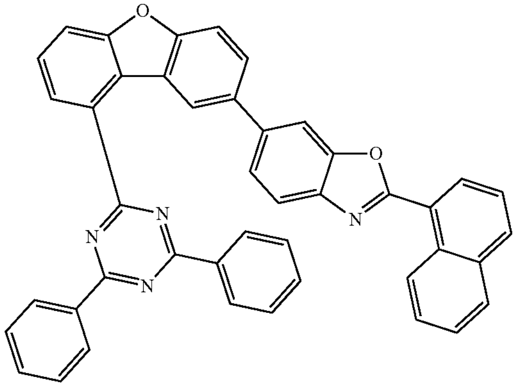

-continued
C-40
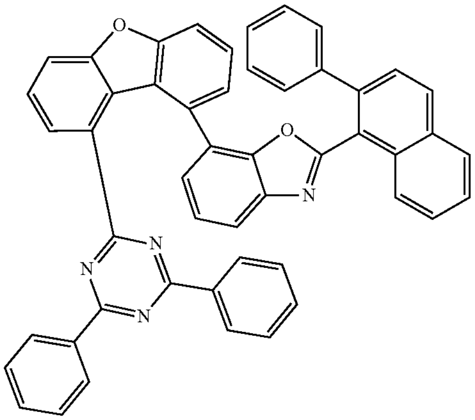
C-41
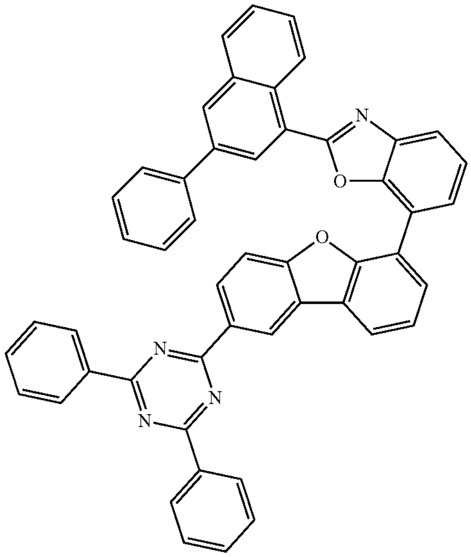
C-42
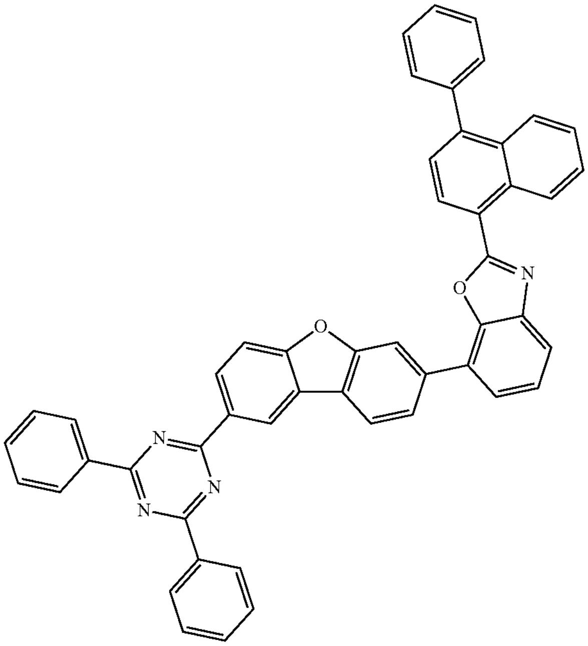
C-43
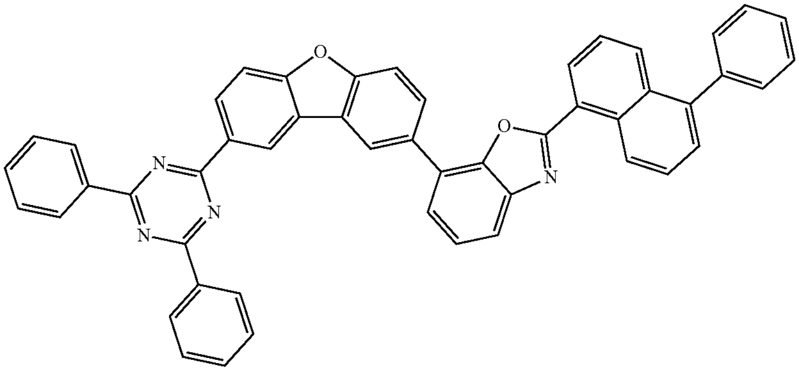

-continued
C-44
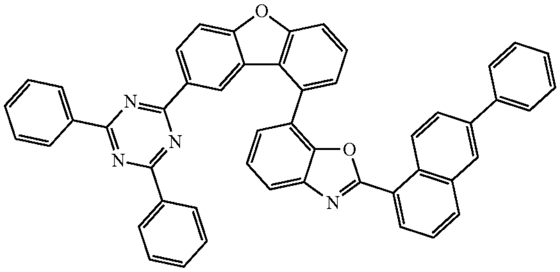
C-45
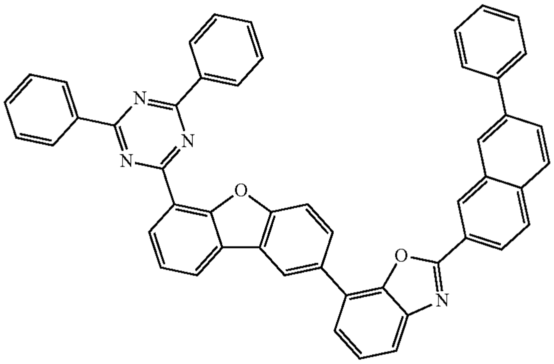
C-46
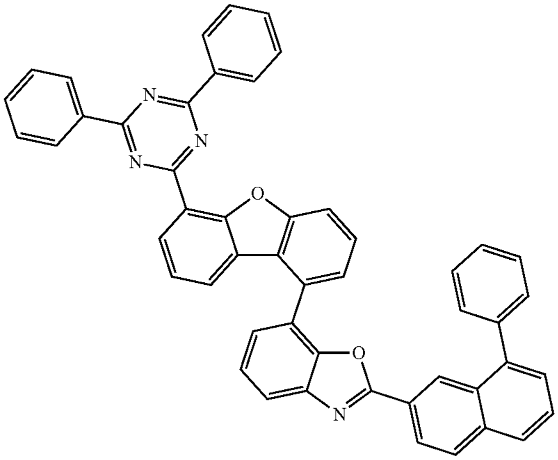
C-47
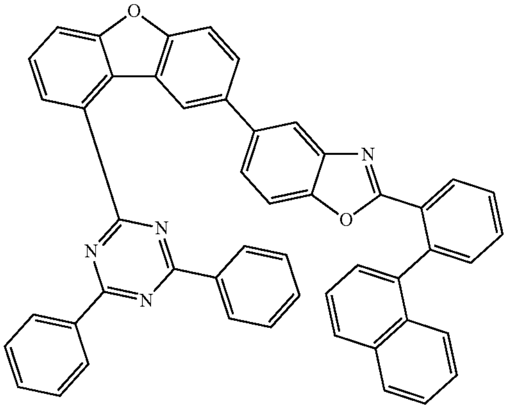
C-48
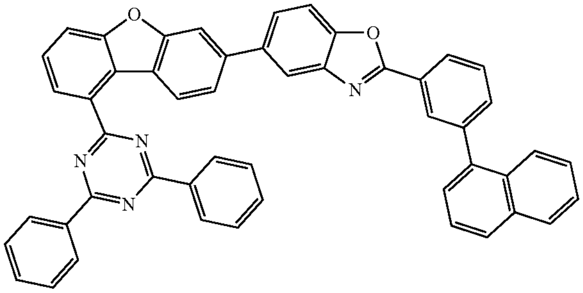
C-49
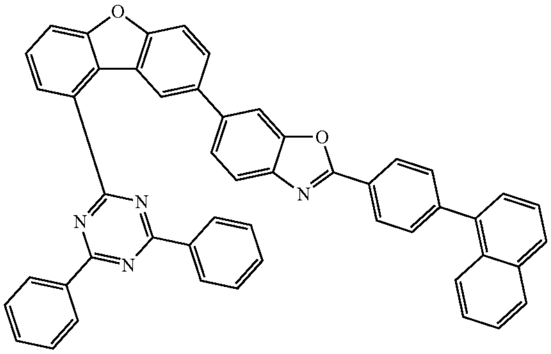

-continued
C-50
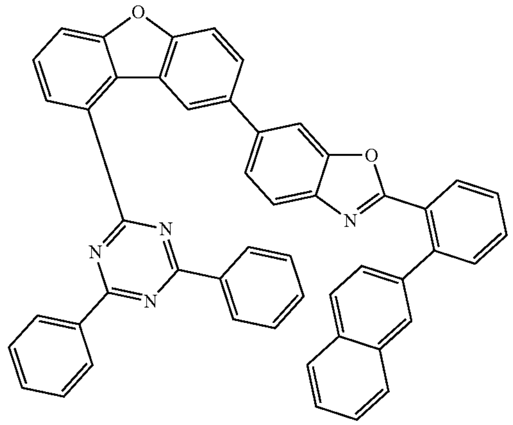
C-51
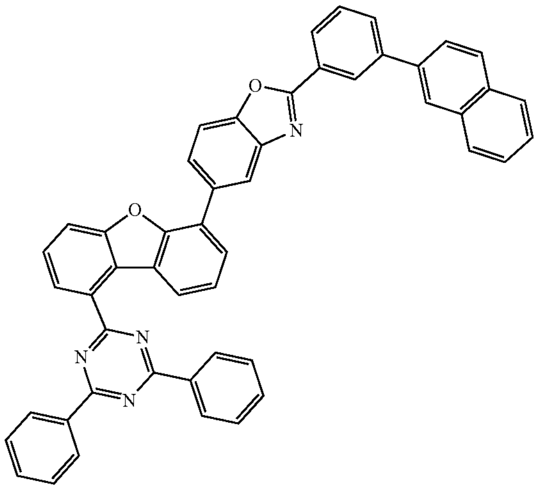
C-52
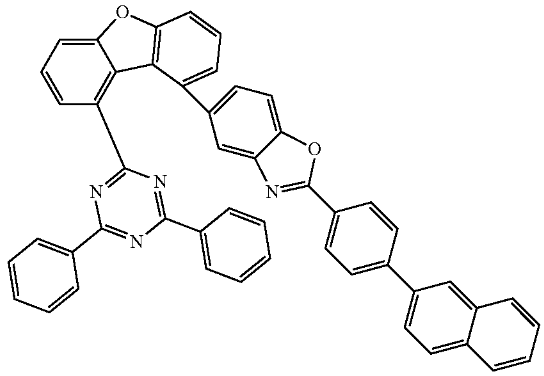
C-53
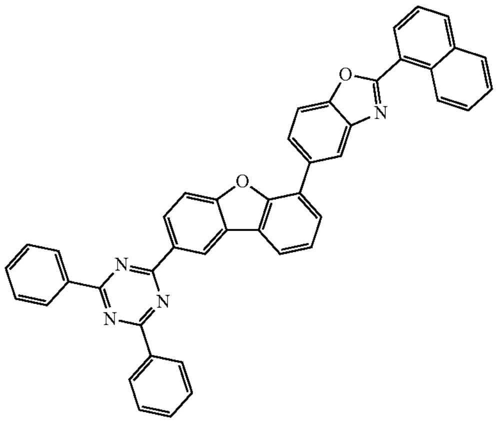
C-54
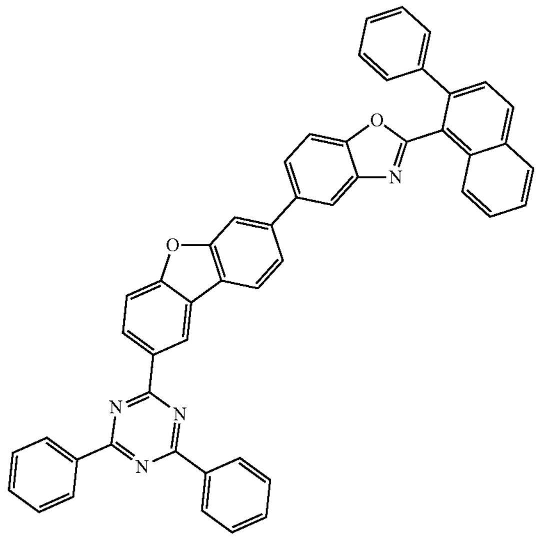
C-55
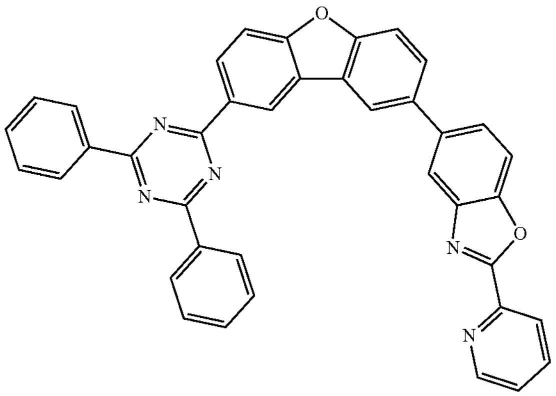

-continued
C-56
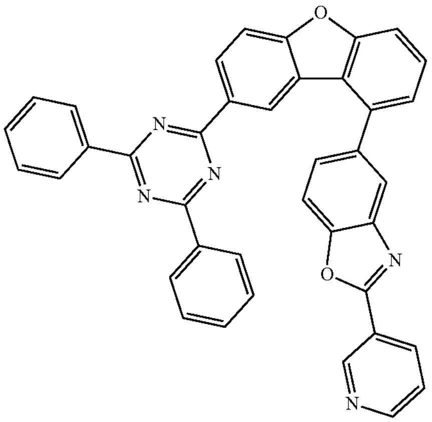
C-57
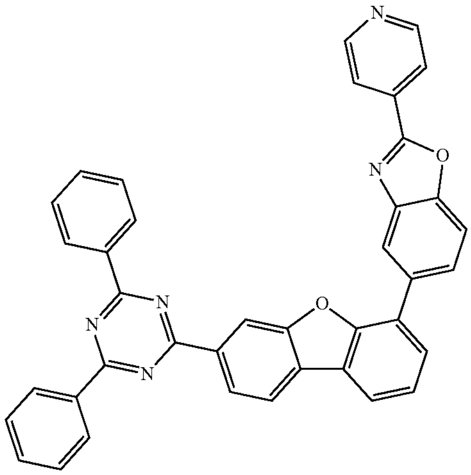
C-58
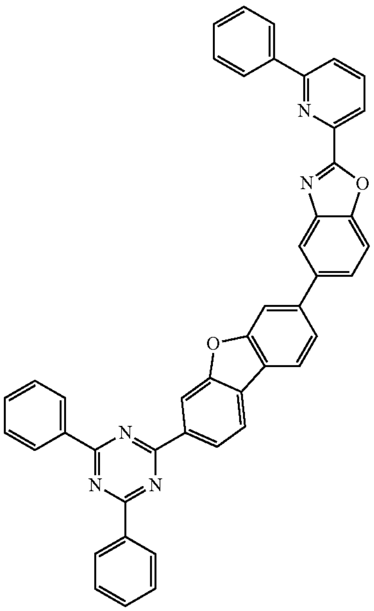
C-59
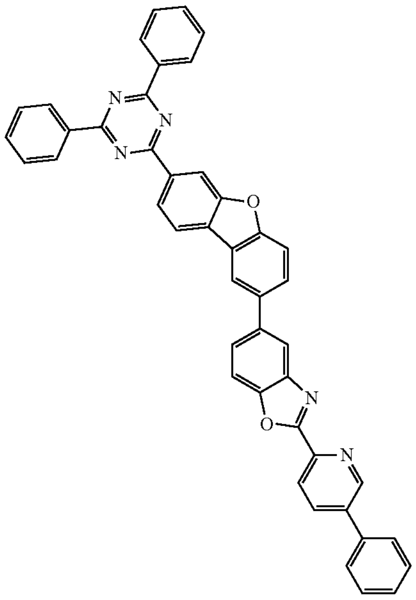

-continued
C-60
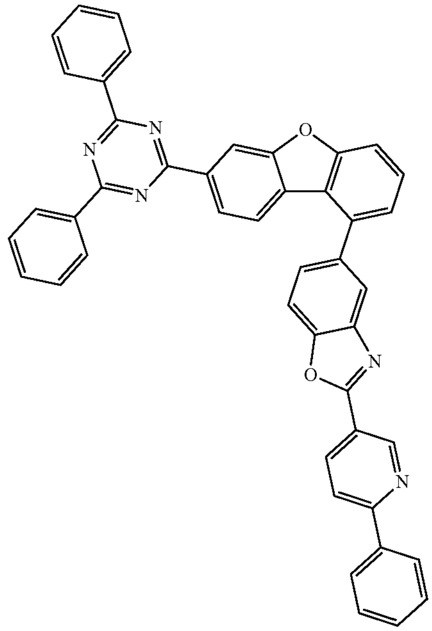
C-61
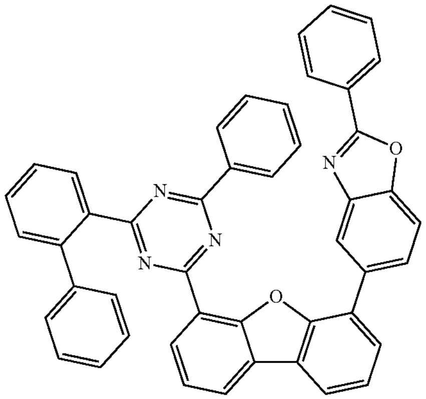
C-62
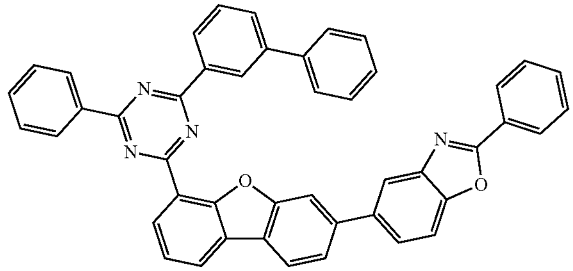
C-63
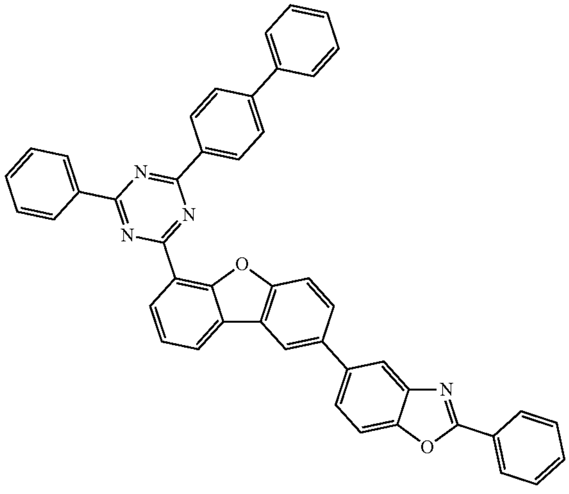

-continued
C-64
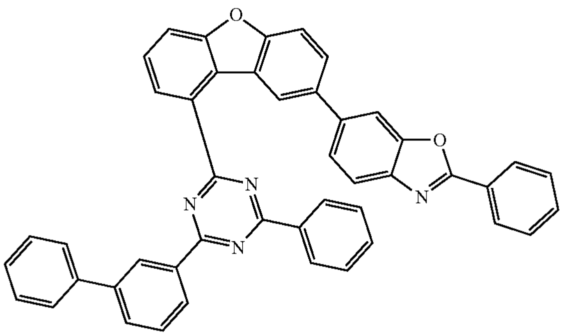
C-65
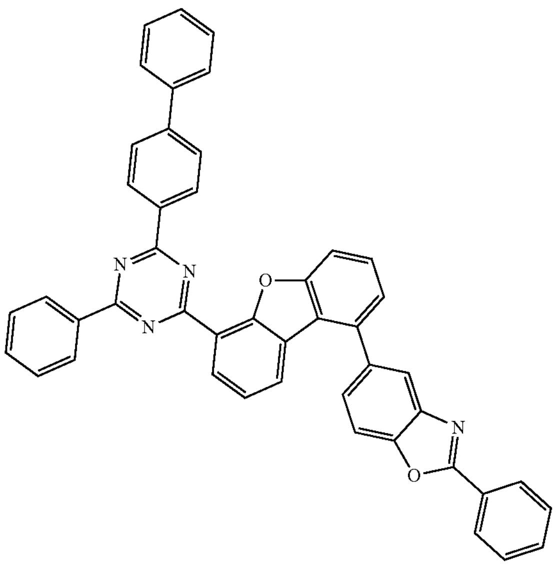
C-66
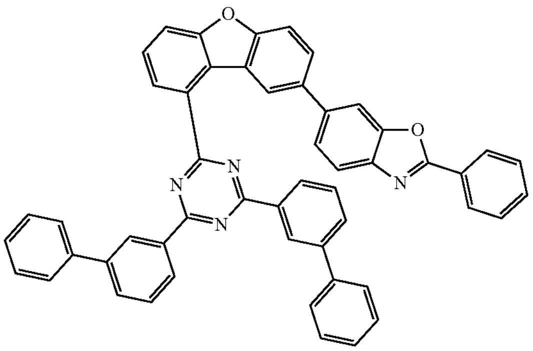
C-67
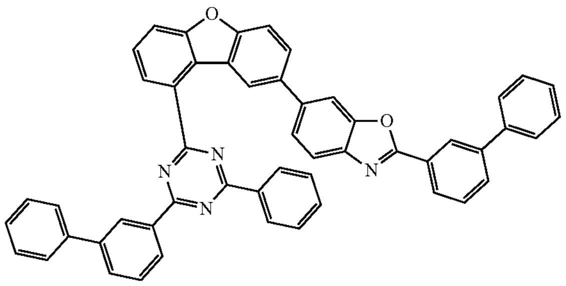
C-68
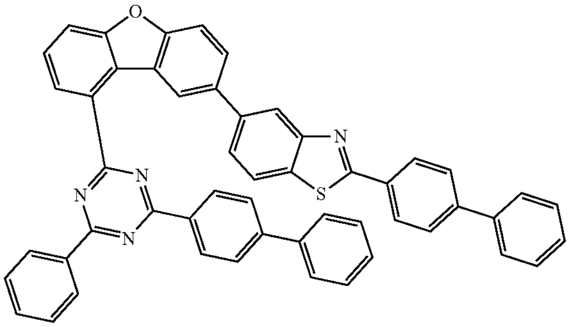
C-69
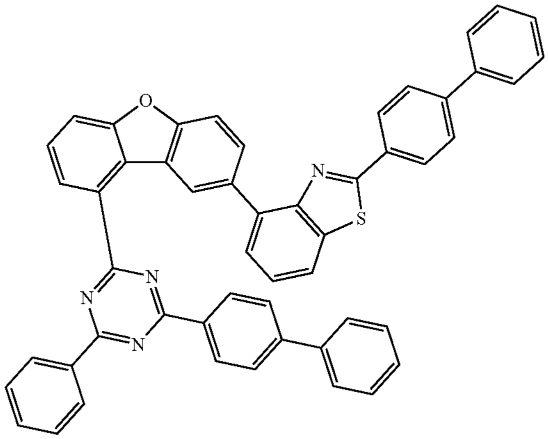

-continued
C-70
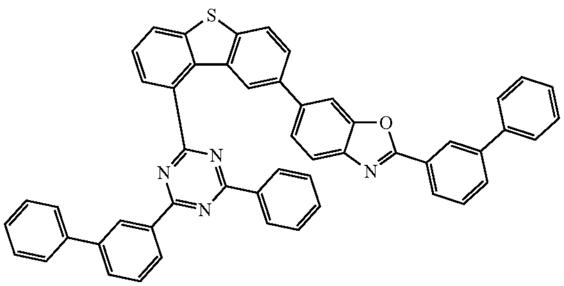
C-71
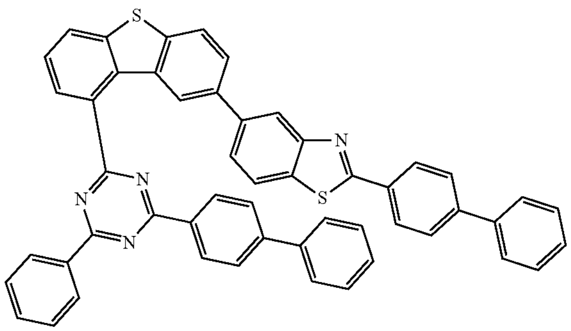
C-72
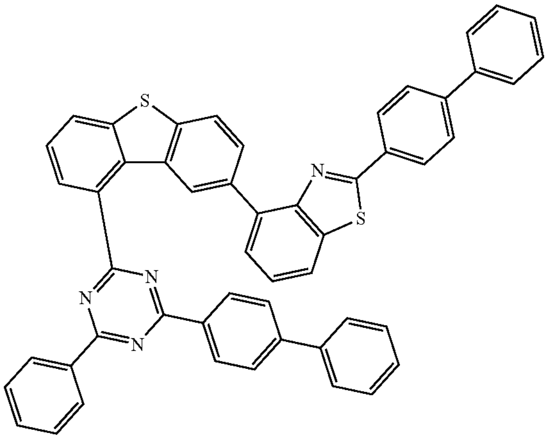
C-73
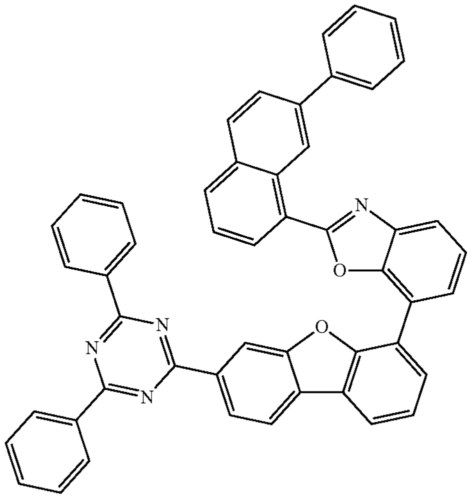
C-74
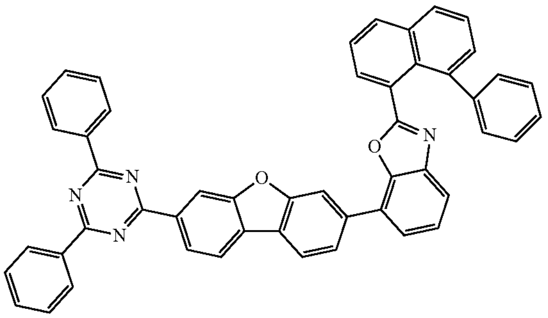
C-75
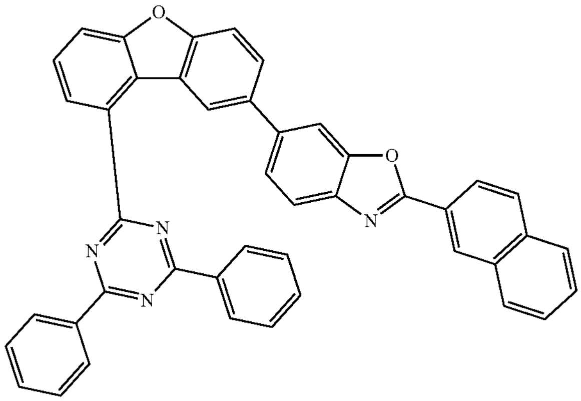

-continued
C-76
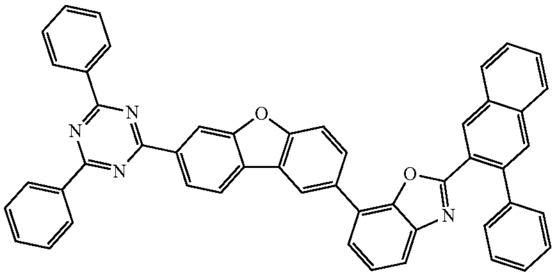
C-77
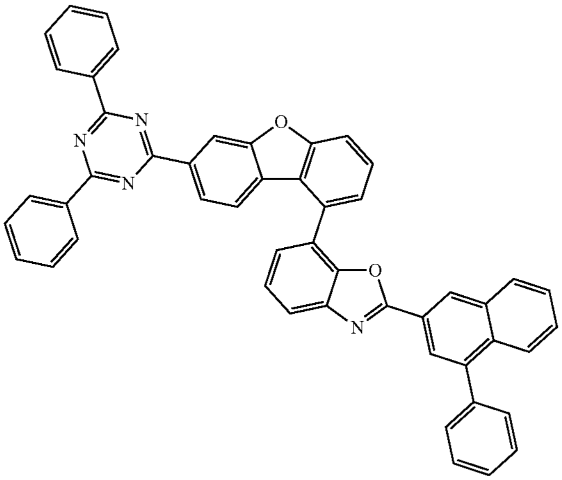
C-78
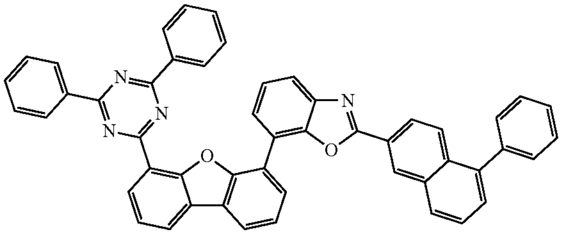
C-79
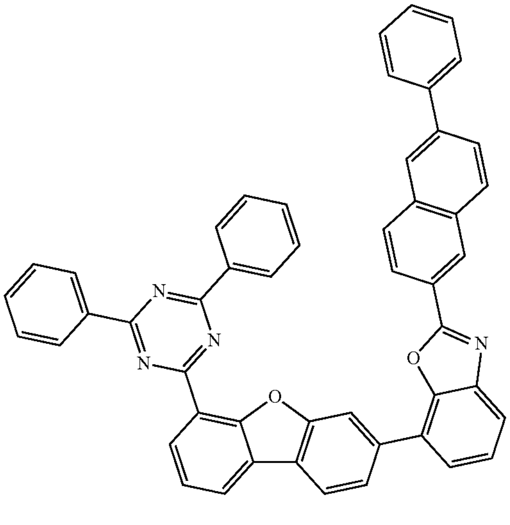
H-1
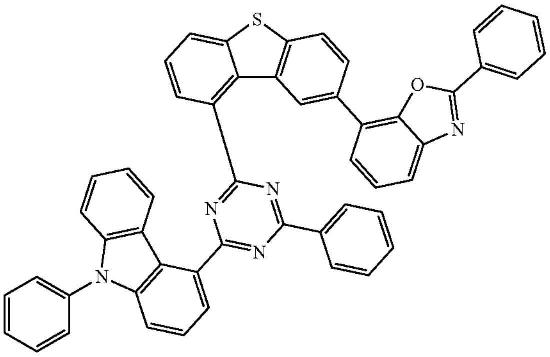
H-2
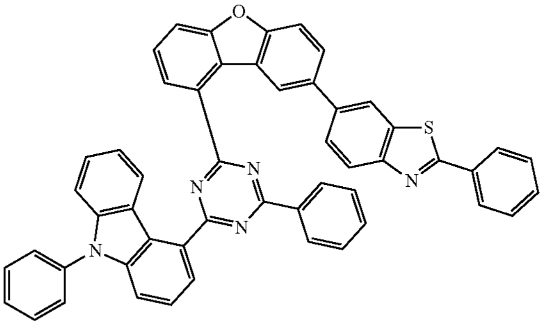

-continued
H-3
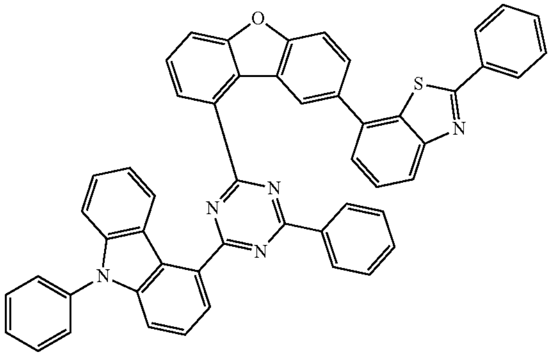
H-4
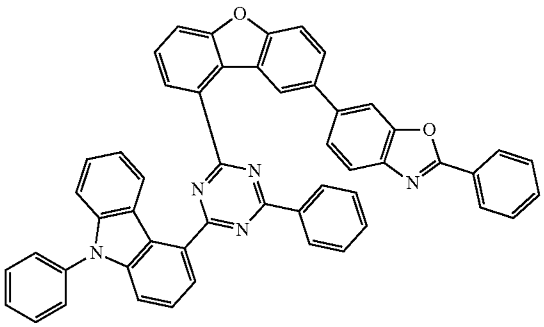
H-5
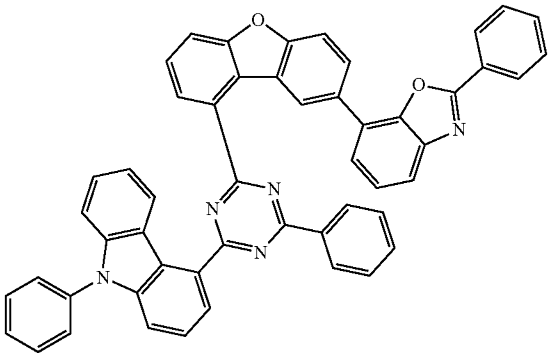
H-6
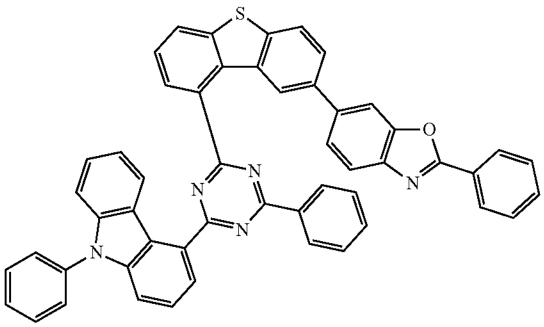
H-7
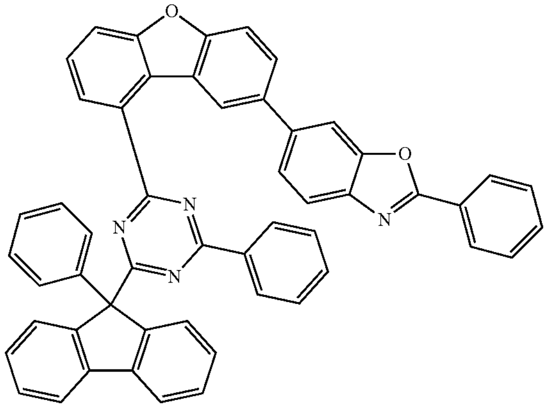
H-8
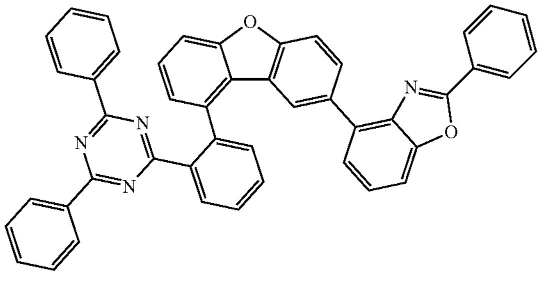

-continued
H-9
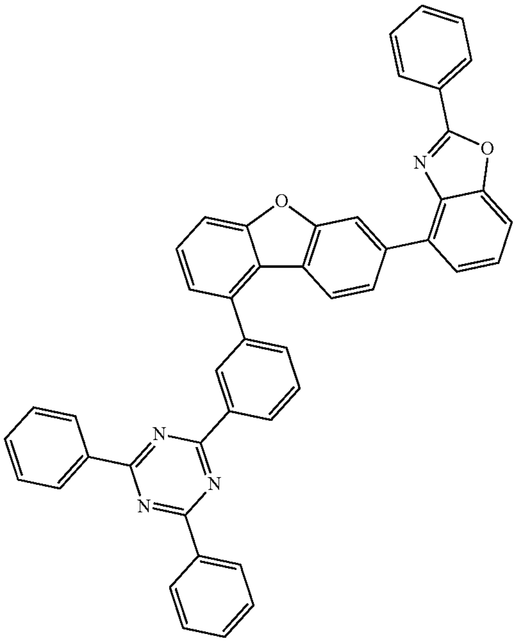
H-10
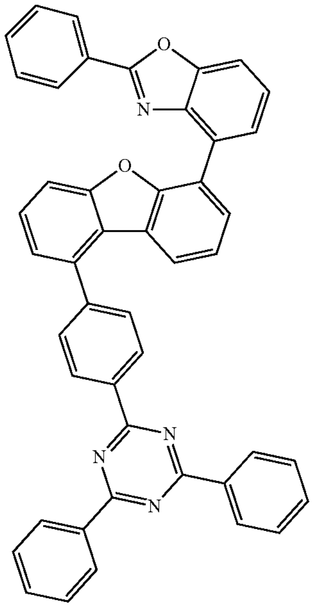
H-11
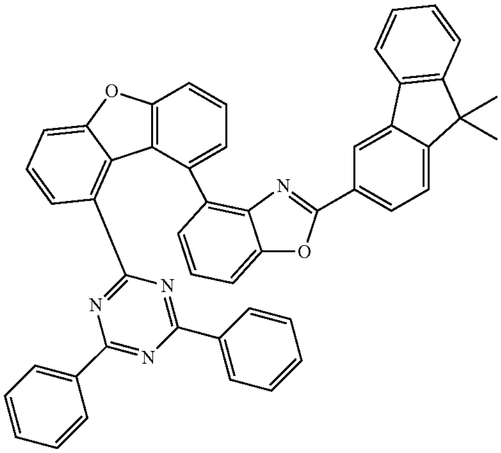
H-12
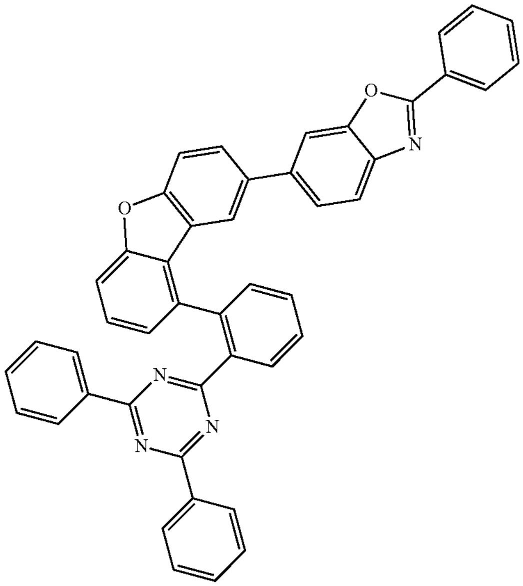

-continued
H-13
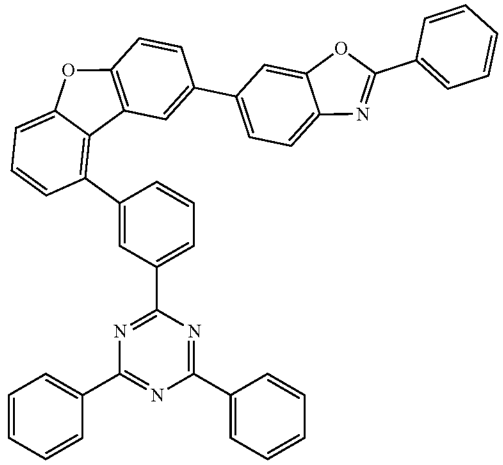
H-14
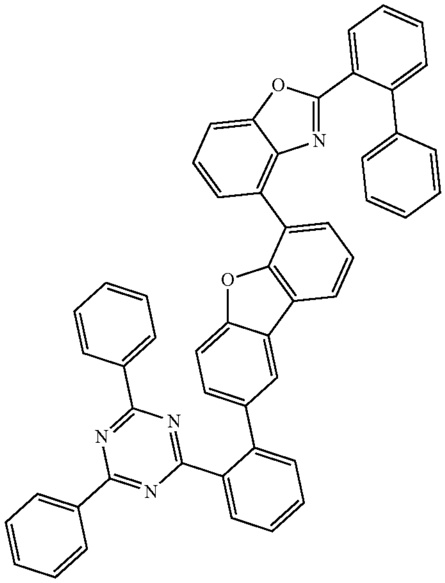
H-15
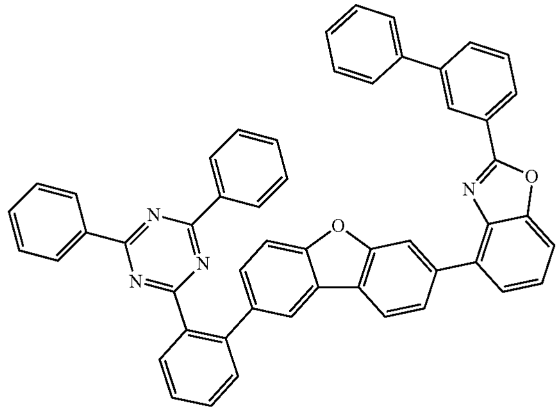
H-16
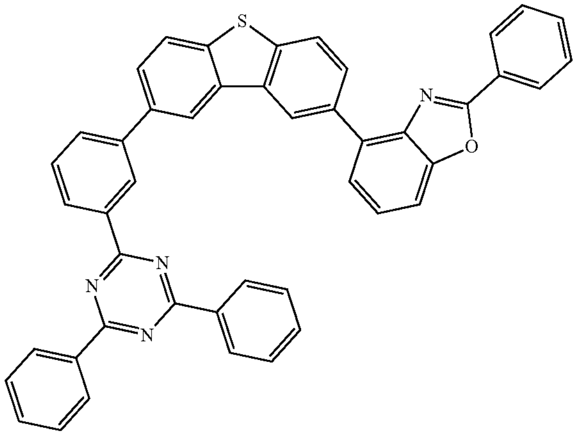
H-17
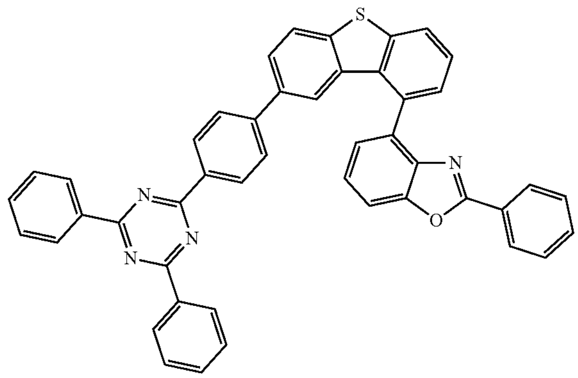
H-18
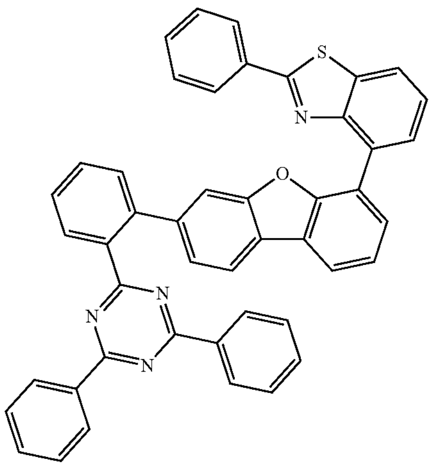

-continued
H-19
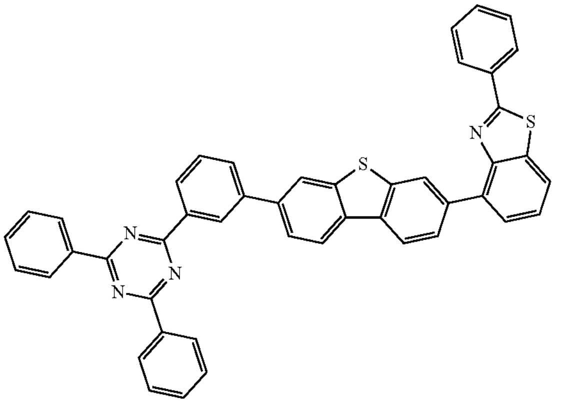
H-20
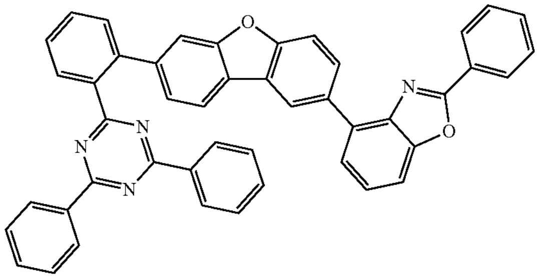
H-21
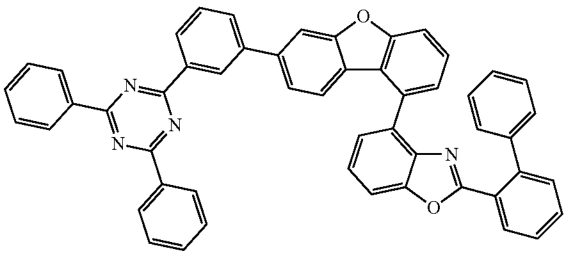
H-22
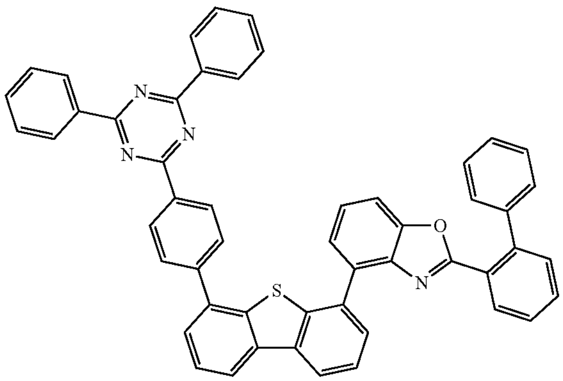
H-23
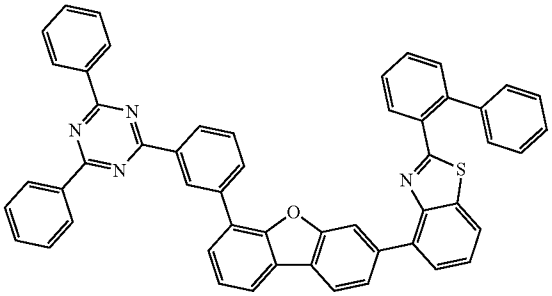
H-24
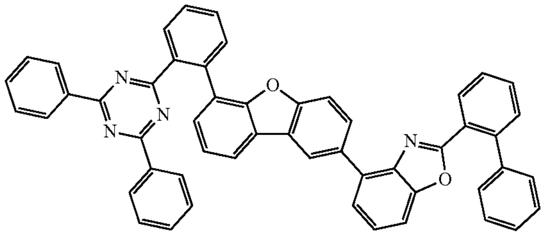
H-25
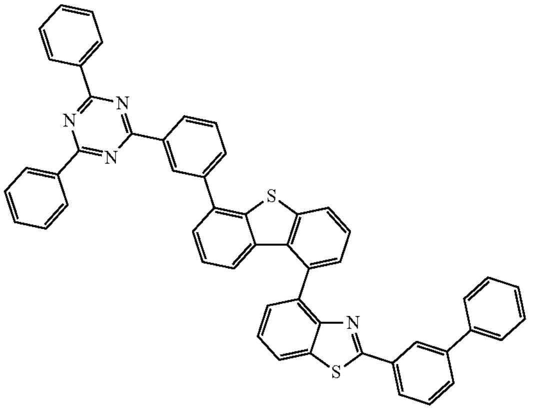
H-26
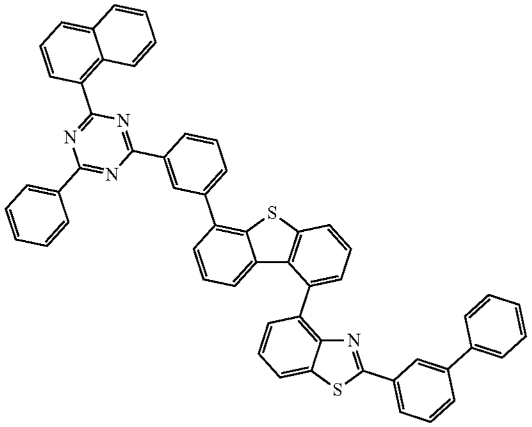

-continued
H-27
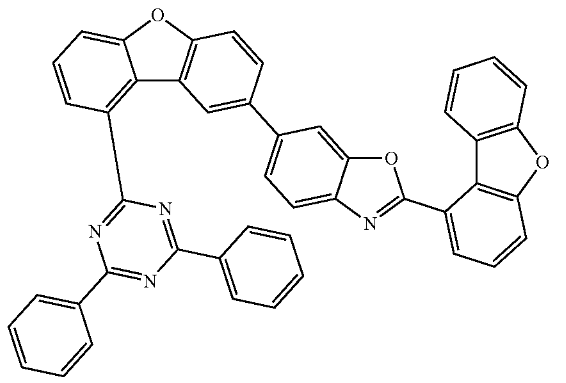
H-28
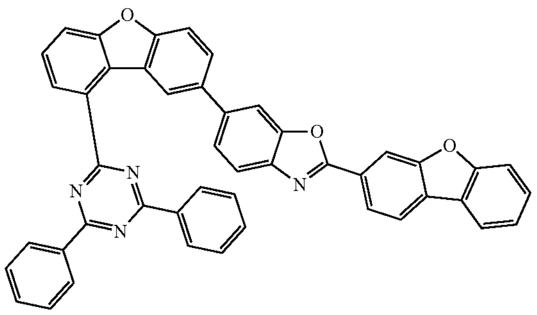
H-29
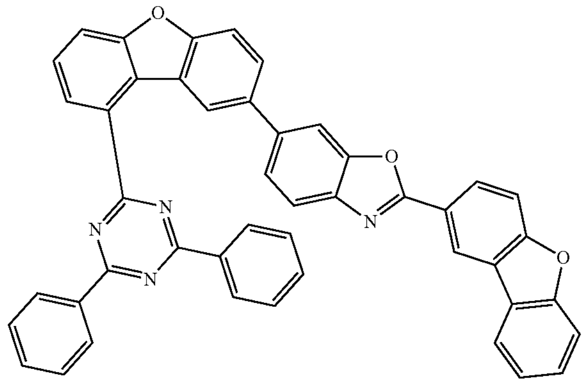
H-30
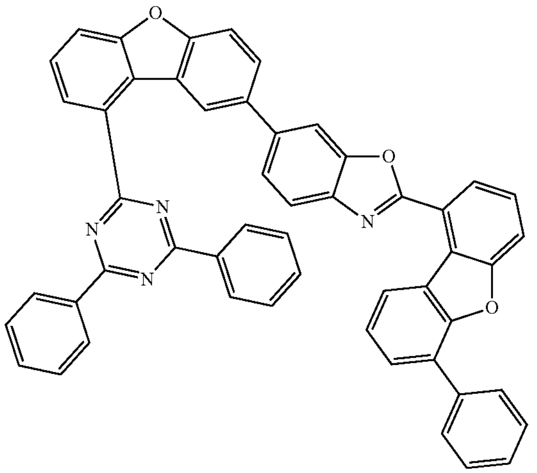
H-31
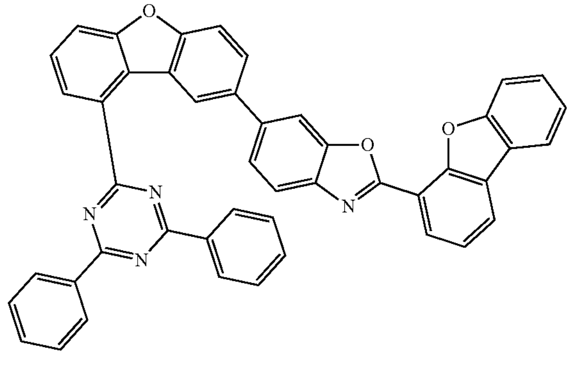
H-32
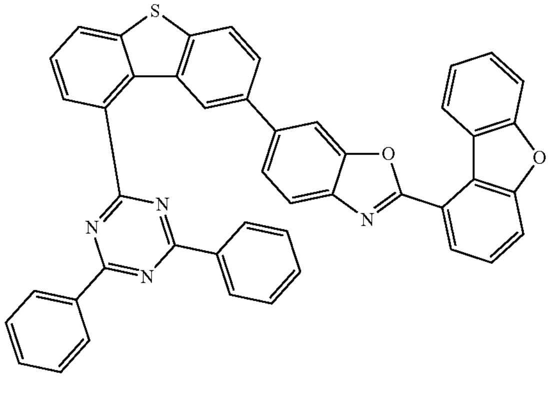

-continued
H-33
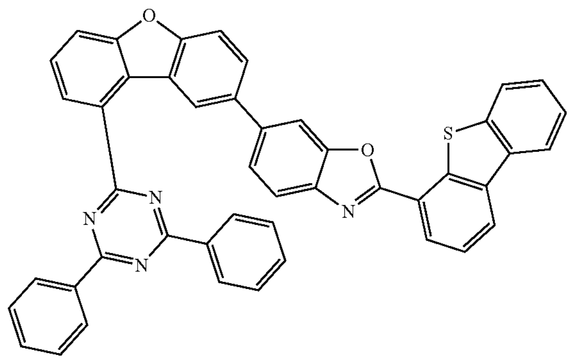
H-34
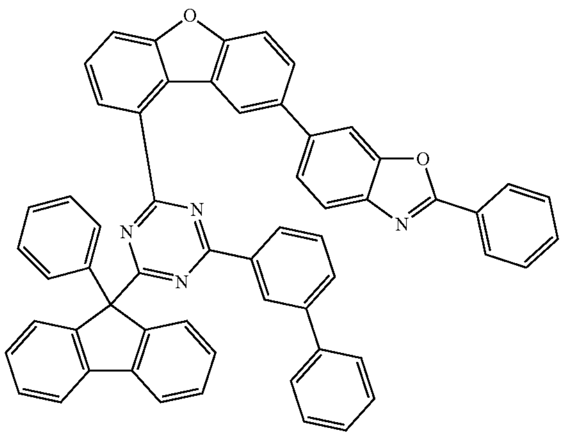
H-35
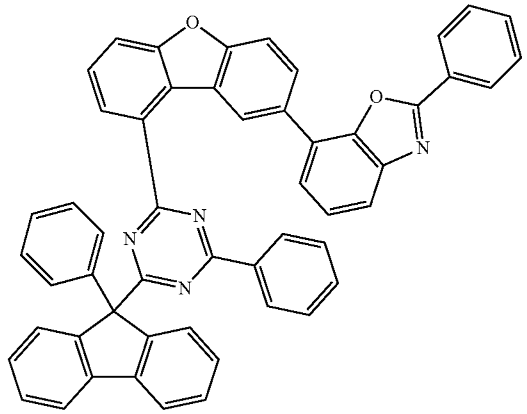
H-36
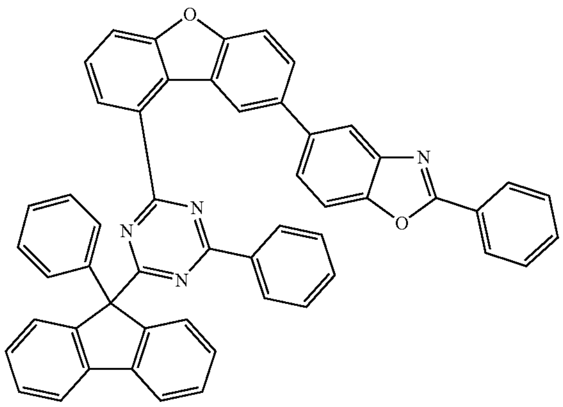
H-37
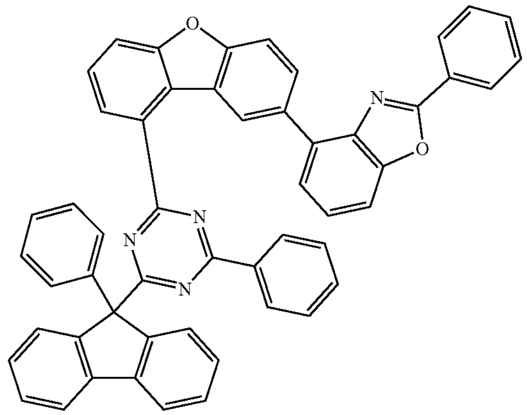
H-38
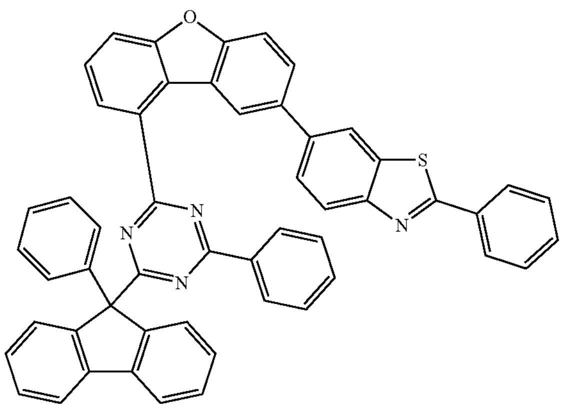

-continued
H-39
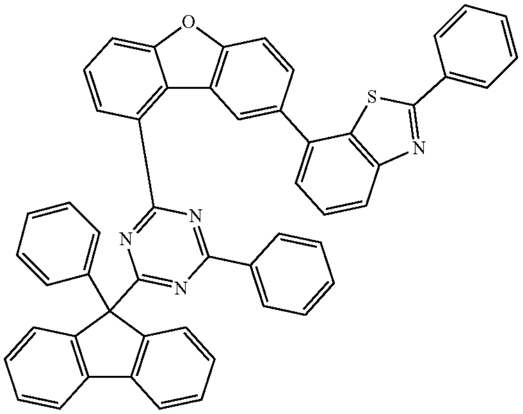
H-40
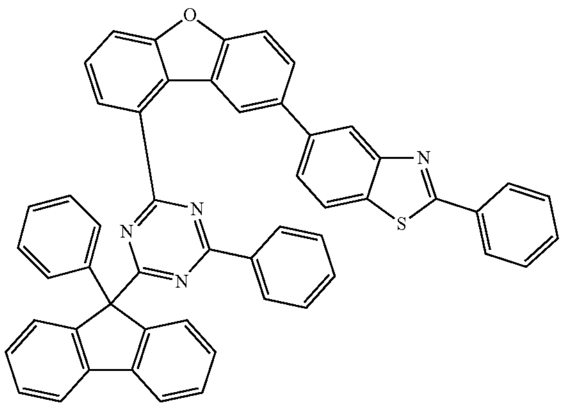
H-41
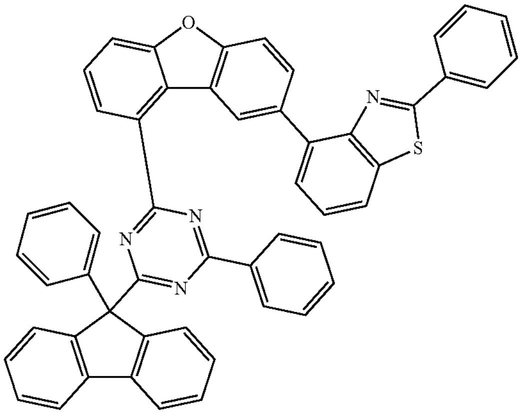
H-42
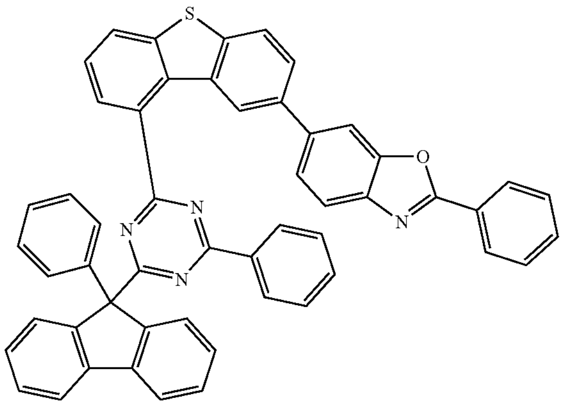
H-43
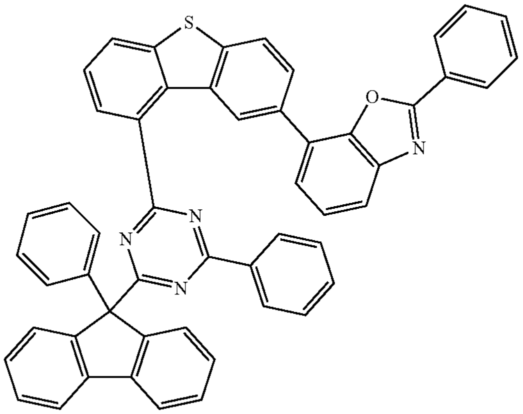
H-44
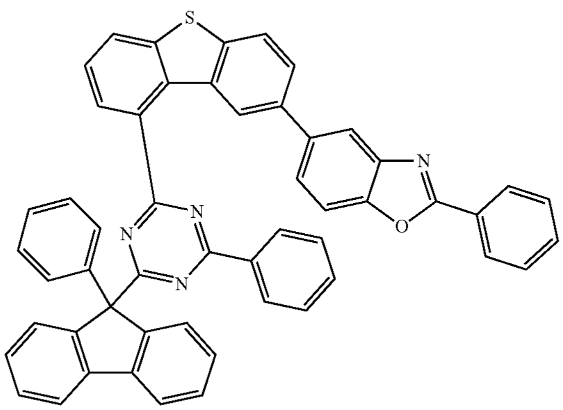

-continued
H-45
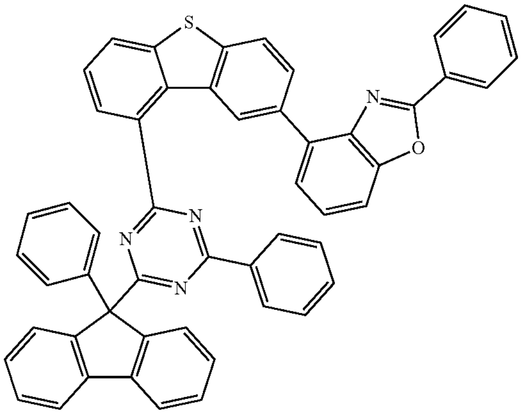
H-46
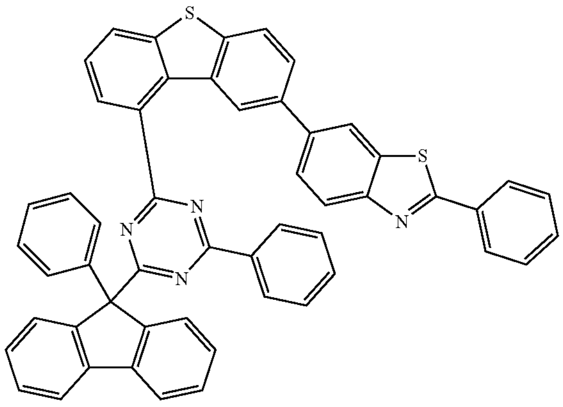
H-47
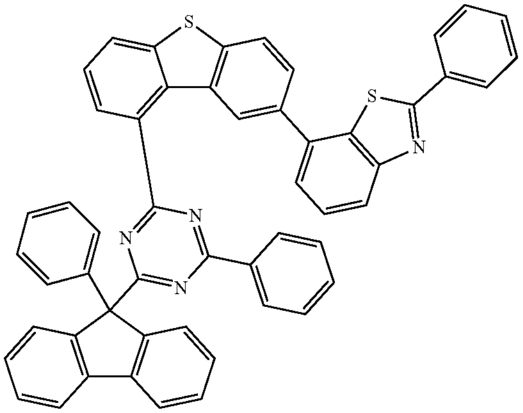
H-48
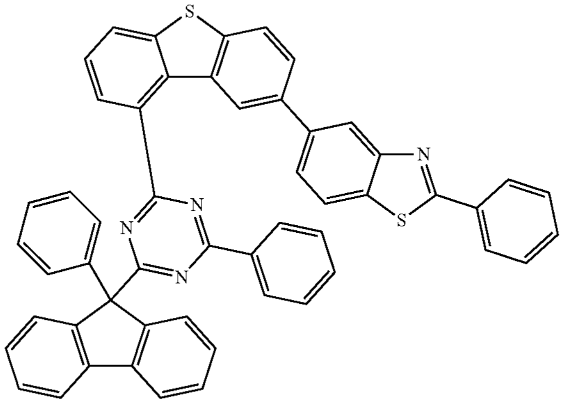
H-49
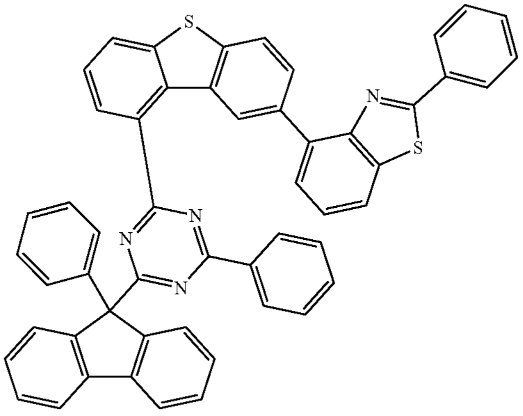
H-50
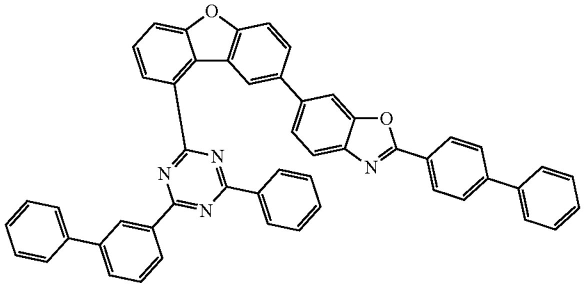

-continued
H-51
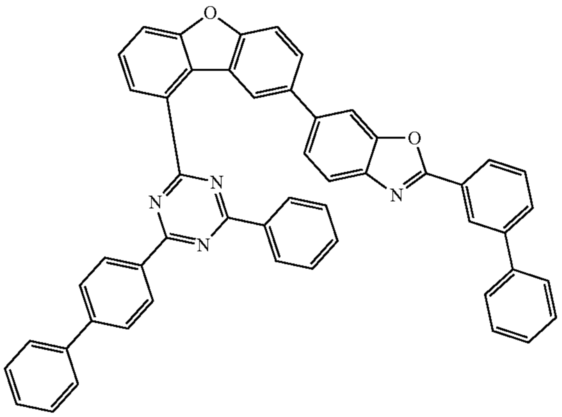
H-52
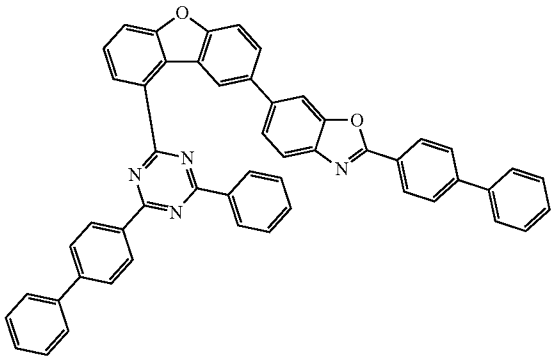
H-53
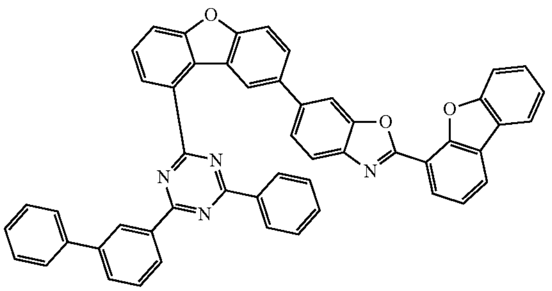
H-54
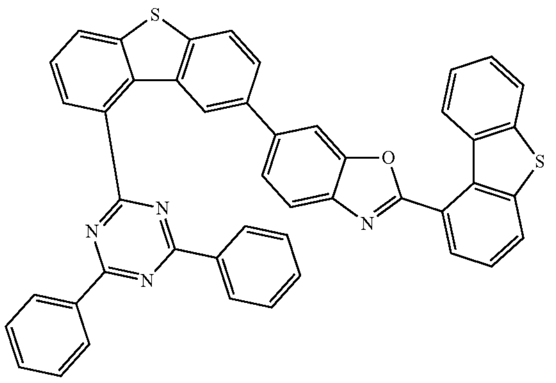
The compound of formula 1 according to the present disclosure may be prepared by a synthetic method known to one skilled in the art, and for example may be prepared as shown in the following reaction scheme 1, but is not limited thereto.
[Reaction Scheme 1]
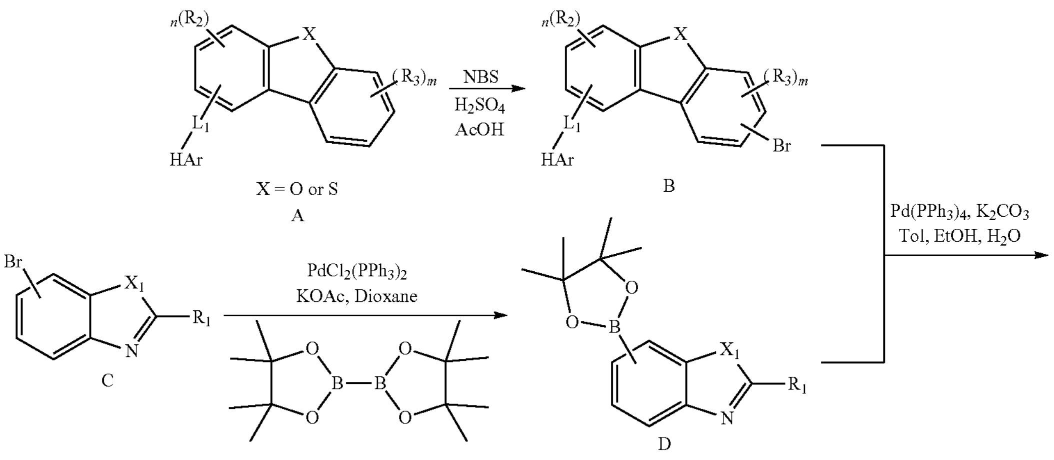

-continued

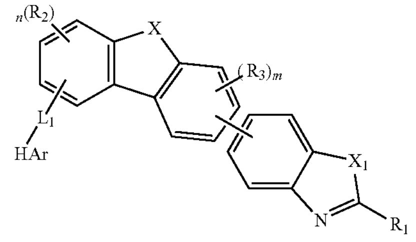

E

In reaction scheme 1, X, $X_1$, HAr, L, $R_1$ to $R_3$, n, and m are as defined in formula 1.

One skilled in the art will be able to readily understand that all synthesis of the compound represented by formula 1 are based on a Buchwald-Hartwig cross-coupling reaction, an N-arylation reaction, a H-mont-mediated etherification reaction, a Miyaura borylation reaction, a Suzuki cross-coupling reaction, an Intramolecular acid-induced cyclization reaction, a Pd(II)-catalyzed oxidative cyclization reaction, a Grignard reaction, a Heck reaction, a Cyclic Dehydration reaction, an $SN_1$ substitution reaction, an $SN_2$ substitution reaction, a Phosphine-mediated reductive cyclization reaction, etc., and the reactions above proceed even when substituents, which are defined in formula 1 above but are not specified in the specific synthesis examples, are bonded.

The present disclosure provides an organic electroluminescent material comprising the organic electroluminescent compound represented by formula 1, and an organic electroluminescent device comprising the organic electroluminescent material. The organic electroluminescent material may consist of the organic electroluminescent compound according to the present disclosure alone, or may further comprise conventional materials included in the organic electroluminescent material.

The organic electroluminescent compound represented by formula 1 of the present disclosure may be comprised in at least one of a light-emitting layer, a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer, preferably, may be comprised in the light-emitting layer. When used in the light-emitting layer, the organic electroluminescent compound represented by formula 1 of the present disclosure may be comprised as a host material. Preferably, the light-emitting layer may further comprise at least one dopant. If necessary, the organic electroluminescent compound of the present disclosure may be used as a co-host material. That is, the light-emitting layer may further include an organic electroluminescent compound other than the organic electroluminescent compound represented by formula 1 of the present disclosure (first host material) as a second host material. The weight ratio between the first host material and the second host material is in a ratio of about 1:99 to about 99:1, preferably in a ratio of about 10:90 to about 90:10, and more preferably in a ratio of about 30:70 to about 70:30. Also, the first host material and the second host material may be combined in an amount of a desired ratio by placing them in a shaker and then mixing them; by placing them in a glass tube, dissolving them by heating, and then collecting the resultant; or by dissolving them in a solvent, etc. When two or more materials are included in one layer, mixed deposition may be performed to form a layer, or co-deposition may be performed separately at the same time to form a layer.

For example, the plurality of host materials for an organic eletroluminescent device of the present disclosure may comprise at least one compound represented by formula 1 and at least one compound represented by the following formula 11:

(11)

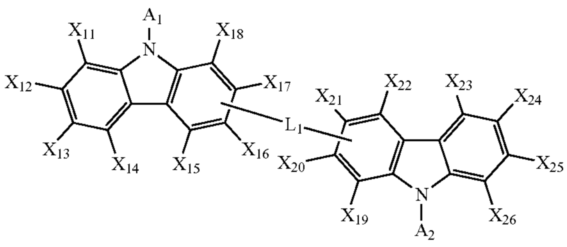

wherein $A_1$ and $A_2$, each independently, represent a substituted or unsubstituted (C6-C30)aryl;

L represents a single bond, or a substituted or unsubstituted (C6-C30)arylene; and $X_{11}$ to $X_{28}$, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C60)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, or a substituted or unsubstituted mono- or di-(C6-C30)arylamino, or may be linked to adjacent one(s) of $X_{11}$ to $X_{26}$ to form a ring(s).

The compound of formula 11 may be represented by any one of the following formulas 12 to 14.

(12)

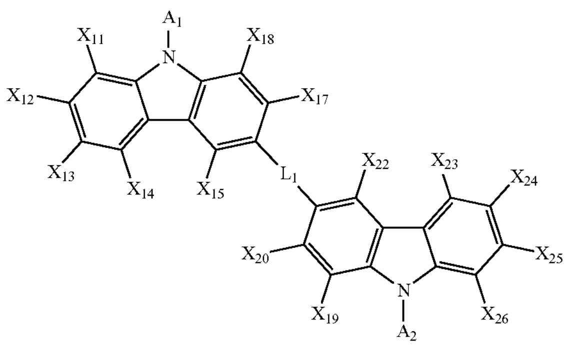

(13)

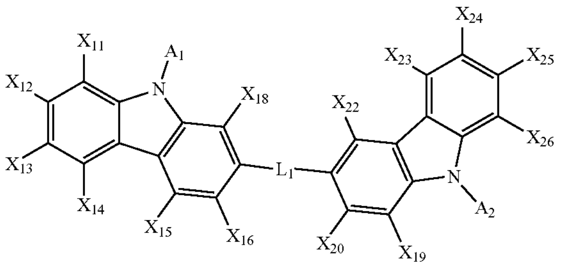

(14)

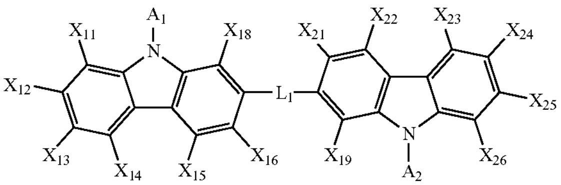

In formulas 12 to 14, $A_1$, $A_2$, $L_1$, and $X_{11}$ to $X_{26}$ are as defined in formula 11.

In formulas 11 to 14, $A_1$ and $A_2$, each independently, represent preferably a substituted or unsubstituted (C6-C25) aryl; and more preferably a (C6-C18)aryl unsubstituted or substituted with at least one selected from the group consisting of a (C1-C6)alkyl(s), a (C6-C18)aryl(s), a (5- to 20-membered)heteroayl(s), and a tri(C6-C12)arylsilyl(s). Specifically, $A_1$ and $A_2$, each independently, may be selected from the group consisting of a substituted or unsubstituted phenyl, a substituted or unsubstituted biphenyl, a substituted or unsubstituted terphenyl, a substituted or unsubstituted naphthyl, a substituted or unsubstituted fluorenyl, a substituted or unsubstituted benzofluorenyl, a substituted or unsubstituted phenanthrenyl, a substituted or unsubstituted anthracenyl, a substituted or unsubstituted indenyl, a substituted or unsubstituted triphenylenyl, a substituted or unsubstituted pyrenyl, a substituted or unsubstituted tetracenyl, a substituted or unsubstituted perylenyl, a substituted or unsubstituted chrysenyl, a substituted or unsubstituted phenylnaphthyl, a substituted or unsubstituted naphthylphenyl, and a substituted or unsubstituted fluoranthenyl. For example, $A_1$ and $A_2$, each independently, represent a substituted or unsubstituted phenyl, a naphthyl, a biphenyl, a naphthylphenyl, a dimethylfluorenyl, a diphenylfluorenyl, or a dimethylbenzofluorenyl, and the substituent(s) of the substituted phenyl may be at least one selected from the group consisting of a methyl, a pyridyl, a pyridyl substituted with a phenyl(s), and a triphenylsilyl.

In formulas 11 to 14, L represents preferably a single bond, or a substituted or unsubstituted (C6-C18)arylene; and more preferably, a single bond, or an unsubstituted (C6-C18)arylene. Specifically, L may represent a single bond, a substituted or unsubstituted phenylene, a substituted or unsubstituted naphthylene, or a substituted or unsubstituted biphenylene.

In formulas 11 to 14, $X_1$ to $X_{26}$, each independently, represent preferably hydrogen, or a substituted or unsubstituted (5- to 20-membered)heteroaryl, or adjacent ones of $X_{11}$ to $X_{26}$ may be linked to each other to form a substituted or unsubstituted mono- or polycyclic (C6-C12) alicyclic or aromatic ring(s); and more preferably, hydrogen, or an unsubstituted (5- to 20-membered)heteroaryl, or adjacent ones of $X_{11}$ to $X_{26}$ may be linked to each other to form an unsubstituted mono- or polycyclic (C6-C12) aromatic ring(s). For example, $X_{11}$ to $X_{26}$, each independently, may represent hydrogen, a dibenzothiophenyl, or a dibenzofuranyl, or adjacent ones of $X_{11}$ to $X_{26}$ may be linked to each other to form a benzene ring(s).

The compound represented by formula 11 may be specifically exemplified by the following compounds, but is not limited thereto.

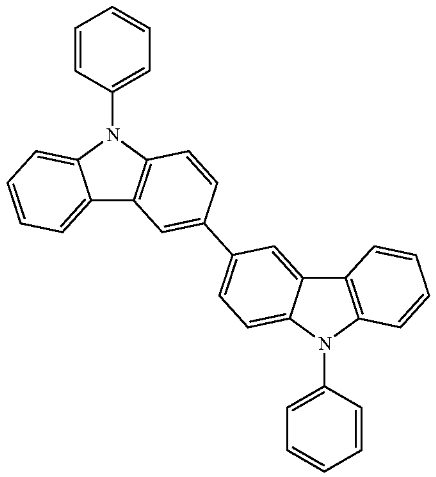

H2-1

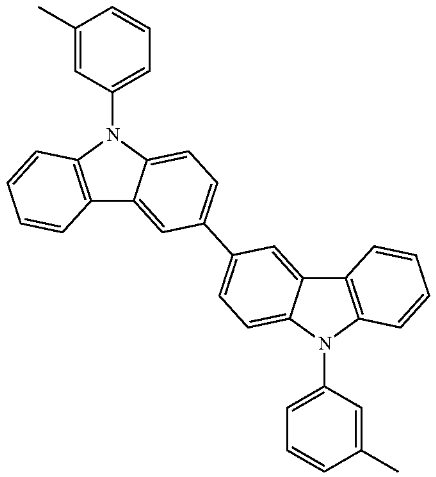

H2-2

-continued
H2-3
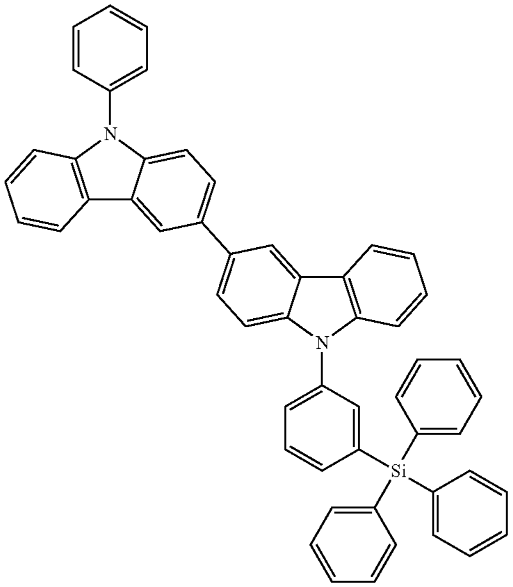
-continued
H2-5
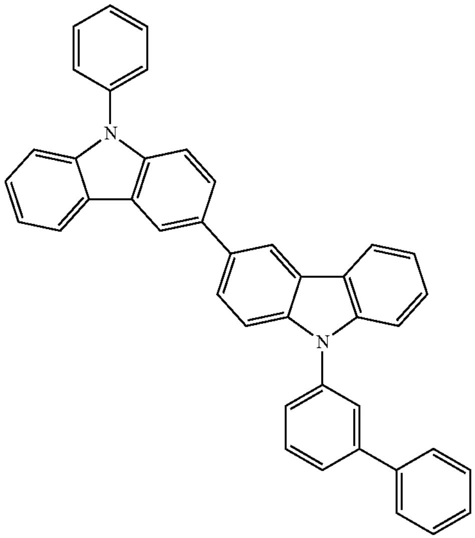
H2-4
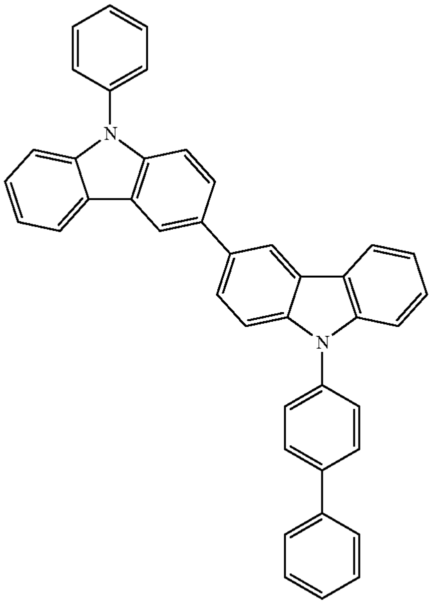
H2-6
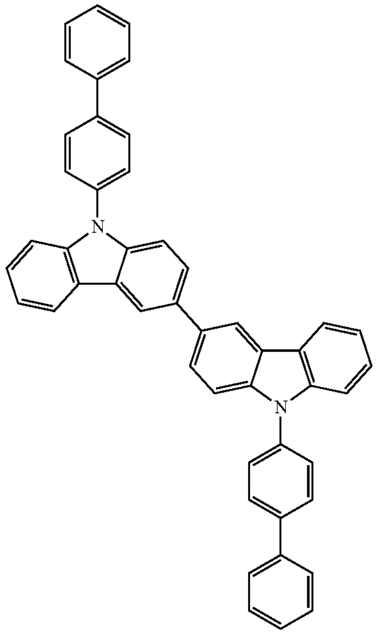

-continued
H2-7
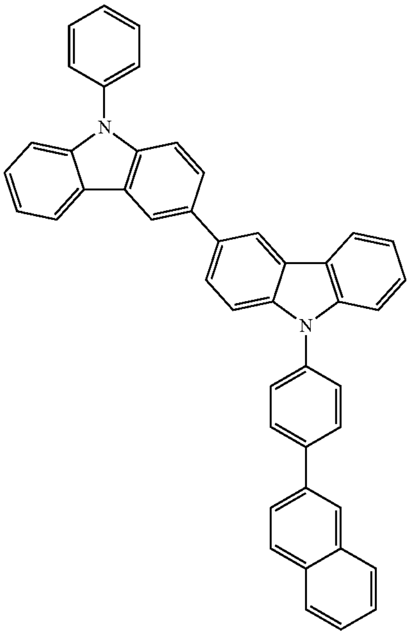
H2-8
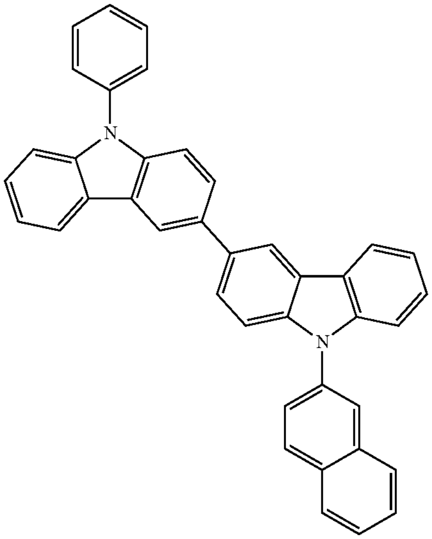
-continued
H2-9
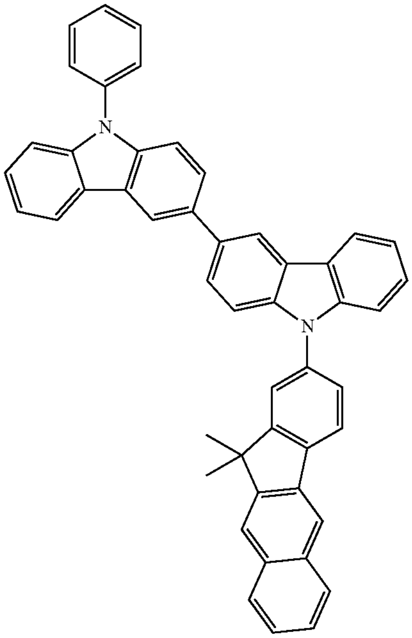
H2-10
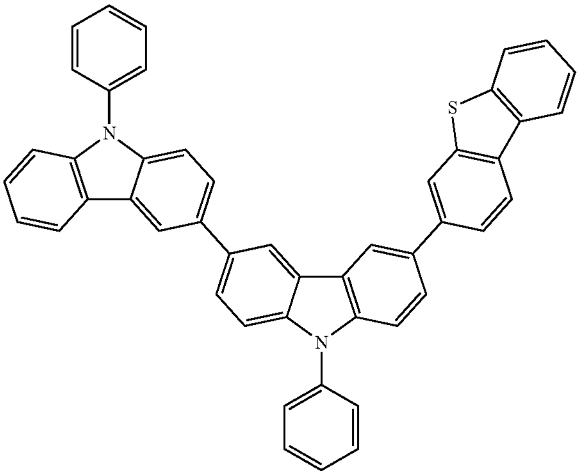
H2-11
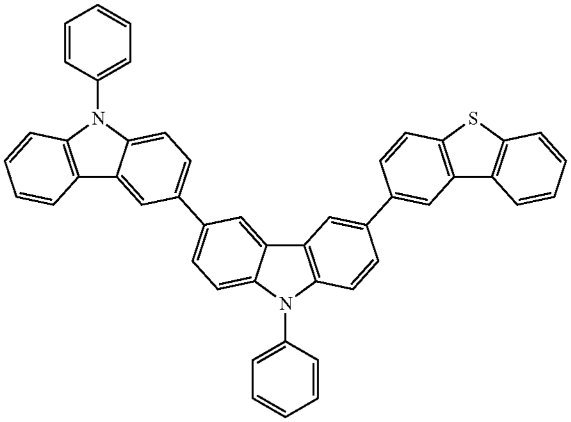

-continued
H2-12
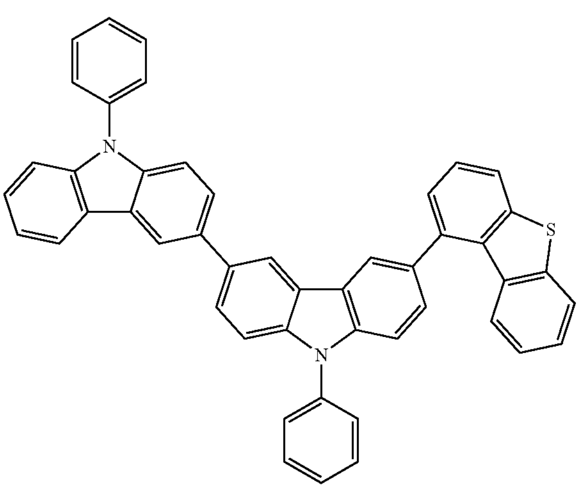
H2-13
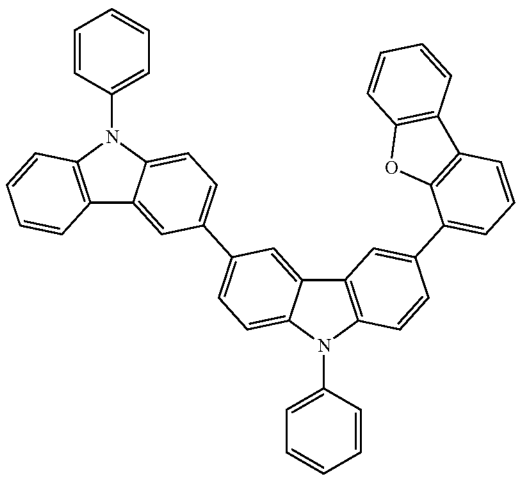
H2-14
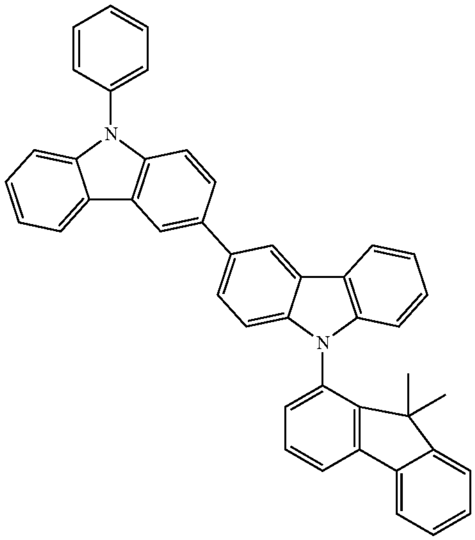
-continued
H2-15
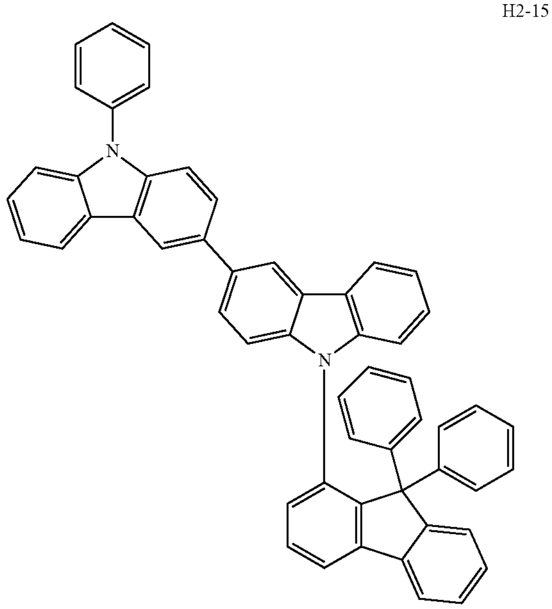
H2-16
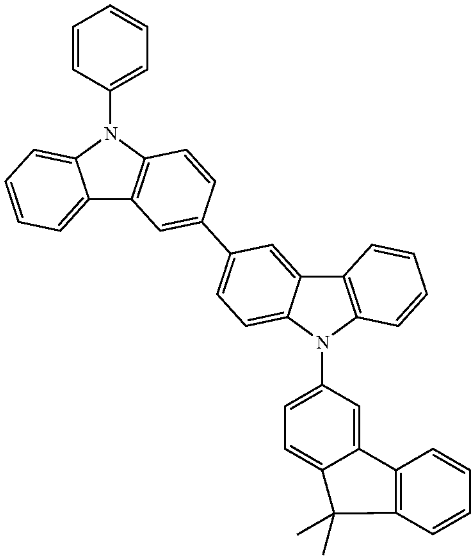

-continued
H2-17
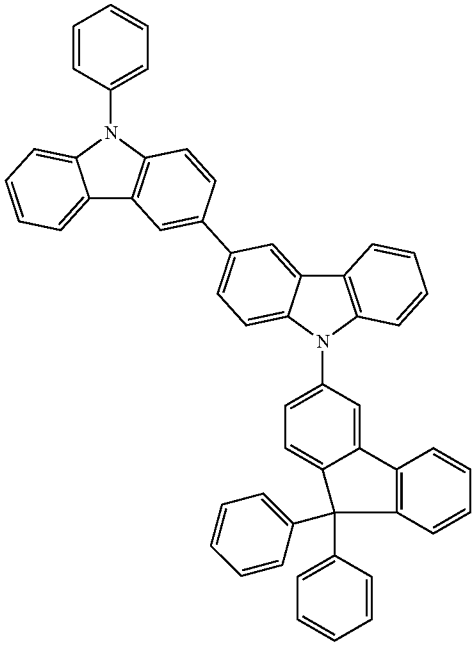
H2-18
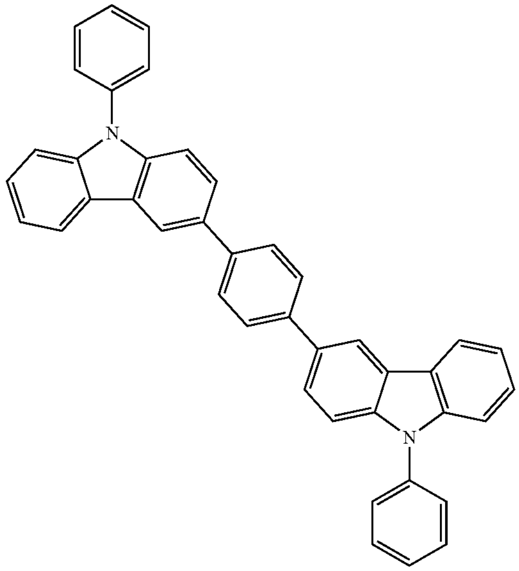
-continued
H2-19
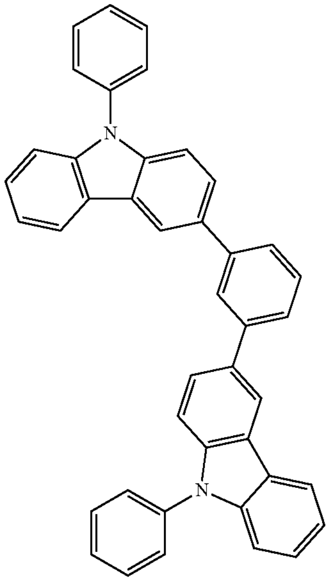
H2-20
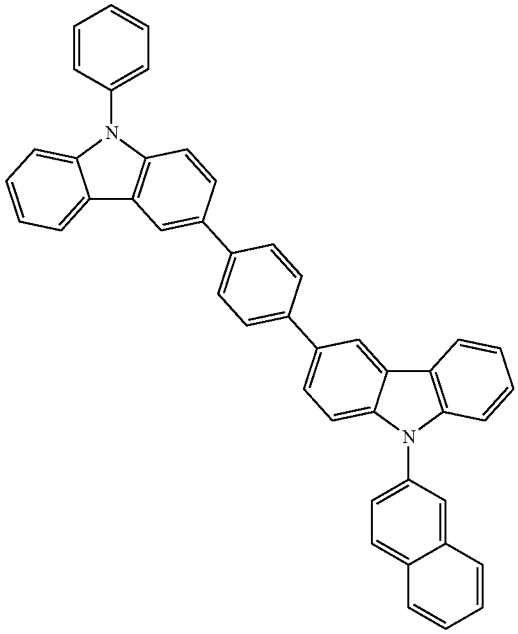

-continued
H2-21
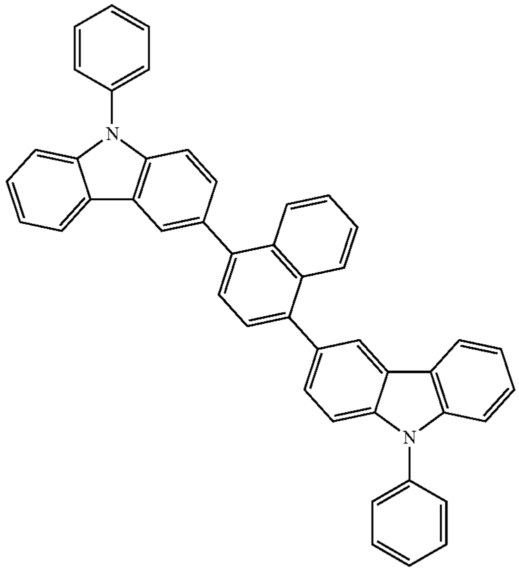
H2-22
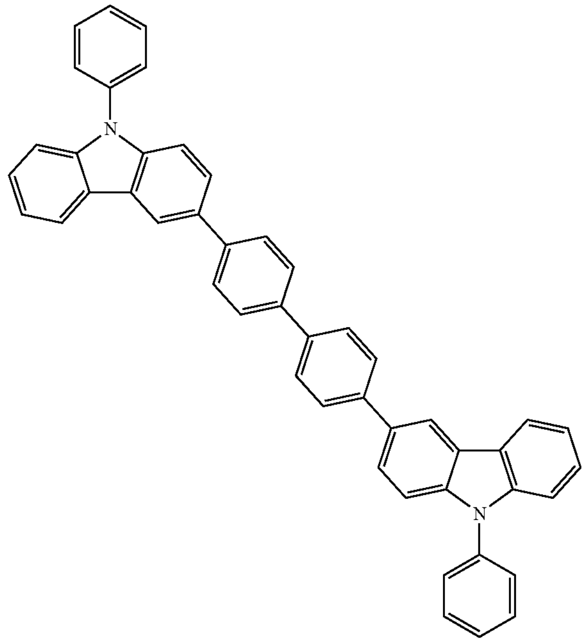
-continued
H2-23
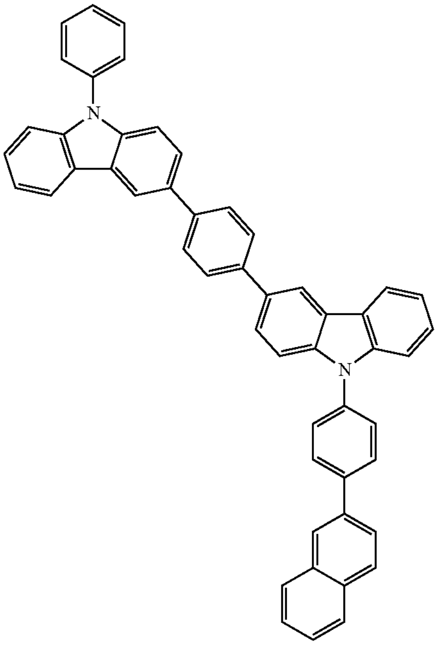
H2-24
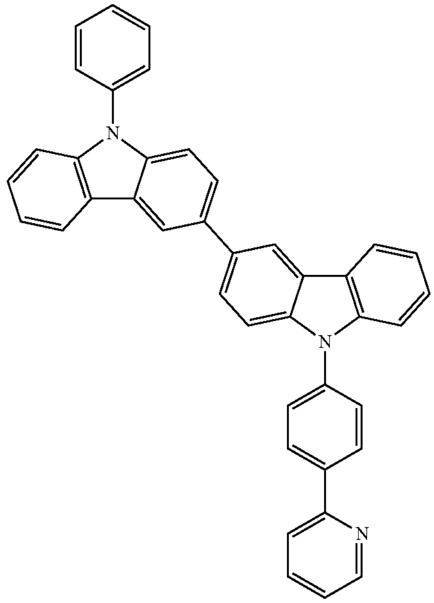

-continued
H2-25
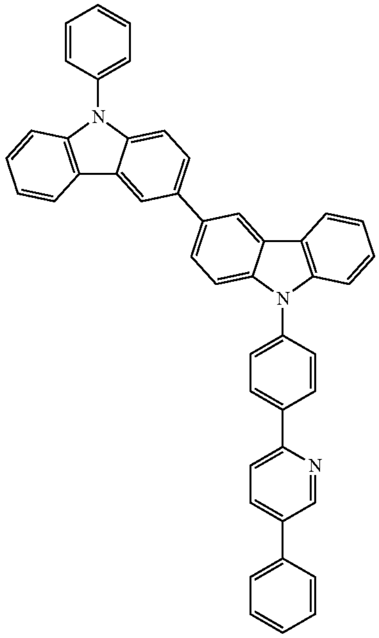
H2-26
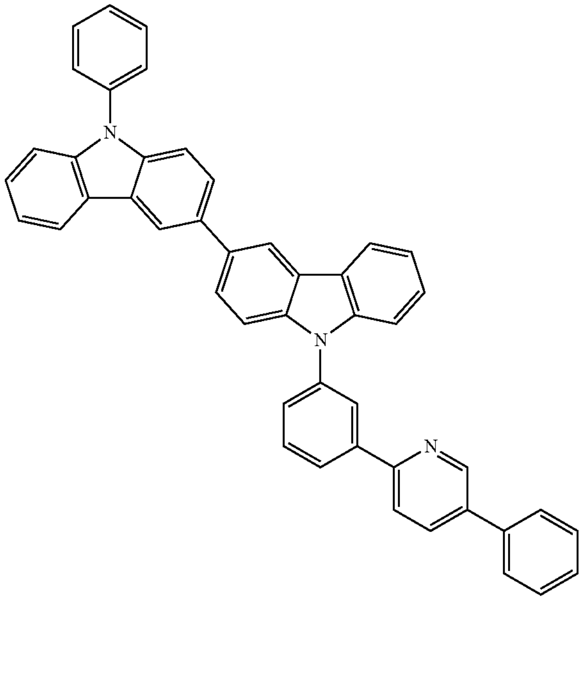
-continued
H2-27
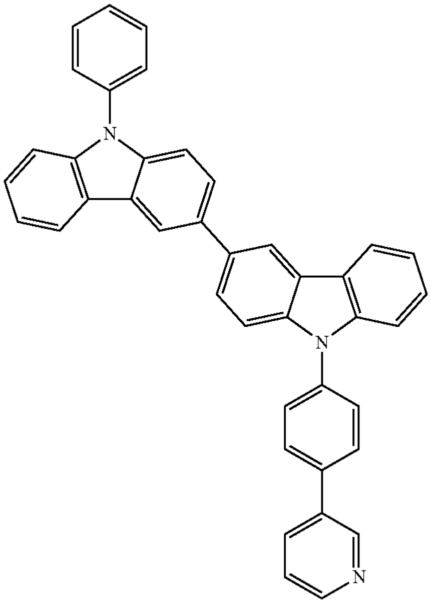
H2-28
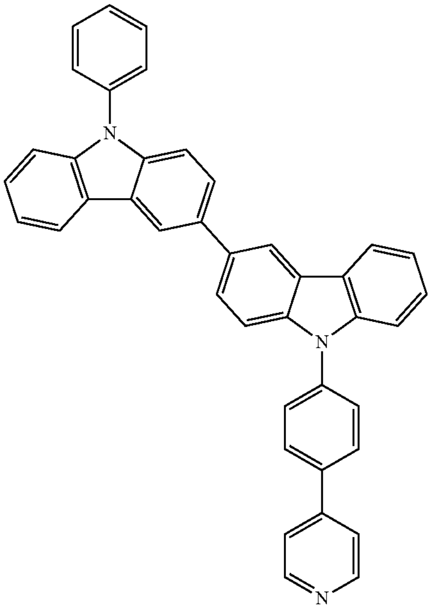

-continued
H2-29
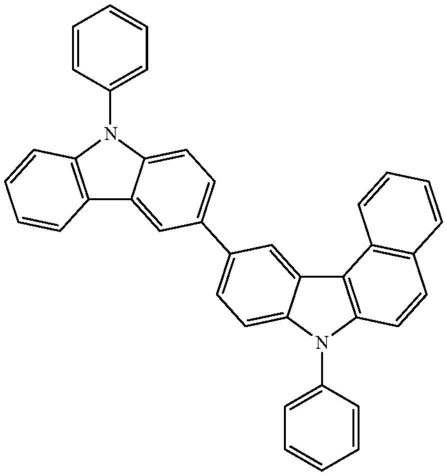
H2-30
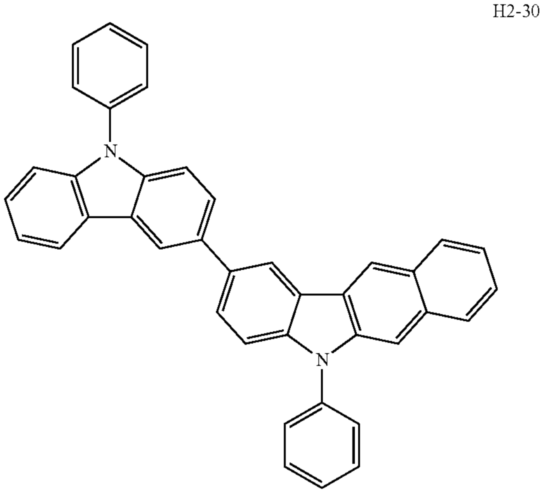
H2-31
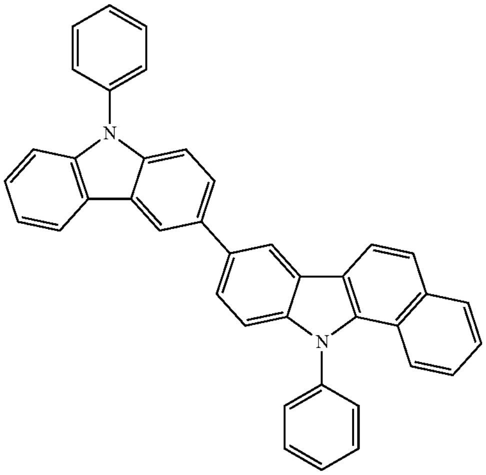
-continued
H2-32
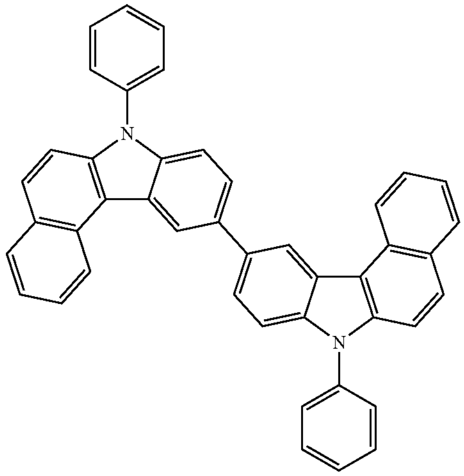
H2-33
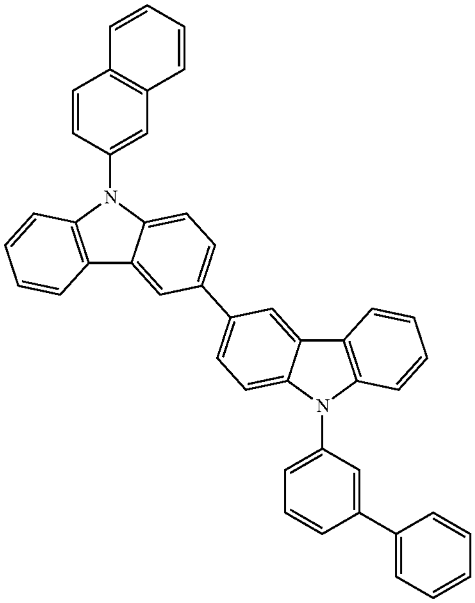

-continued

H2-34

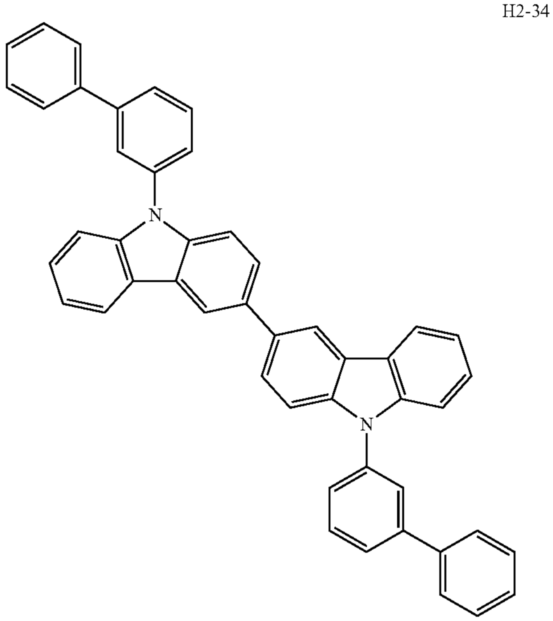 [SMILES: c1ccc(-c2cccc(-n3c4ccccc4c4cc(-c5ccc6c(c5)c5ccccc5n6-c5cccc(-c6ccccc6)c5)ccc43)c2)cc1]

The compound of formula 11 according to the present disclosure may be prepared by a synthetic method known to one skilled in the art. For example, it can be prepared by referring to JP Patent No. JP 3139321 B (published on Feb. 26, 2001) and International Patent Publication No. WO 2011/162162 A (published on Dec. 29, 2011), but is not limited thereto.

The dopant comprised in the organic electroluminescent device of the present disclosure may be at least one phosphorescent or fluorescent dopant, preferably at least one phosphorescent dopant. The phosphorescent dopant material applied to the organic electroluminescent device of the present disclosure is not particularly limited, but may be preferably selected from the metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant comprised in the organic electroluminescent device of the present disclosure may comprise the compound represented by the following formula 101, but is not limited thereto.

(101)

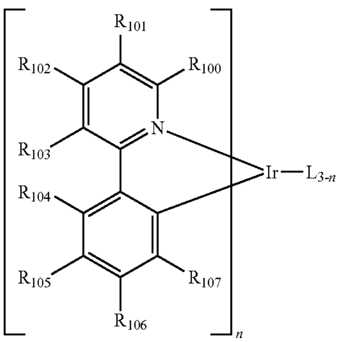

In formula 101, L is an one selected from the following structures 1 to 3:

[Structure 1]

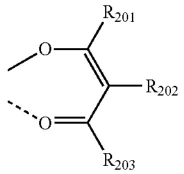

[Structure 2]

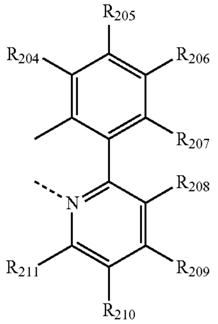

[Structure 3]

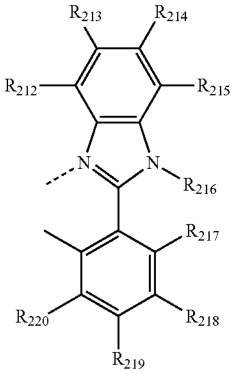

$R_{100}$ to $R_{103}$, each independently, represent hydrogen, deuterium, a halogen, a (C1-C30)alkyl unsubstituted or substituted with deuterium or a halogen, a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or may be linked to adjacent one(s) of $R_{100}$ to $R_{103}$, to form a substituted or unsubstituted fused ring with a pyridine, e.g., a substituted or unsubstituted quinoline, a substituted or unsubstituted isoquinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline or a substituted or unsubstituted indenoquinoline;

$R_{104}$ to $R_{107}$, each independently, represent hydrogen, deuterium, a halogen, a (C1-C30)alkyl unsubstituted or substituted with deuterium or a halogen, a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or may be linked to adjacent one(s) of $R_{104}$ to $R_{17}$ to form a substituted or unsubstituted fused ring with a benzene, e.g., a substituted or unsubstituted naphthalene, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine;

$R_{201}$ to $R_{220}$, each independently, represent hydrogen, deuterium, a halogen, a (C1-C30)alkyl unsubstituted or substituted with deuterium or a halogen, a substituted or unsubstituted (C3-C30)cycloalkyl, or a substituted or unsubstituted (C6-C30)aryl; or may be linked to adjacent one(s) of $R_{201}$ to $R_{220}$ to form a substituted or unsubstituted fused ring; and n represents an integer of 1 to 3.

The specific examples of the dopant compound are as follows, but are not limited thereto.

D-1

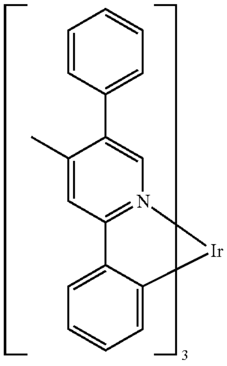

D-2

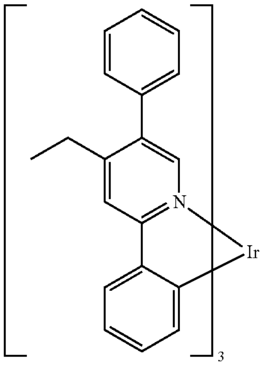

D-3

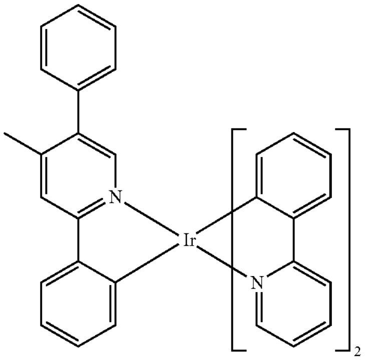

-continued

D-4

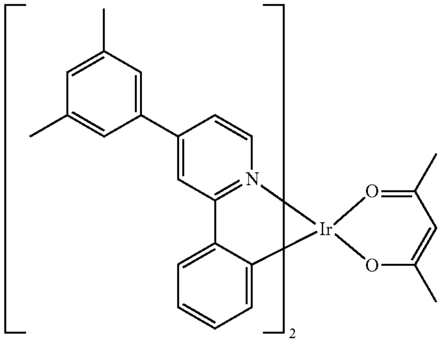

D-5

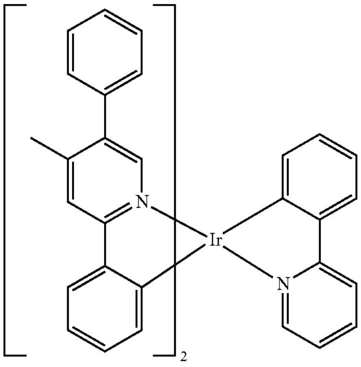

D-6

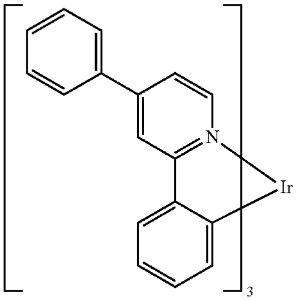

D-7

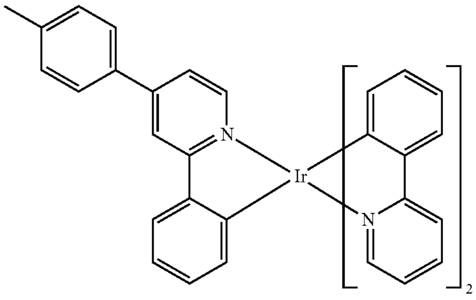

-continued
D-8
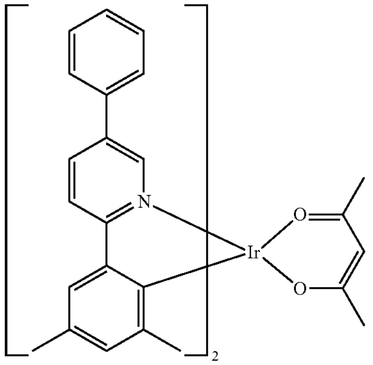
D-9
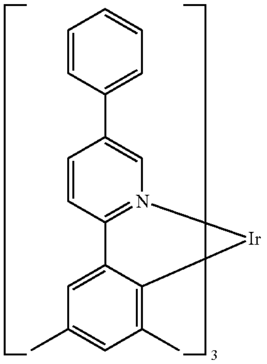
D-10
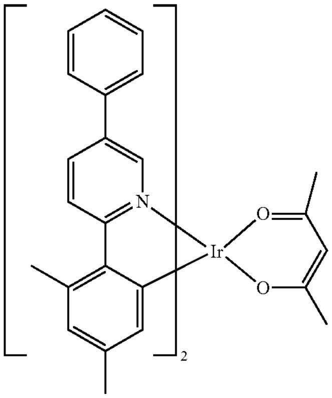
D-11
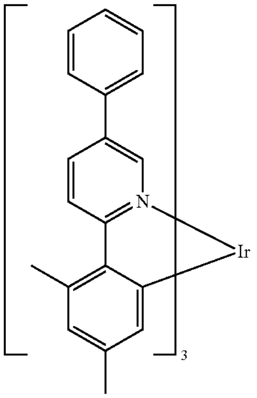
-continued
D-12
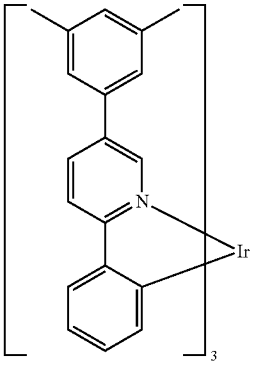
D-13
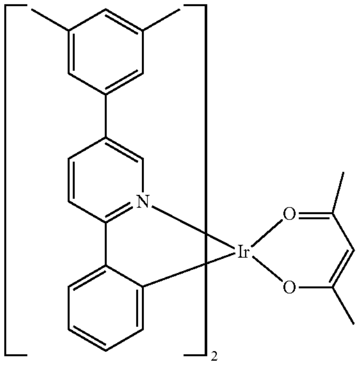
D-14
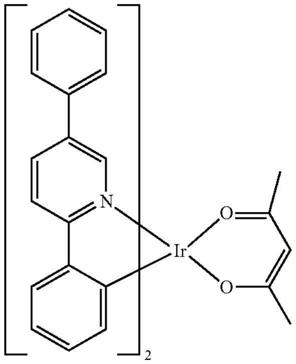
D-15
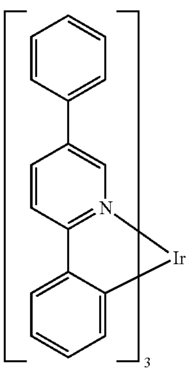

-continued
D-16
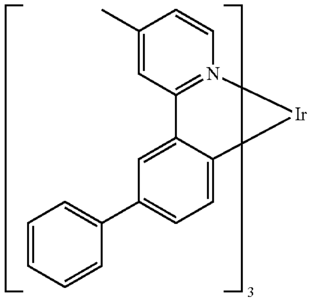
D-17
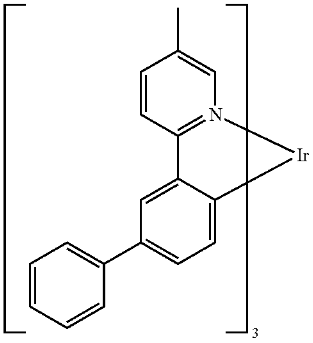
D-18
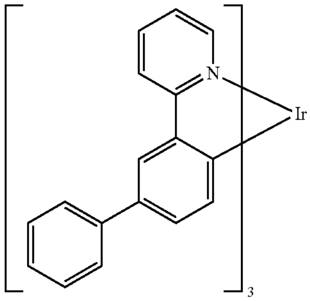
D-19
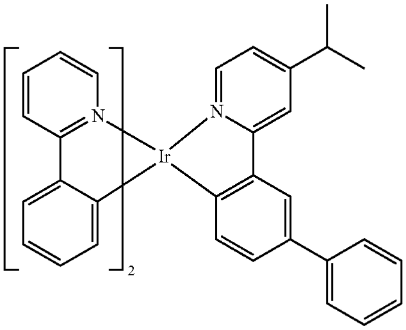
D-20
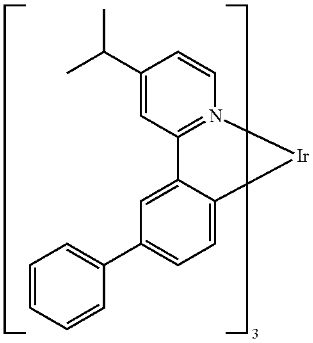
-continued
D-21
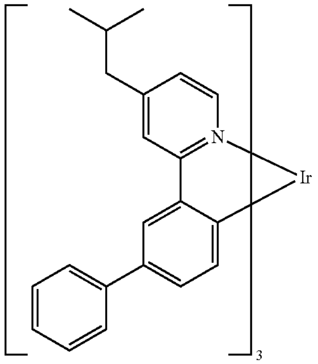
D-22
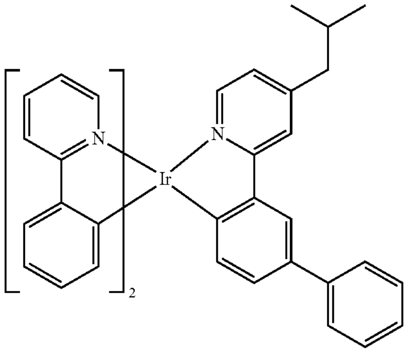
D-23
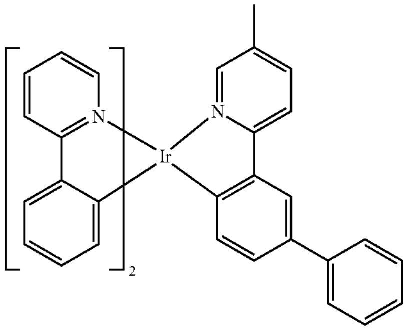
D-24
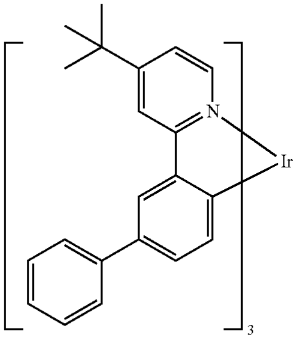

-continued
D-25
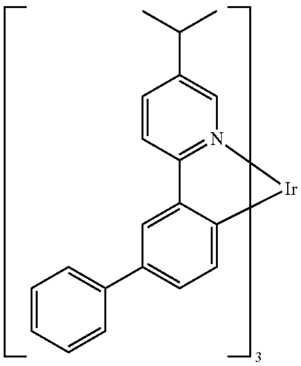
D-26
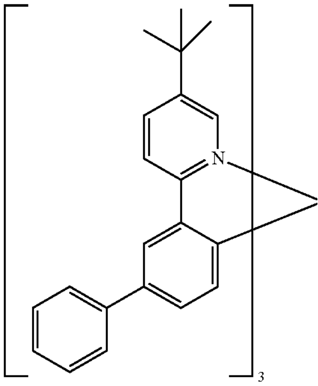
D-27
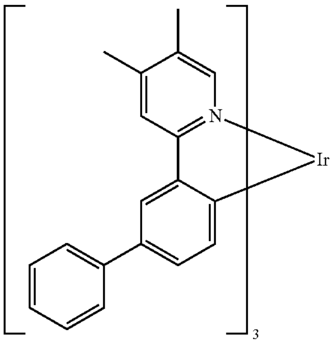
D-28
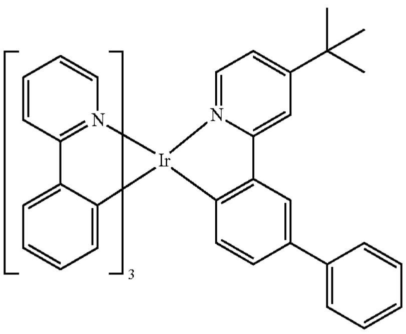
-continued
D-29
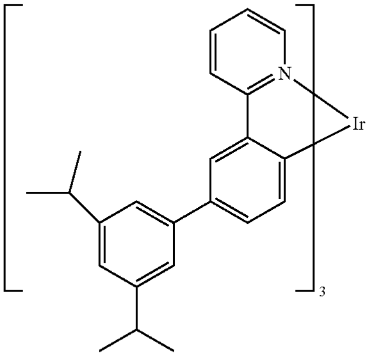
D-30
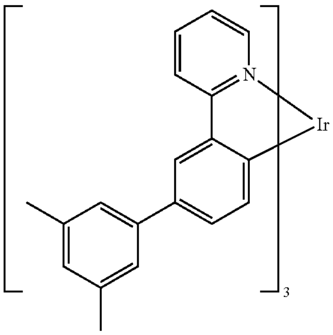
D-31
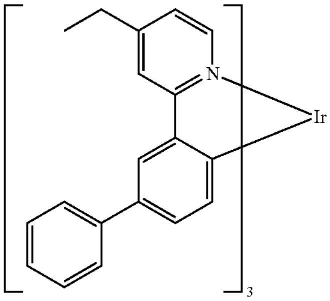
D-32
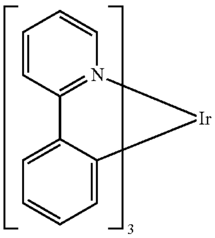
D-33
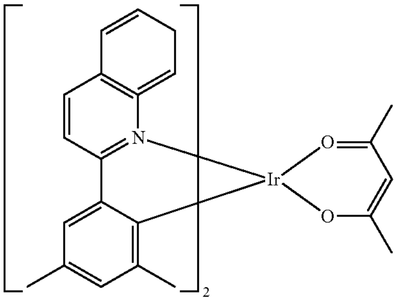

D-34
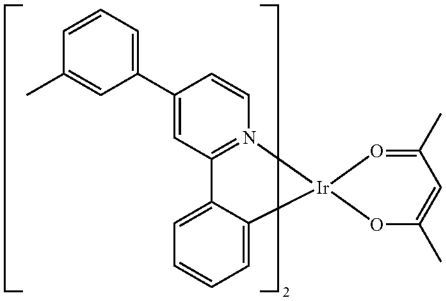
D-35
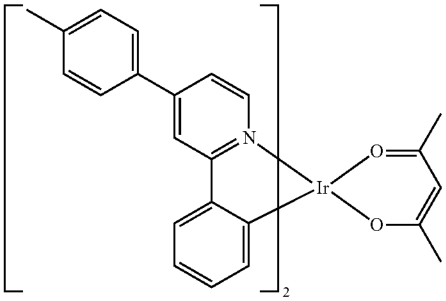
D-36
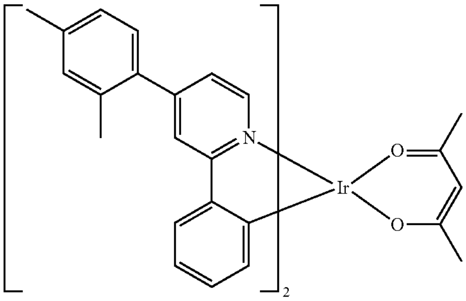
D-37
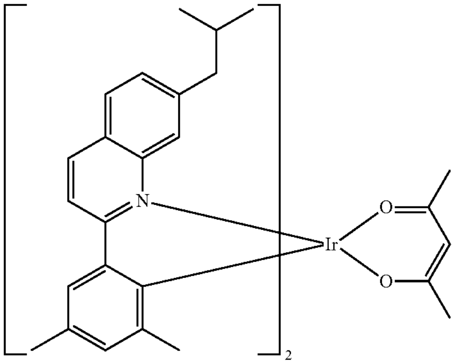
D-38
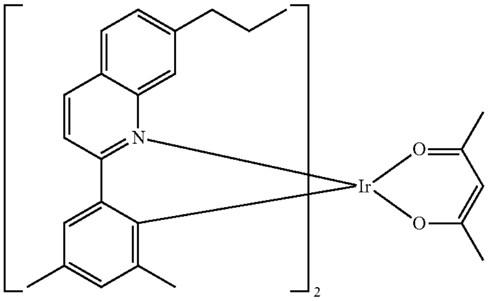
D-39
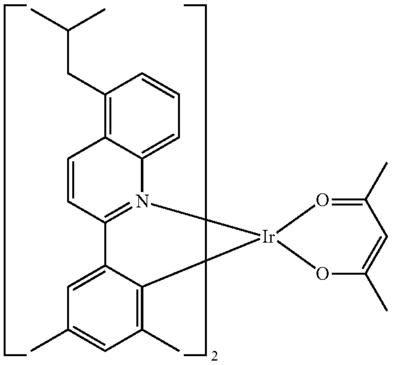
D-40
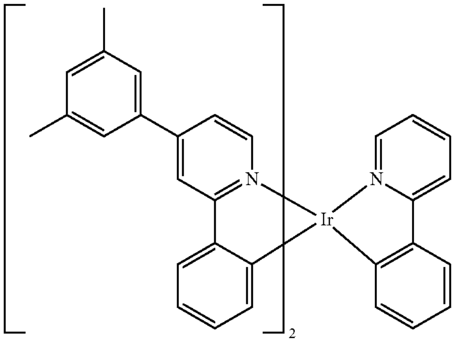
D-41
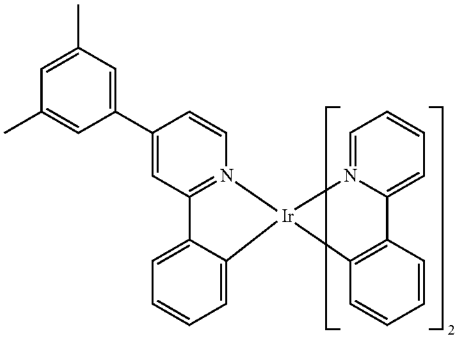
D-42
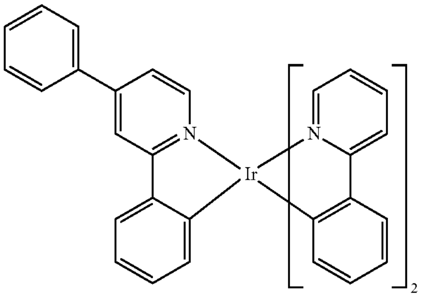

-continued
D-43
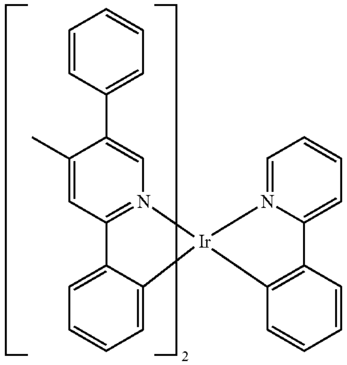
D-44
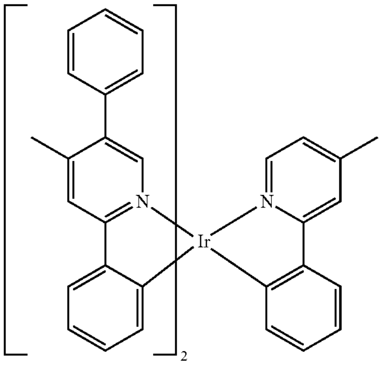
D-45
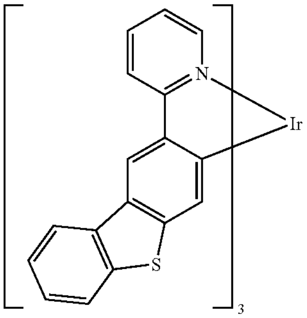
D-46
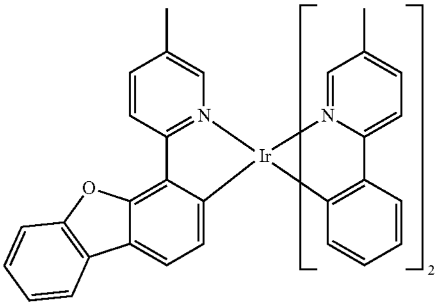
-continued
D-47
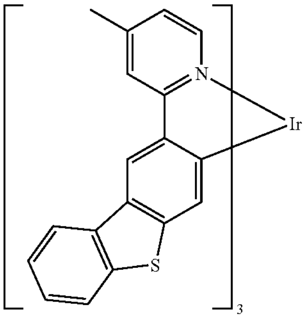
D-48
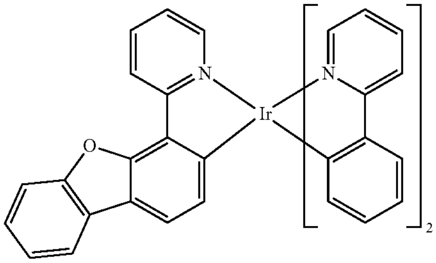
D-49
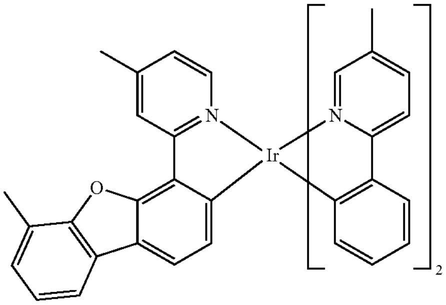
D-50
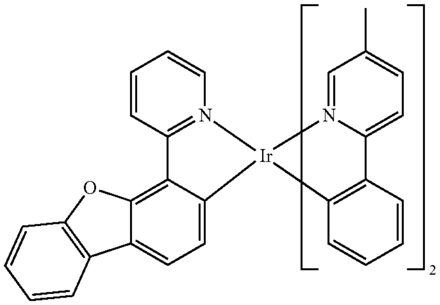
D-51
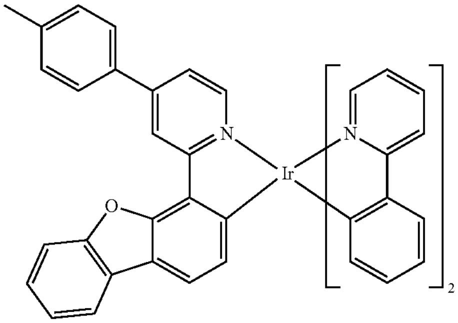

-continued
D-52
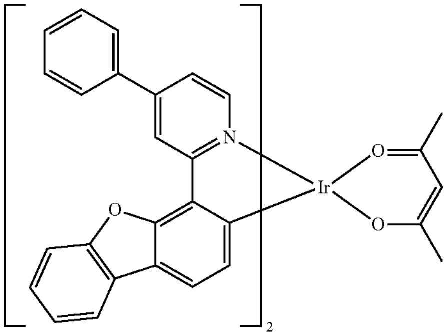
D-53
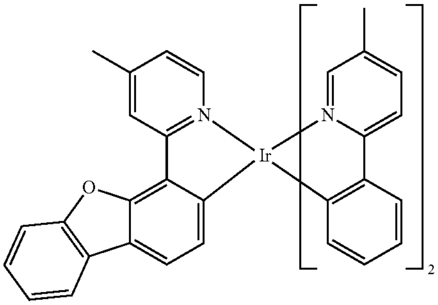
D-54
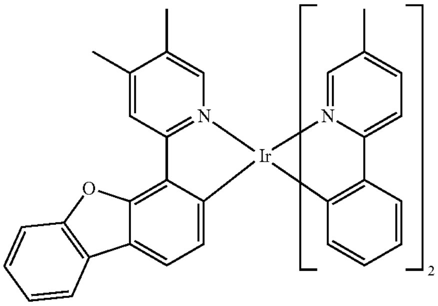
D-55
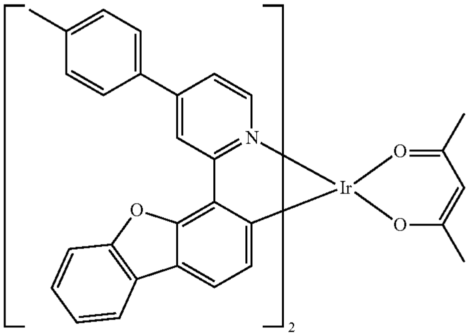
D-56
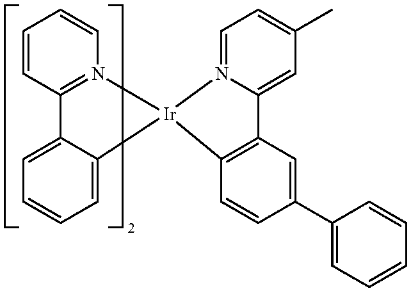
-continued
D-57
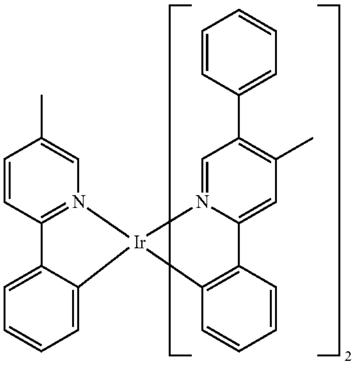
D-58
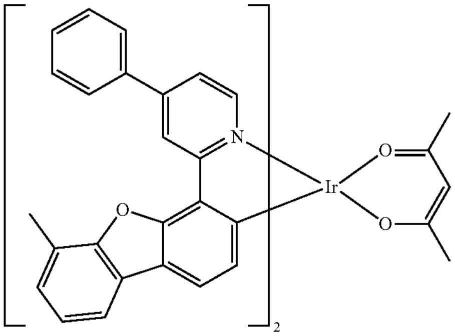
D-59
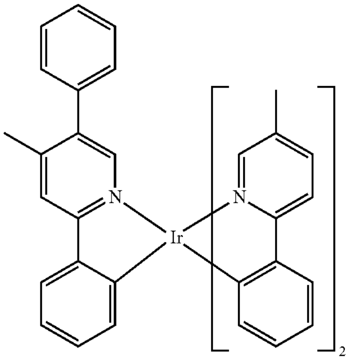
D-60
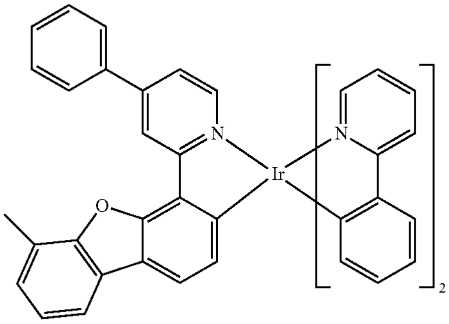

-continued
D-61
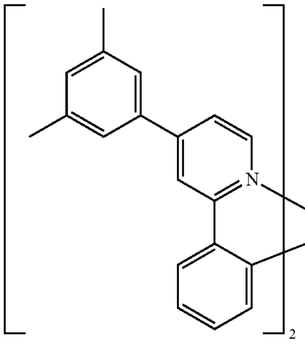
D-62
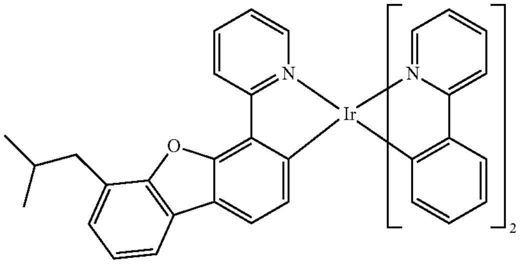
D-63
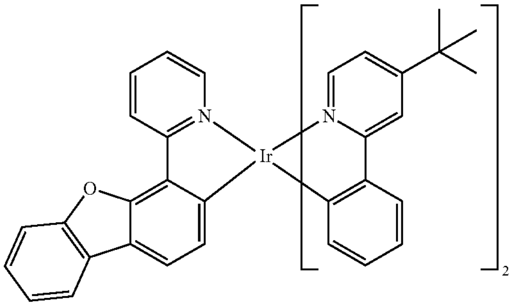
D-64
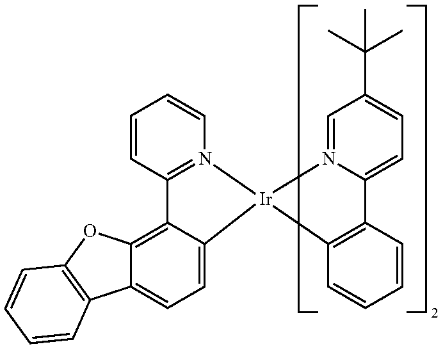
-continued
D-65
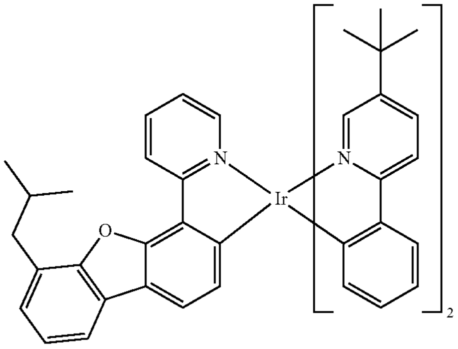
D-66
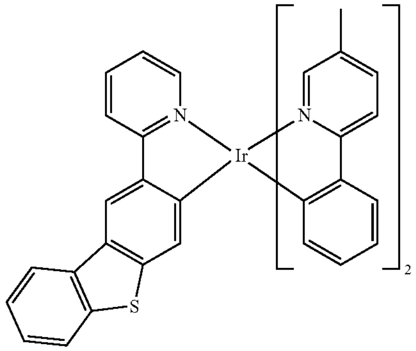
D-67
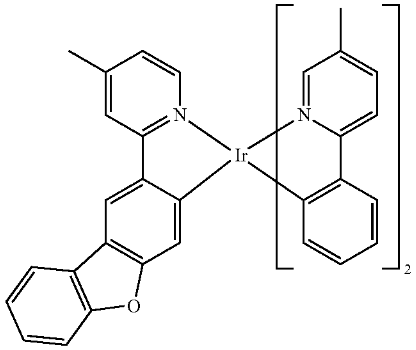
D-68
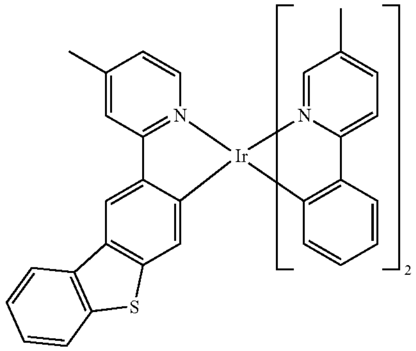

-continued
D-69
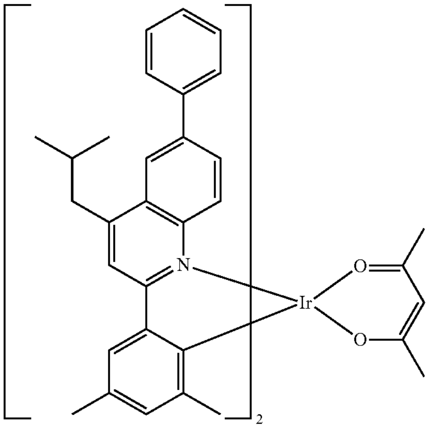
D-70
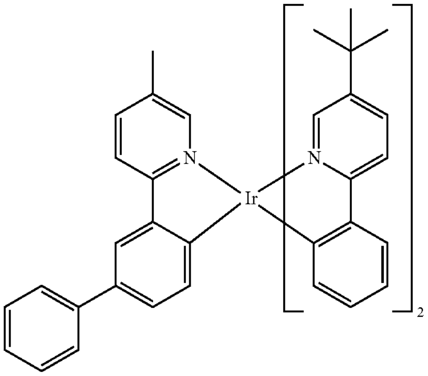
D-71
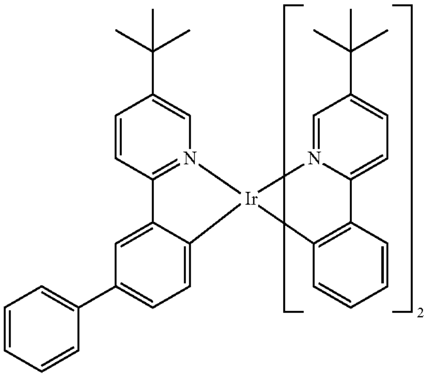
D-72
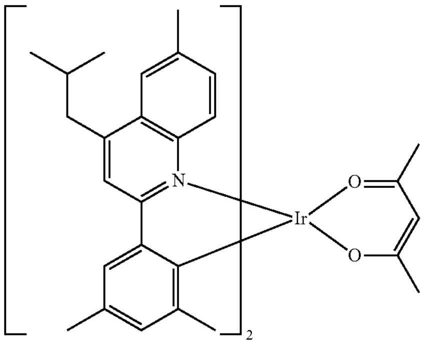
-continued
D-73
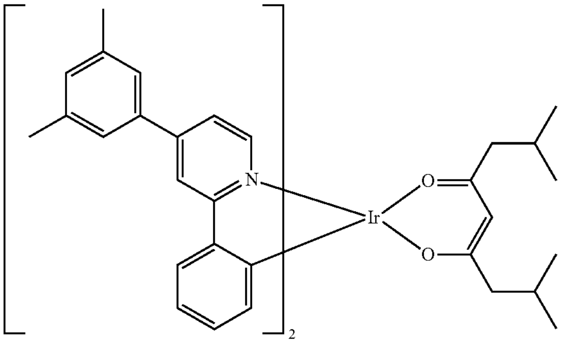
D-74
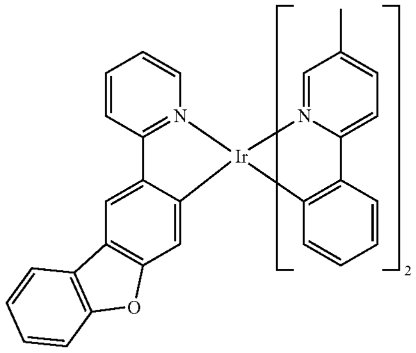
D-75
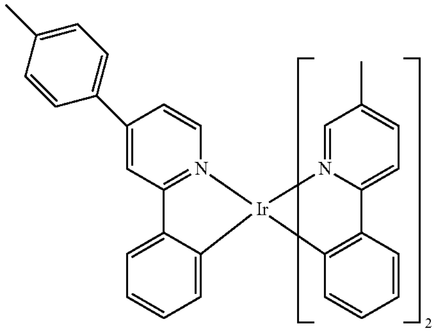
D-76
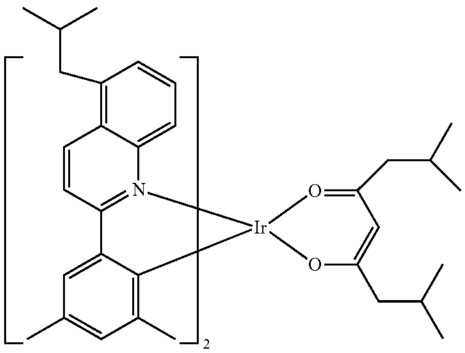

-continued
D-77
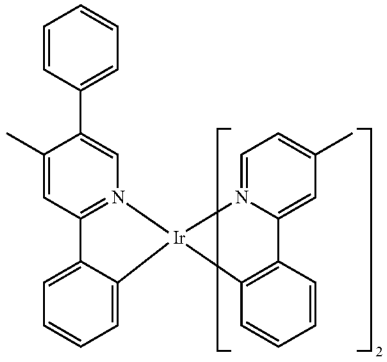
D-78
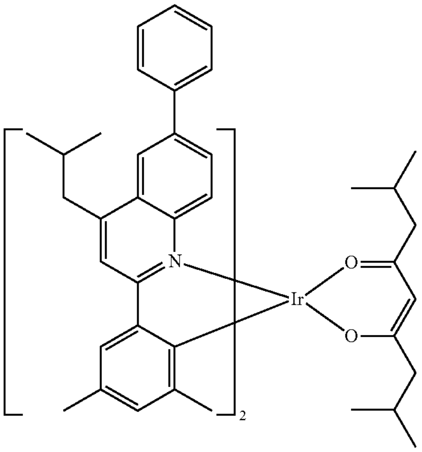
D-79
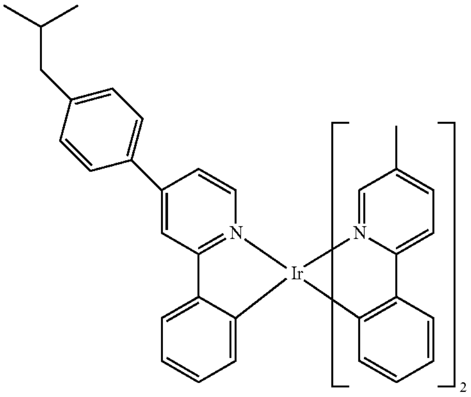
D-80
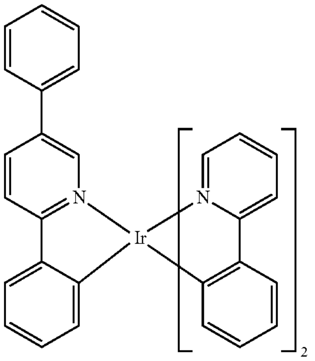
-continued
D-81
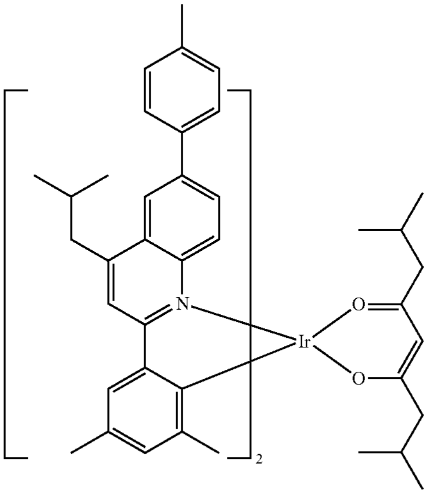
D-82
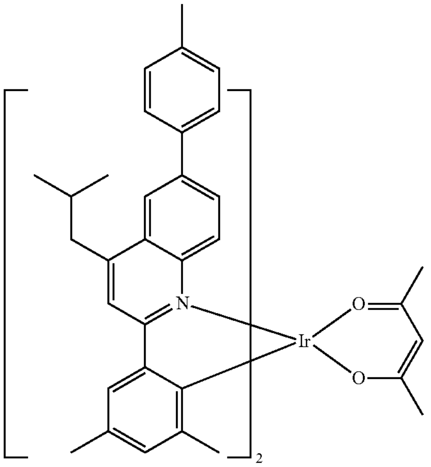
D-83
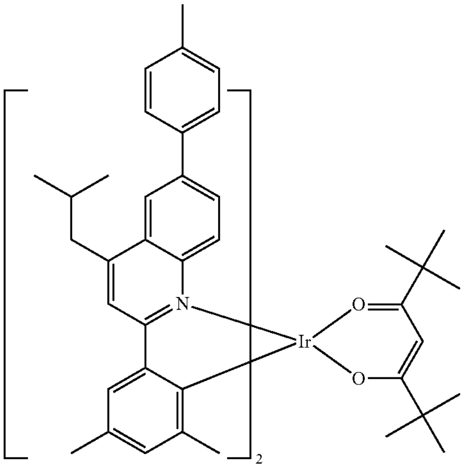

-continued
D-84
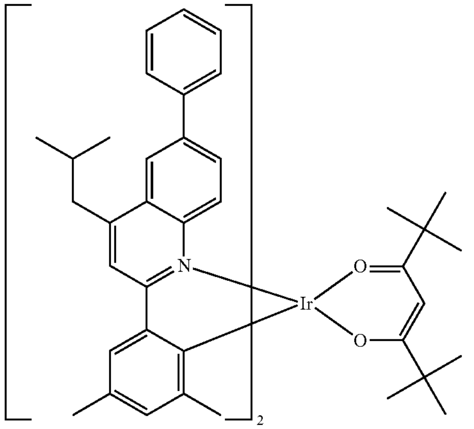
D-85
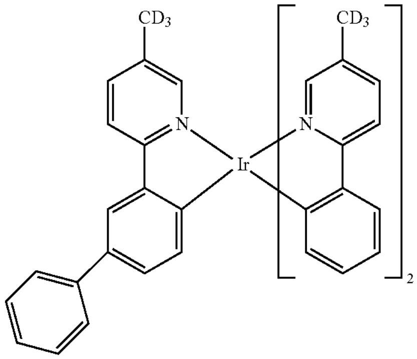
D-86
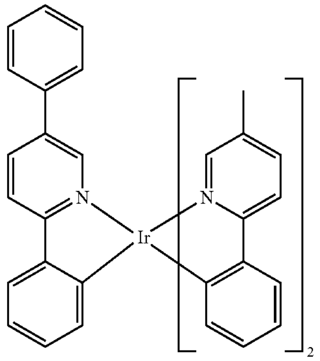
D-87
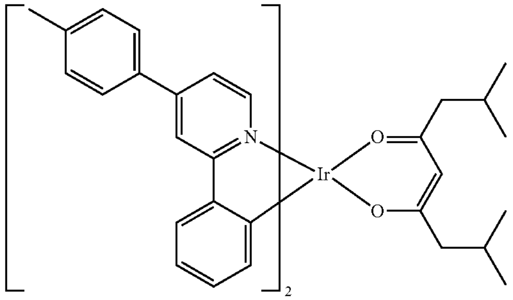
-continued
D-88
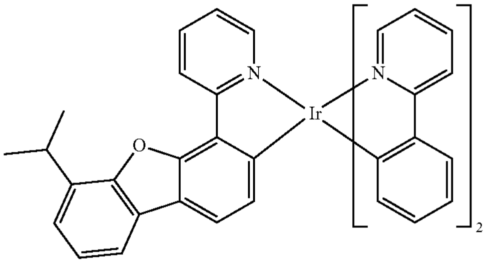
D-89
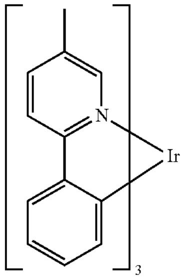
D-90
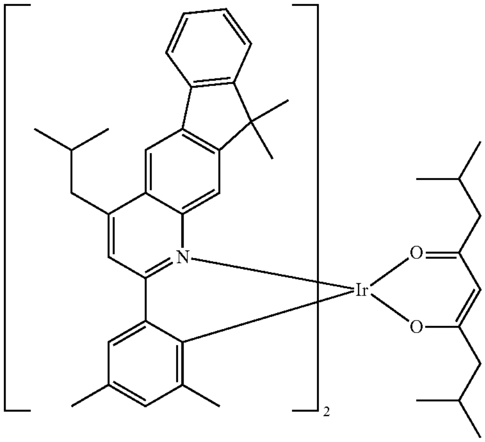
D-91
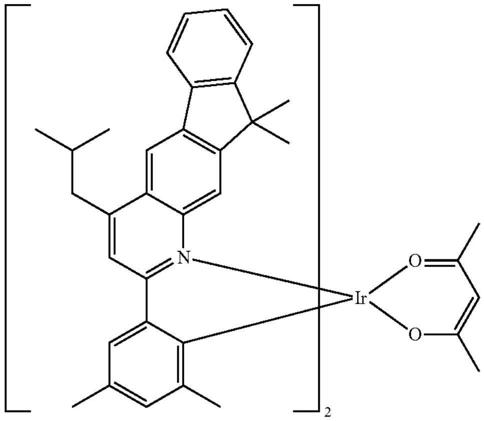

-continued
D-92
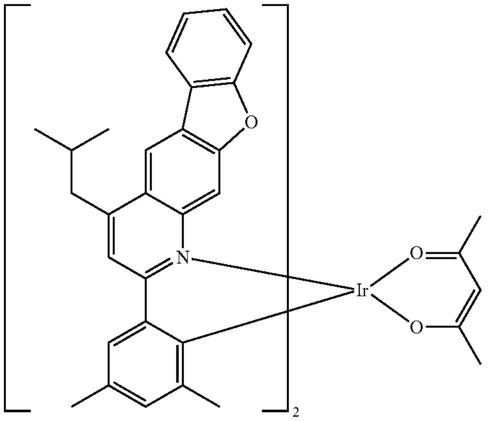
D-93
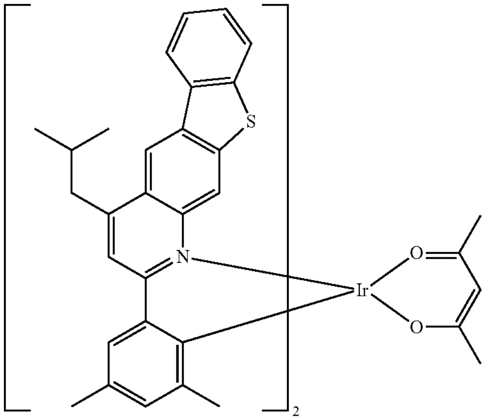
D-94
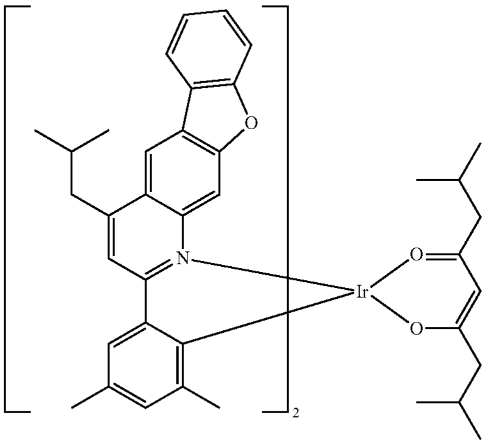
-continued
D-95
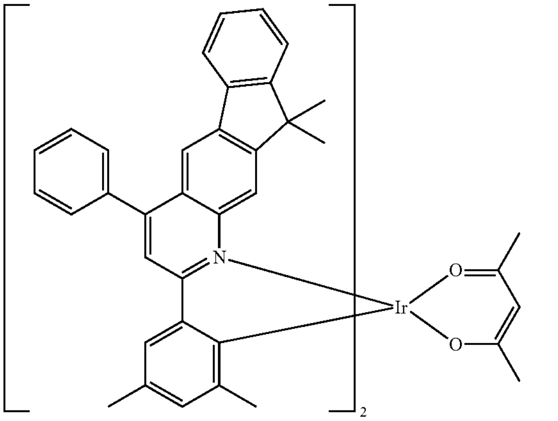
D-96
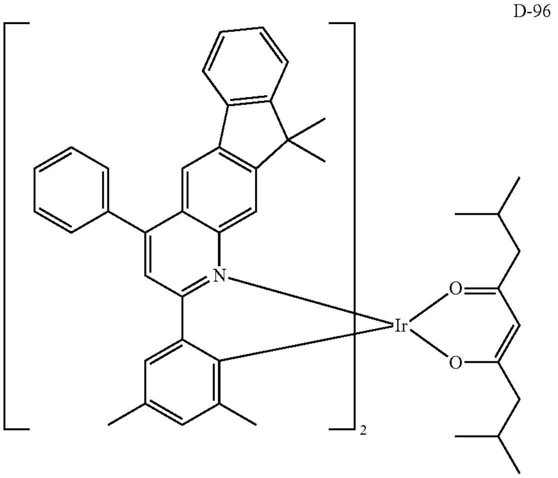
D-97
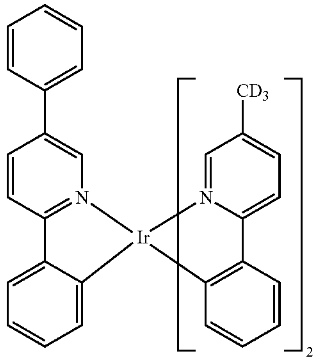
D-98
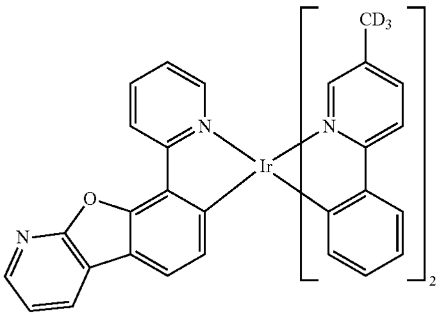

-continued
D-99
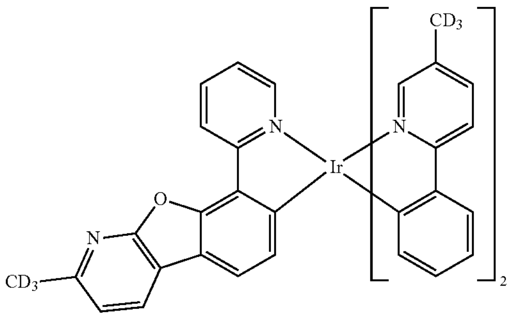
D-100
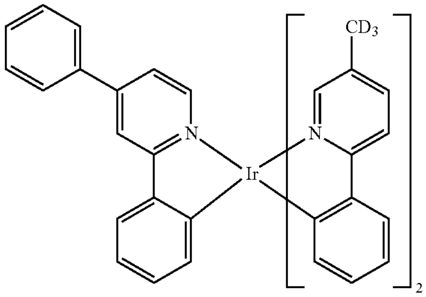
D-101
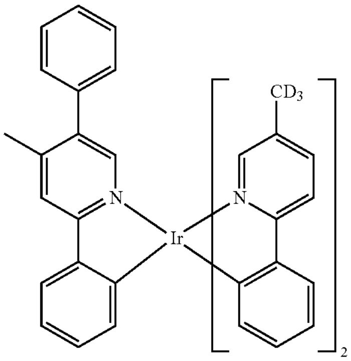
D-102
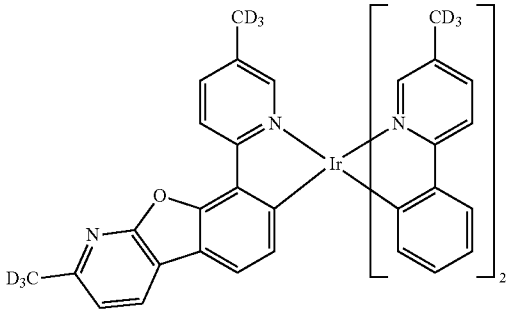
-continued
D-103
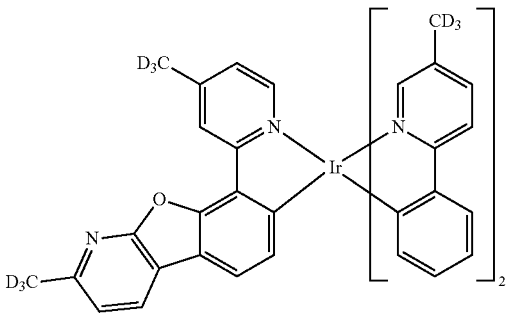
D-104
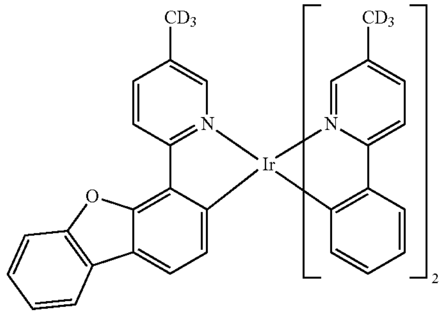
D-105
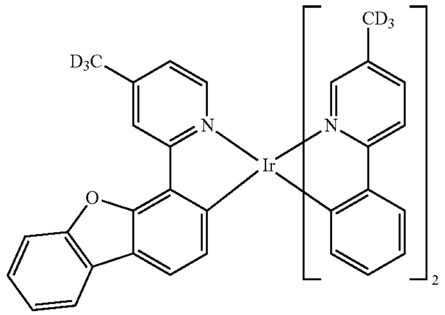
D-106
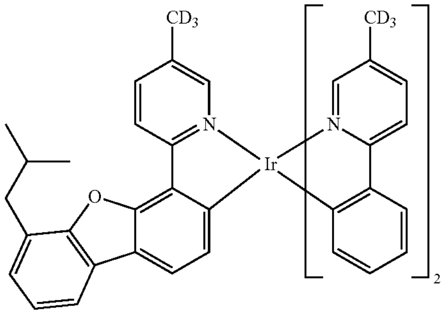
D-107
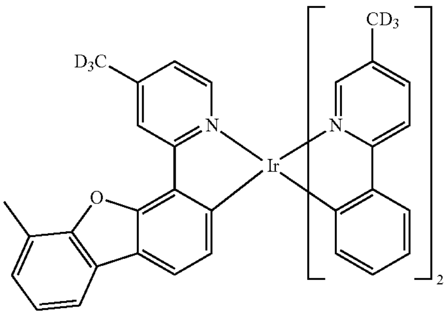

-continued
D-108
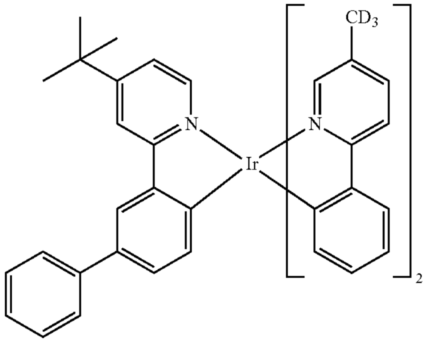
D-109
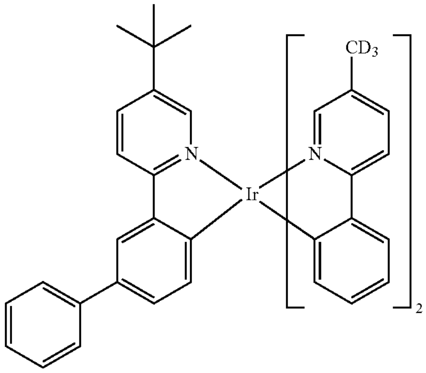
D-110
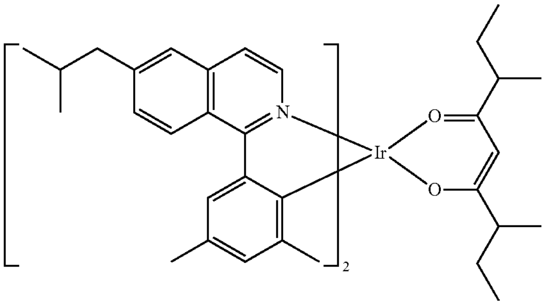
D-111
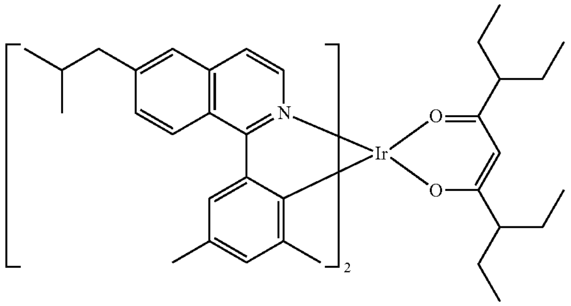
-continued
D-112
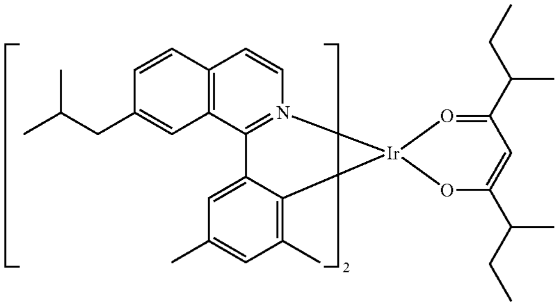
D-113
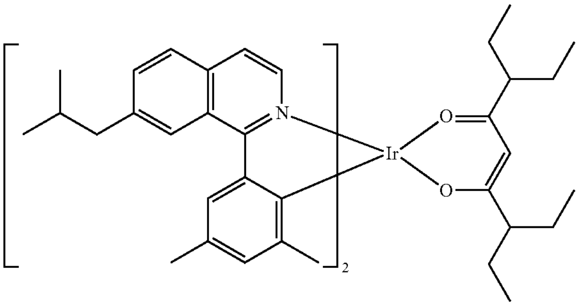
D-114
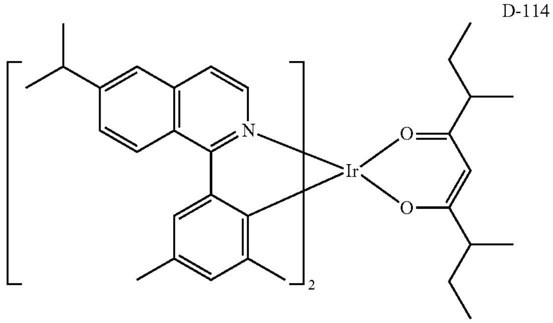
D-115
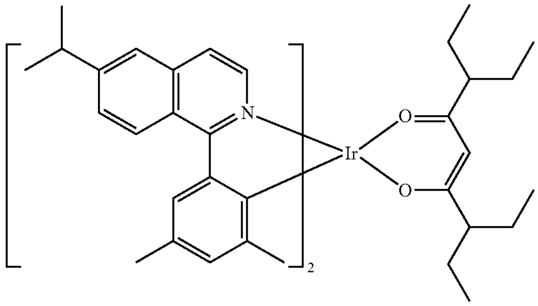
D-116
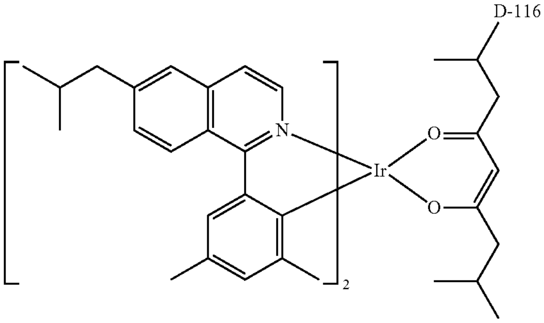

-continued
D-117
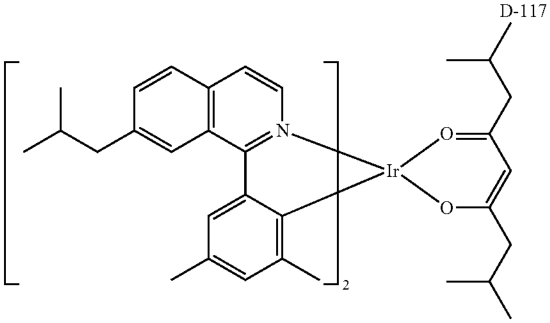
D-118
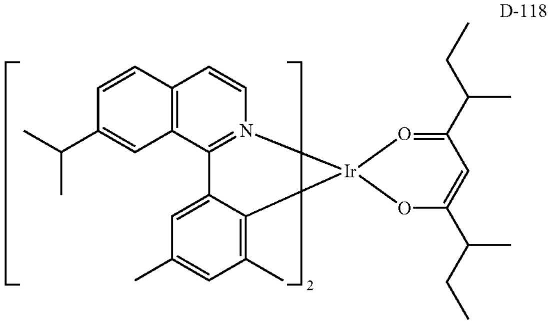
D-119
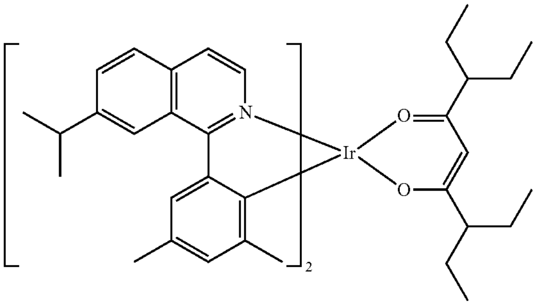
D-120
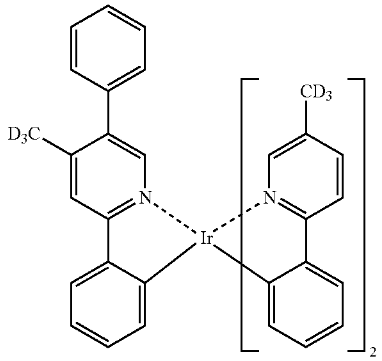
-continued
D-121
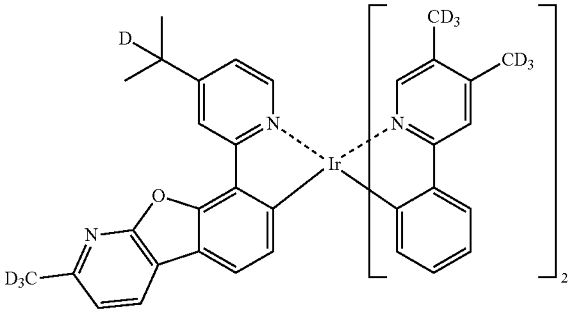
D-122
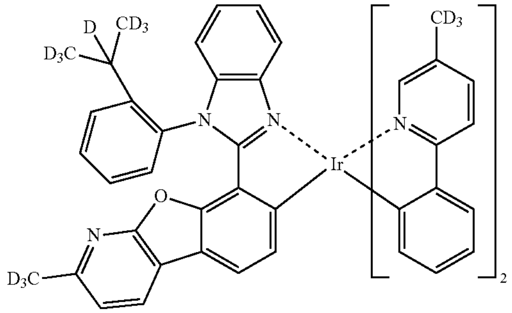
D-123
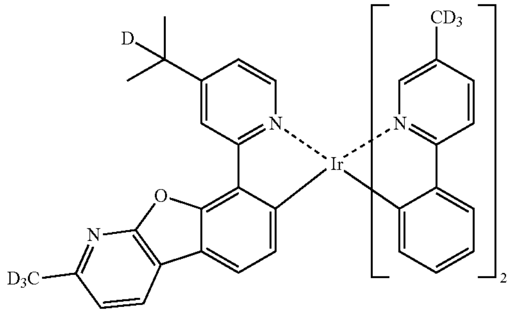
D-124
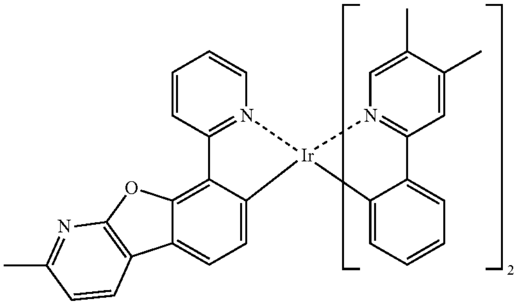
D-125
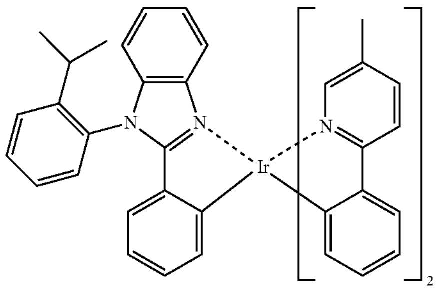

-continued

D-126

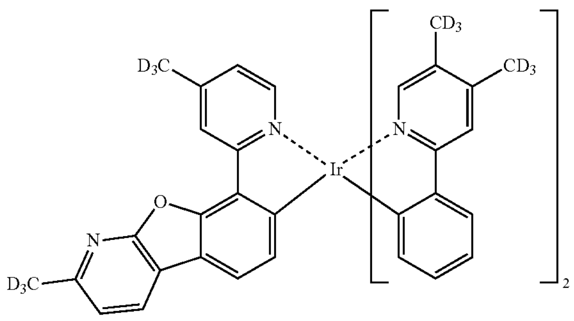

D-127

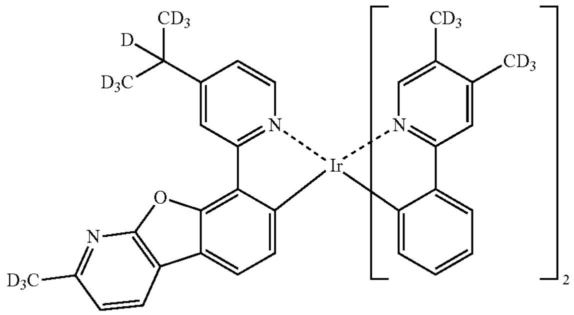

D-128

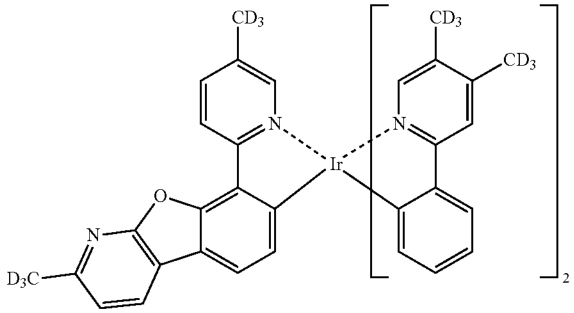

D-129

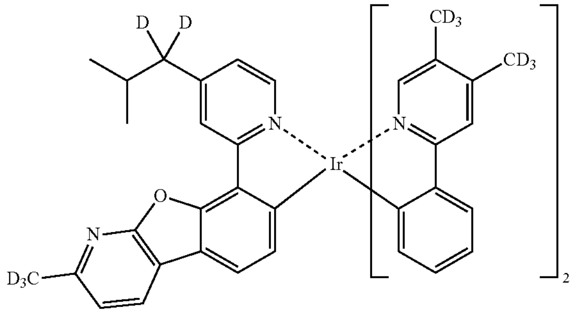

-continued

D-130

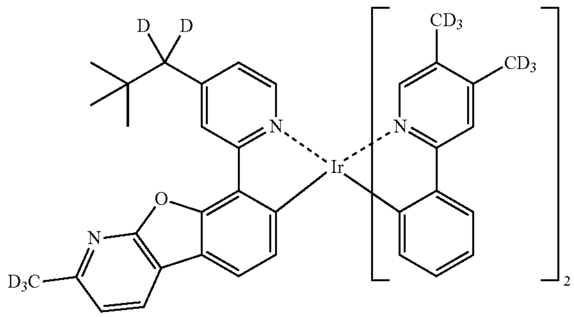

The organic electroluminescent device according to the present disclosure comprises a first electrode, a second electrode, and at least one organic layer between the first and second electrodes. One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer. Each of the layers may further consist of multi-layers.

The first electrode and the second electrode may each be formed with a transmissive conductive material, a transflective conductive material, or a reflective conductive material. The organic electroluminescent device may be a top emission type, a bottom emission type, or both-sides emission type according to the kinds of the material forming the first electrode and the second electrode. In addition, the hole injection layer may be further doped with a p-dopant, and the electron injection layer may be further doped with an n-dopant.

The organic layer may further comprise at least one compound selected from the group consisting of arylamine-based compounds and styrylarylamine-based compounds. In addition, in the organic electroluminescent device of the present disclosure, the organic layer may further comprise at least one metal selected from the group consisting of metals of Group 1, metals of Group 2, transition metals of the 4$^{th}$ period, transition metals of the 5$^{th}$ period, lanthanides and organic metals of d-transition elements of the Periodic Table, or at least one complex compound comprising said metal.

The organic electroluminescent device of the present disclosure may emit white light by further including at least one light-emitting layer containing a blue, red or green light-emitting compound, which is known in the art, besides the compound of the present disclosure. In addition, it may further include a yellow or orange light-emitting layer, if necessary.

In the organic electroluminescent device of the present disclosure, at least one layer selected from a chalcogenide layer, a metal halide layer and a metal oxide layer (hereinafter, "a surface layer") may be preferably placed on an inner surface(s) of one or both electrodes. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. The surface layer may provide operating stability for the organic electroluminescent device. Preferably, the chalcogenide includes SiOx ($1 \leq X \leq 2$), AlOx ($1 \leq X \leq 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, or an electron blocking layer, or a combination thereof may be used between the anode and the light-emitting layer. The hole injection layer may be multilayers in order to lower the hole injection barrier (or hole injection voltage) from the anode to the hole transport layer or the electron blocking layer, wherein each of the multilayers may use two compounds simultaneously. The hole transport layer or the electron blocking layer may also be multilayers.

An electron buffer layer, a hole blocking layer, an electron transport layer, or an electron injection layer, or a combination thereof can be used between the light-emitting layer and the cathode. The electron buffer layer may be multilayers in order to control the injection of the electron and improve the interfacial properties between the light-emitting layer and the electron injection layer, wherein each of the multilayers may use two compounds simultaneously. The hole blocking layer or the electron transport layer may also be multilayers, wherein each of the multilayers may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. In addition, the hole auxiliary layer may be placed between the hole transport layer (or hole injection layer) and the light-emitting layer, and may be effective to promote or block the hole transport rate (or the hole injection rate), thereby enabling the charge balance to be controlled. Further, the electron blocking layer may be placed between the hole transport layer (or hole injection layer) and the light-emitting layer, and may block overflowing electrons from the light-emitting layer and confine the excitons in the light-emitting layer to prevent light leakage. When an organic electroluminescent device includes two or more hole transport layers, the hole transport layer, which is further included, may be used as a hole auxiliary layer or an electron blocking layer. The light-emitting auxiliary layer, the hole auxiliary layer or the electron blocking layer may have an effect of improving the efficiency and/or the lifetime of the organic electroluminescent device.

In the organic electroluminescent device of the present disclosure, a mixed region of an electron transport compound and a reductive dopant, or a mixed region of a hole transport compound and an oxidative dopant is preferably placed on at least one surface of a pair of electrodes. In this case, the electron transport compound is reduced to an anion, and thus it becomes easier to inject and transport electrons from the mixed region to an electroluminescent medium. Further, the hole transport compound is oxidized to a cation, and thus it becomes easier to inject and transport holes from the mixed region to the electroluminescent medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be employed as a charge-generating layer to prepare an organic electroluminescent device having two or more light-emitting layers, which emits white light.

An organic electroluminescent material according to one embodiment of the present disclosure may be used as light-emitting materials for a white organic light-emitting device. The white organic light-emitting device has been suggested to have various structures such as a side-by-side structure or a stacking structure depending on the arrangement of R (red), G (green) or YG (yellow green), and B (blue) light-emitting parts, or a color conversion material (CCM) method, etc. In addition, the organic electroluminescent material according to one embodiment of the present disclosure may also be applied to the organic electroluminescent device comprising QD (quantum dot).

In order to form each layer of the organic electroluminescent device of the present disclosure, dry film-forming methods such as vacuum evaporation, sputtering, plasma, ion plating, etc., or wet film-forming methods such as spin coating, dip coating, flow coating, etc., can be used. The first and second host compounds of the present disclosure may be co-evaporated or mixture-evaporated to form a film.

When using a wet film-forming method, a thin film can be formed by dissolving or diffusing the materials forming each layer into any suitable solvent such as ethanol, chloroform, tetrahydrofuran, dioxane, etc. The solvent is not specifically limited as long as the material constituting each layer is soluble or dispersible in the solvents, which do not cause any problems in forming a film.

It is possible to produce a display system, e.g., a display system for smartphones, tablets, notebooks, PCs, TVs, or cars, or a lighting system, e.g., an outdoor or indoor lighting system, by using the organic electroluminescent device of the present disclosure.

Hereinafter, the preparation method of the compound of the present disclosure, and the properties thereof will be explained in detail with reference to the representative compounds of the present disclosure. However, the present disclosure is not limited to the following examples.

Example 1: Preparation of Compound A-1

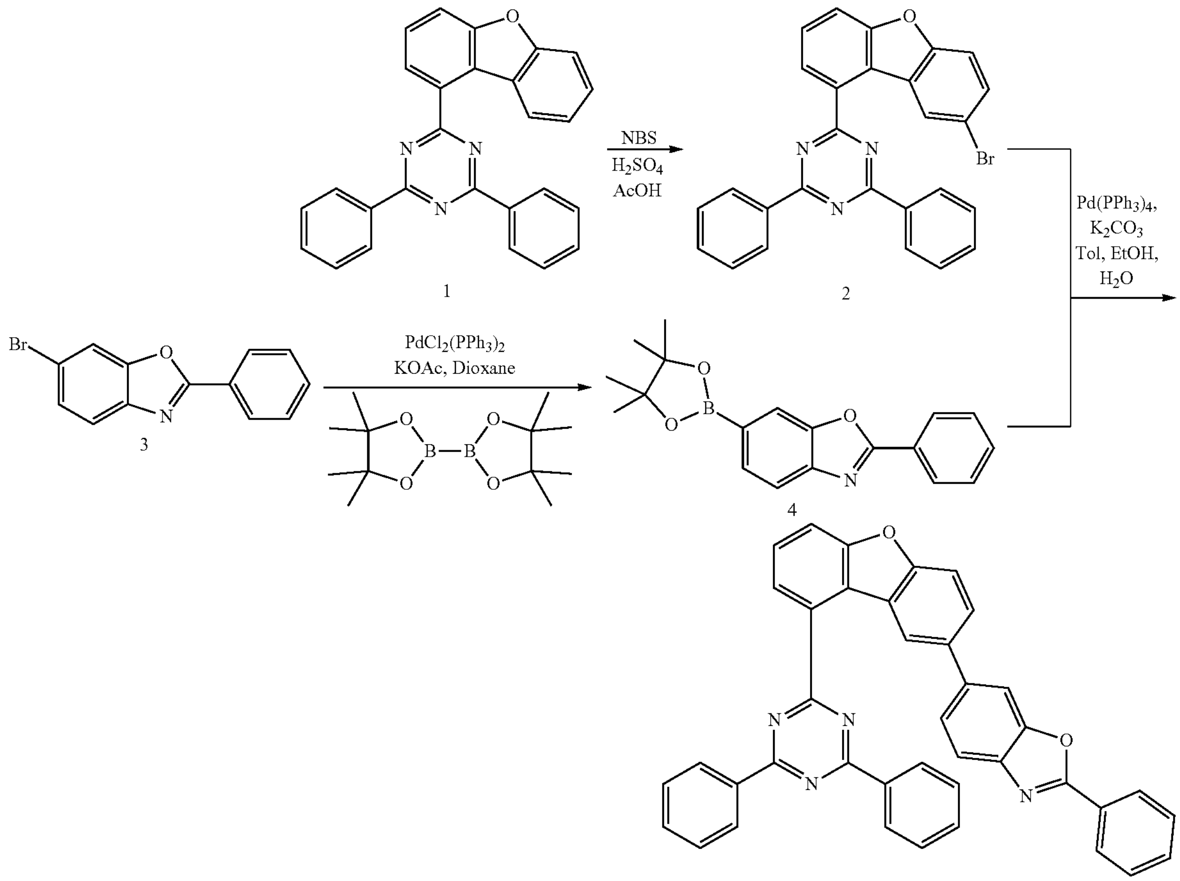

1

2

3

4

A-1

1) Synthesis of Compound 2

In a reaction vessel, 7.3 g of compound 1 (18.2 mmol), 3.9 g of N-bromosuccinimide (NBS) (21.8 mmol), 180 mL of sulfuric acid, and 180 mL of acetic acid were added, and the mixture was stirred at room temperature for 18 hours. After completion of the reaction, water was added thereto to neutralize. The resulting solid was obtained and then dried. The residue was purified by column chromatography to obtain 5.7 g of compound 2 (yield: 66%).

2) Synthesis of compound 4

In a reaction vessel, 10 g of compound 3 (36.4 mmol), 11 g of bis(pinacolato)diboron (43.6 mmol), 0.32 g of bis (triphenylphosphine)palladium (II) dichloride (1.82 mmol), 10 g of potassium acetate (109.2 mmol), and 180 mL of 1,4-dioxane were added, and the mixture was stirred at 130'C for 2 hours. After completion of the reaction, the reaction mixture was cooled to room temperature and an organic layer was extracted with ethyl acetate. The extracted organic layer was dried with magnesium sulfate and the solvent was removed by a rotary evaporator. The residue was purified by column chromatography to obtain 11.5 g of compound 4 (yield: 98%).

3) Synthesis of Compound A-1

In a reaction vessel, 5.7 g of compound 2 (11.9 mmol), 4.2 g of compound 4 (13.0 mmol), 0.69 g of tetrakis(triphenylphosphine)palladium (0.6 mmol), 4.1 g of potassium carbonate (29.8 mmol), 60 mL of toluene, 15 mL of ethanol, and 15 mL of distilled water were added, and the mixture was stirred at 140'C for 3 hours. After completion of the reaction, the reaction mixture was cooled to room temperature and an organic layer was extracted with ethyl acetate. The extracted organic layer was dried with magnesium sulfate and the solvent was removed by a rotary evaporator. The residue was purified by column chromatography to obtain 3.2 g of compound A-1 (yield: 46%).

| | MW | M.P. |
|---|---|---|
| A-1 | 592.66 | 242° C. |

$^1$H-NMR Data $^1$H NMR (600 MHz, $CDCl_3$, δ) 8.899-8.896 (d, 1H), 8.771-8.757 (d, 4H), 8.470-8.456 (d, 1H), 8.250-8.234 (m, 2H), 7.865-7.850 (d, 1H), 7.810-7.792 (dd, 1H), 7.726-7.712 (d, 1H), 7.714-7.688 (t, 1H), 7.574-7.553 (m, 3H), 7.551-7.527 (t, 2H), 7.485-7.460 (t, 4H), 7.482-7.469 (d, 2H), 7.343-7.326 (dd, 1H)

Hereinafter, the properties of an organic electroluminescent device (OLED) comprising the compound according to the present disclosure will be explained in detail. However, the following examples merely illustrate the properties of an OLED according to the present disclosure, but the present disclosure is not limited to the following examples.

Device Example 1: Producing an OLED Comprising the Compound According to the Present Disclosure as a Host An OLED according to the present disclosure was produced as follows: A transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and then was stored in isopropanol. The ITO substrate was mounted on a substrate holder of a vacuum vapor deposition apparatus. Compound HI-1 shown in Table 3 below as a first hole injection compound was introduced into a cell of the vacuum vapor deposition apparatus, and compound HT-1 as a first hole transport compound was introduced into another cell of the vacuum vapor deposition apparatus. The two materials were evaporated at different rates and the first hole injection compound was deposited in a doping amount of 3 wt % based on the total amount of the first hole injection compound and the first hole transport compound to form a first hole injection layer having a thickness of 10 nm on the ITO substrate. Next, compound HT-1 was deposited as a first hole transport layer having a thickness of 80 nm on the first hole injection layer. Compound HT-2 was then introduced into another cell of the vacuum vapor deposition apparatus and was evaporated by applying an electric current to the cell, thereby forming a second hole transport layer having a thickness of 30 nm on the first hole transport layer. After forming the hole injection layer and the hole transport layers, a light-emitting layer was formed thereon as follows: The host shown in Table 1 was introduced into one cell of the vacuum vapor deposition apparatus as a host, and compound D-50 was introduced into another cell as a dopant. The two materials were evaporated at different rates and the dopant was deposited in a doping amount of 10 wt % based on the total amount of the host and dopant to form a light-emitting layer having a thickness of 40 nm on the second hole transport layer. Next, compound ETL-1 and compound EIL-1 were deposited at a weight ratio of 40:60 to form an electron transport layer having a thickness of 35 nm on the light-emitting layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, an OLED was produced. All the materials used for producing the OLED were purified by vacuum sublimation at $10^{-6}$ torr.

Comparative Example 1: Producing an OLED Comprising a Conventional Compound as a Host An OLED was produced in the same manner as in Device Example 1, except that compound Com. 1 was used as a host of a light-emitting layer.

The driving voltage and light-emitting color at a luminance of 1,000 nit, and the time taken for luminance to decrease from 100% to 95% at a luminance of 20,000 nit (lifetime; T95) of the OLEDs produced in Device Example 1 and Comparative Example 1, are shown in Table 1 below.

TABLE 1

| | Host | Driving Voltage [V] | Light-Emitting Color | Lifetime (T95) [hr] |
|---|---|---|---|---|
| Device Example 1 | A-1 | 2.8 | Green | 14.7 |
| Comparative Example 1 | Com. 1 | 2.9 | Green | 4.3 |

Device Example 2: Producing an OLED Comprising the Compound According to the Present Disclosure as a Second Host An OLED was produced in the same manner as in Device Example 1, except that a light-emitting layer was formed as follows: The first host and the second host shown in Table 2 below were introduced into two cells of the vacuum vapor deposition apparatus, respectively, as hosts, and compound D-50 was introduced into another cell as a dopant. The two host materials were evaporated at different rates of 2:1, and at the same time the dopant material was evaporated at a different rate to deposit the dopant in a doping amount of 10 wt % based on the total amount of the hosts and dopant thereby forming a light-emitting layer having a thickness of 40 nm on the second hole transport layer.

Comparative Example 2: Producing an OLED Comprising a Conventional Compound as a Second Host An OLED was produced in the same manner as in Device Example 2, except that compound Com.1 was used as a second host of a light-emitting layer.

The driving voltage, luminous efficiency, and light-emitting color at a luminance of 1,000 nit, and the time taken for luminance to decrease from 100% to 95% at a luminance of 20,000 nit (lifetime; T95) of the OLEDs produced in Device Example 2 and Comparative Example 2, are shown in Table 2 below.

TABLE 2

| | First Host | Second Host | Driving Voltage [V] | Luminous Efficiency [cd/A] | Light-Emitting Color | Lifetime (T95) [hr] |
|---|---|---|---|---|---|---|
| Device Example 2 | H2-6 | A-1 | 2.9 | 80.8 | Green | 174 |
| Comparative Example 2 | H2-6 | Com. 1 | 3.0 | 80.6 | Green | 52 |

From Tables 1 and 2 above, it can be confirmed that the luminous properties of the organic electroluminescent compounds developed in the present disclosure are superior to those of the conventional materials. In addition, the OLED using the compound according to the present disclosure as a host material in a light-emitting layer exhibits not only excellent luminous properties but also especially improved lifetime properties.

Compound Com.1 used in the comparative examples has a structure, in which benzoxazole is linked to dibenzofuran at 2-position of benzoxazole. This compound has the characteristic of fast electron mobility. On the other hand, the compound according to the present disclosure has a structure in which benzoxazole is linked to dibenzofuran or dibenzothiophene at the following position a, b, c, or d of benzoxazole, which can reduce electron mobility. Due to this, it is thought that the organic electroluminescent device comprising the compound of the present disclosure can improve lifetime properties while having equivalent or improved power efficiency compared to the conventional organic electroluminescent device.

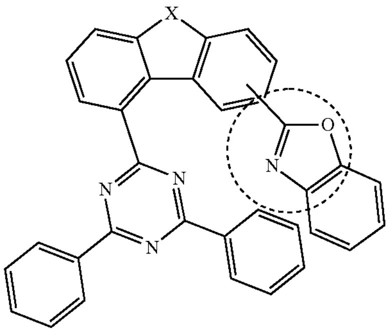

X: O, S
Prior Art

-continued

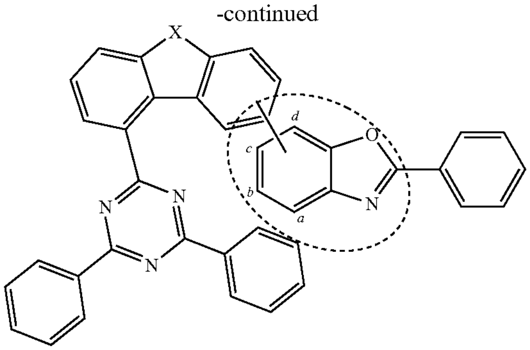

X: O, S
Present Disclosure

The compounds used in the Device Examples and the Comparative Examples are shown in Table 3 below.

TABLE 3

| | |
|---|---|
| Hole Injection Layer/ Hole Transport Layer | 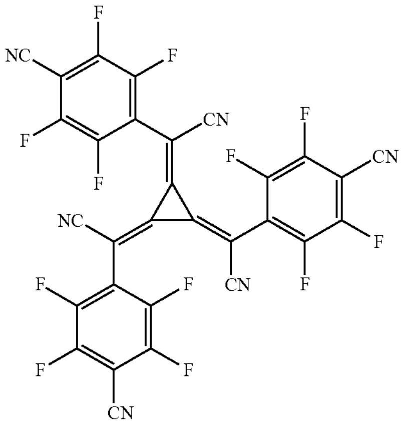 HI-1 |
| | 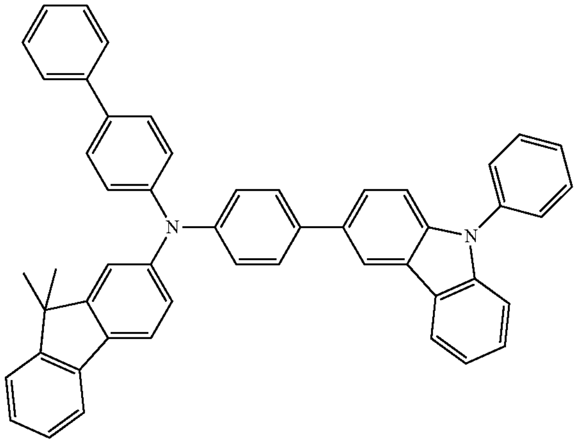 HT-1 |

TABLE 3-continued
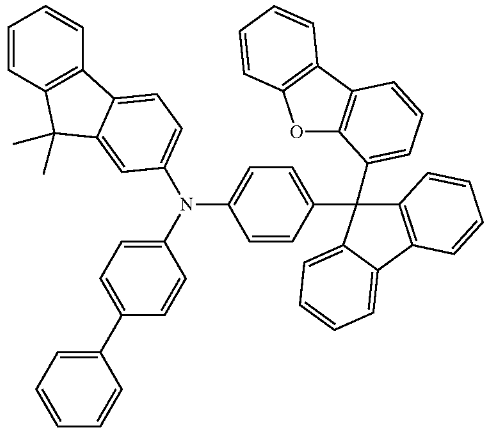
HT-2
Light-Emitting Layer
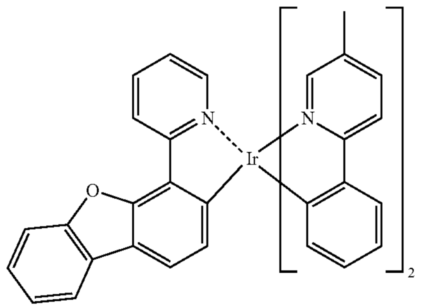
D-50
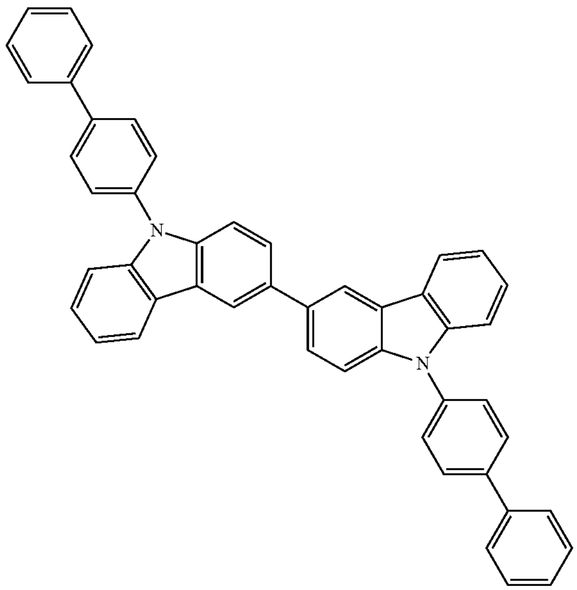
H2-6

TABLE 3-continued
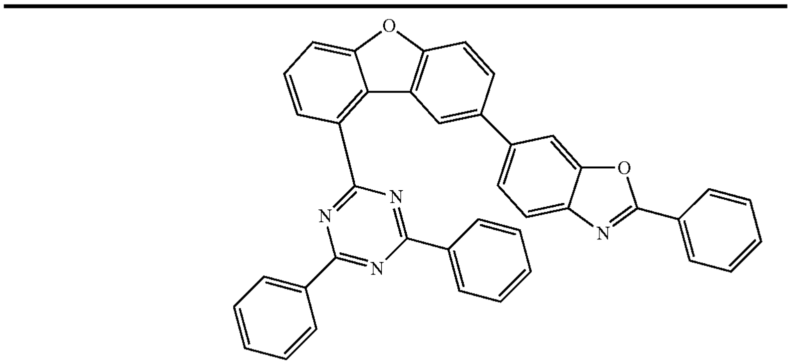
A-1
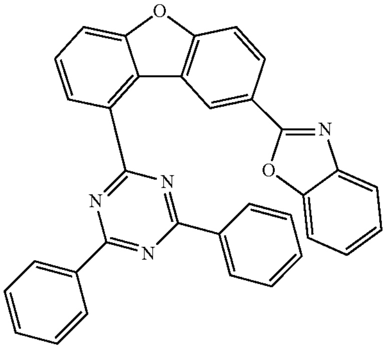
Com. 1
Electron transport Layer/
Electron Injection Layer
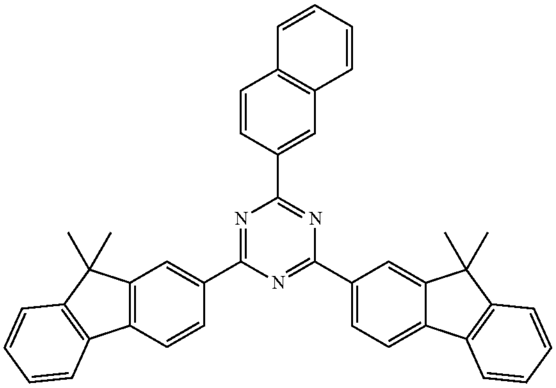
ETL-1
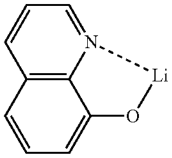
EIL-1

The invention claimed is:

1. An organic electroluminescent compound represented by the following formula 1:

(1)

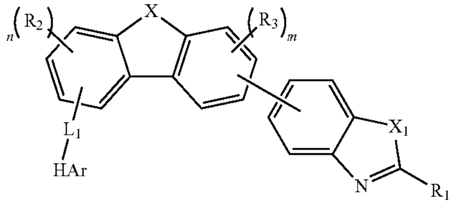

wherein

X and $X_1$, each independently, represent O or S;

HAr represents a substituted or unsubstituted (3- to 30-membered)heteroaryl;

$L_1$ represents a single bond, a substituted or unsubstituted (C6-C30)arylene, or a substituted or unsubstituted (3- to 30-membered)heteroaryene;

$R_1$ represents a substituted or unsubstituted (C1-C30) alkyl, a substituted or unsubstituted (C6-C30)aryl, a substituted or unsubstituted (3- to 30-membered)heteroaryl, or a substituted or unsubstituted (C3-C30) cycloalkyl;

$R_2$ and $R_3$, each independently, represent hydrogen, deuterium, a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30)cycloalkyl, or may be linked to adjacent one(s) of $R_2$ and $R_3$ to form a ring(s); and n and m represent an integer of 1 to 3; in which if n and m, each independently, are an integer of 2 or more, each of $R_2$ or each of $R_3$ may be the same or different.

2. The organic electroluminescent compound according to claim 1, wherein the formula 1 is represented by at least one of the following formulas 1-1 to 1-8:

(1-1)

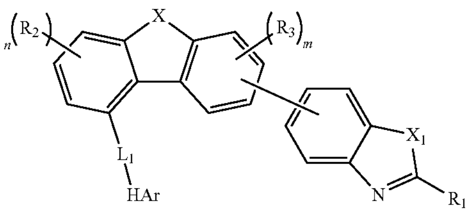

(1-2)

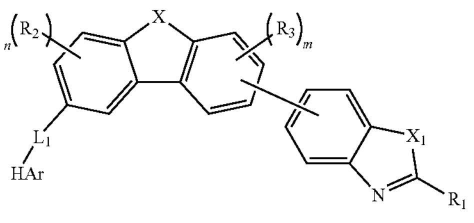

-continued (1-3)

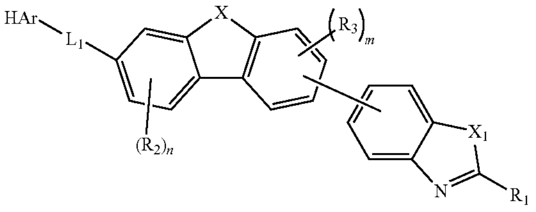

(1-4)

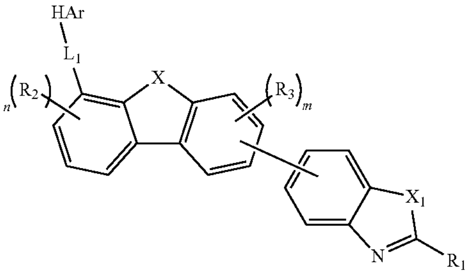

(1-5)

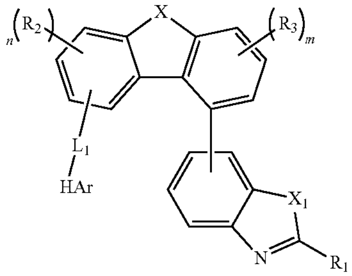

(1-6)

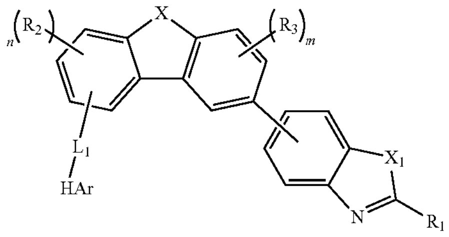

(1-7)

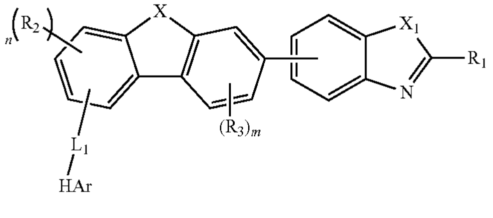

(1-8)

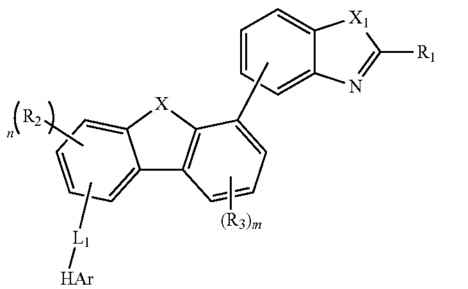

wherein, X, $X_1$, HAr, $L_1$, $R_1$ to $R_3$, n, and m are as defined in claim 1.

3. The organic electroluminescent compound according to claim 1, wherein the substituents of the substituted alkyl, the substituted aryl(ene), the substituted heteroaryl(ene), and the substituted cycloalkyl, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with a (C6-C30)aryl(s); a (C6-C30)aryl unsubstituted or substituted with a (3- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino unsubstituted or substituted with a (C1-C30)alkyl(s); a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

4. The organic electroluminescent compound according to claim 1, wherein HAr is any one selected from the following group 1:

[Group 1]

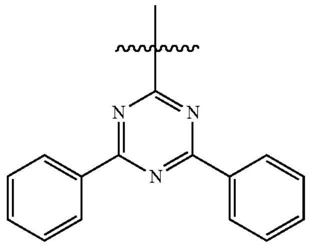

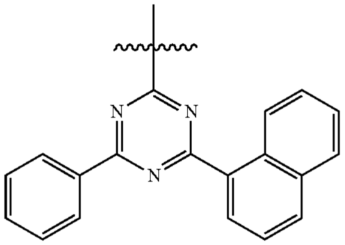

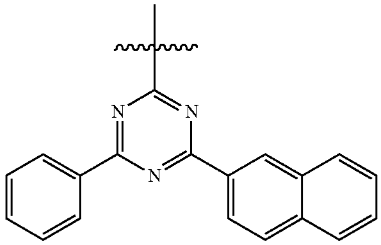

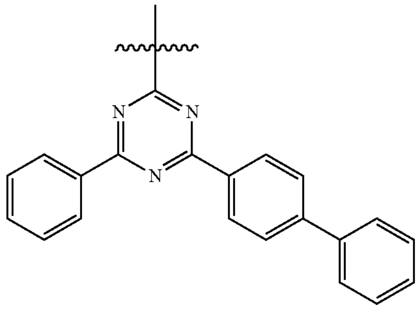

-continued

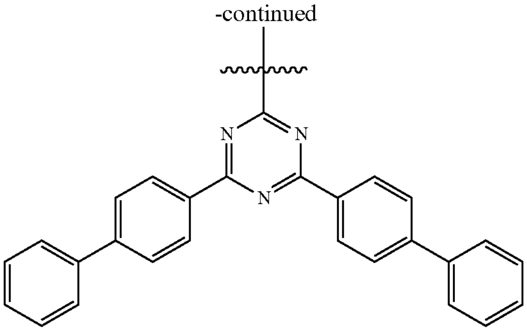

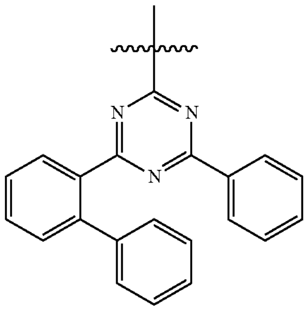

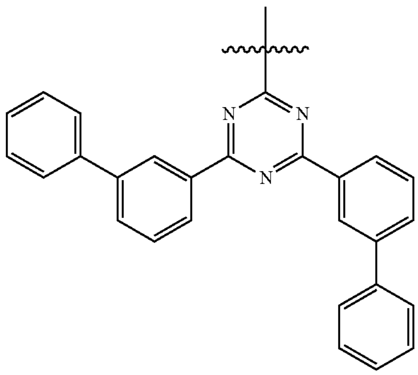

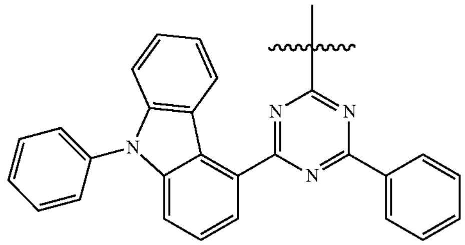

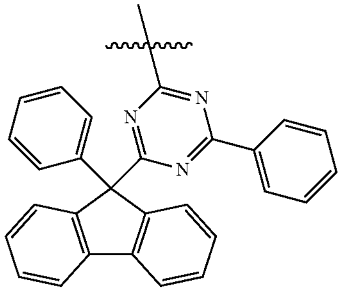

-continued
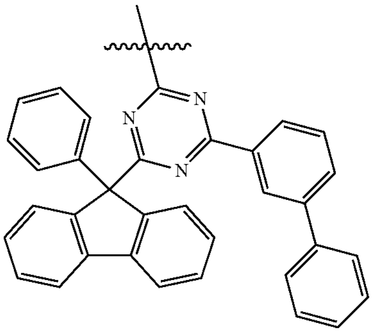
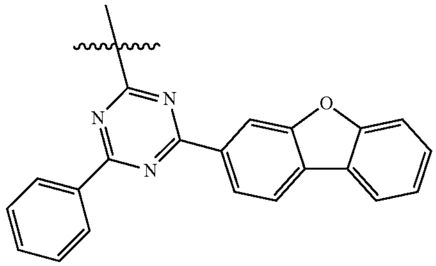
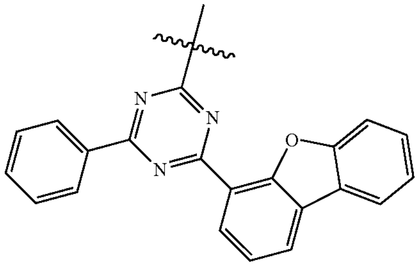
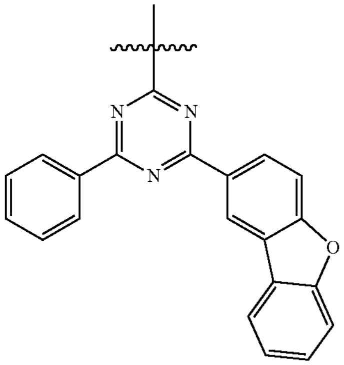
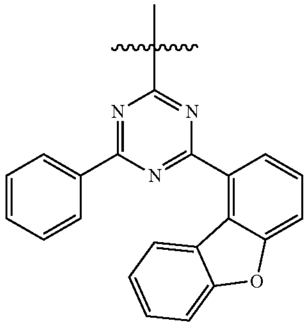
-continued
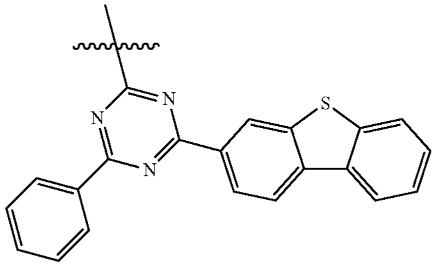
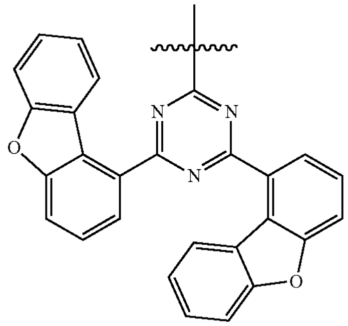
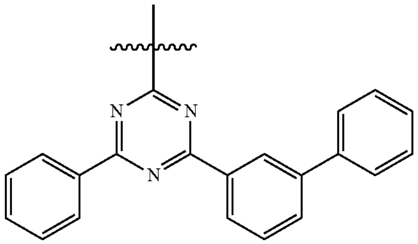
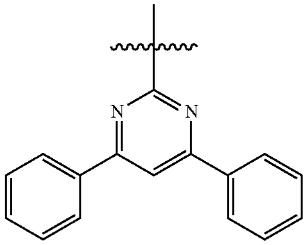
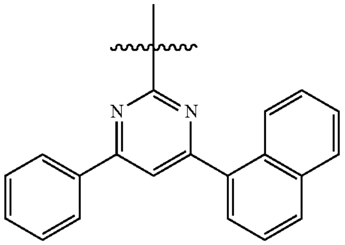
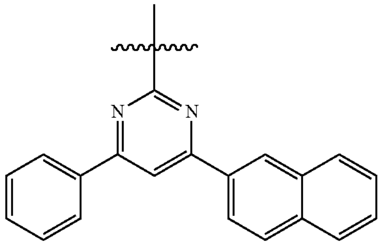

-continued
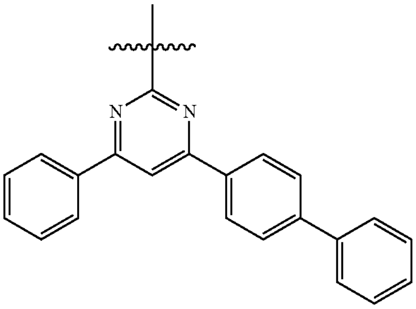
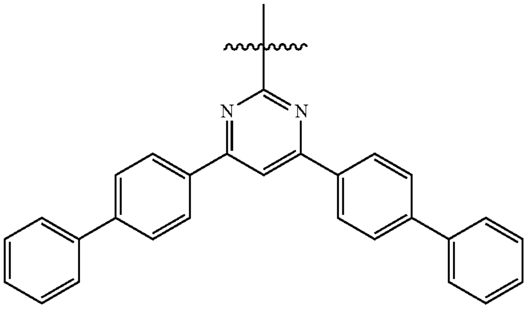
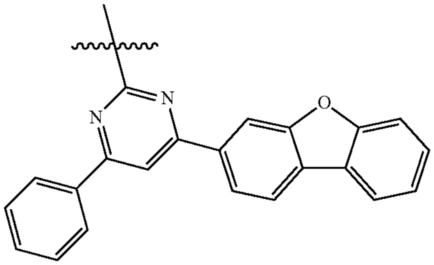
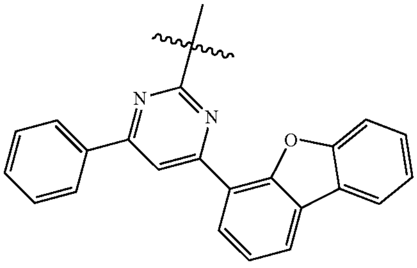
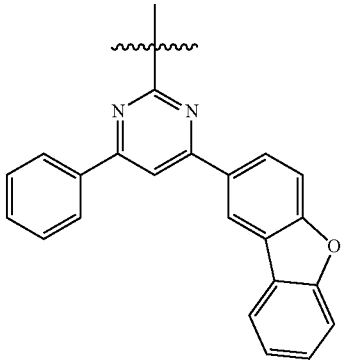
-continued
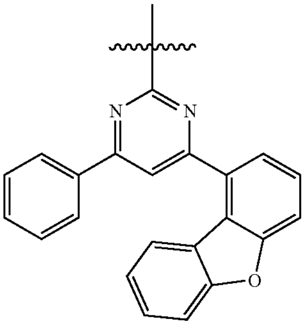
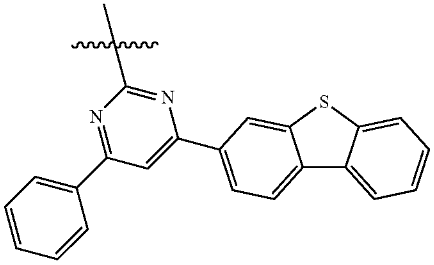
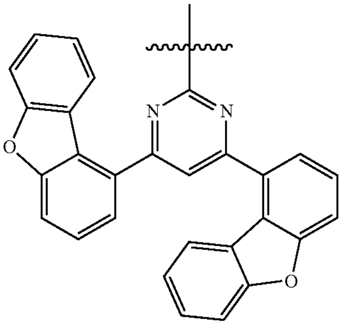
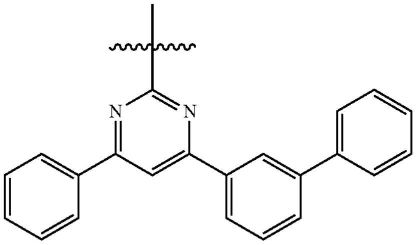
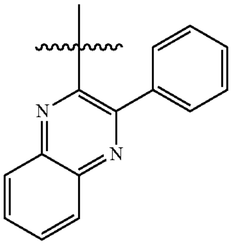
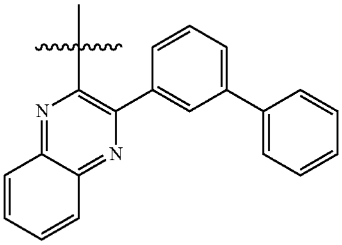
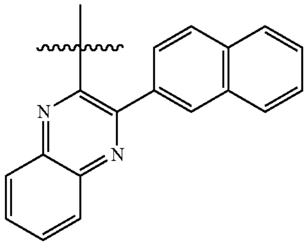

-continued
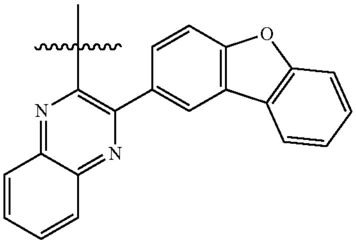
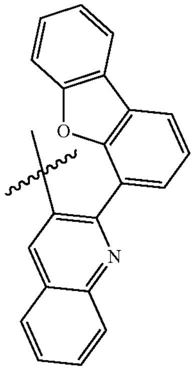
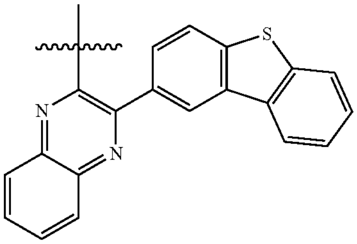
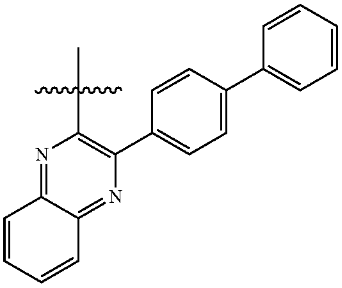
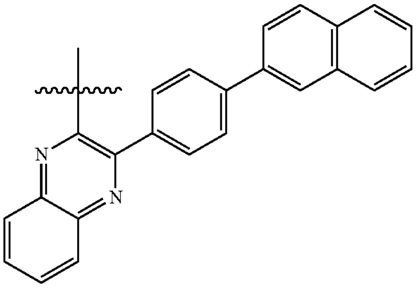
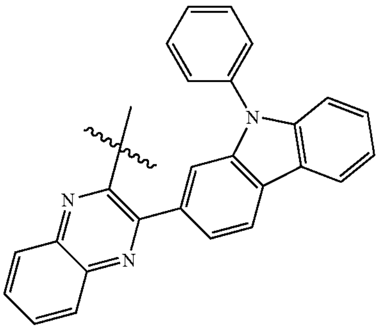
-continued
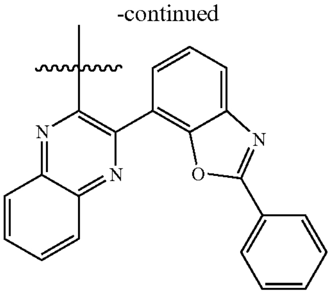
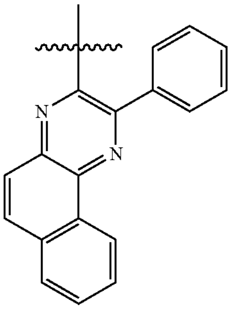
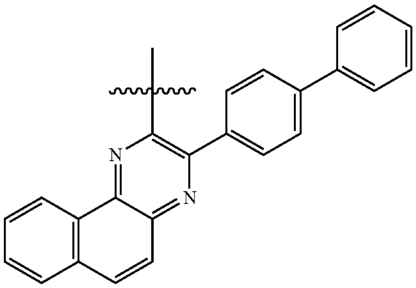
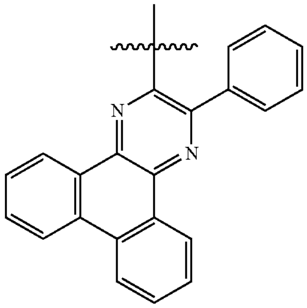
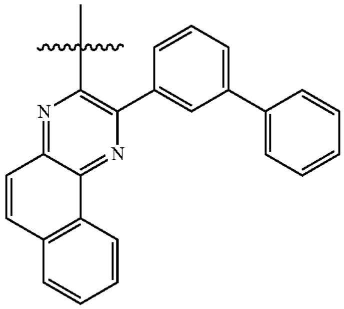
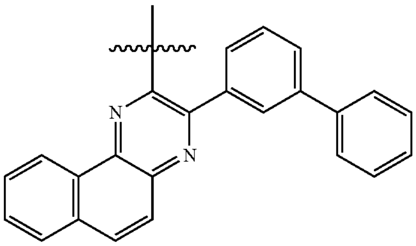

-continued
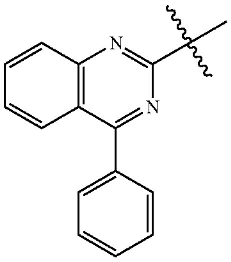
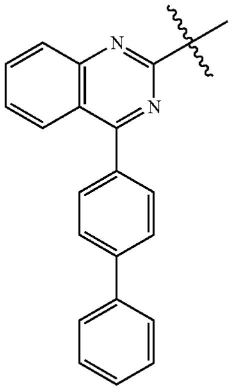
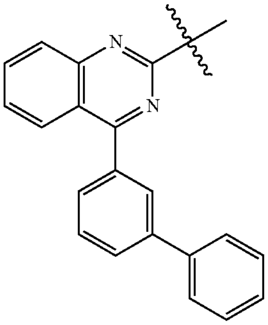
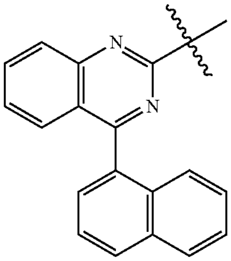
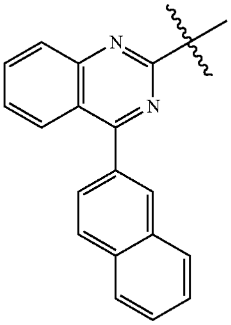
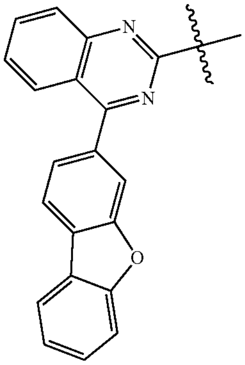
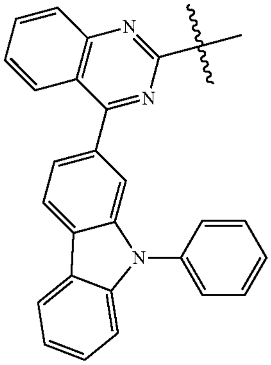
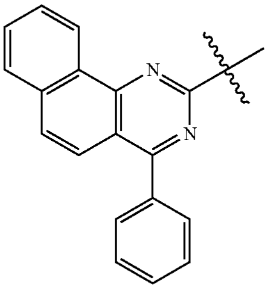
-continued
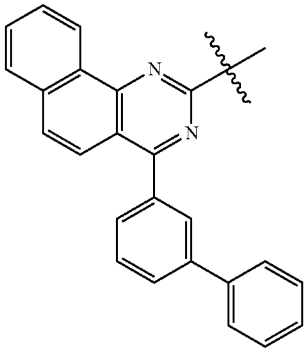
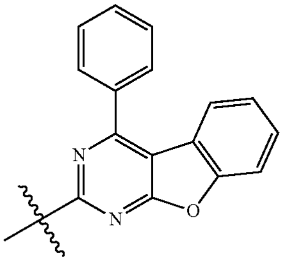
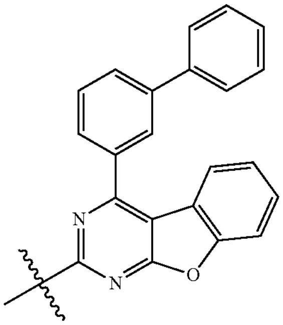
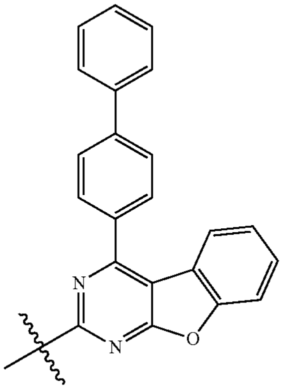
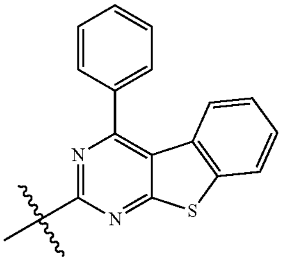
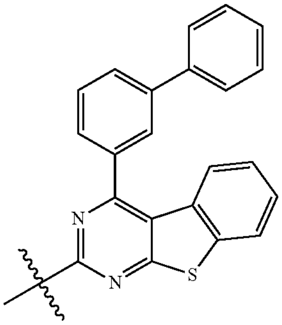
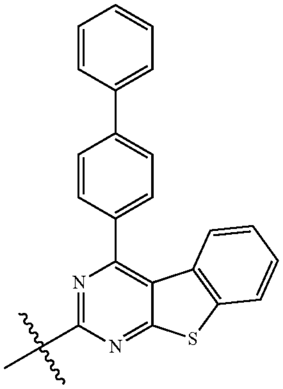

-continued
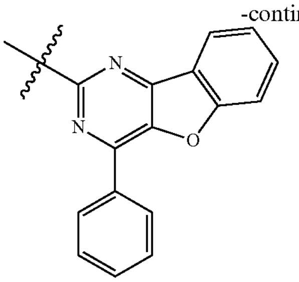
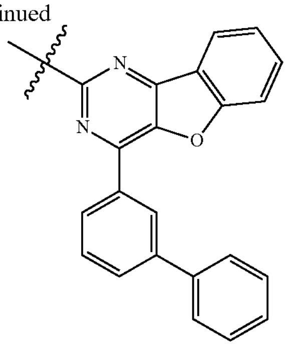
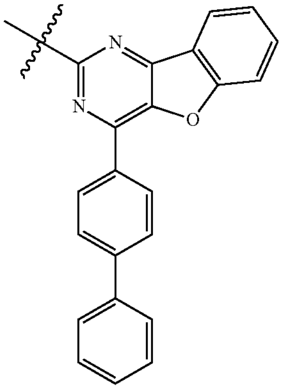
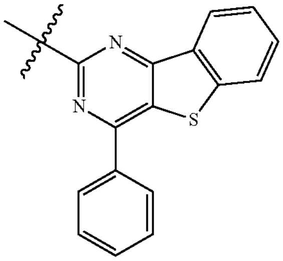
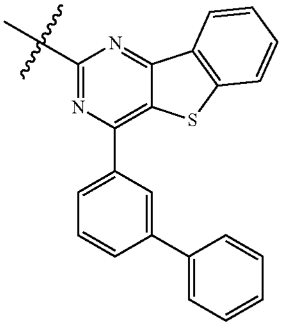
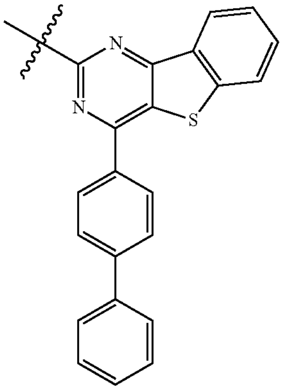
-continued
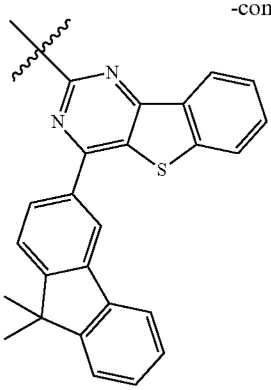
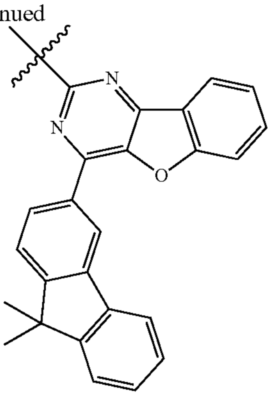
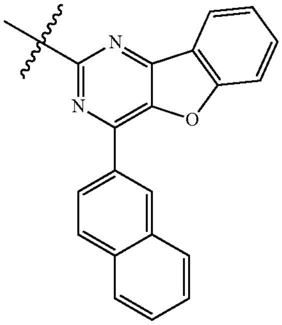
.
5. The organic electroluminescent compound according to claim 1, wherein the compound represented by formula 1 is selected from the group consisting of the following compounds:
A-1
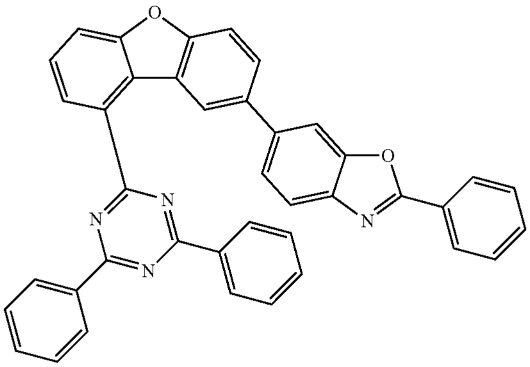
A-2
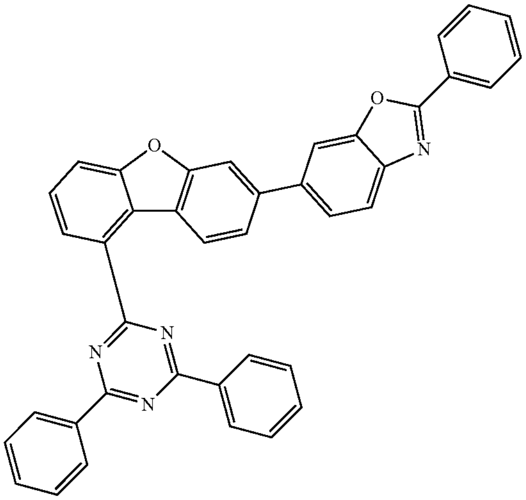

-continued
A-3
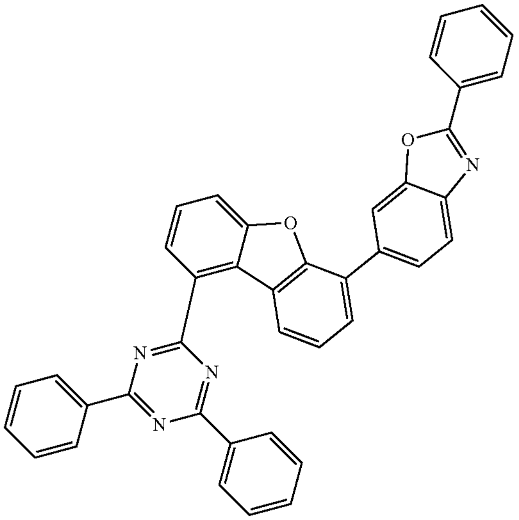
A-4
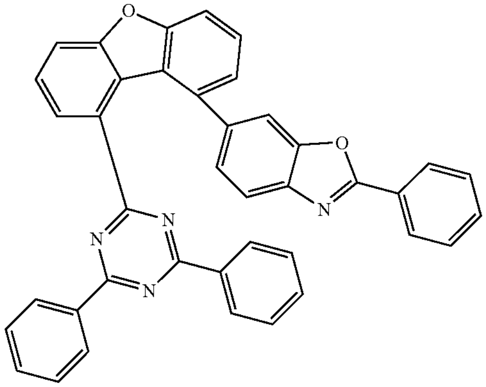
A-5
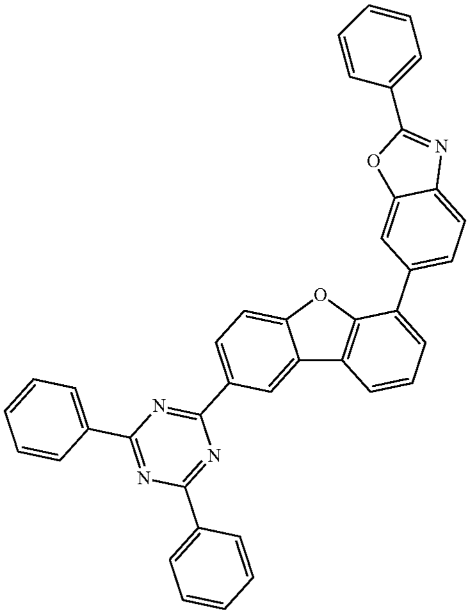
A-6
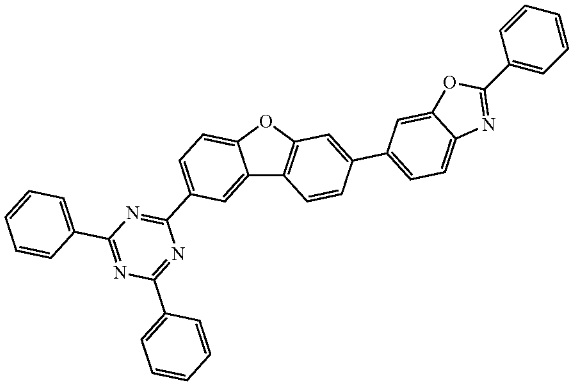
A-7
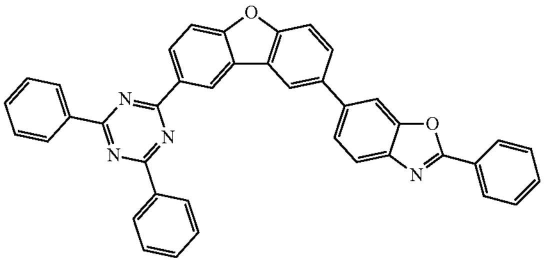
A-8
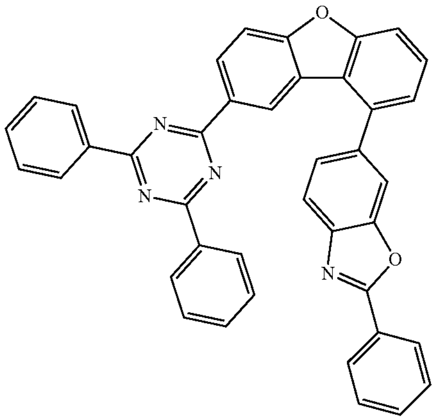

-continued
A-9
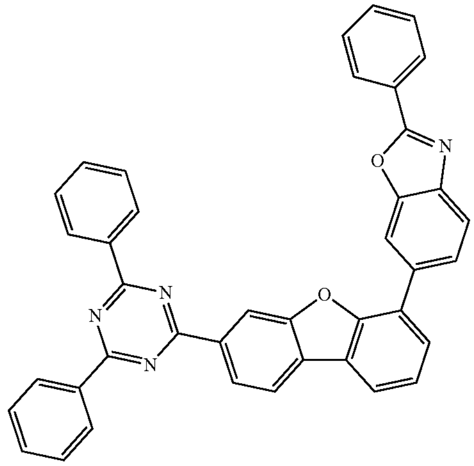
A-10
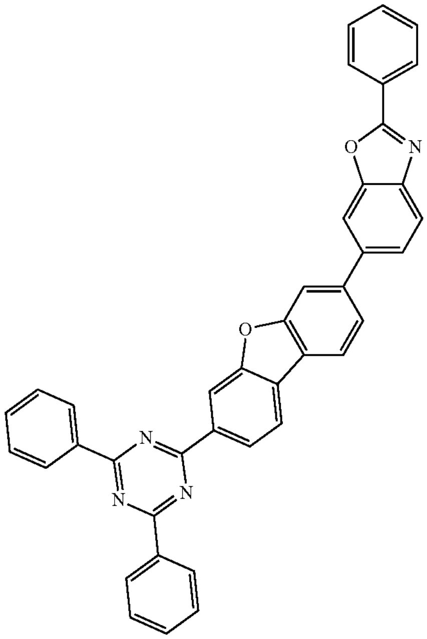
A-11
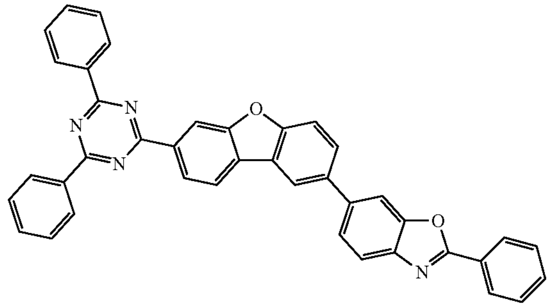
A-12
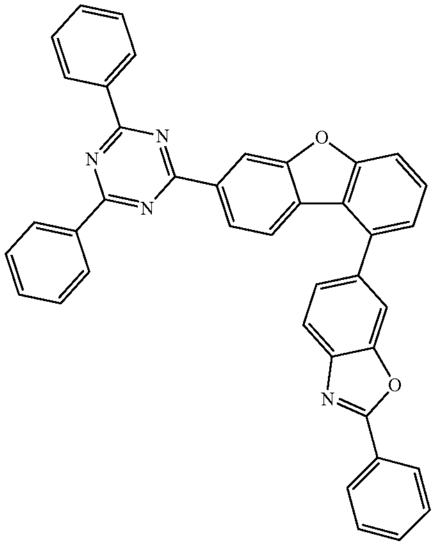
A-13
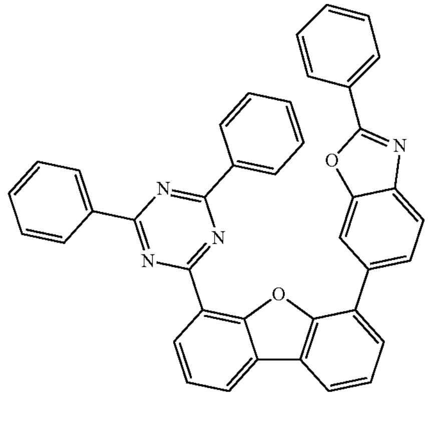
A-14
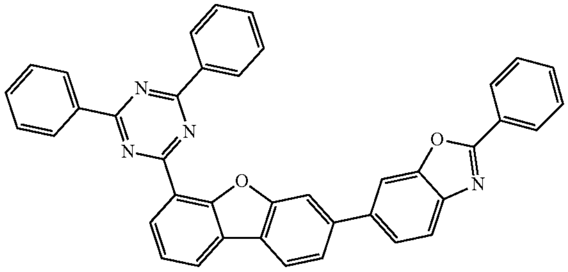

-continued
A-15
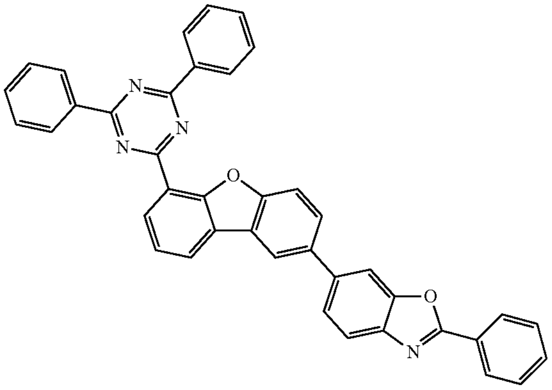
A-16
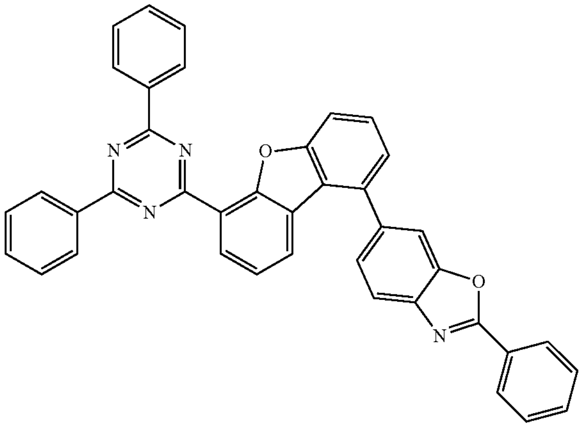
A-17
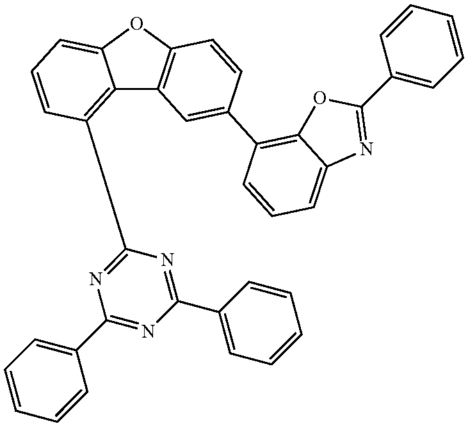
A-18
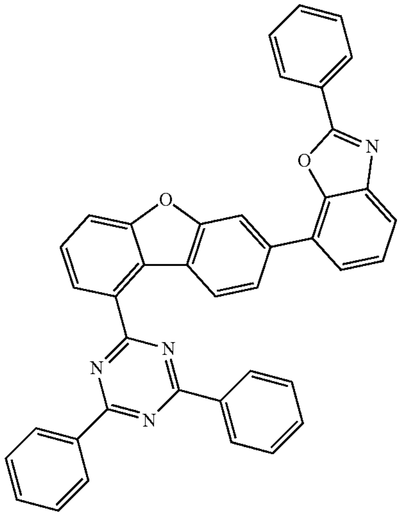
A-19
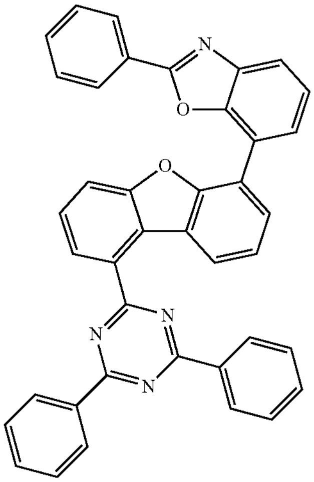
A-20
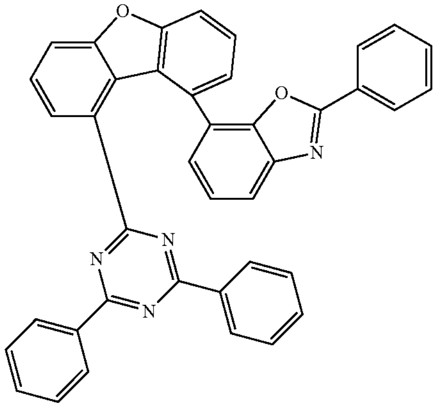

-continued
A-21
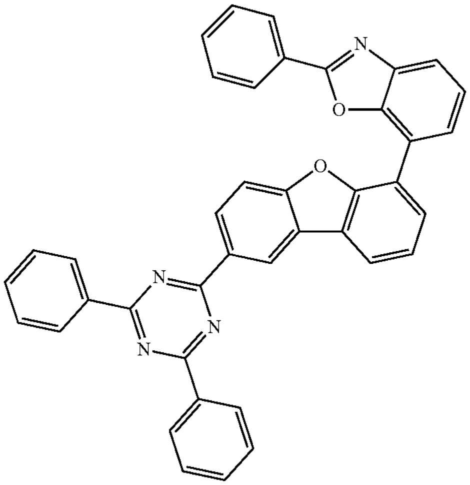
A-22
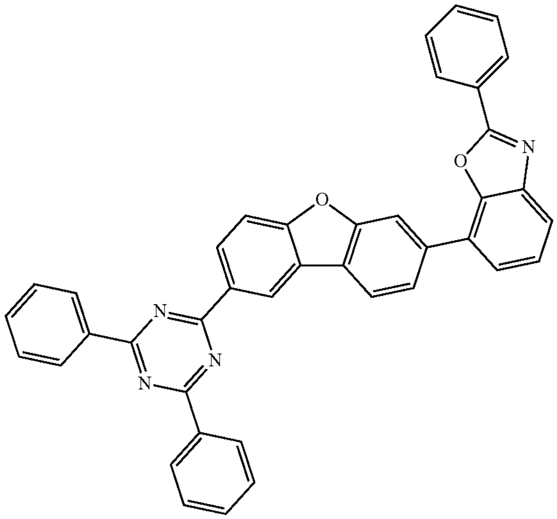
A-23
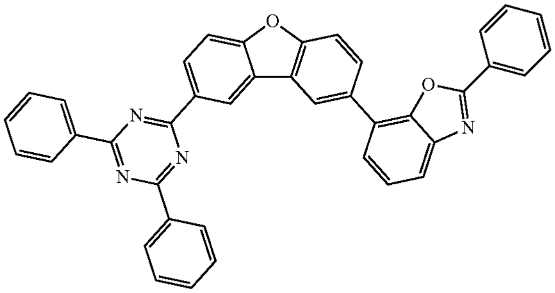
A-24
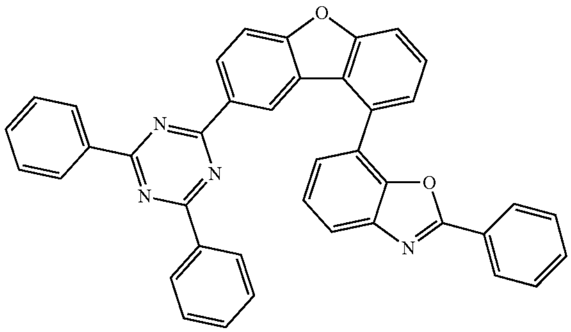
A-25
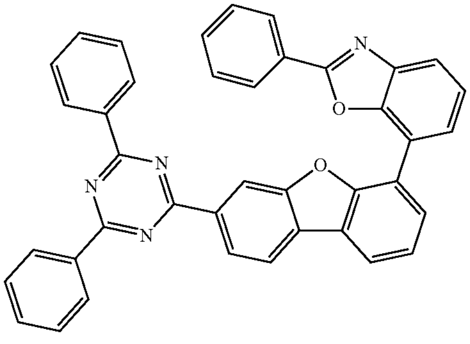
A-26
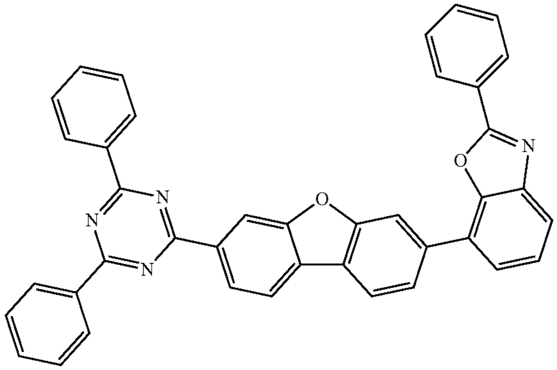

-continued
A-27
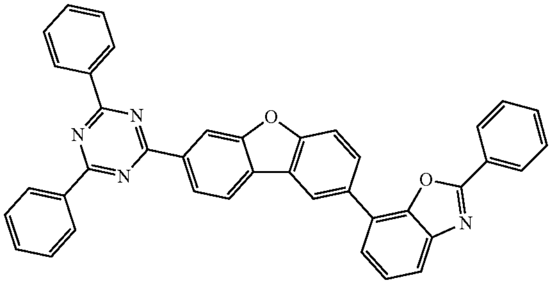
A-28
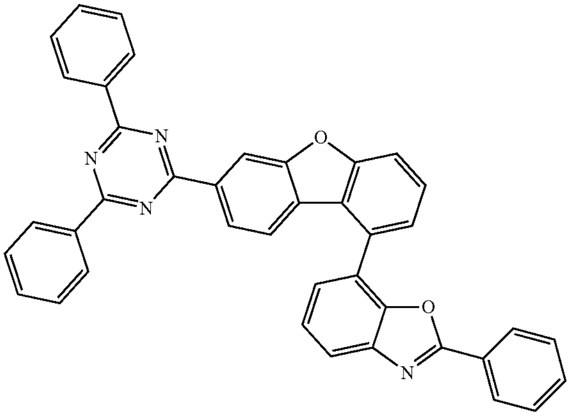
A-29
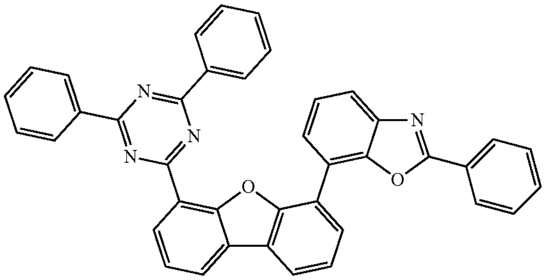
A-30
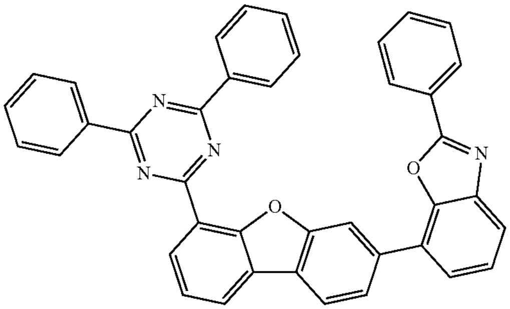
A-31
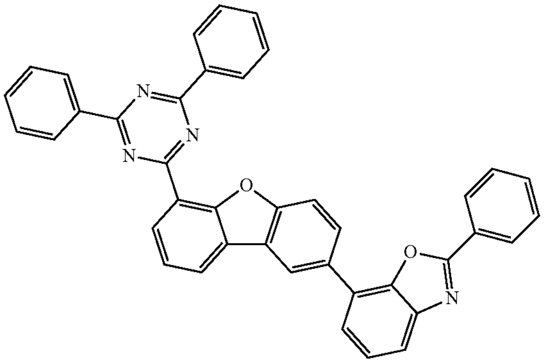
A-32
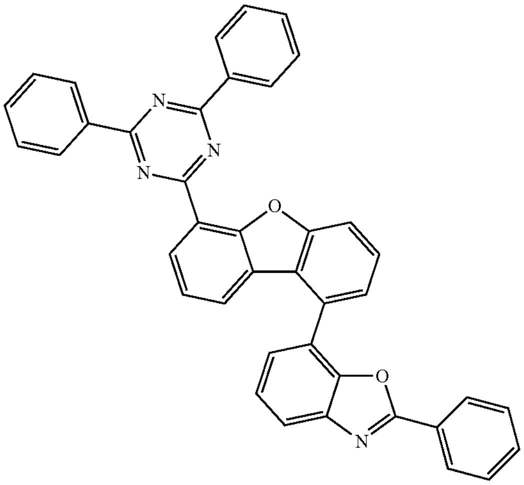

-continued
A-33
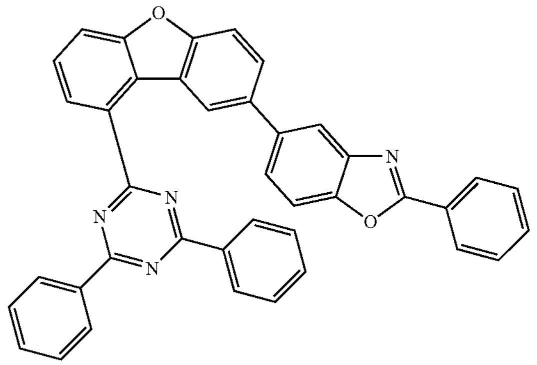
A-34
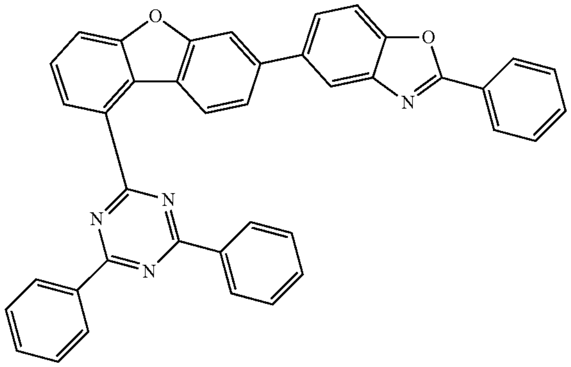
A-35
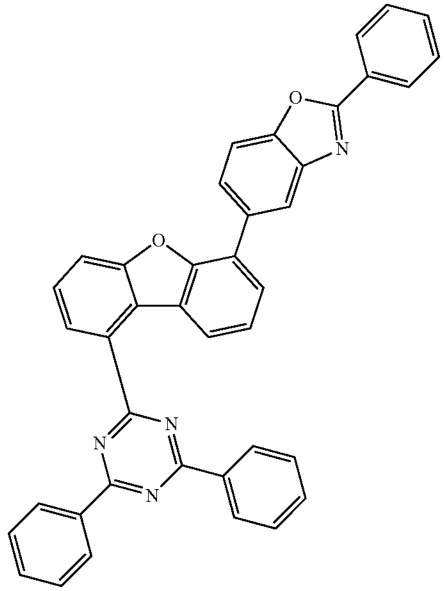
A-36
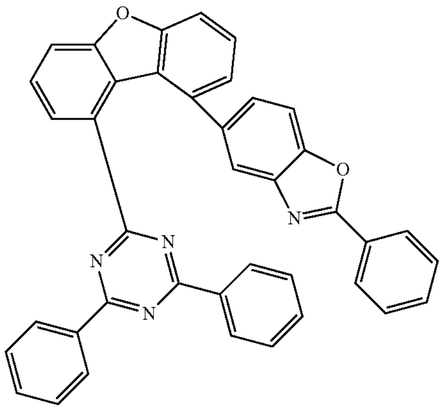
A-37
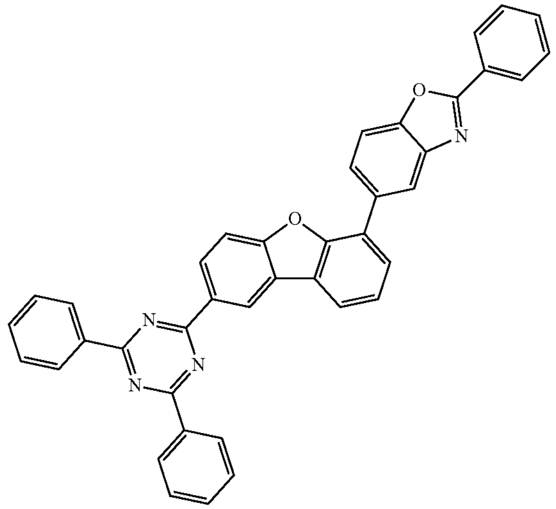
A-38
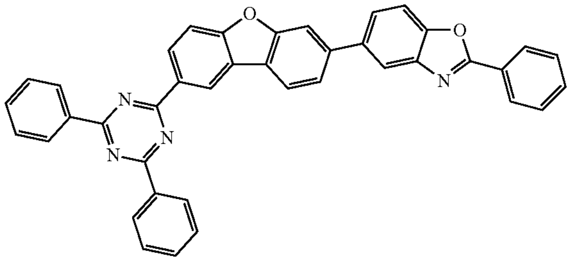

-continued
A-39
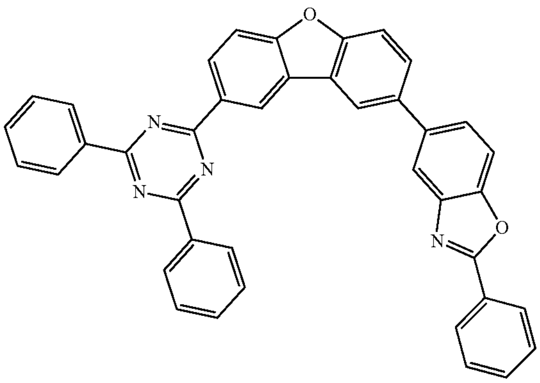
A-40
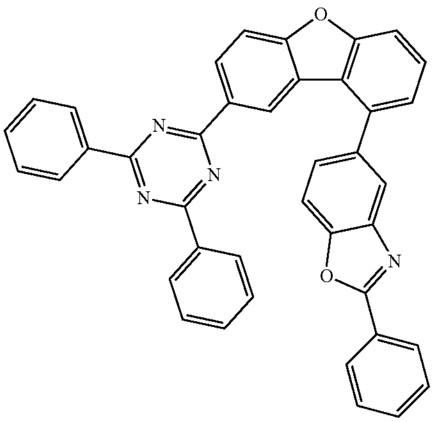
A-41
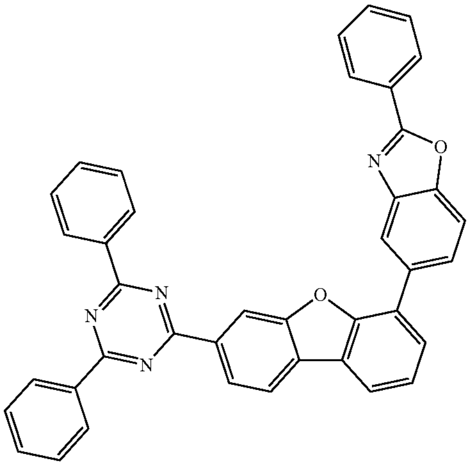
A-42
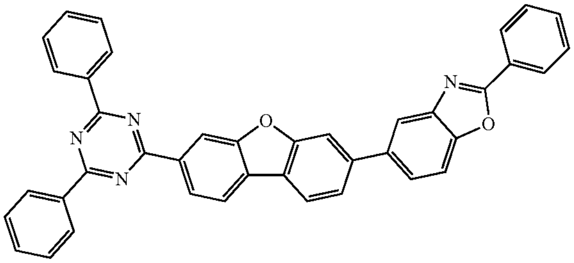
A-43
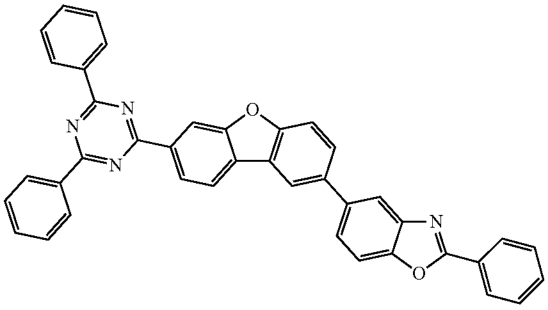
A-44
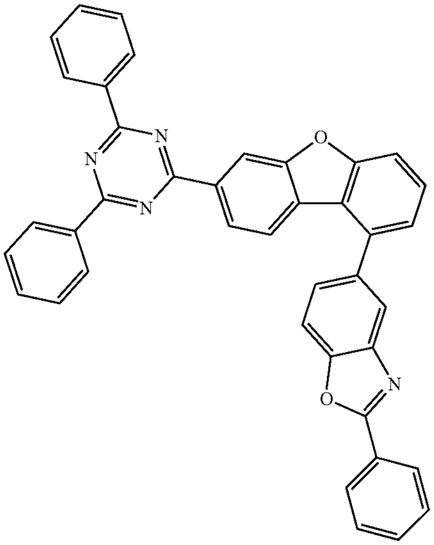

-continued
A-45
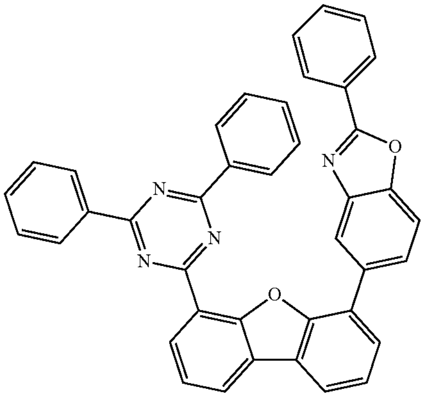
A-46
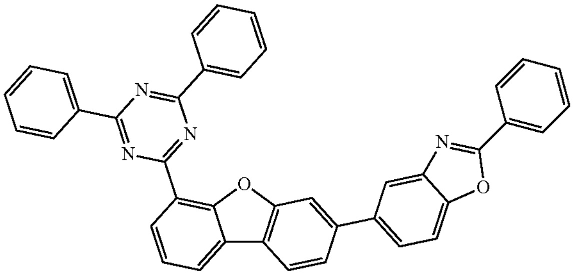
A-47
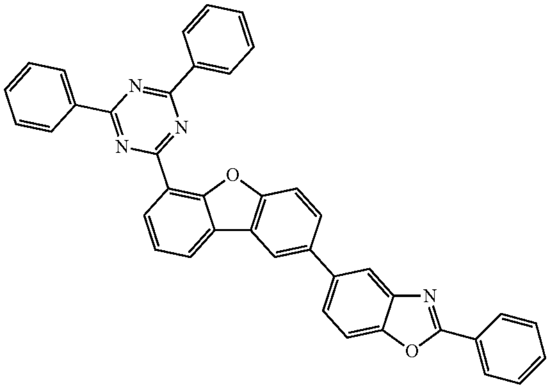
A-48
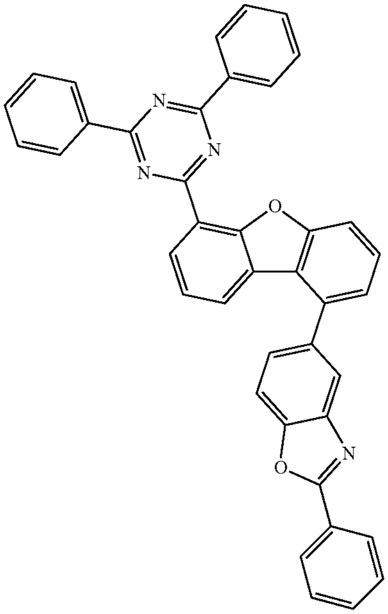
A-49
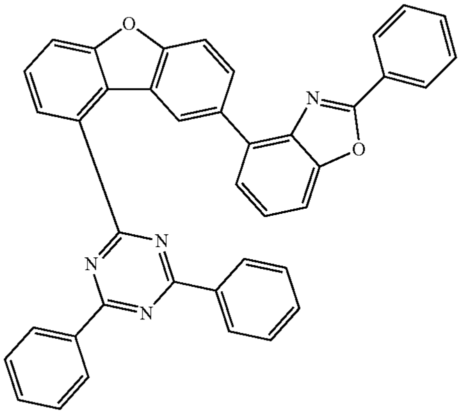
A-50
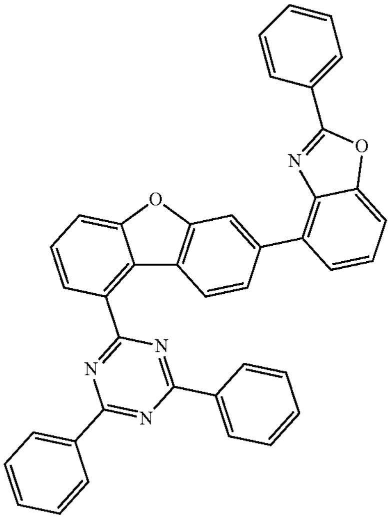

-continued
A-51
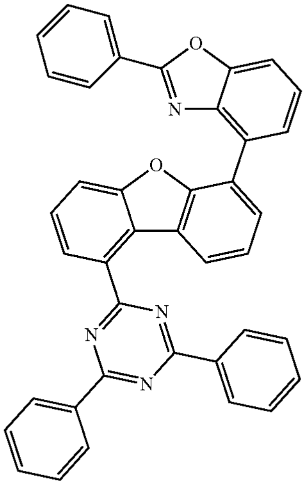
A-52
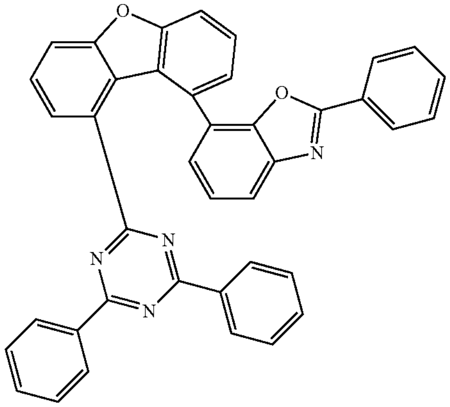
A-53
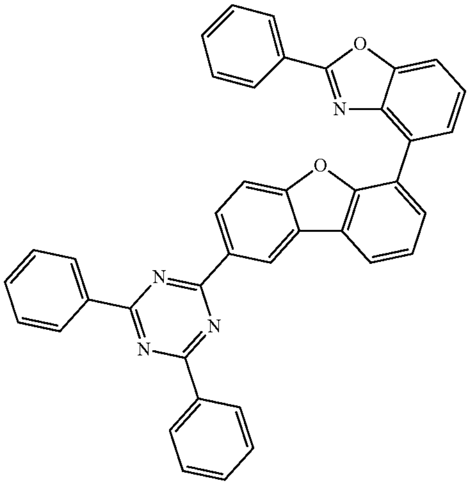
A-54
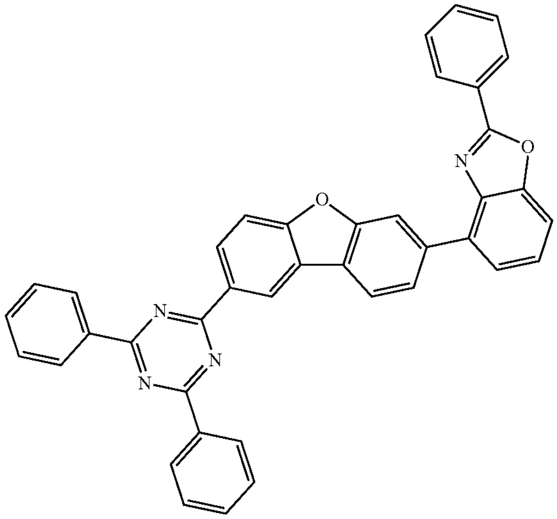
A-55
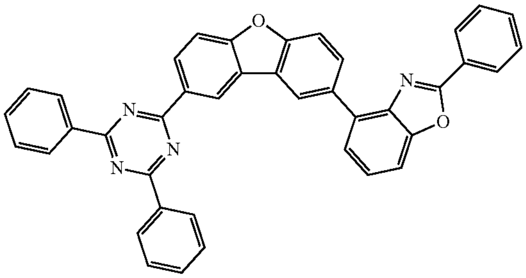
A-56
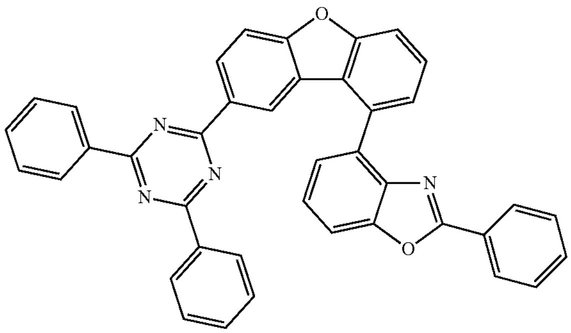

-continued
A-57
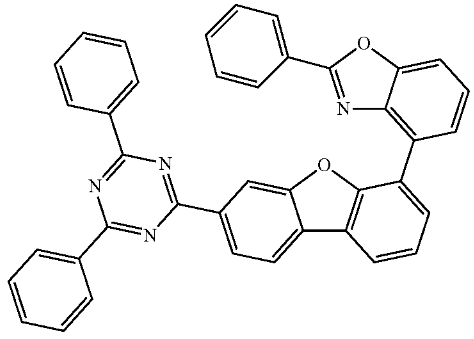
A-58
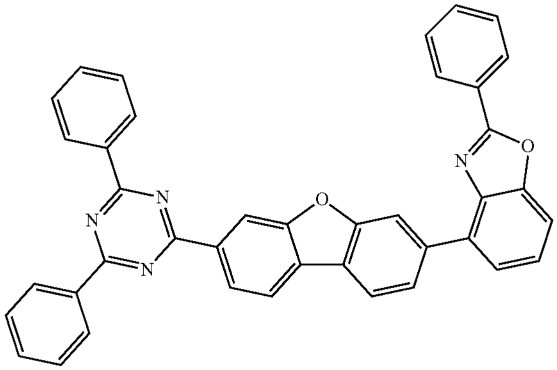
A-59
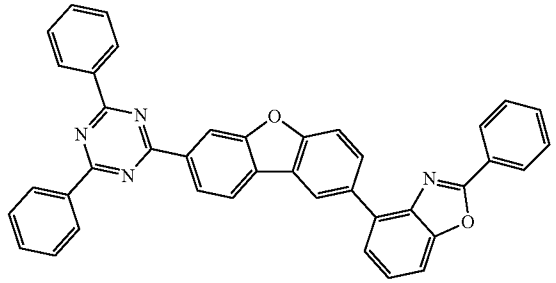
A-60
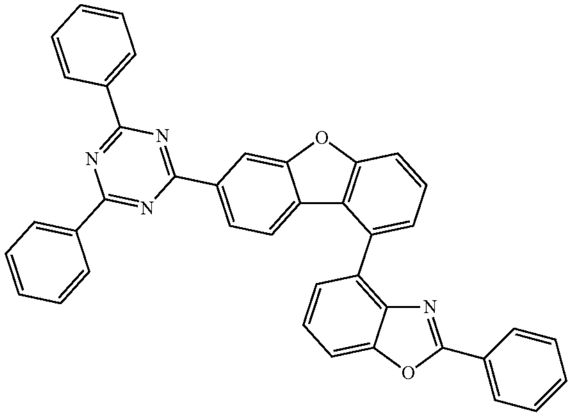
A-61
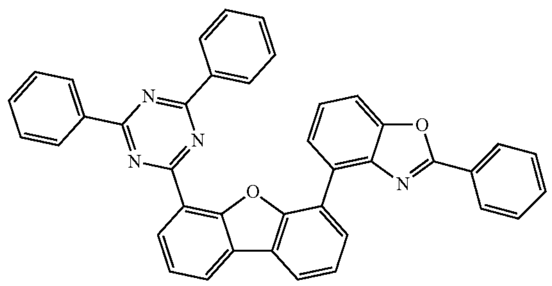
A-62
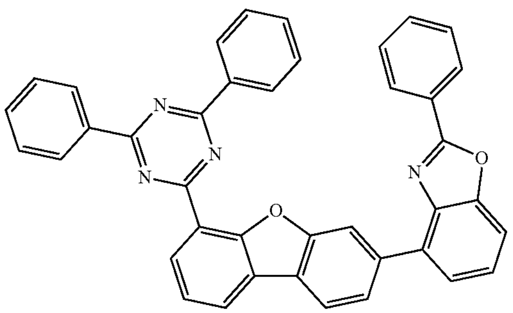

-continued
A-63
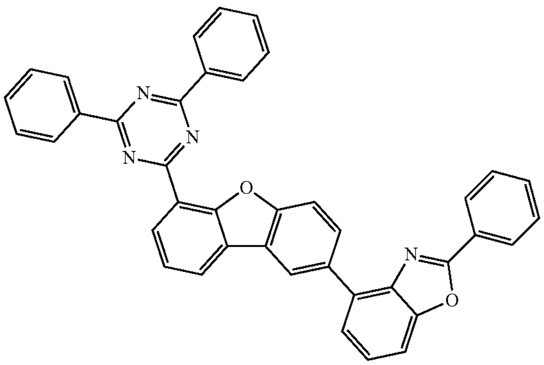
A-64
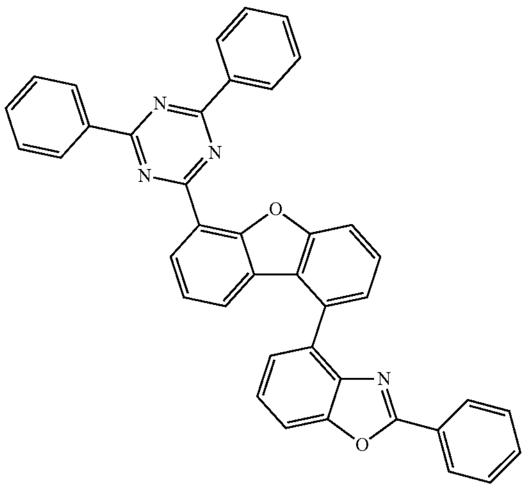
B-1
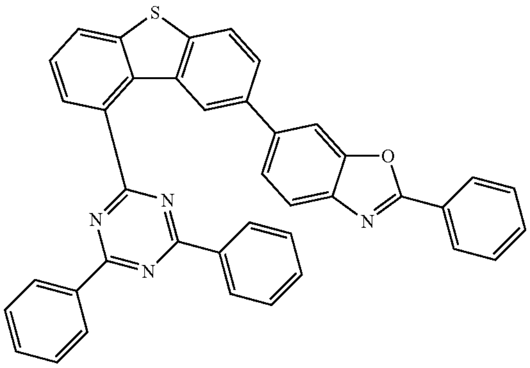
B-2
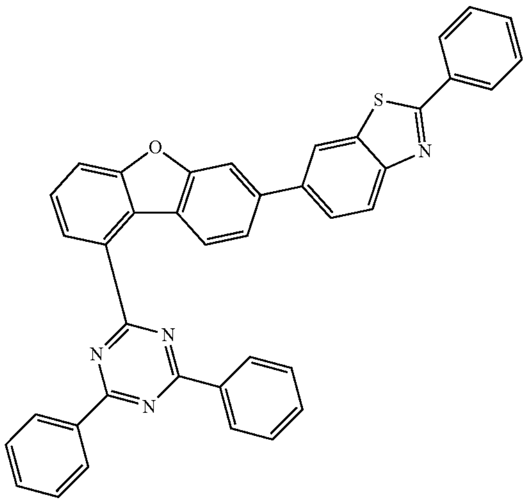
B-3
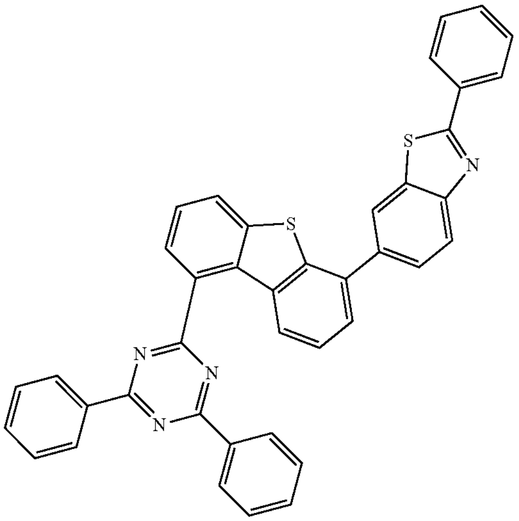
B-4
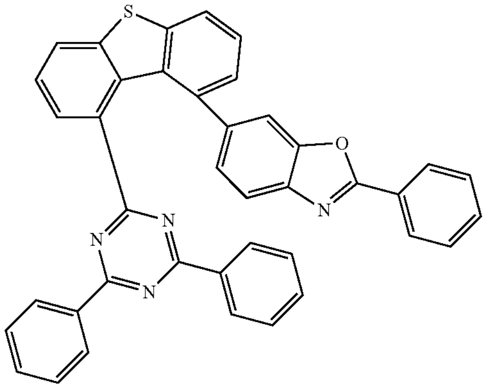

-continued
B-5
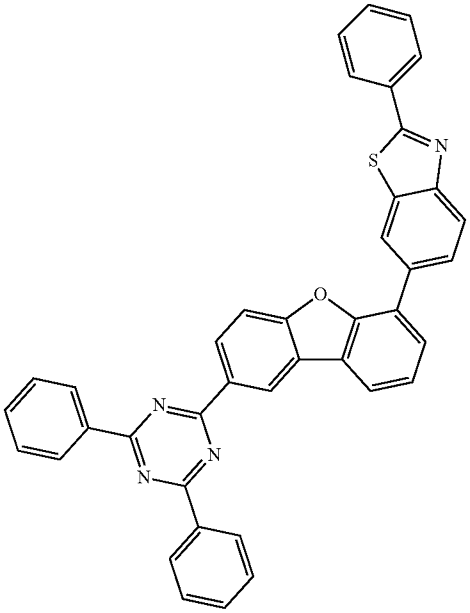
B-6
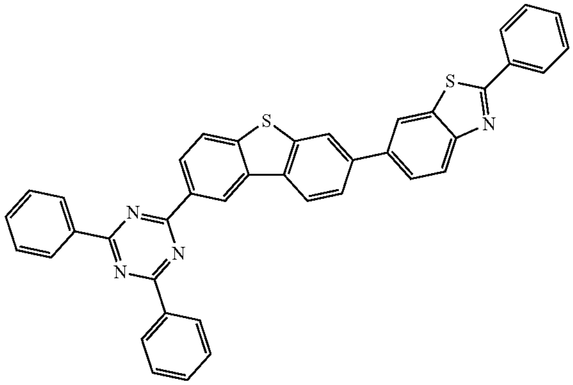
B-7
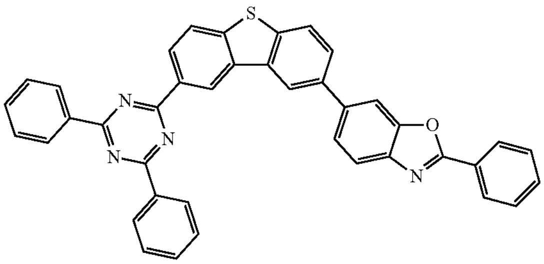
B-8
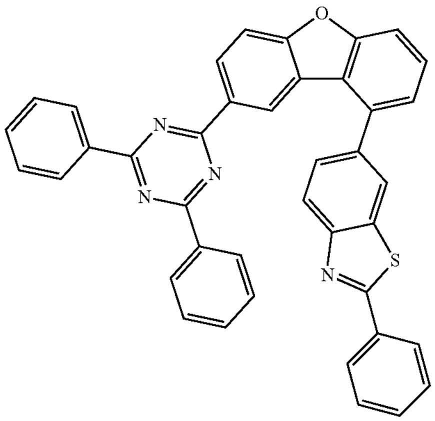
B-9
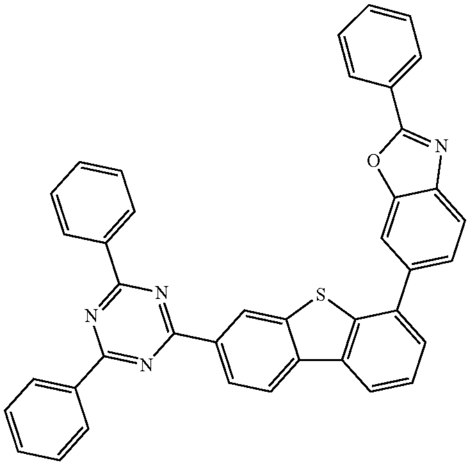
B-10
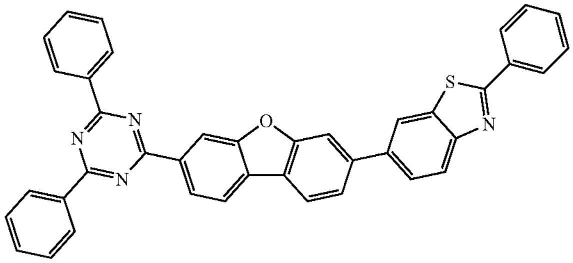

-continued
B-11
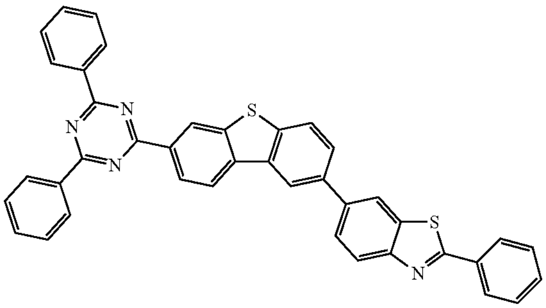
B-12
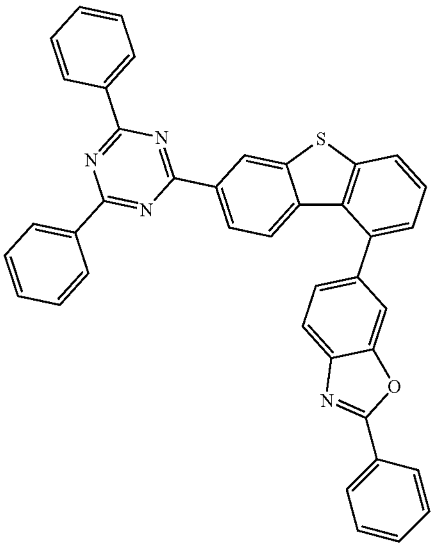
B-13
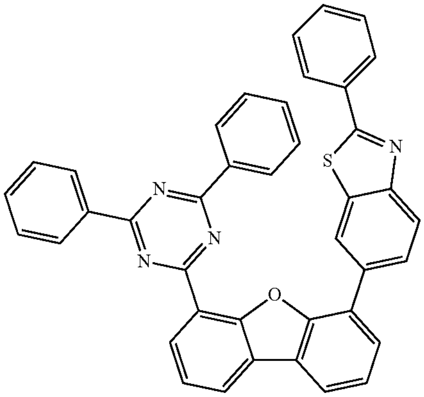
B-14
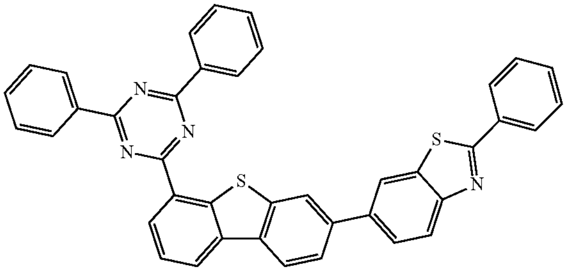
B-15
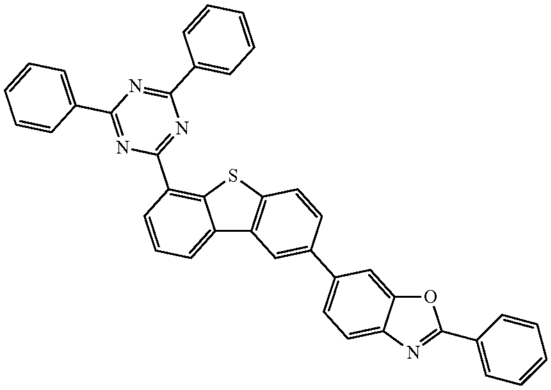
B-16
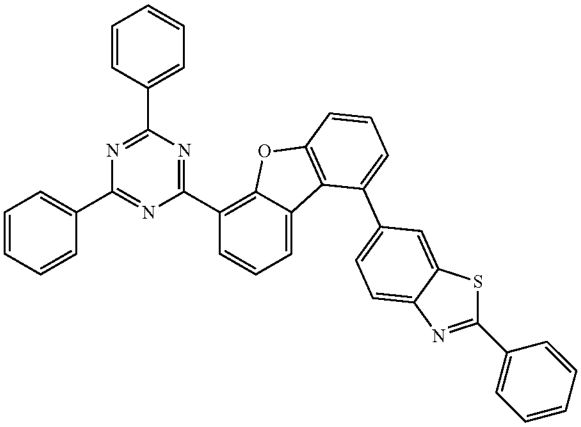

-continued
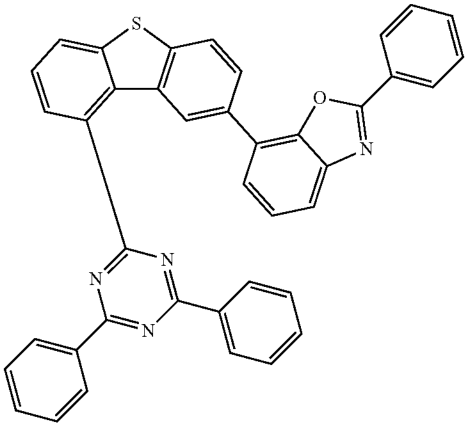
B-17
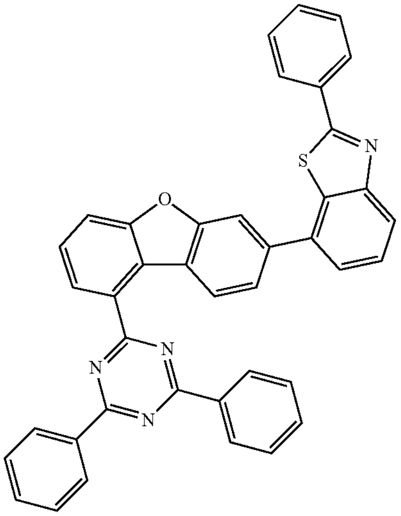
B-18
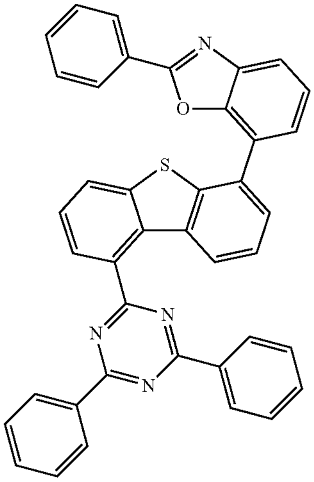
B-19
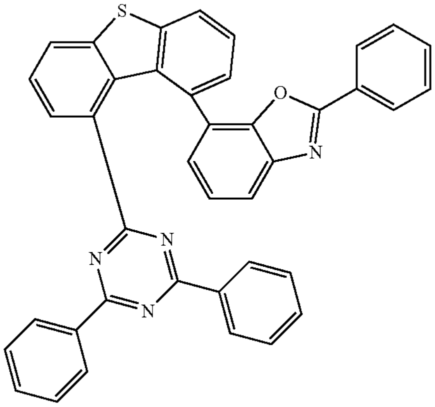
B-20
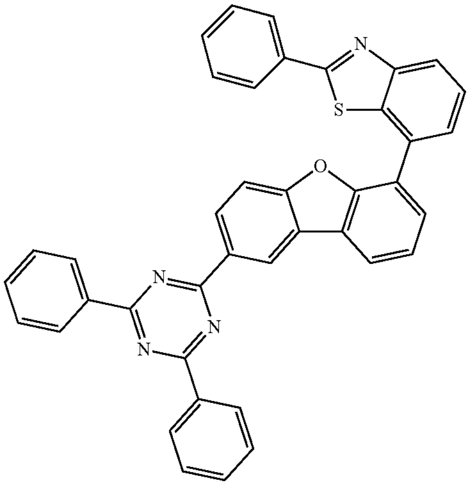
B-21
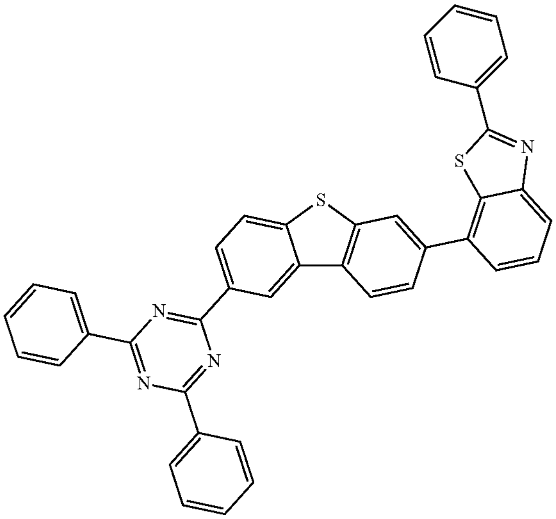
B-22

-continued
B-23
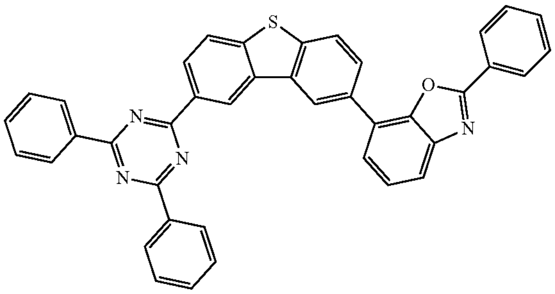
B-24
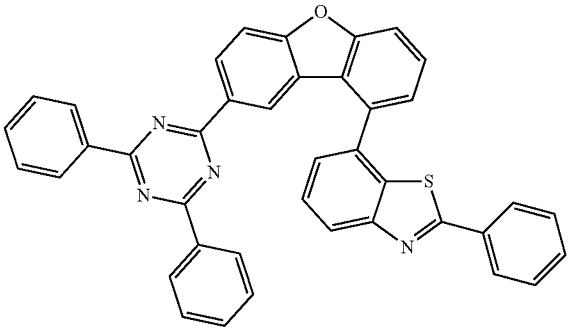
B-25
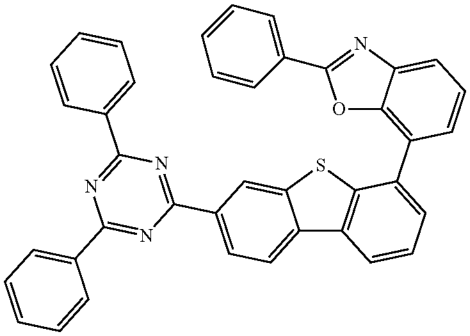
B-26
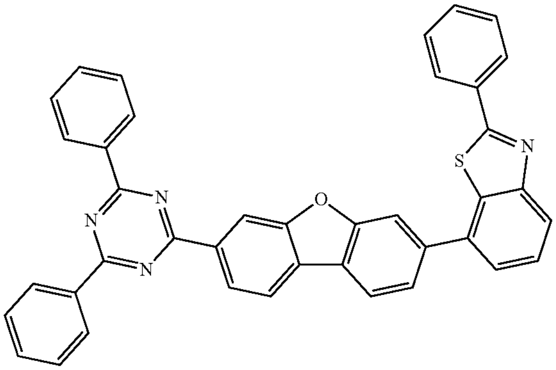
B-27
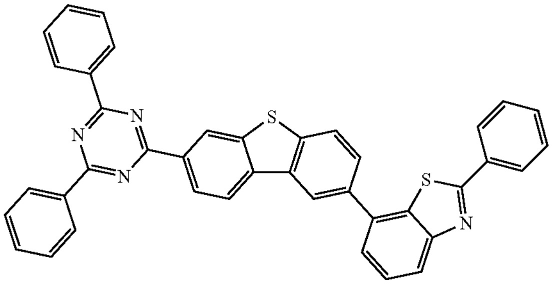
B-28
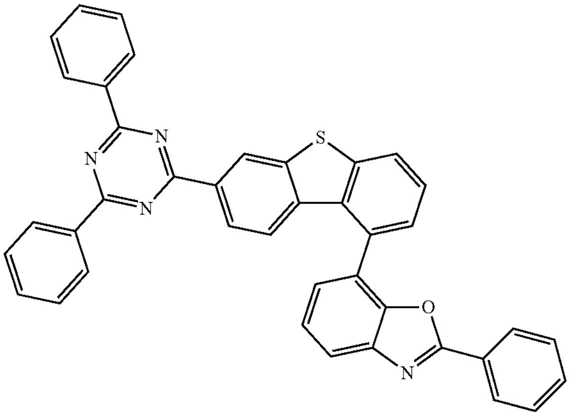
B-29
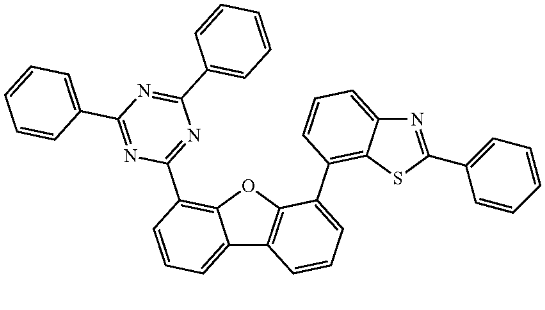
B-30
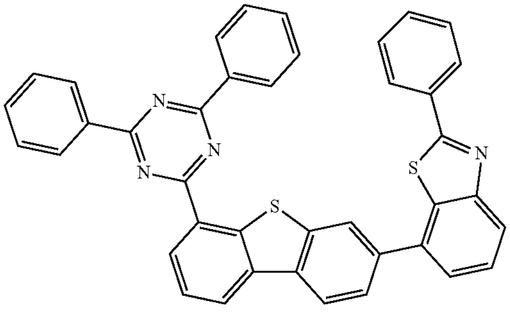

-continued
B-31
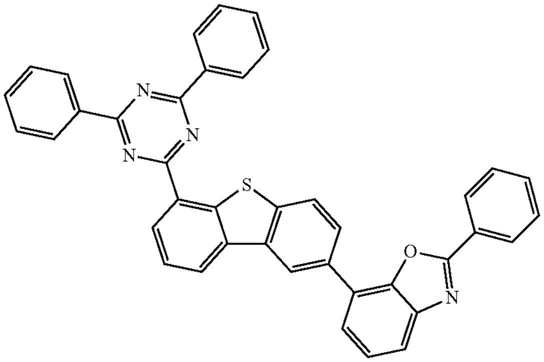
B-32
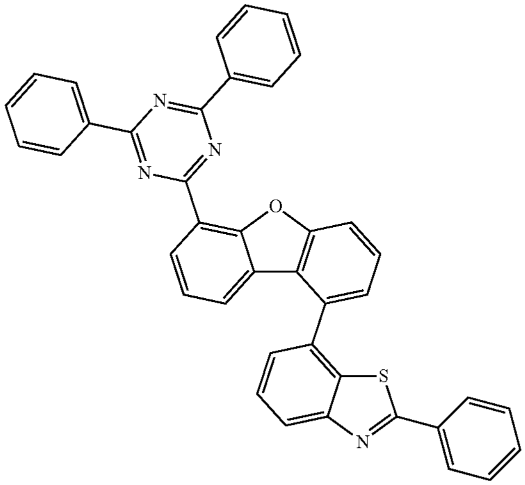
B-33
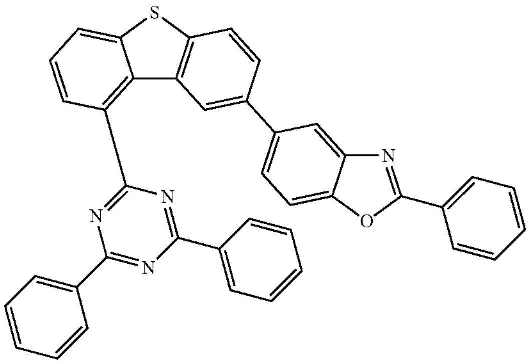
B-34
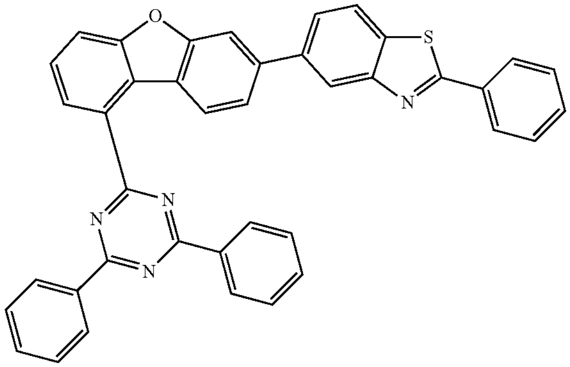
B-35
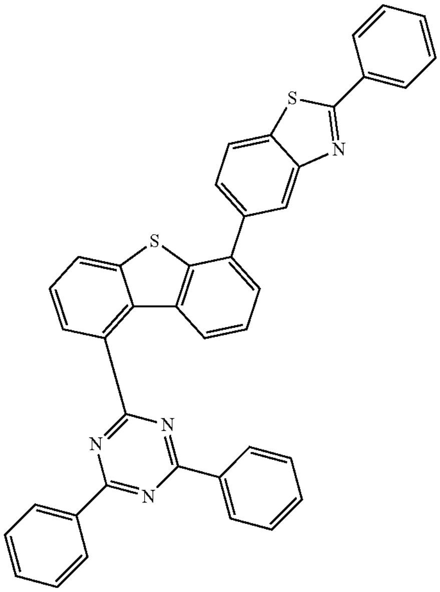
B-36
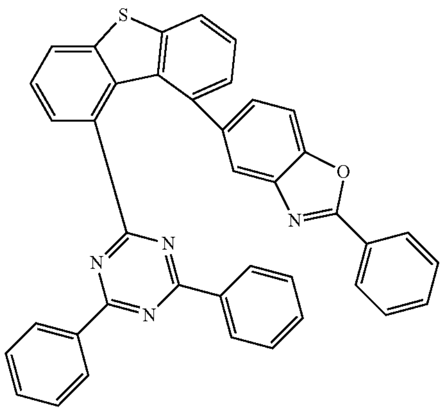

-continued
B-37
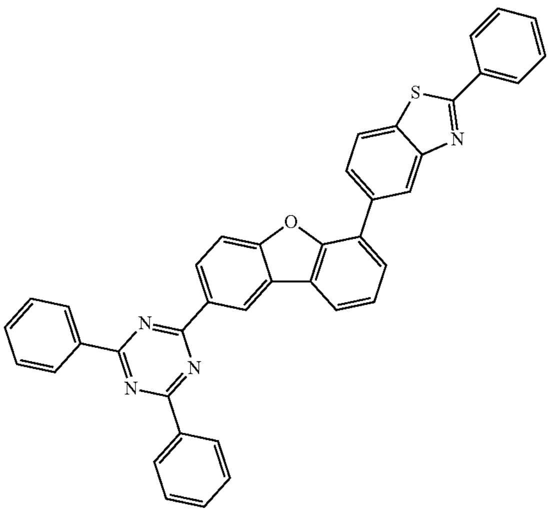
B-38
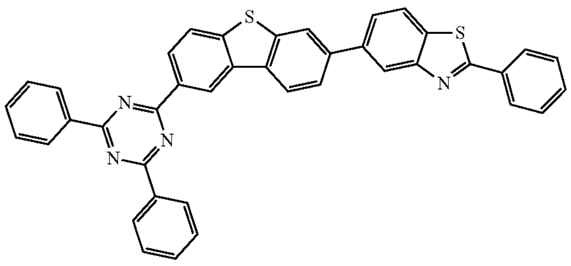
B-39
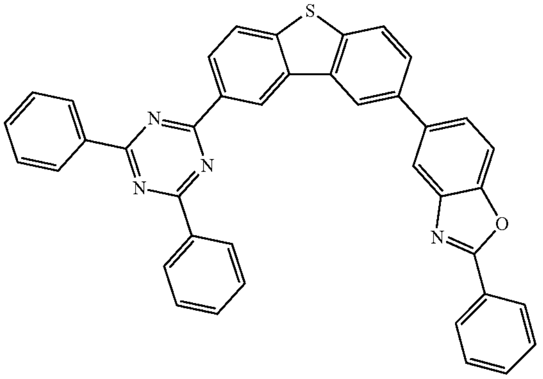
B-40
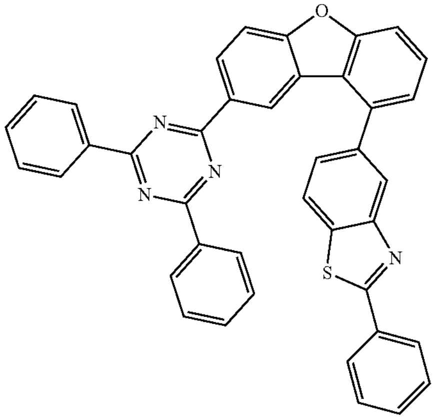
B-41
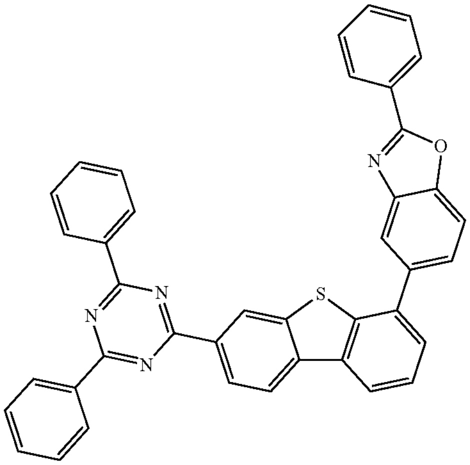
B-42
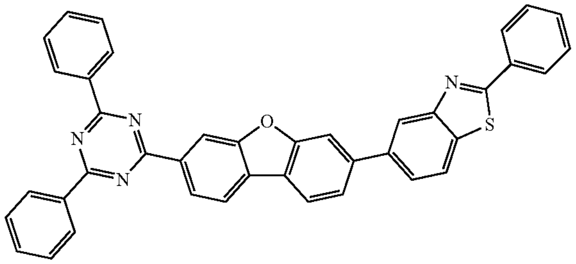

-continued
B-43
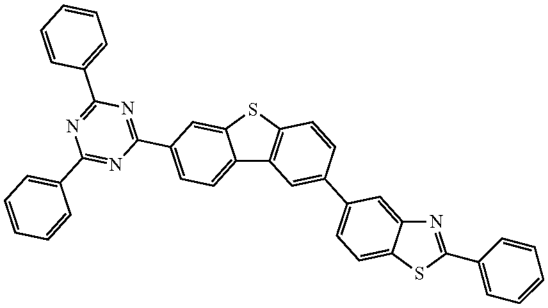
B-44
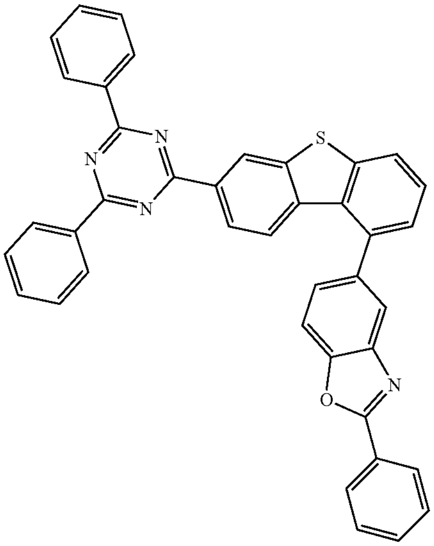
B-45
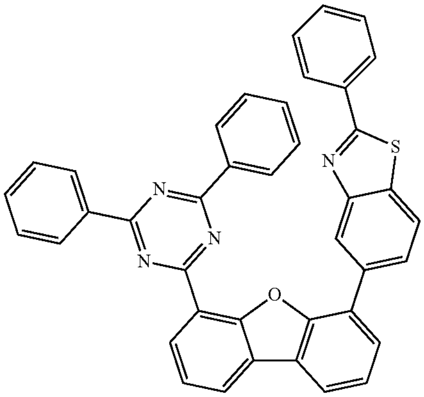
B-46
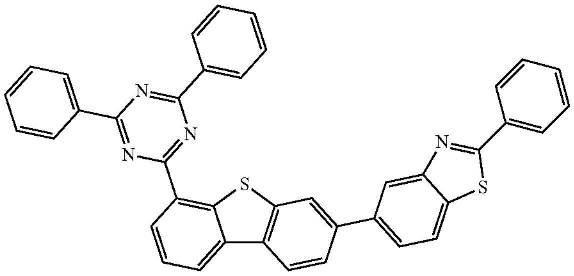
B-47
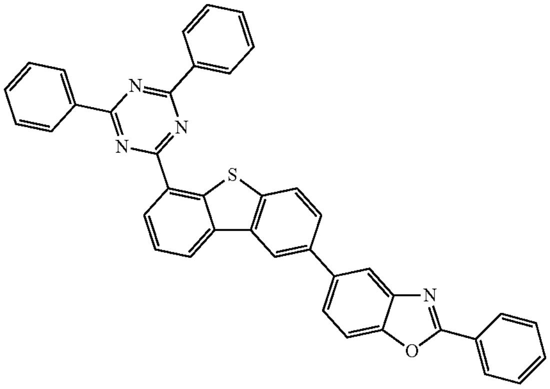
B-48
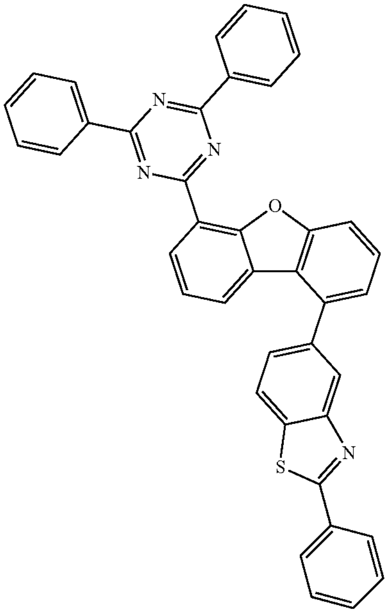

-continued
B-49
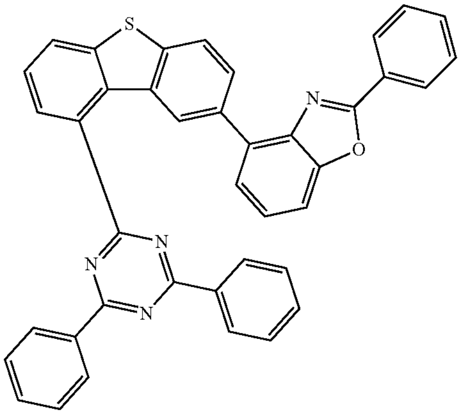
B-50
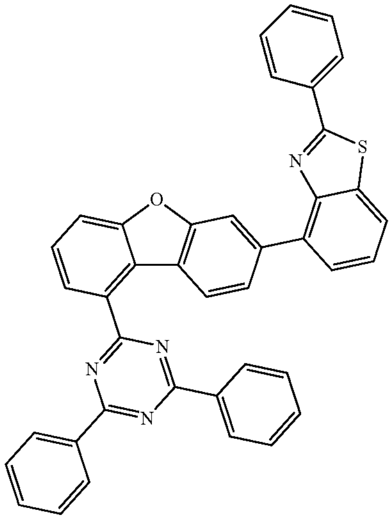
B-51
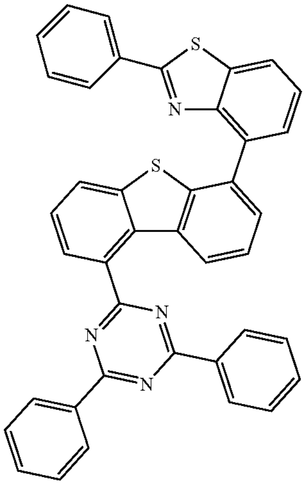
B-52
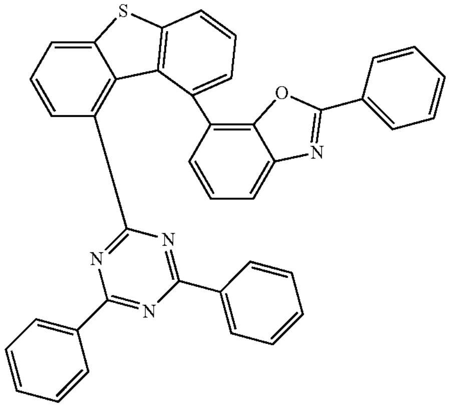
B-53
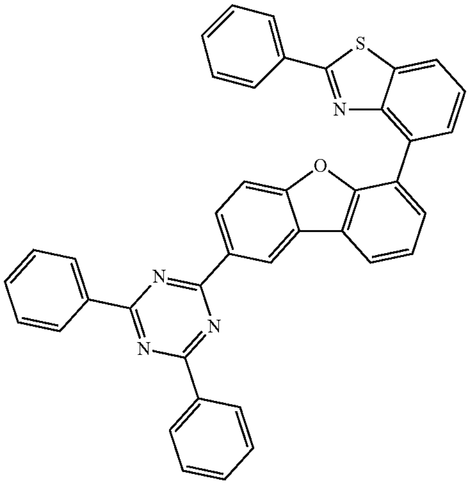
B-54
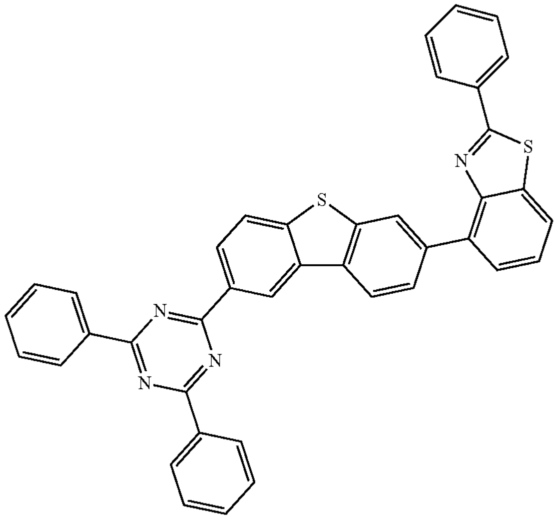

-continued
B-55
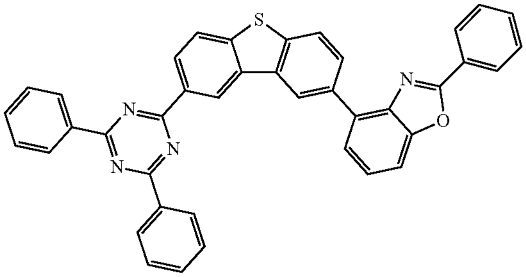
B-56
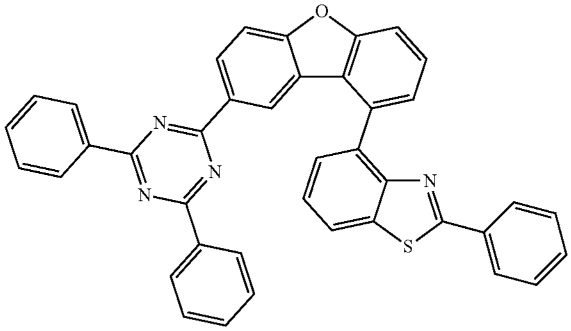
B-57
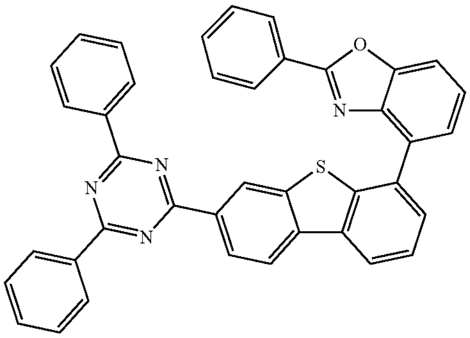
B-58
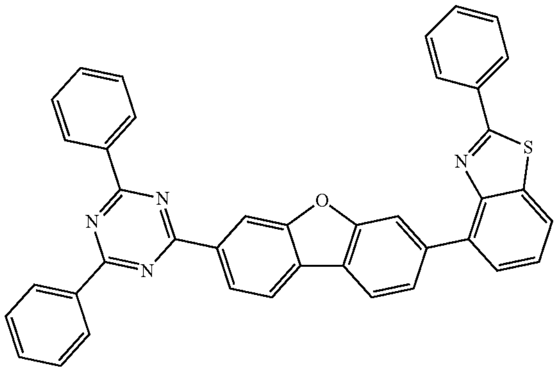
B-59
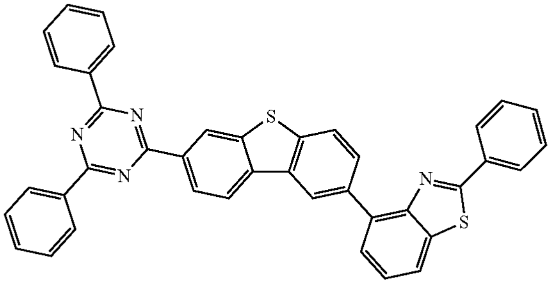
B-60
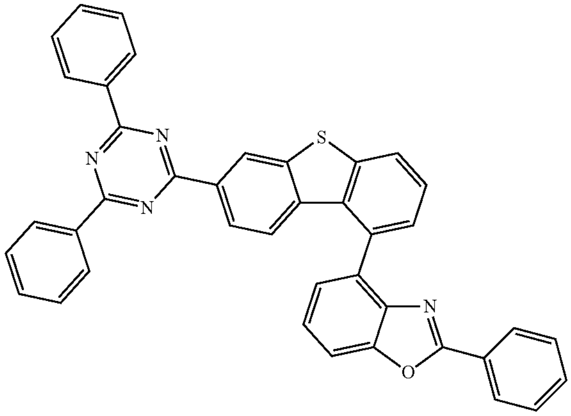
B-61
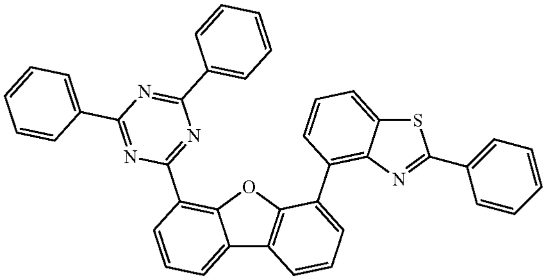
B-62
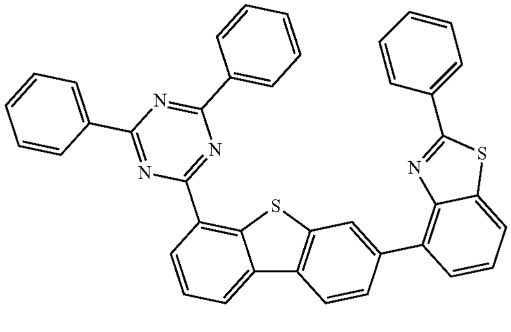

-continued
B-63
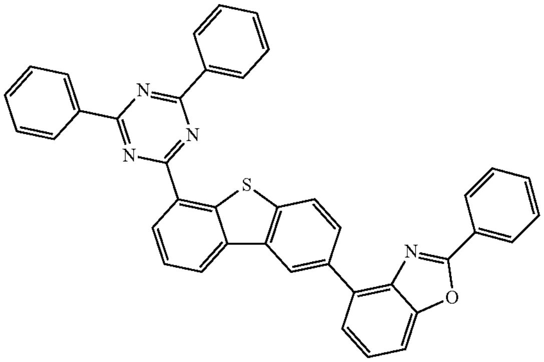
B-64
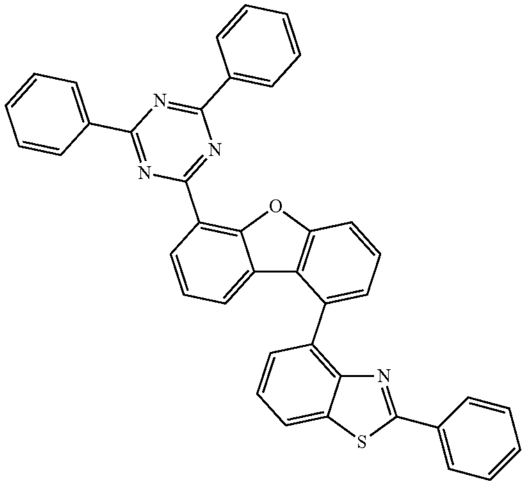
C-1
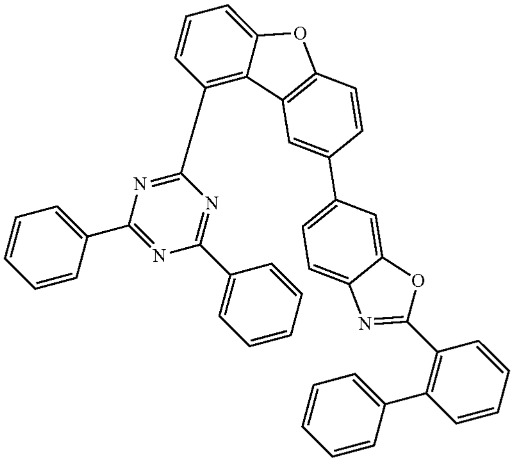
C-2
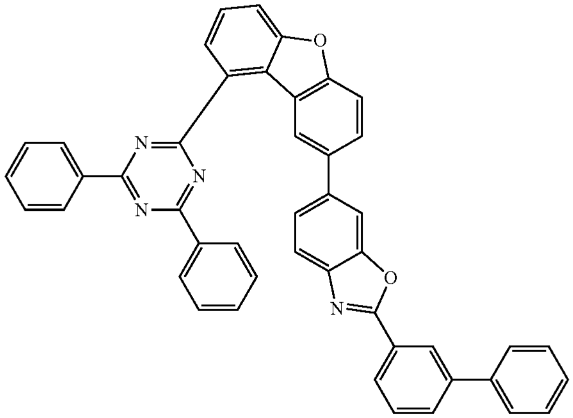
C-3
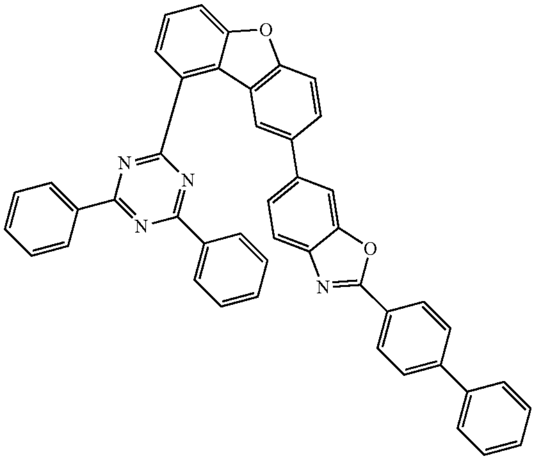
C-4
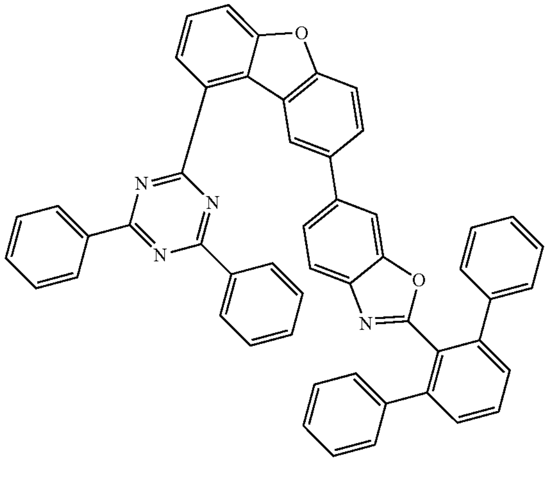

-continued
C-5
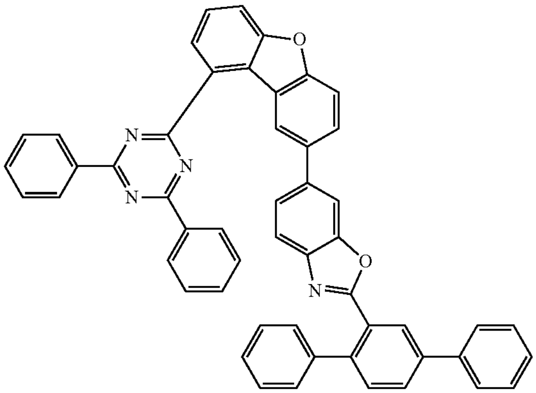
C-6
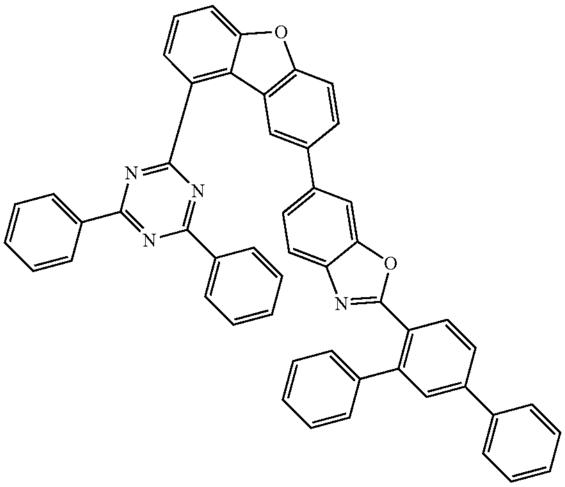
C-7
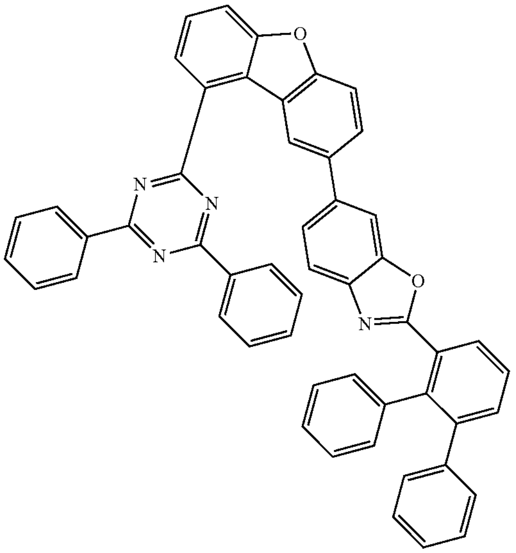
C-8
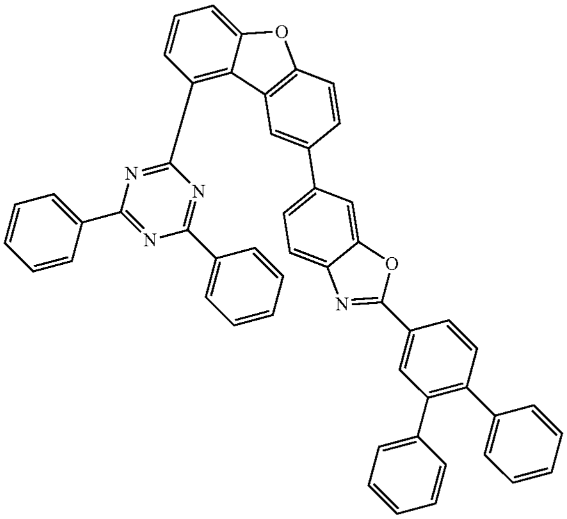
C-9
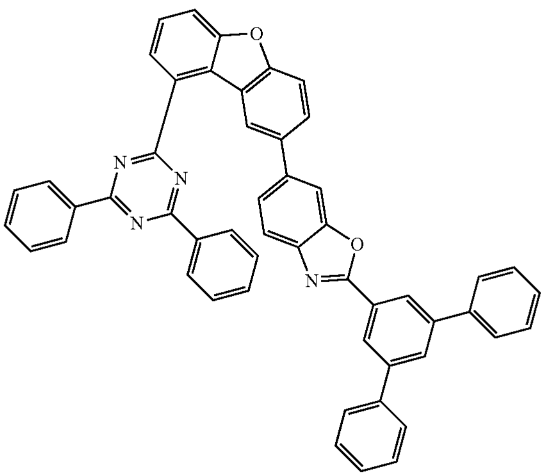
C-10
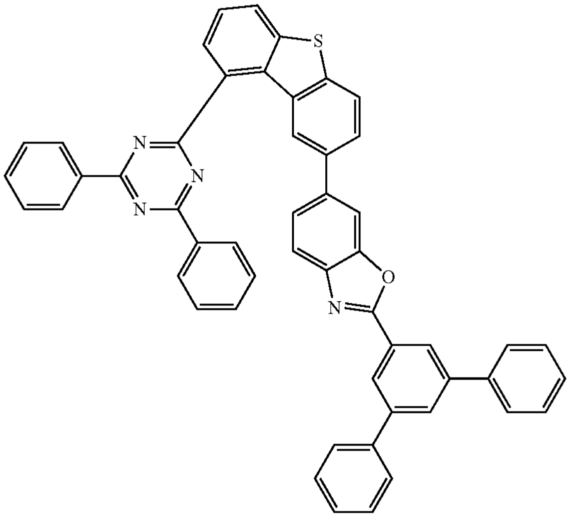

-continued
C-11
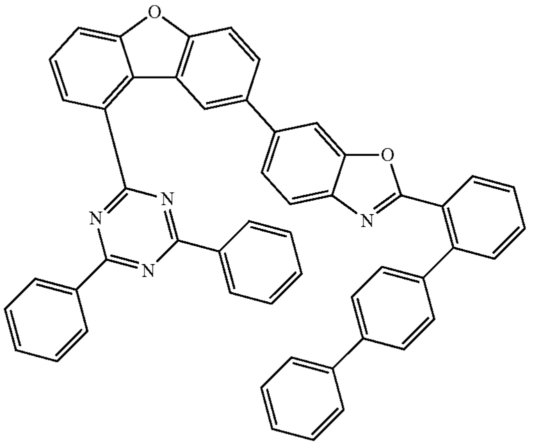
C-12
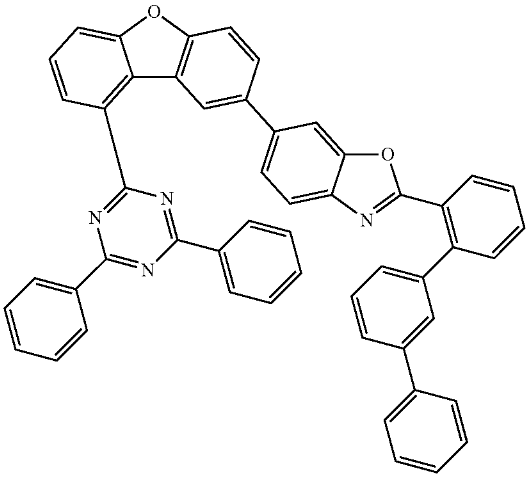
C-13
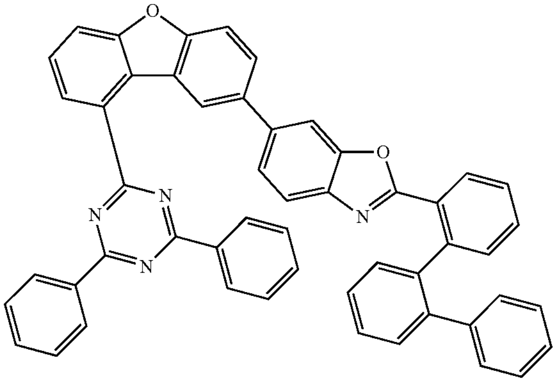
C-14
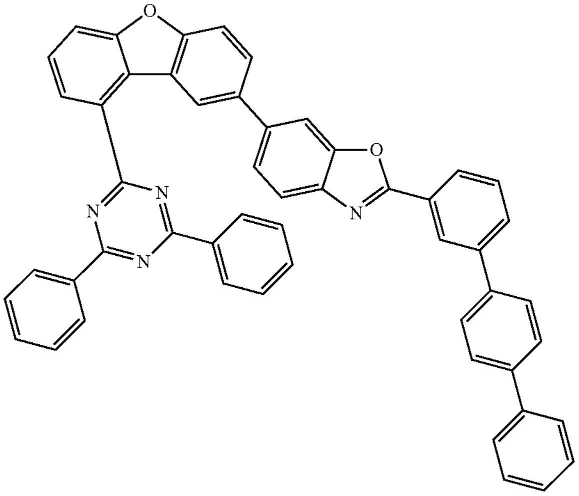
C-15
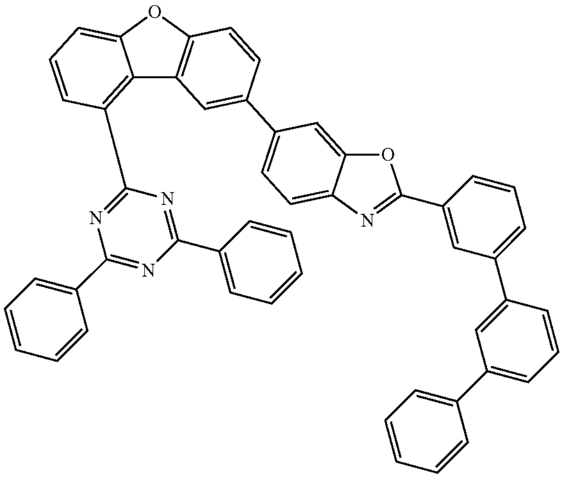
C-16
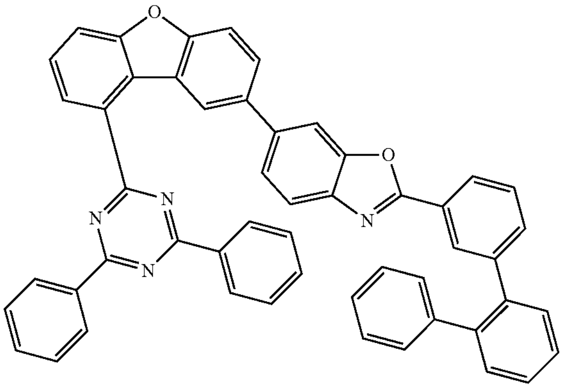

-continued
C-17
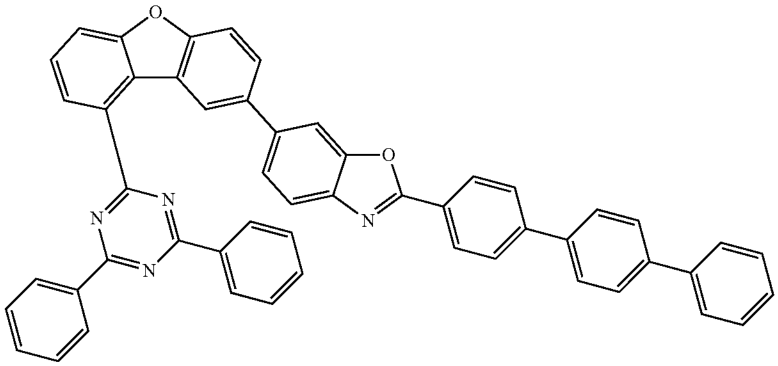
C-18
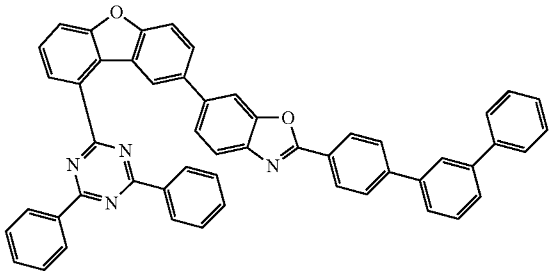
C-19
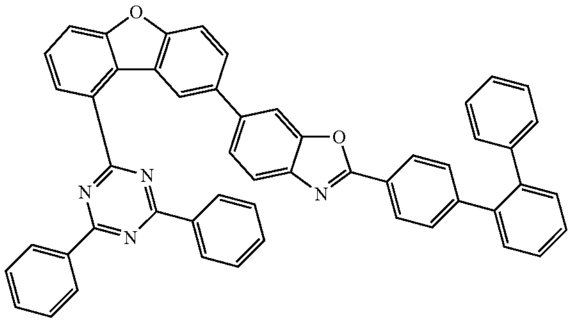
C-20
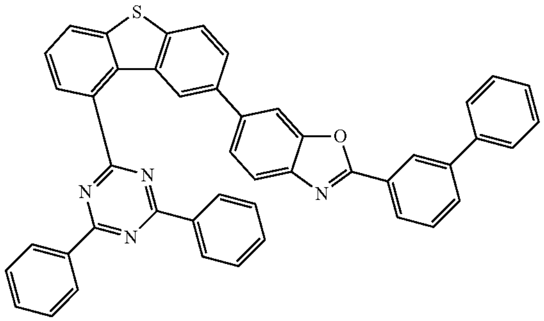
C-21
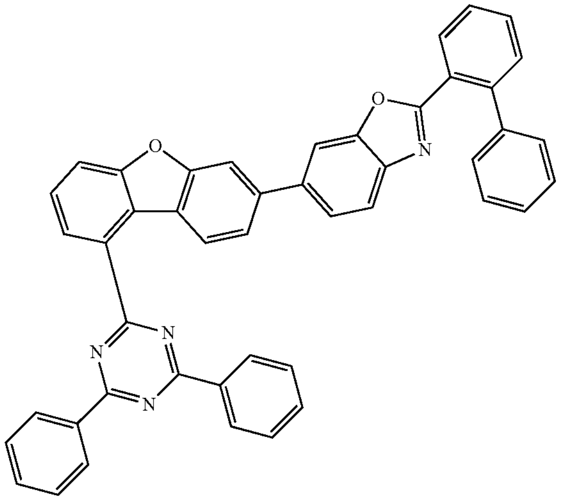

-continued
C-22
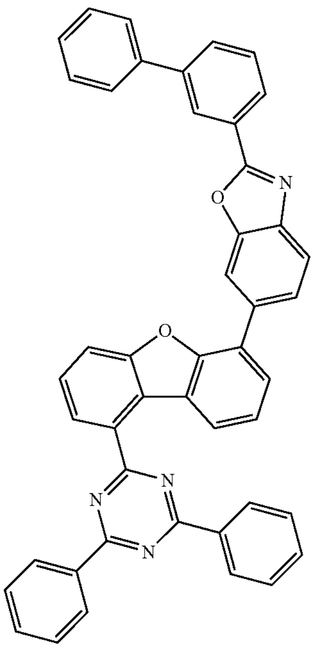
C-23
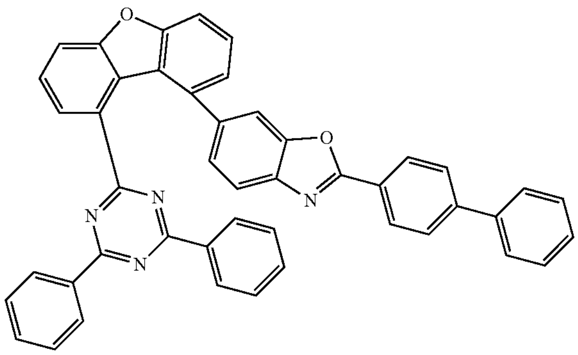
C-24
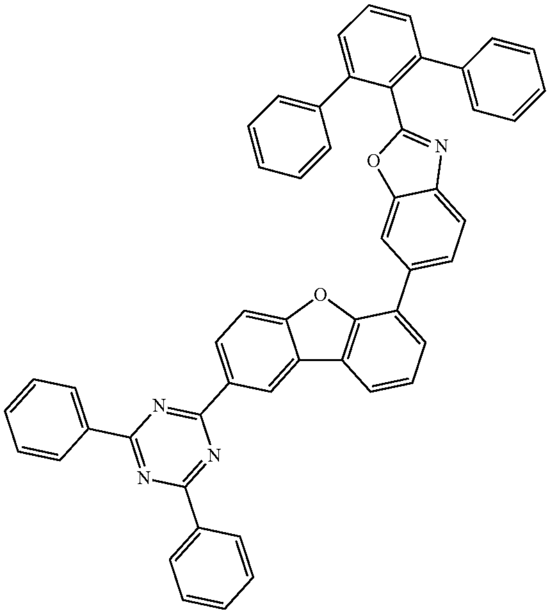
C-25
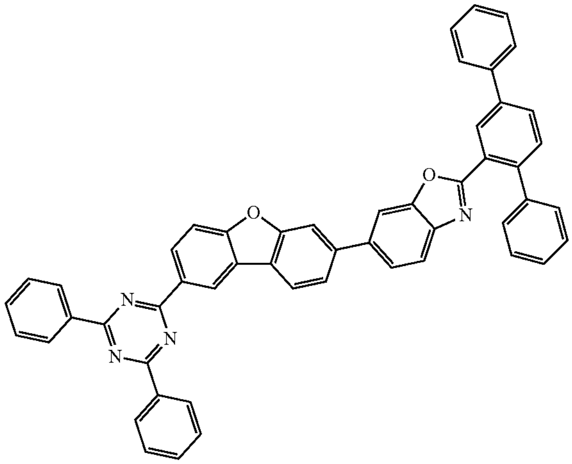
C-26
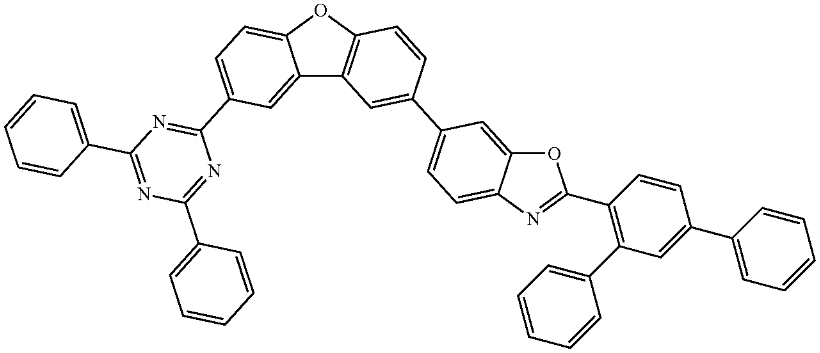

-continued
C-27
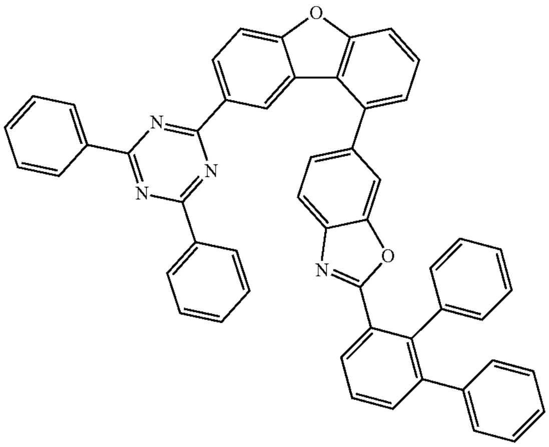
C-28
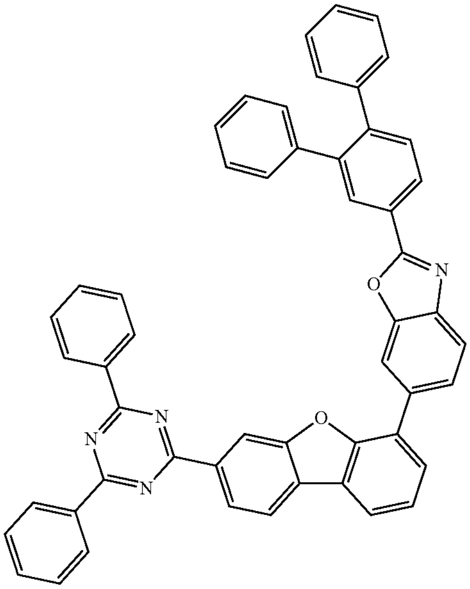
C-29
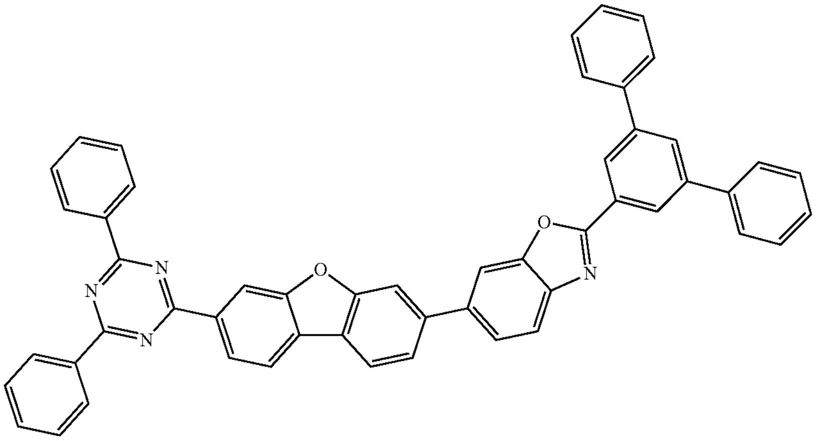
C-30
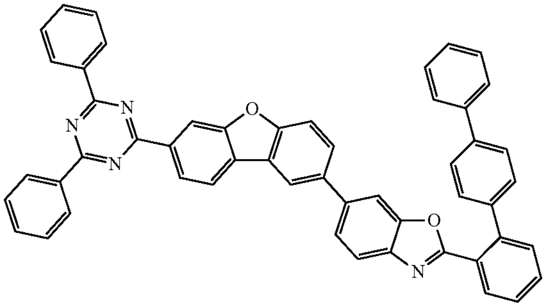
C-31
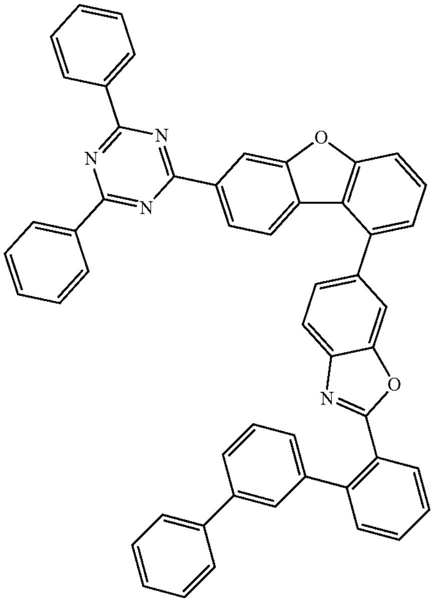

-continued
C-32
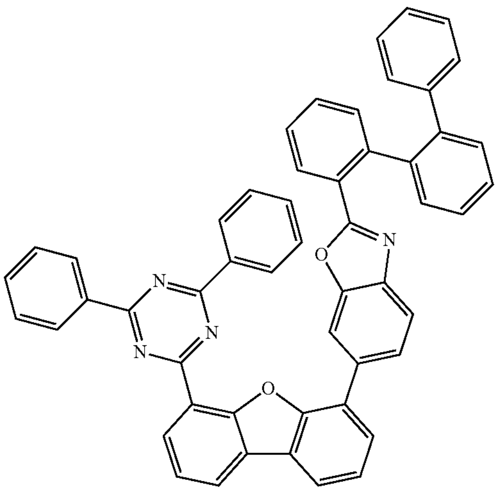
C-33
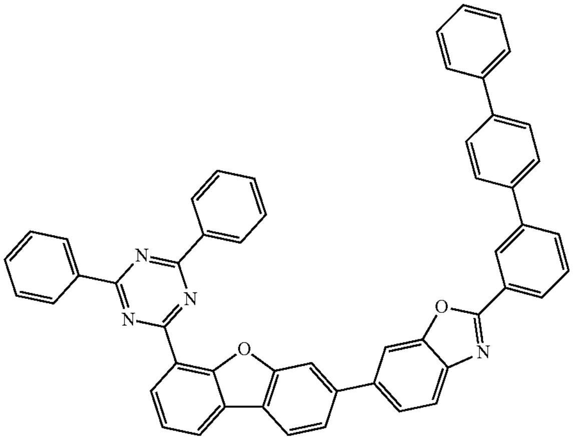
C-34
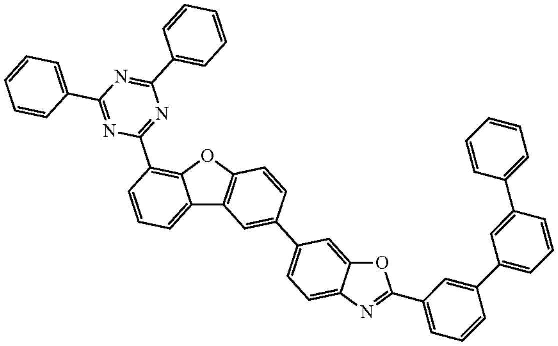
C-35
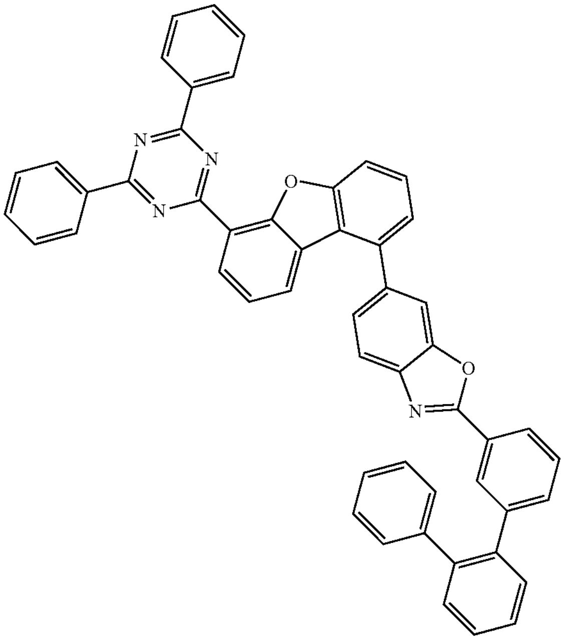

-continued
C-36
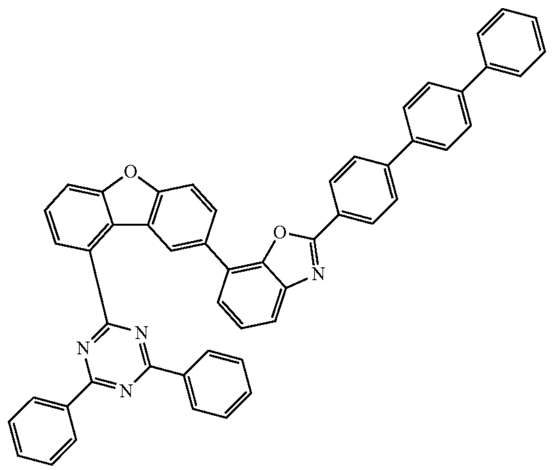
C-37
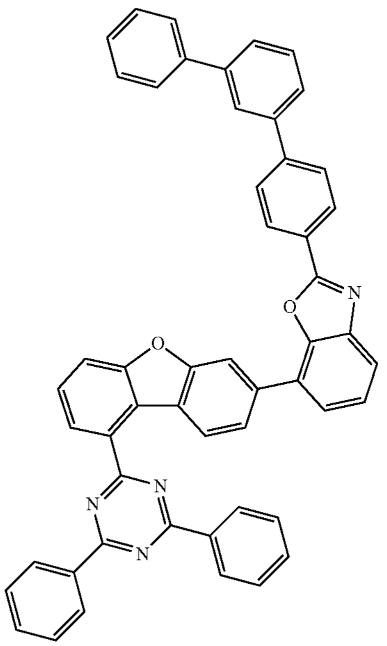
C-38
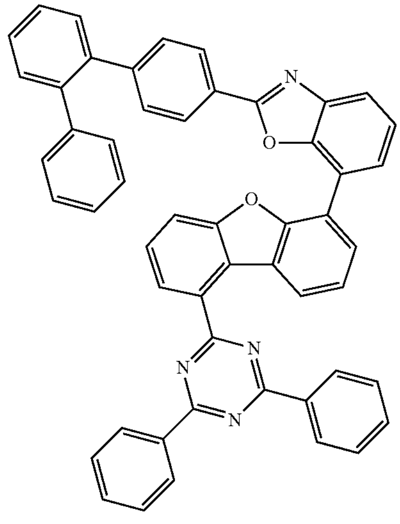
C-39
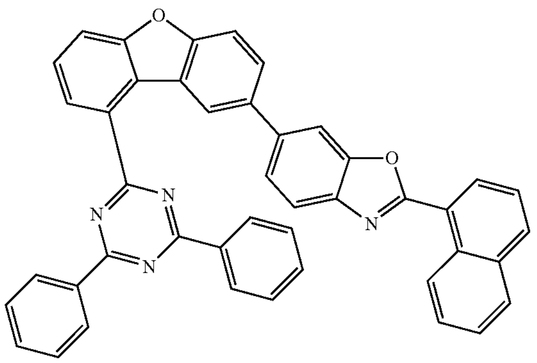

-continued
C-40
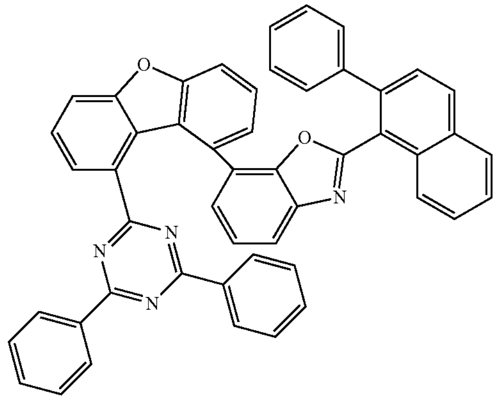
C-41
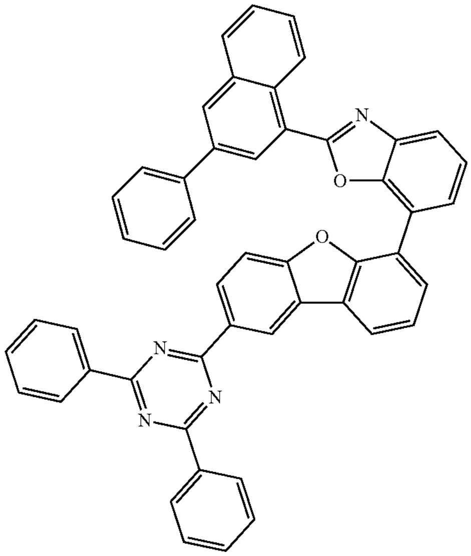
C-42
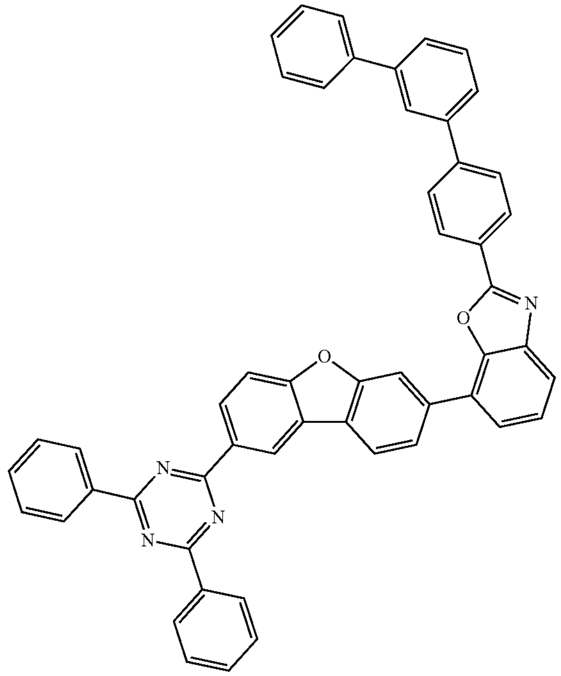
C-43
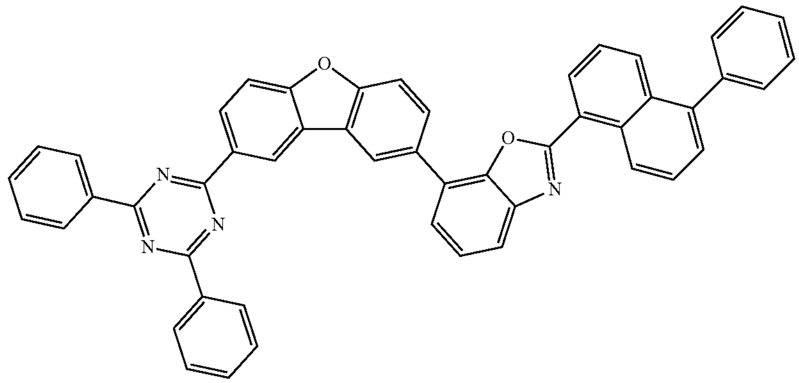

-continued
C-44
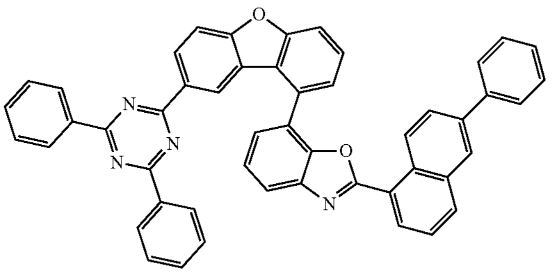
C-45
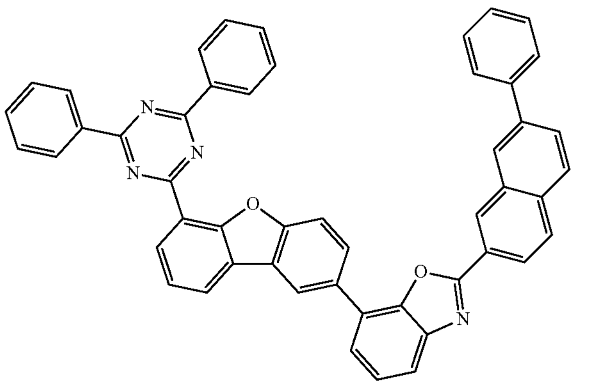
C-46
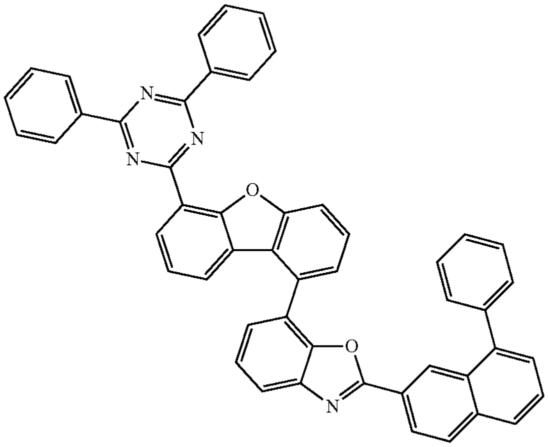
C-47
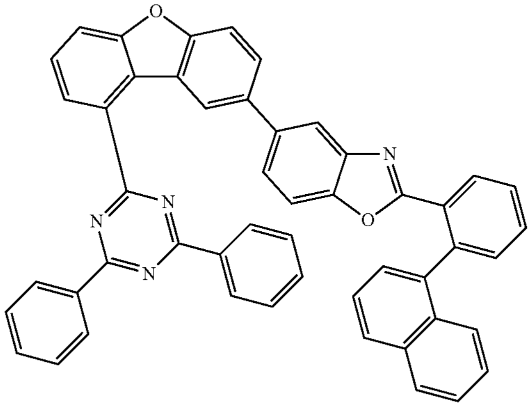
C-48
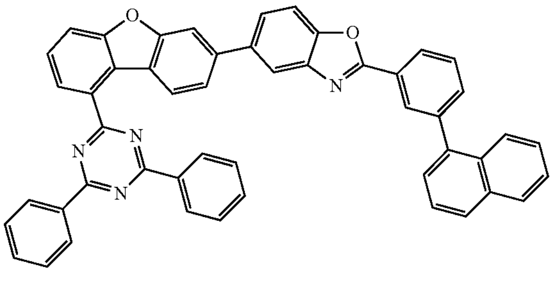
C-49
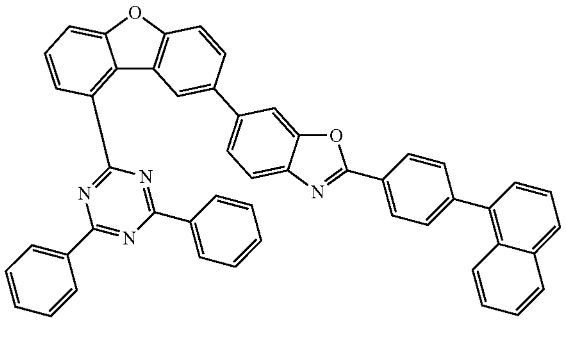

-continued
C-50
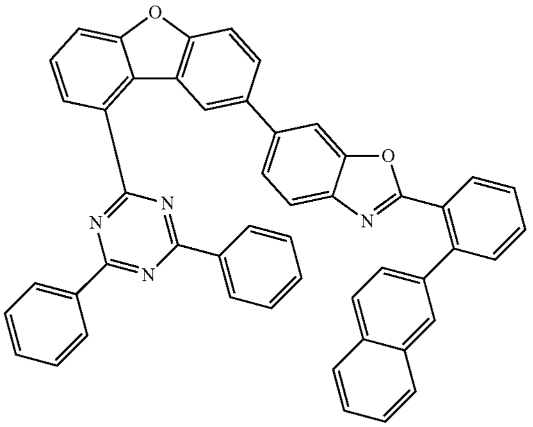
C-51
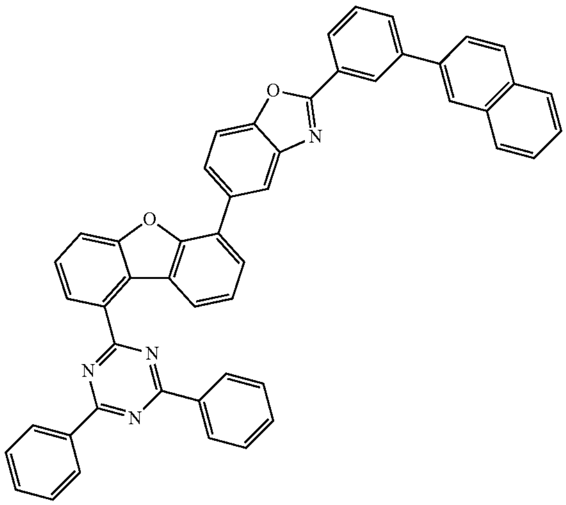
C-52
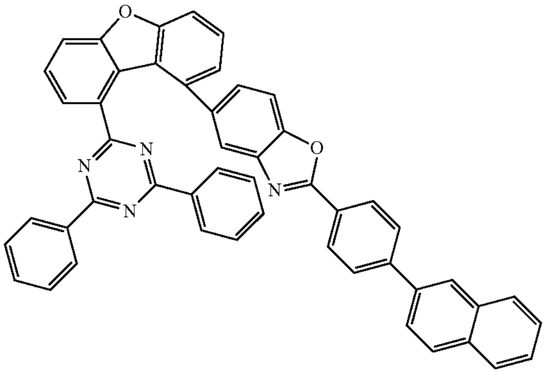
C-53
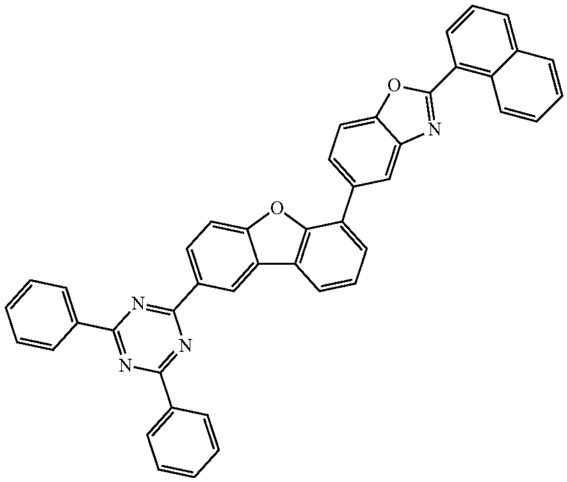
C-54
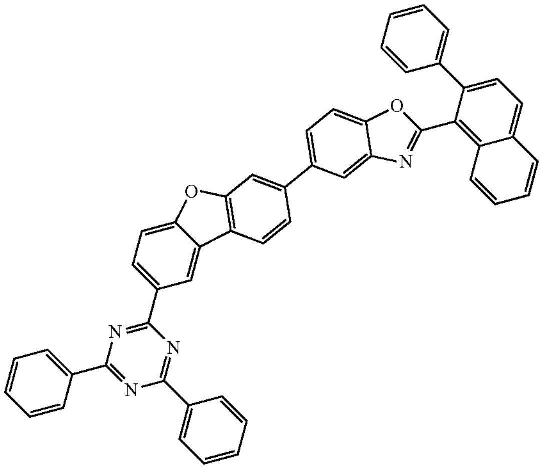
C-55
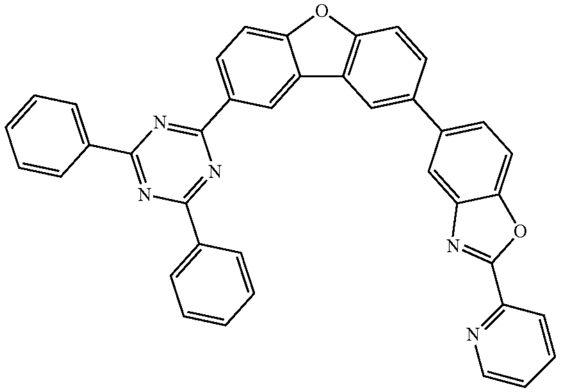

-continued
C-56
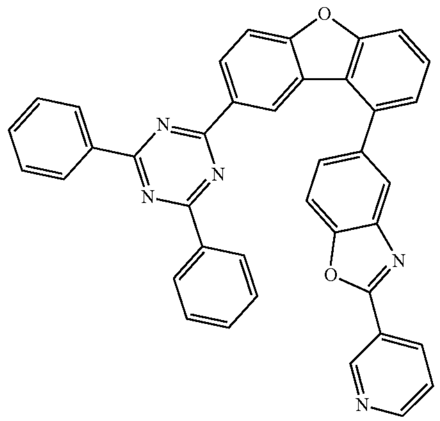
C-57
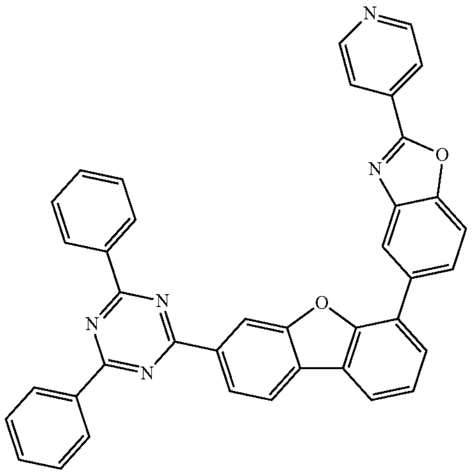
C-58
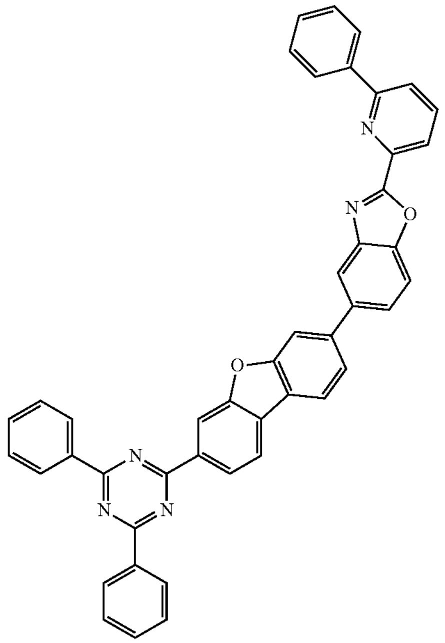
C-59
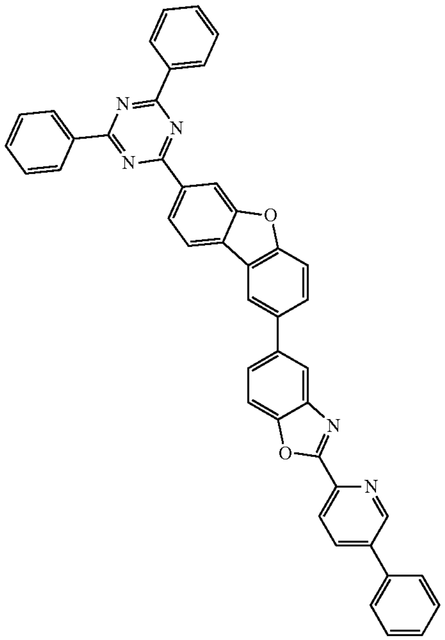

-continued
C-60
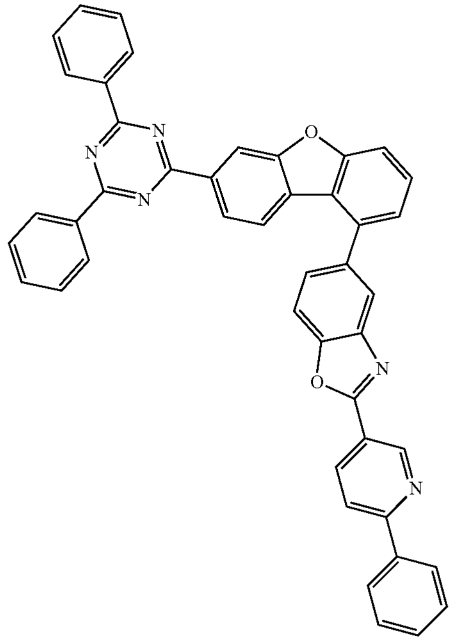
C-61
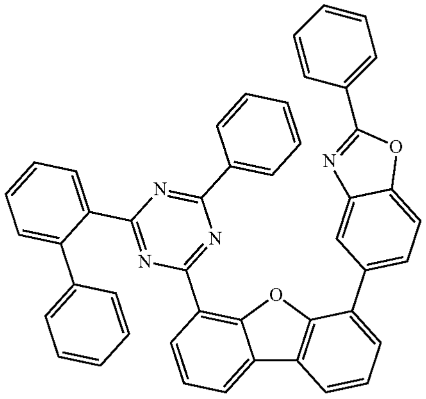
C-62
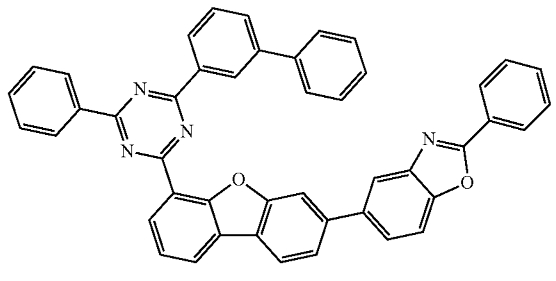
C-63
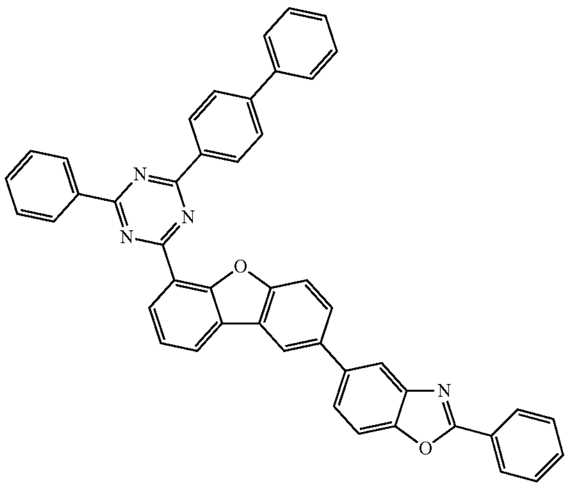

-continued
C-64
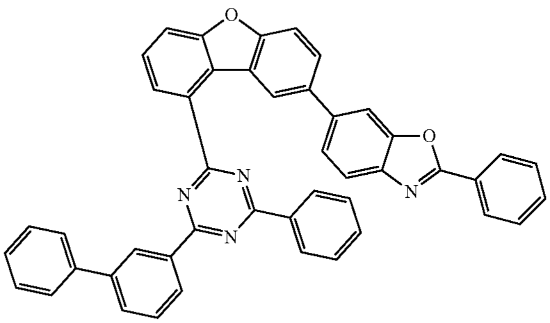
C-65
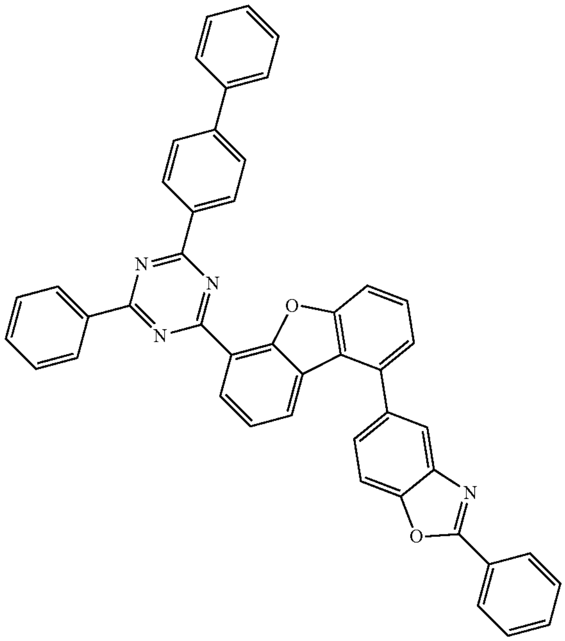
C-66
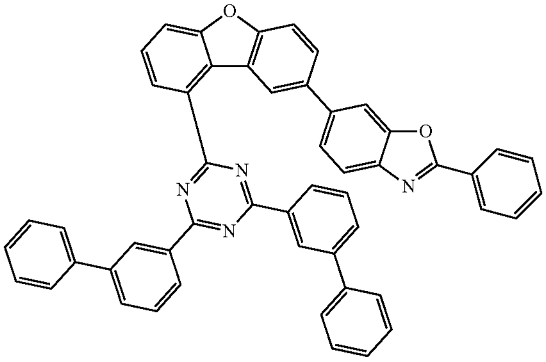
C-67
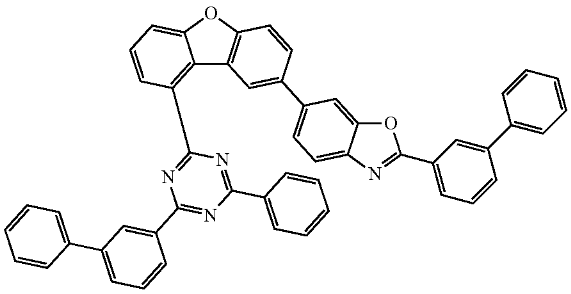
C-68
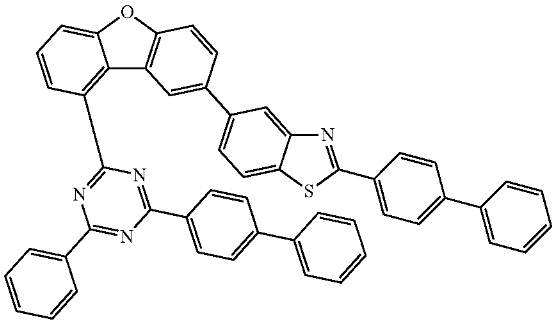
C-69
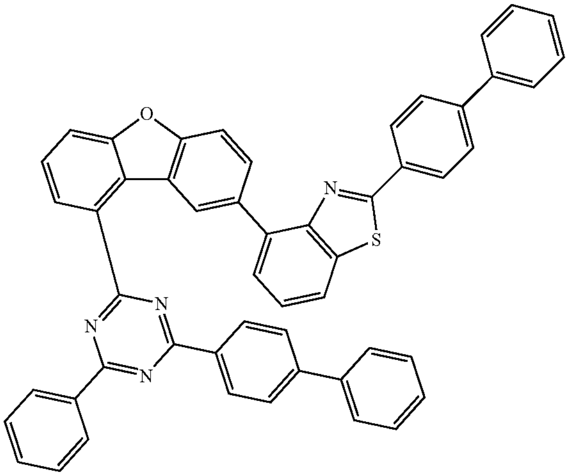

-continued
C-70
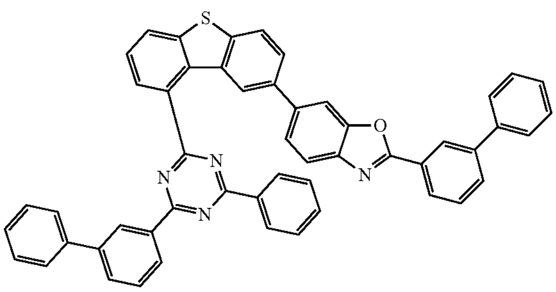
C-71
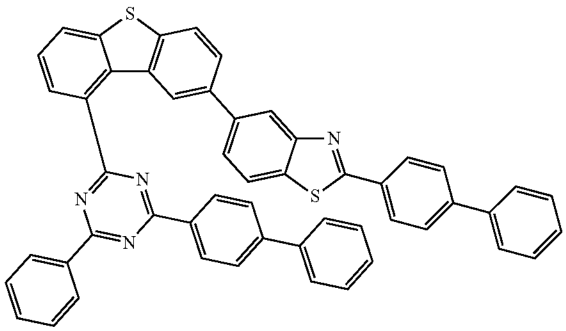
C-72
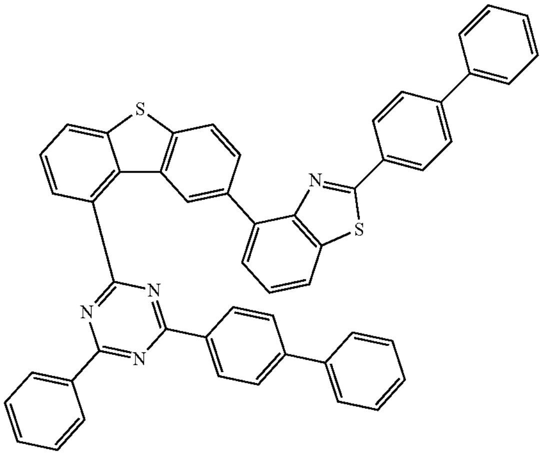
C-73
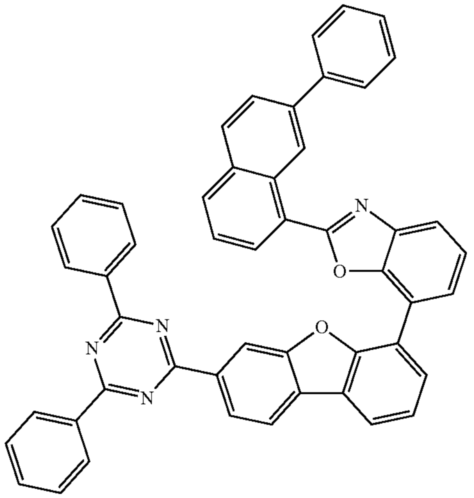
C-74
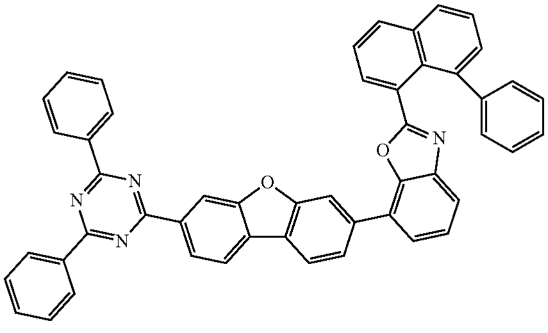
C-75
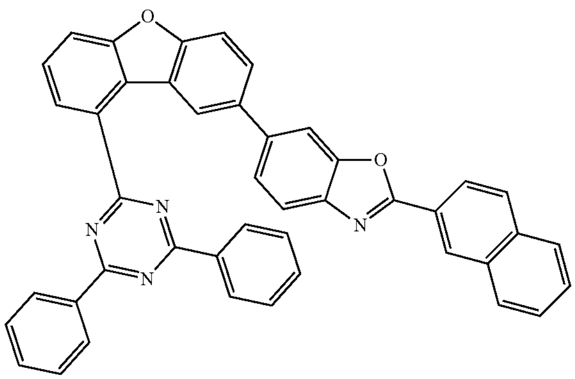

-continued
C-76
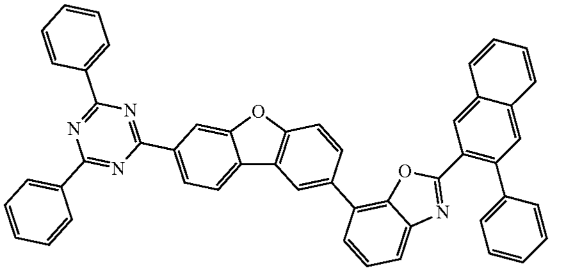
C-77
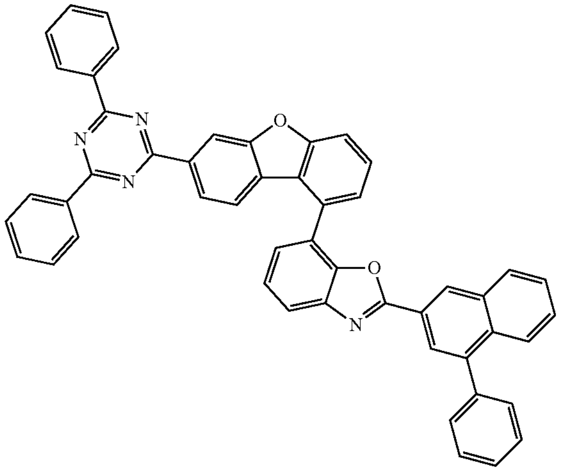
C-78
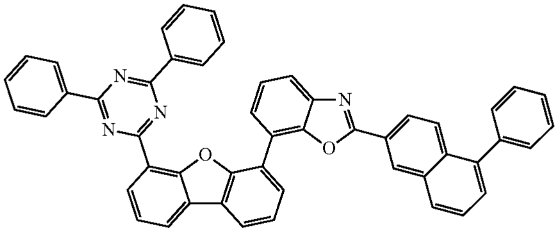
C-79
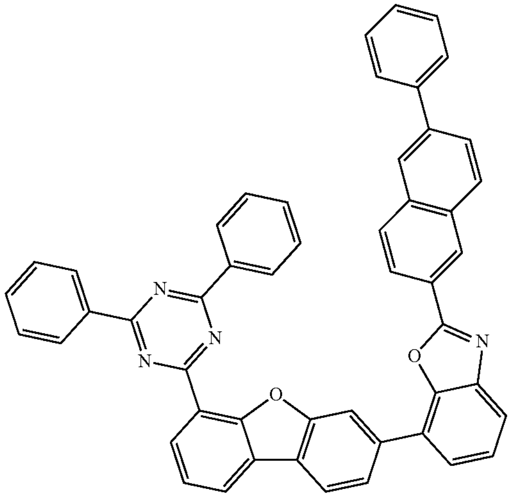
H-1
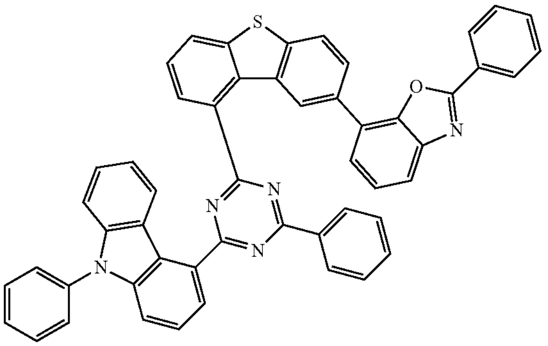
H-2
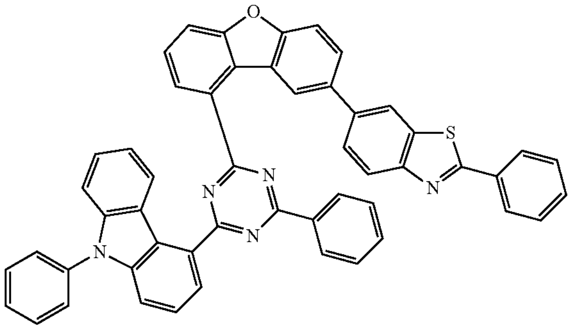

-continued
H-3
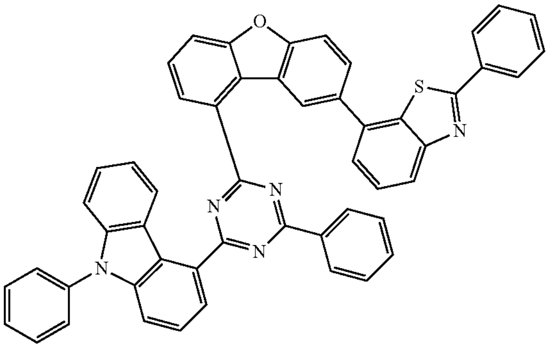
H-4
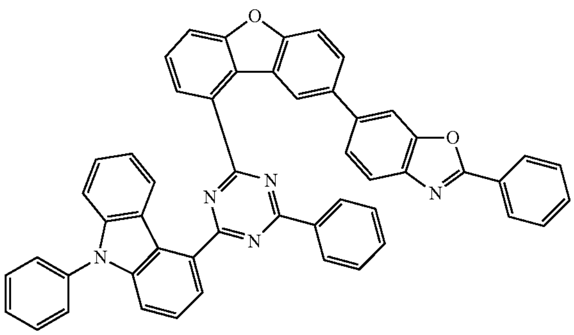
H-5
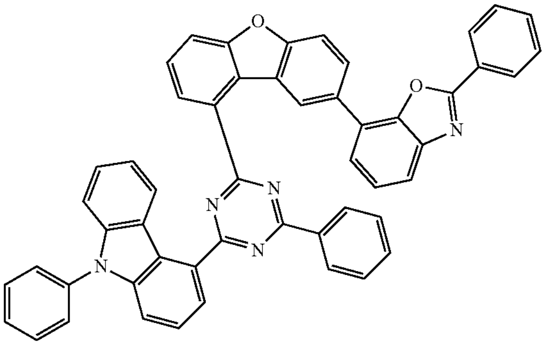
H-6
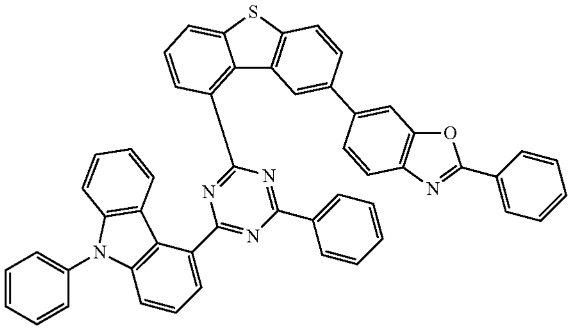
H-7
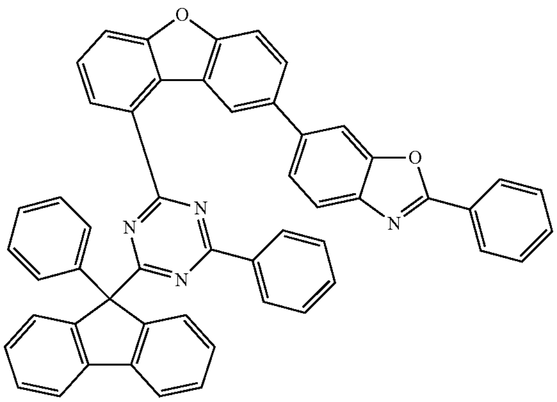
H-8
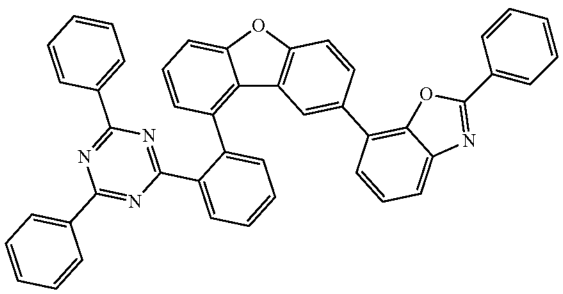

-continued
H-9
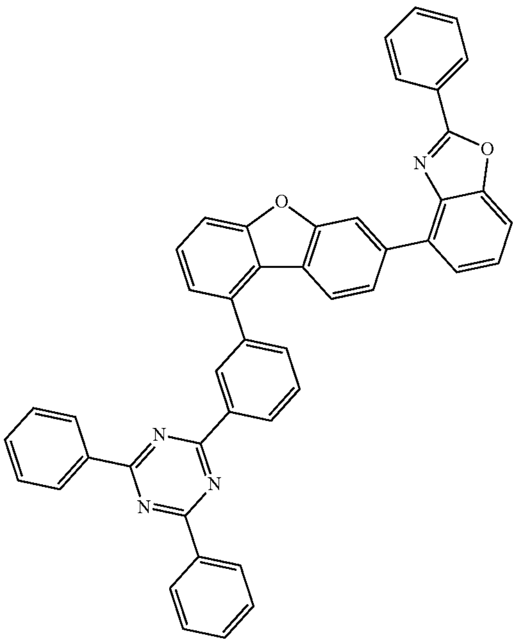
H-10
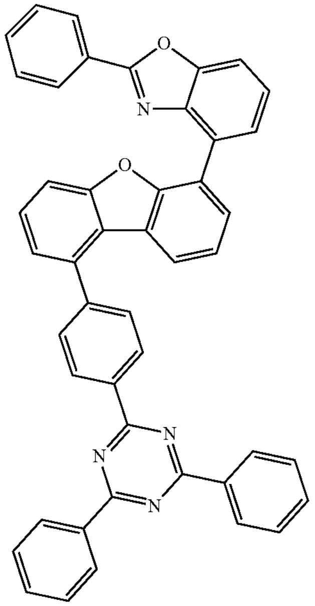
H-11
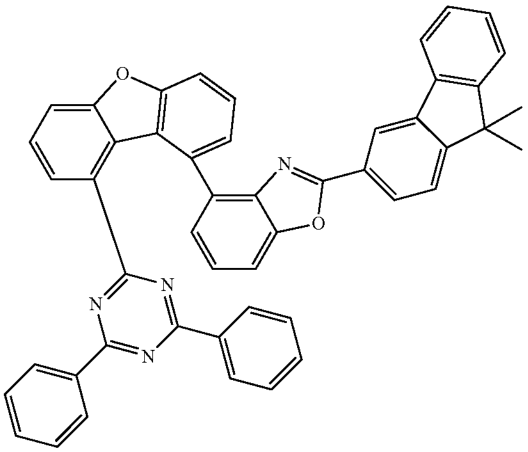
H-12
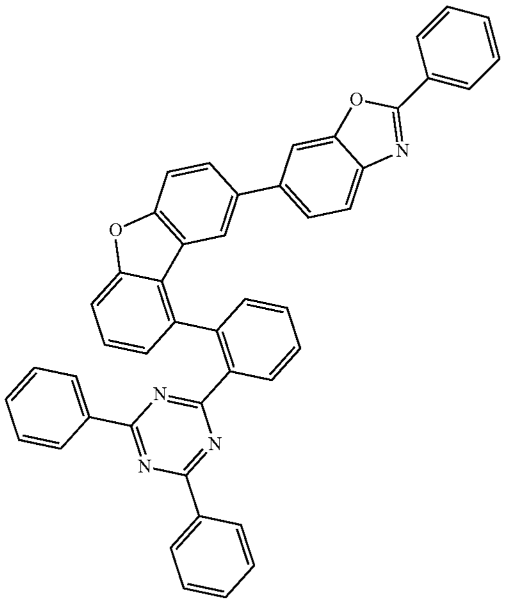

-continued
H-13
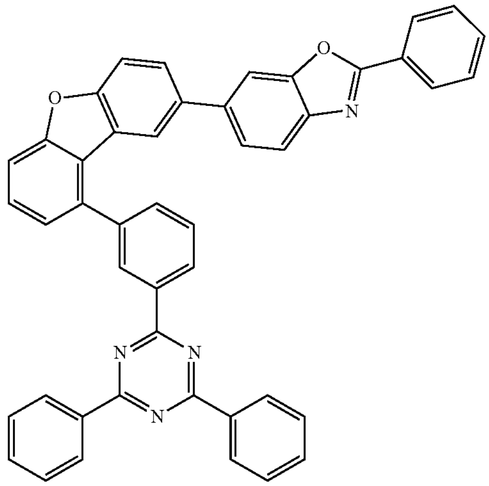
H-14
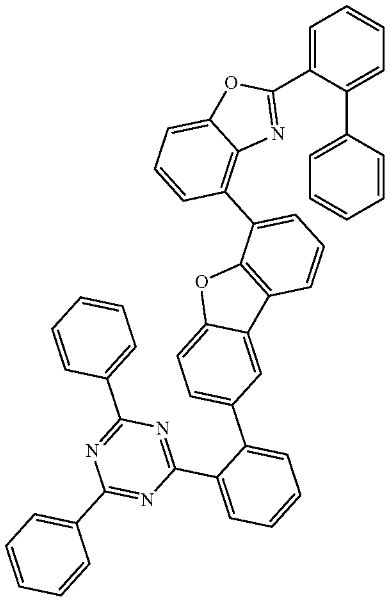
H-15
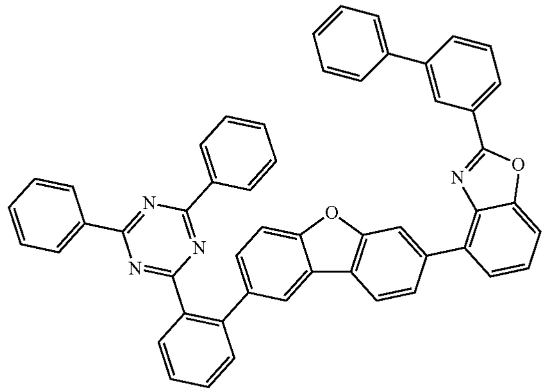
H-16
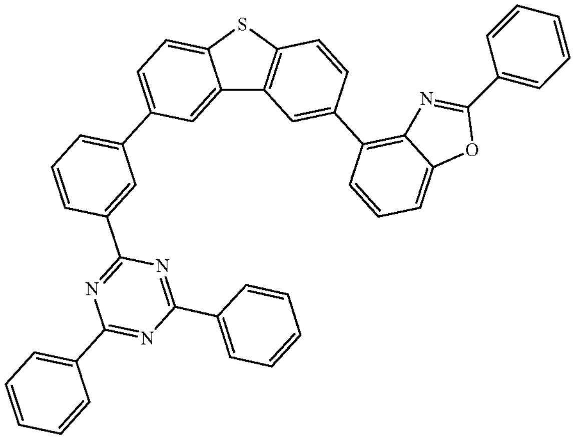
H-17
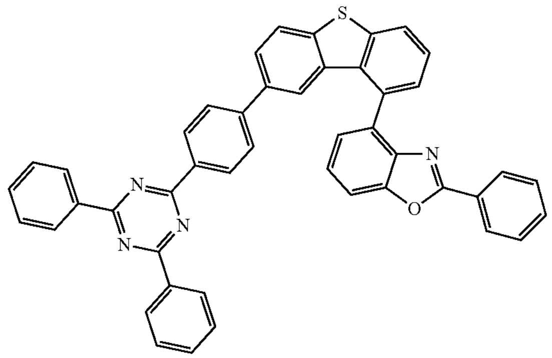
H-18
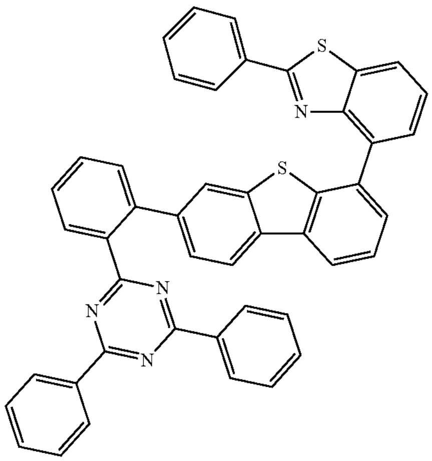

-continued
H-19
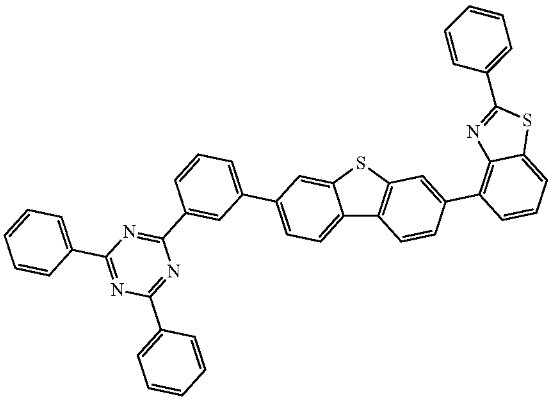
H-20
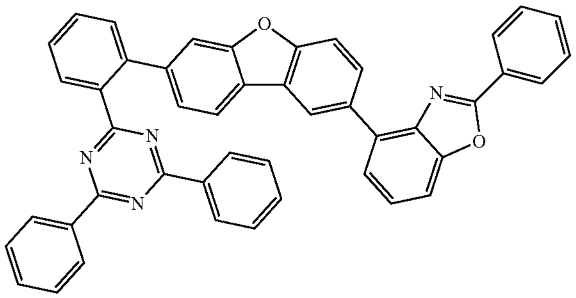
H-21
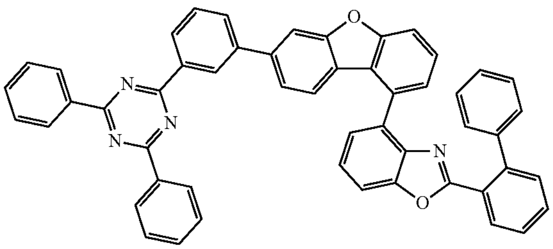
H-22
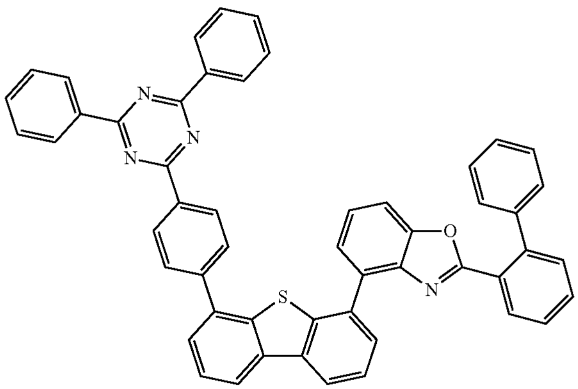
H-23
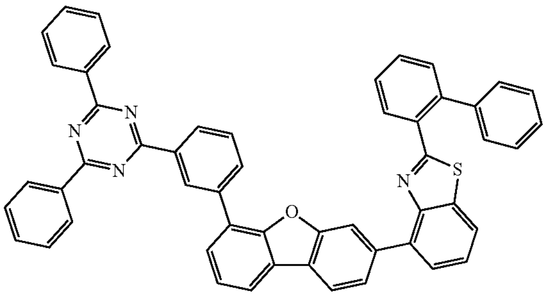
H-24
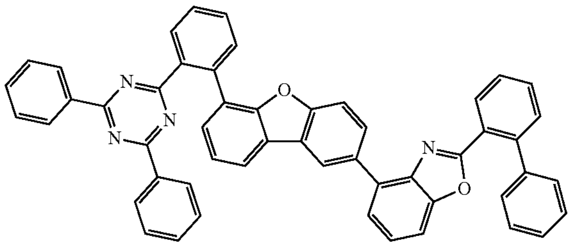
H-25
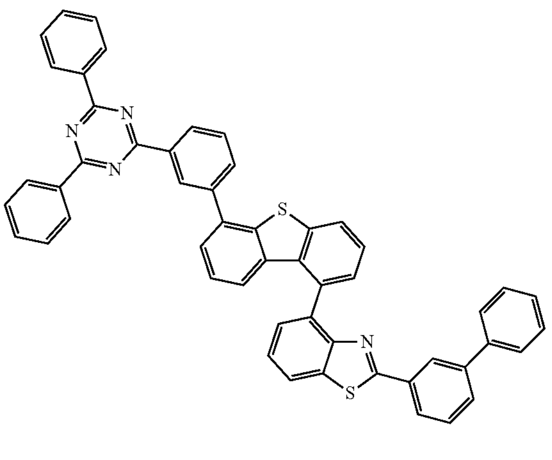
H-26
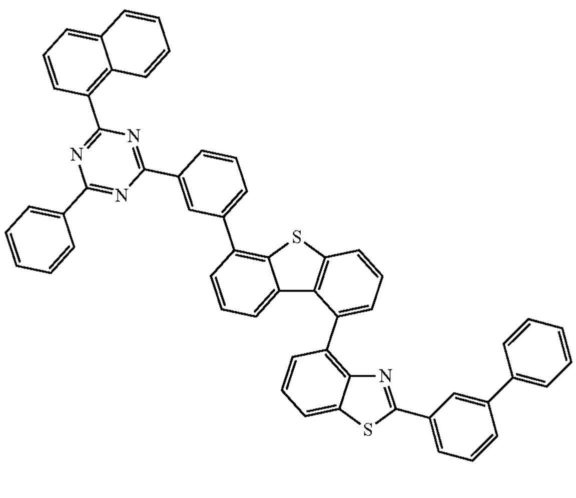

-continued
H-27
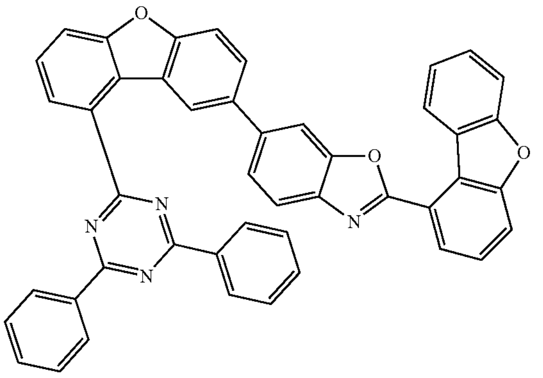
H-28
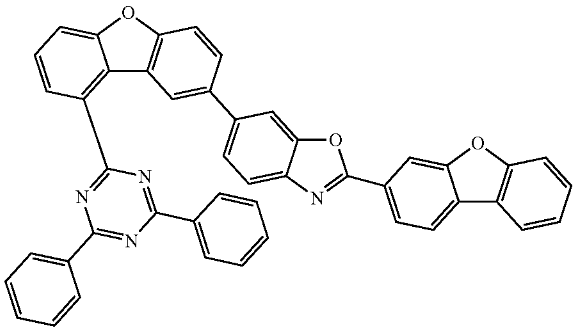
H-29
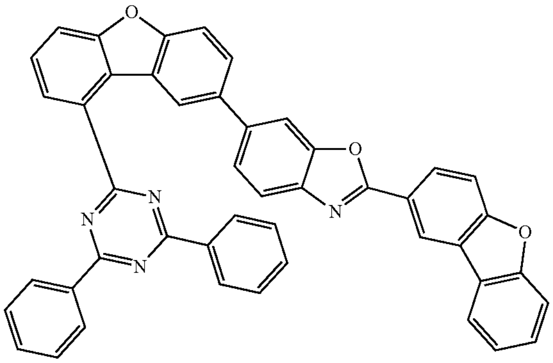
H-30
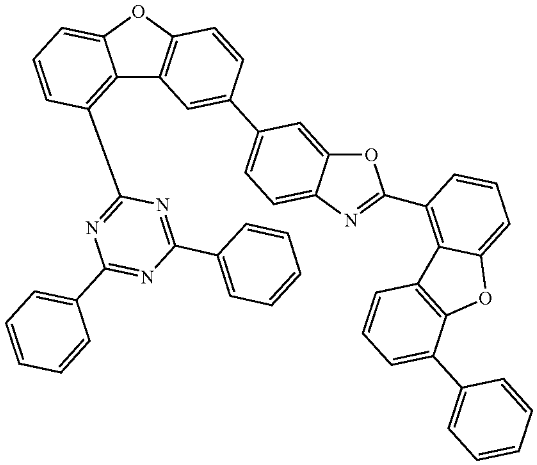
H-31
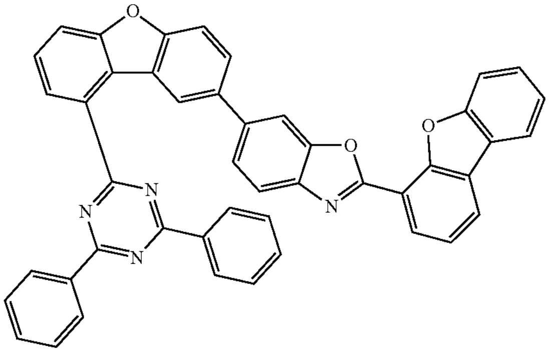
H-32
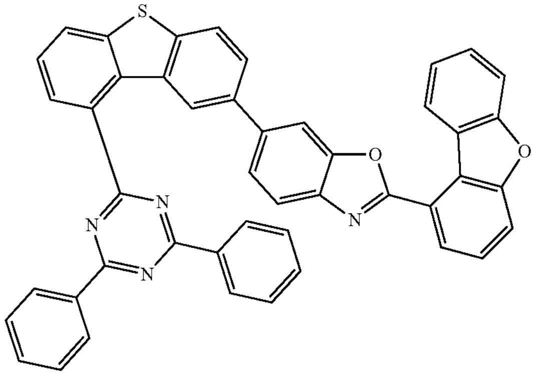

-continued
H-33
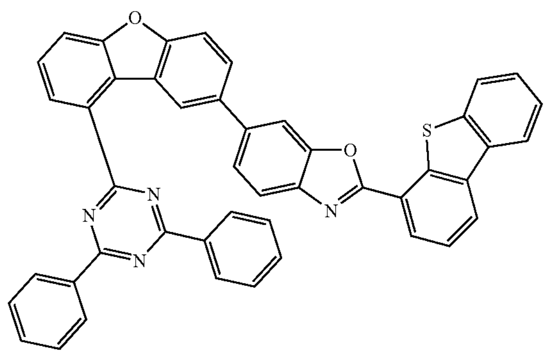
H-34
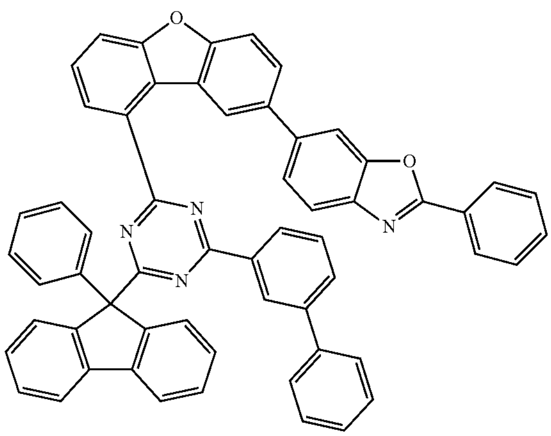
H-35
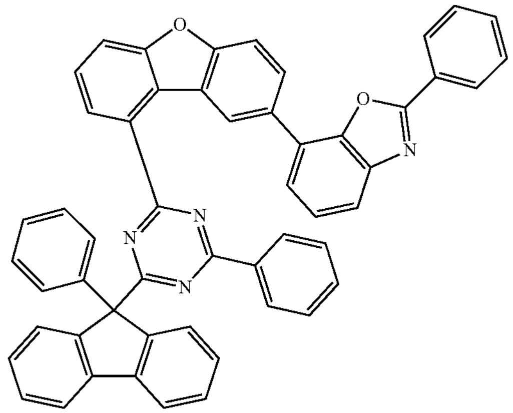
H-36
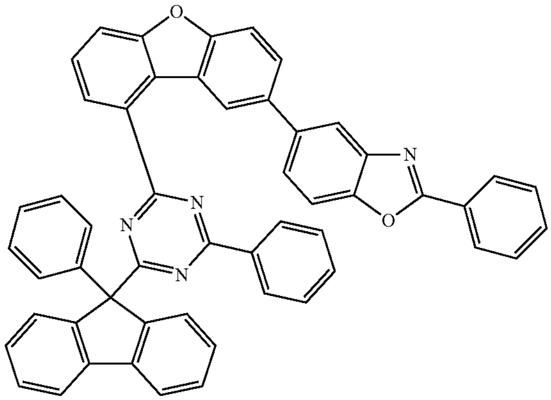
H-37
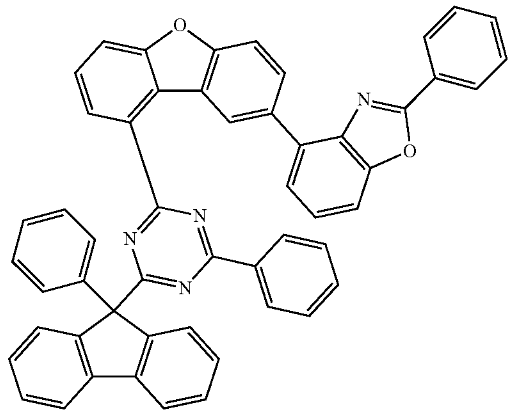
H-38
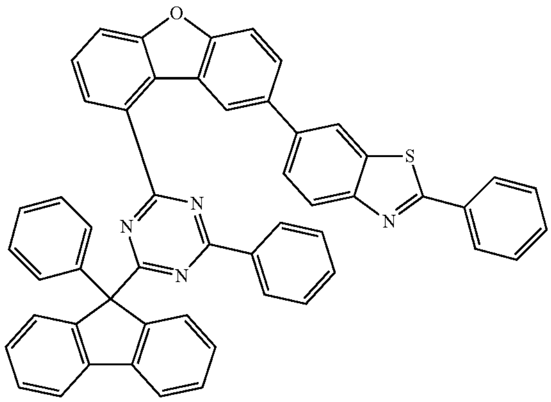

-continued
H-39
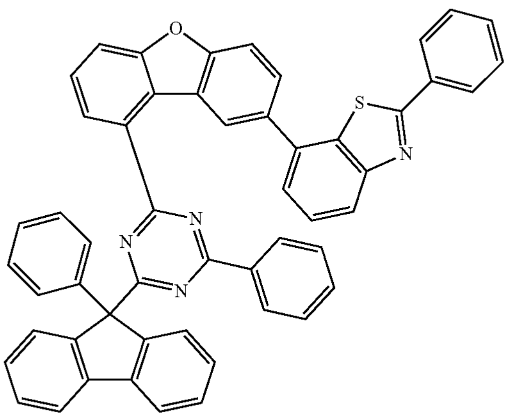
H-40
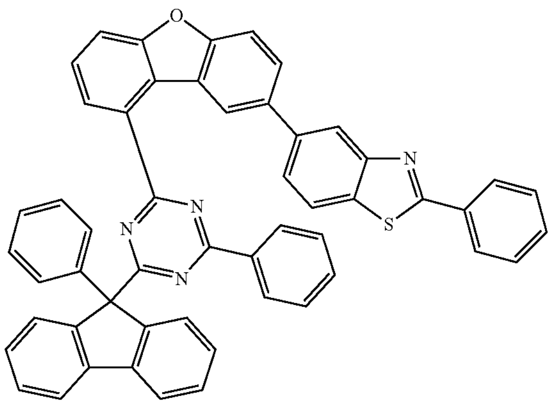
H-41
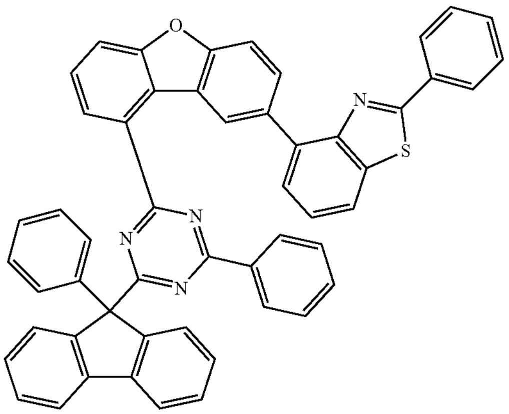
H-42
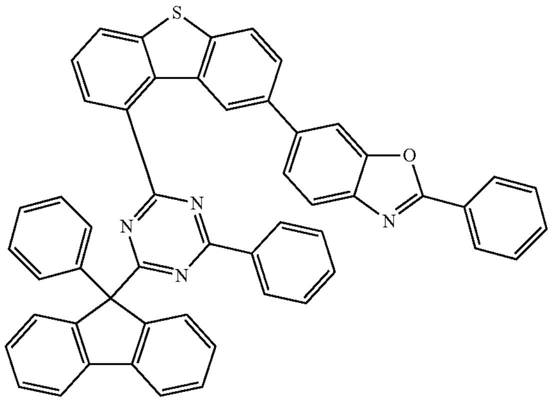
H-43
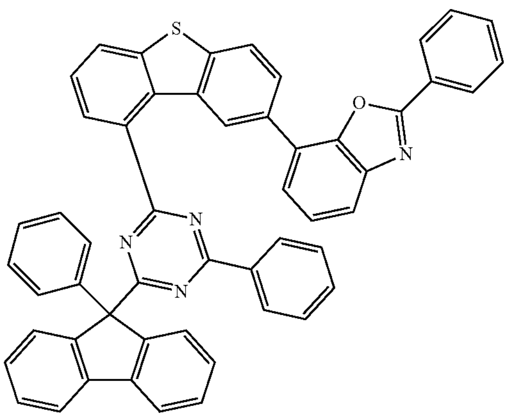
H-44
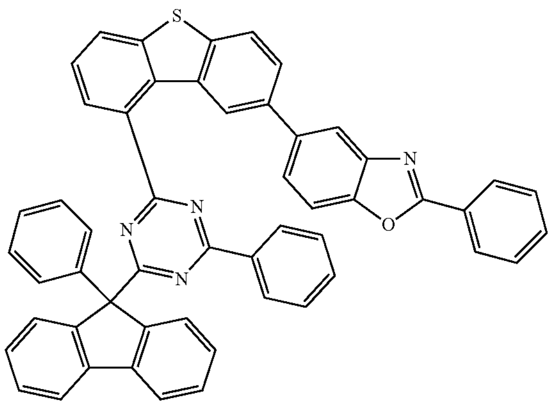

-continued
H-45
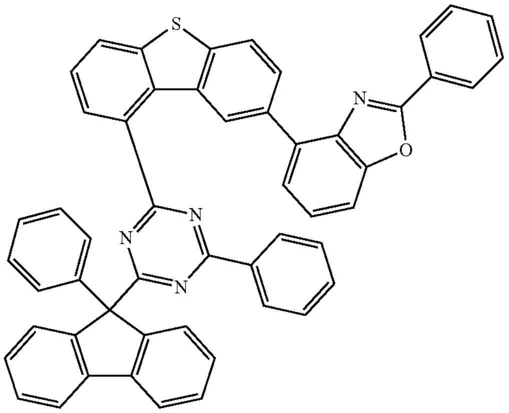
H-46
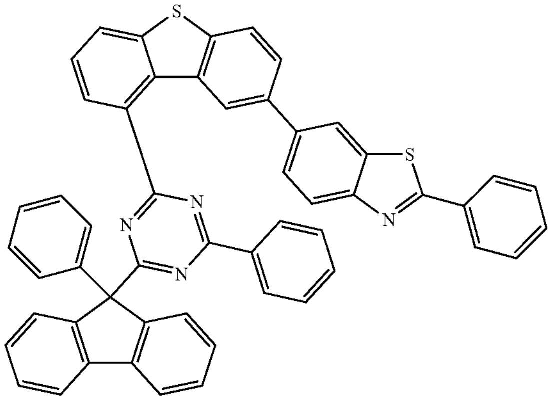
H-47
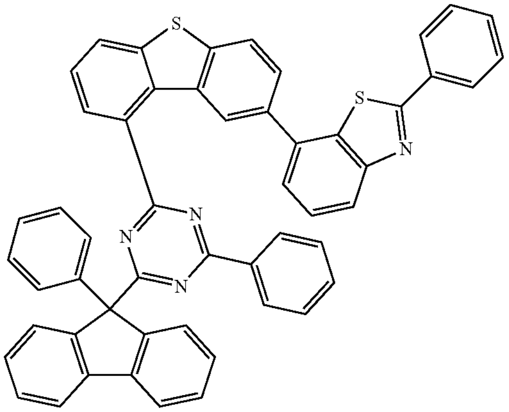
H-48
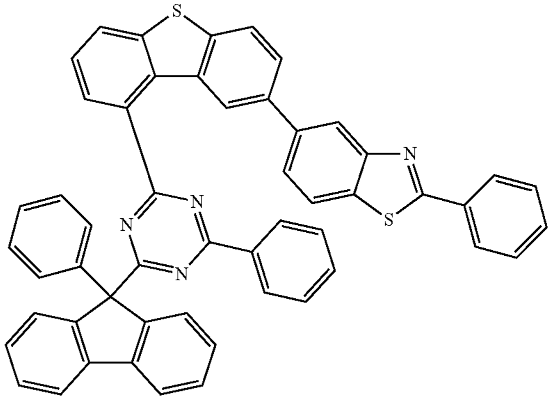
H-49
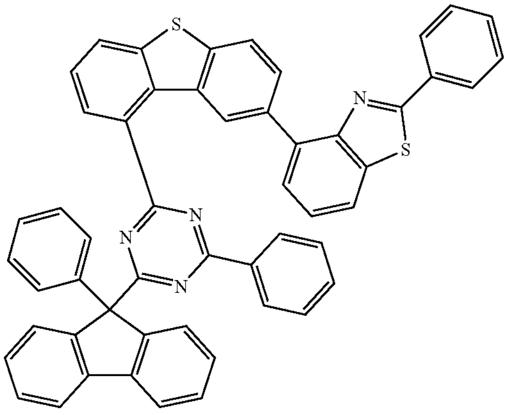
H-50
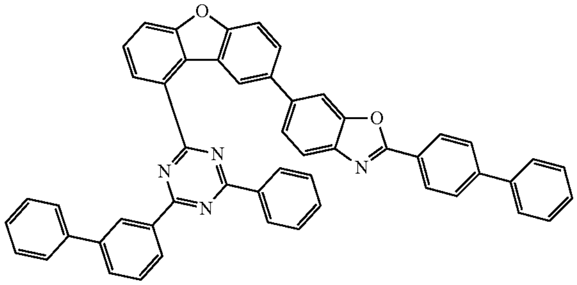

-continued

H-51

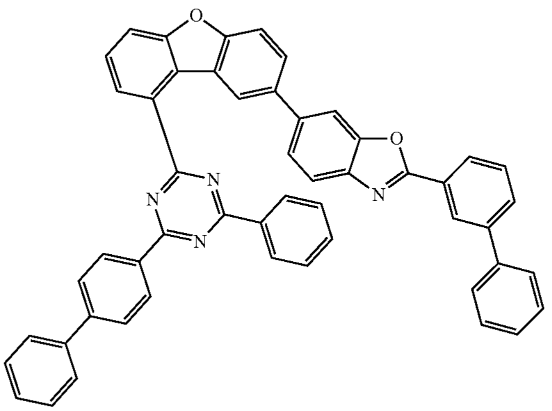

H-52

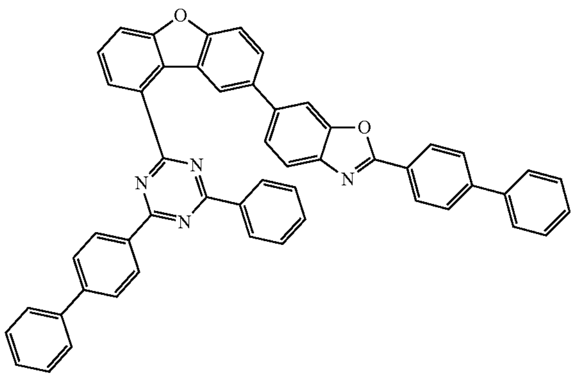

H-53

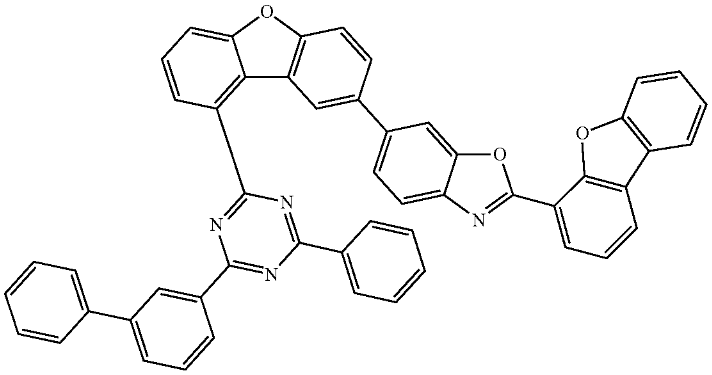

and

H-54

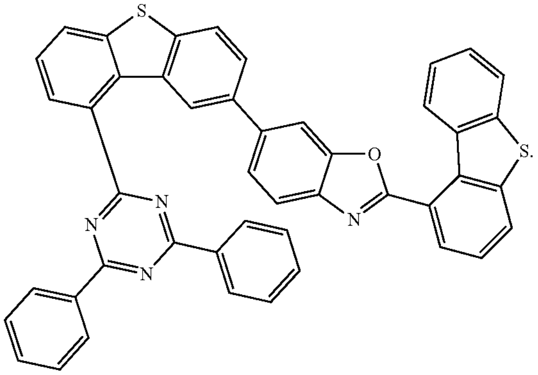

6. An organic electroluminescent material comprising the organic electroluminescent compound according to claim 1.

7. A plurality of host materials comprising the organic electroluminescent material according to claim 6 as a first host material, and at least one organic electroluminescent compound as a second host material, wherein the first host material and the second host material are different from each other.

8. The plurality of host materials according to claim 7, wherein the at least one organic electroluminescent compound is at least one of the compounds represented by the following formula 11:

(11)

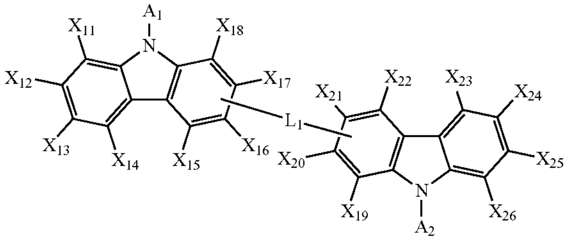

wherein $A_1$ and $A_2$, each independently, represent a substituted or unsubstituted (C6-C30)aryl;

$L_1$ represents a single bond, or a substituted or unsubstituted (C6-C30)aryene; and $X_{11}$ to $X_{26}$, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30) cycloalkyl, a substituted or unsubstituted (C6-C60)aryl, a substituted or unsubstituted (3- to 30-membered) heteroaryl, a substituted or unsubstituted tri(C1-C30) alkylsilyl, a substituted or unsubstituted tri(C6-C30) arysilyl, a substituted or unsubstituted di(C1-C30)alkyl (C6-C30)arylsilyl, a substituted or unsubstituted (C1-C30)alkyldi(C6-C30)arysilyl, a substituted or unsubstituted mono- or di-(C1-C30)alkylamino, or a substituted or unsubstituted mono- or di-(C6-C30)arylamino, or may be linked to adjacent one(s) of $X_{11}$ to $X_{26}$ to form a ring(s).

9. The plurality of host materials according to claim 8, wherein the compound represented by formula 11 is selected from the group consisting of the following compounds:

H2-1

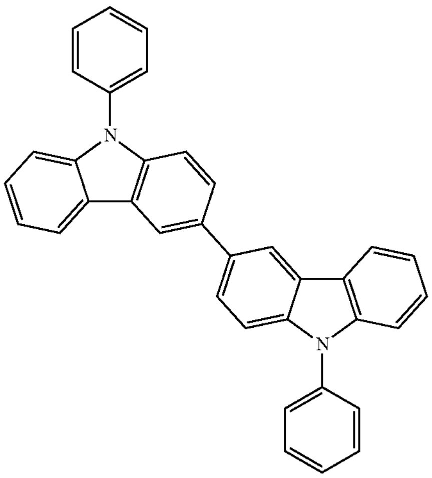

H2-2

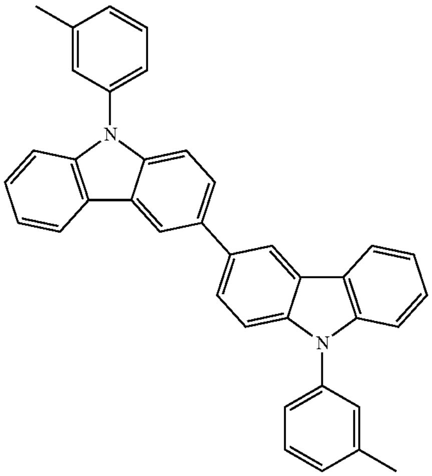

-continued

H2-3

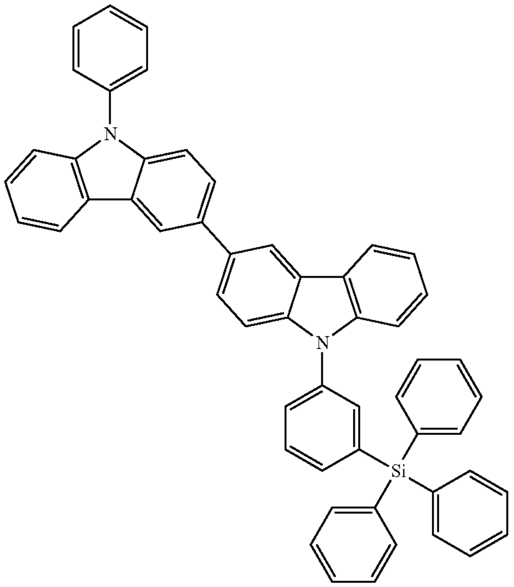

H2-4

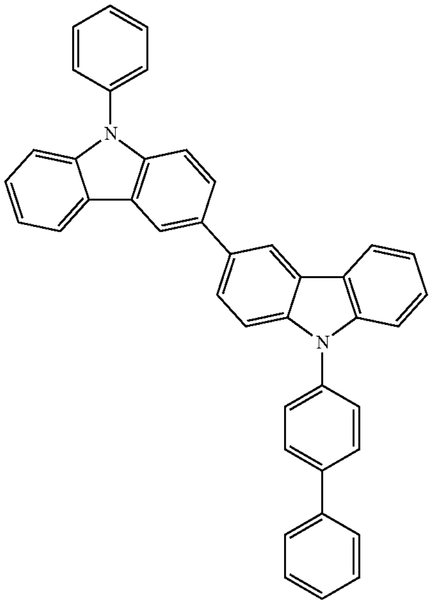

-continued
H2-5
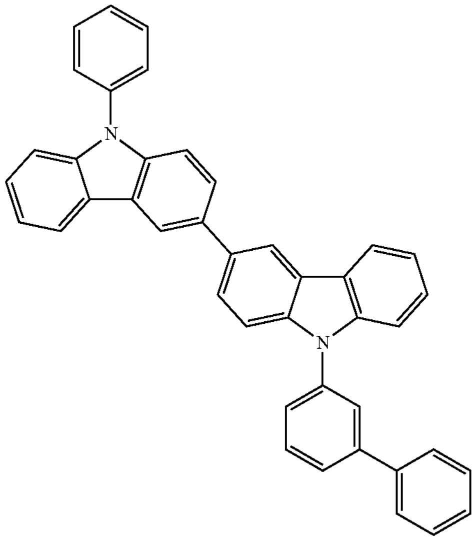
H2-6
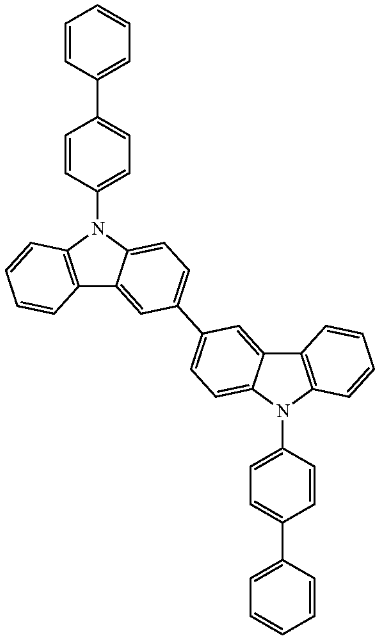
-continued
H2-7
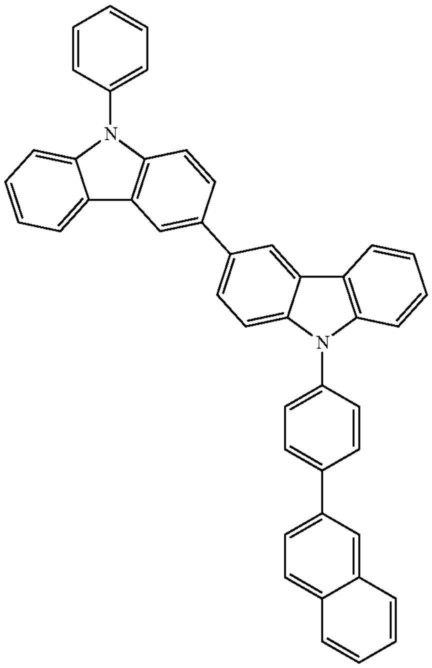
H2-8
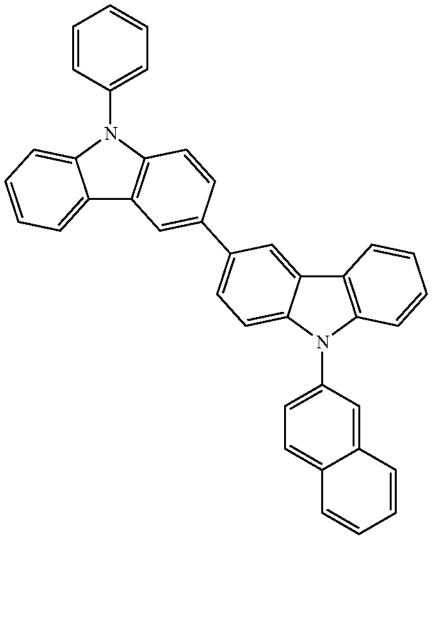

-continued
H2-9
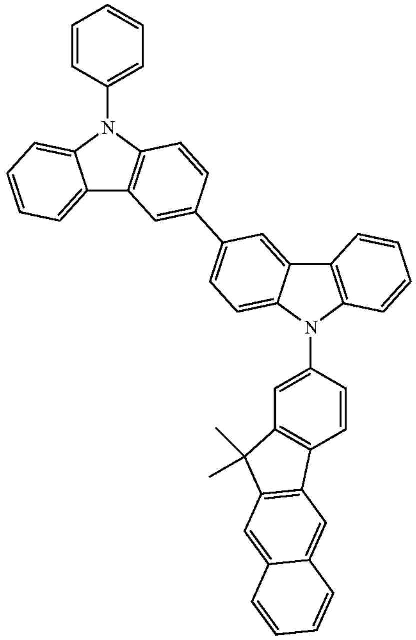
H2-10
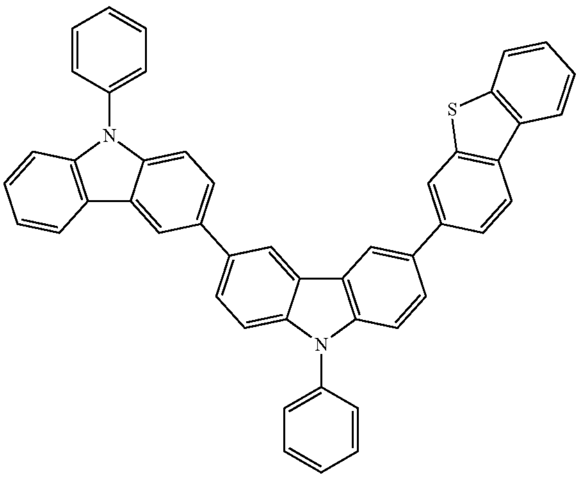
H2-11
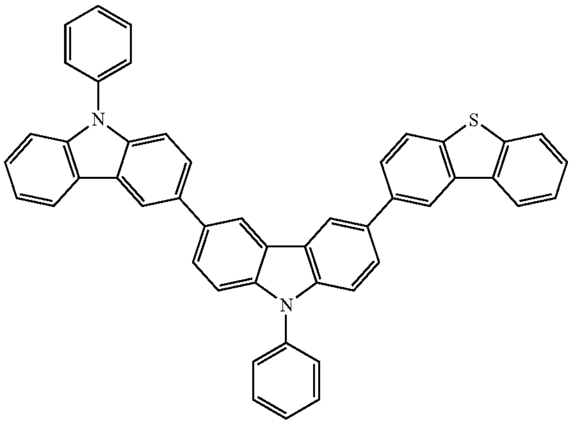
-continued
H2-12
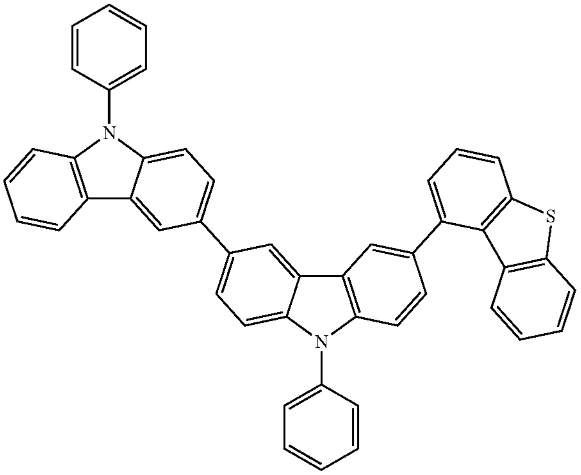
H2-13
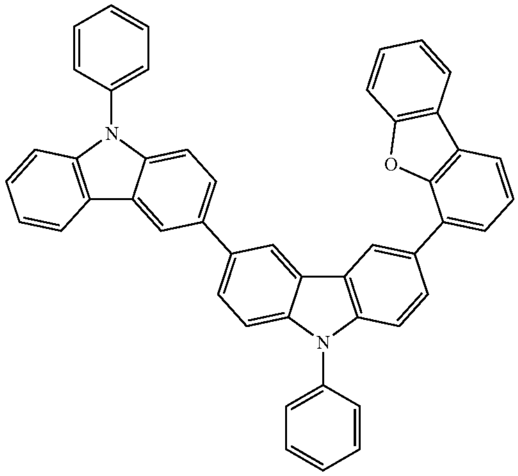
H2-14
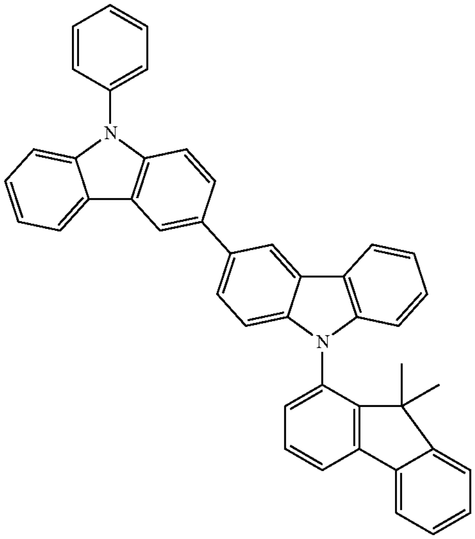

-continued
H2-15
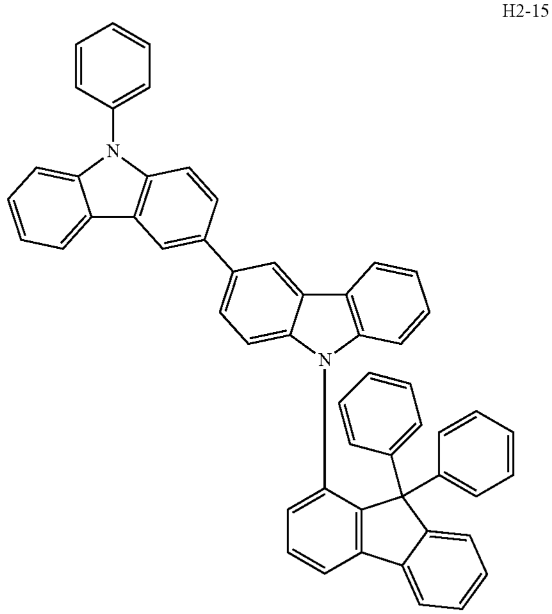
H2-16
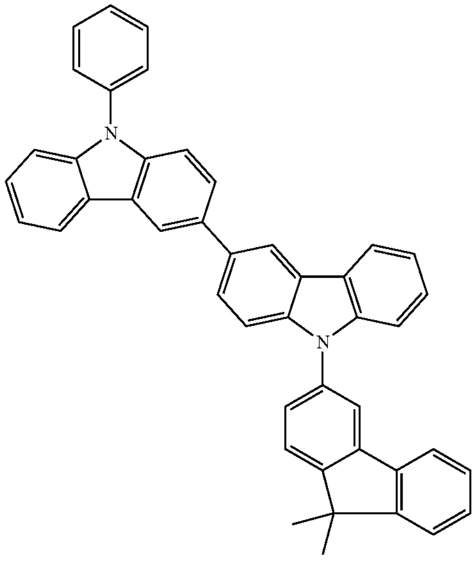
-continued
H2-17
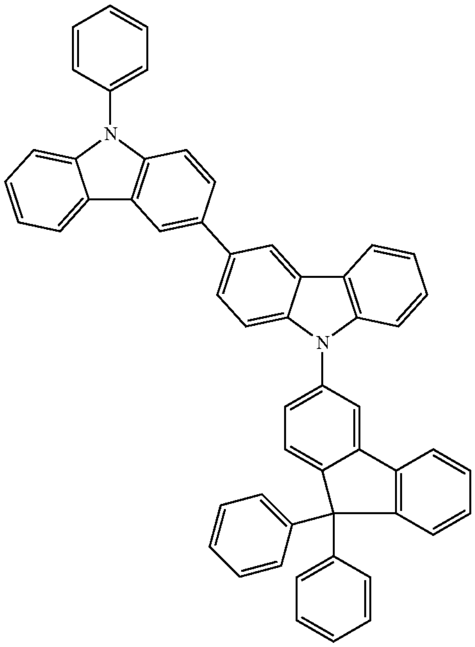
H2-18
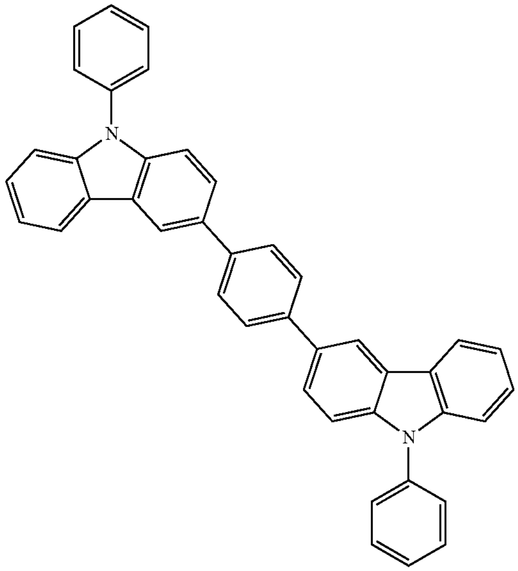

-continued
H2-19
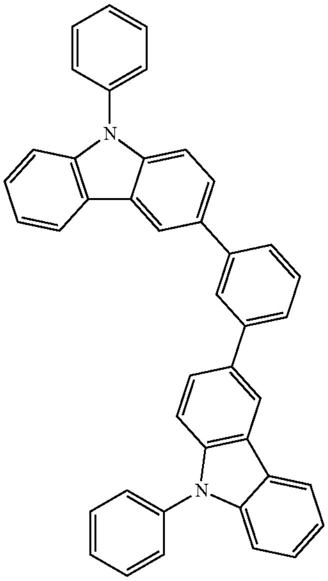
H2-20
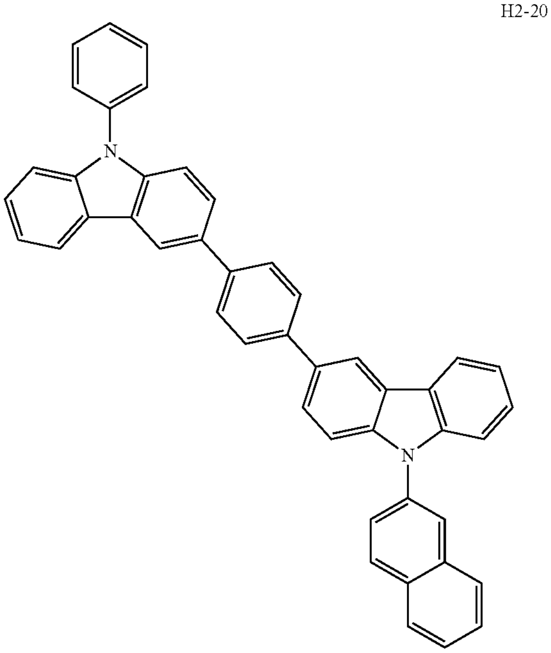
-continued
H2-21
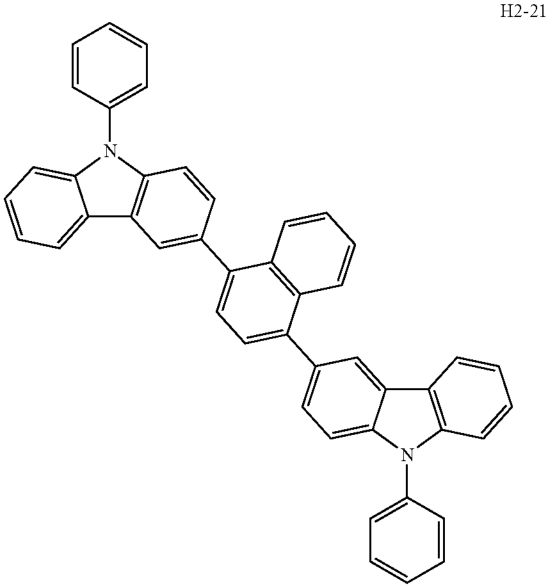
H2-22
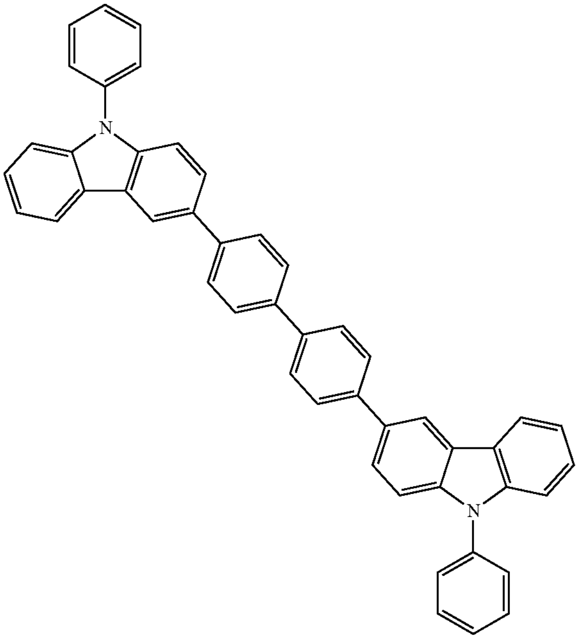

-continued
H2-23
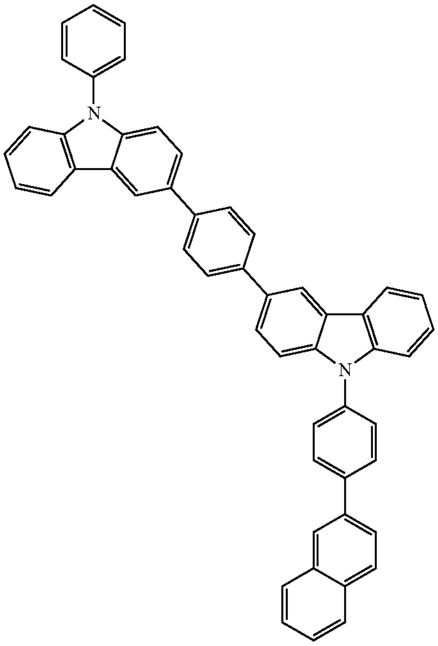
H2-24
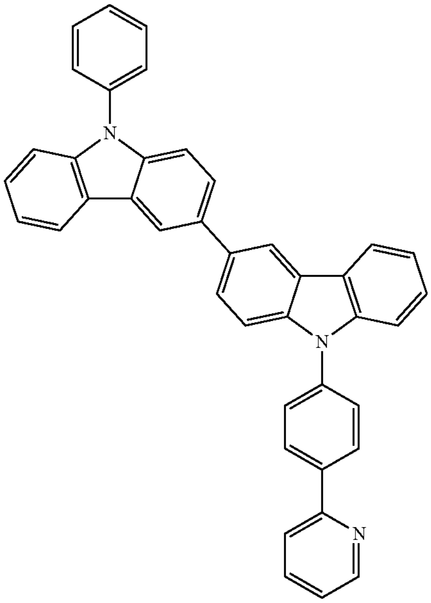
-continued
H2-25
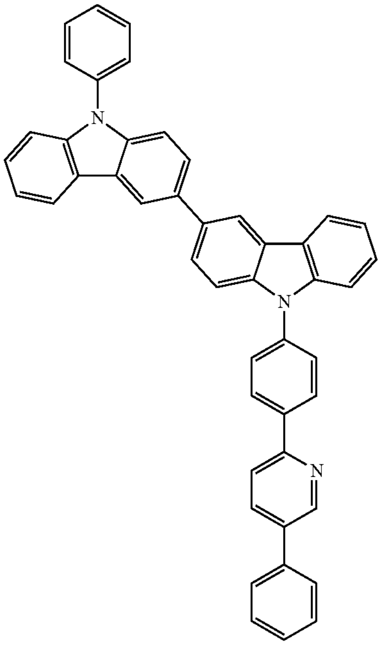
H2-26
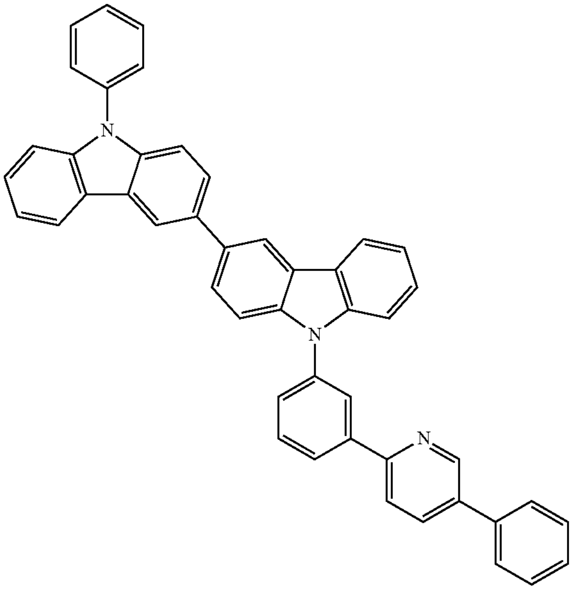

-continued
H2-27
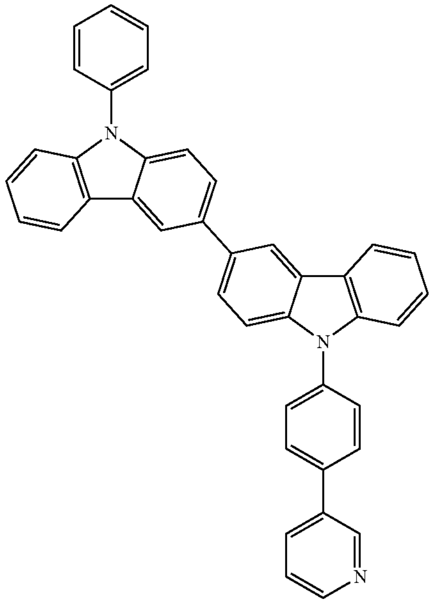
H2-28
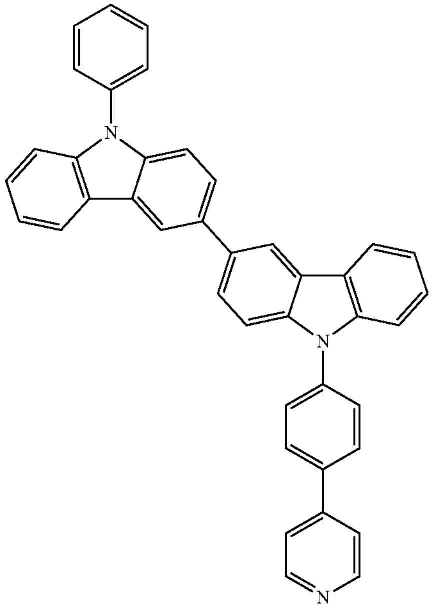
-continued
H2-29
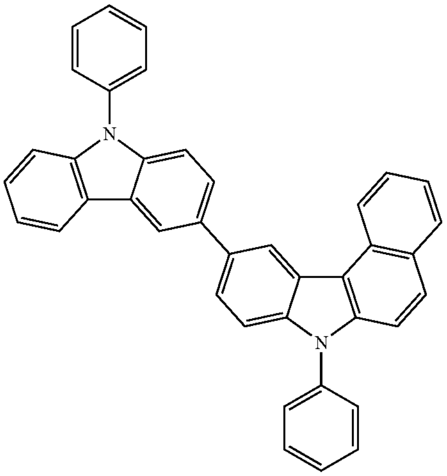
H2-30
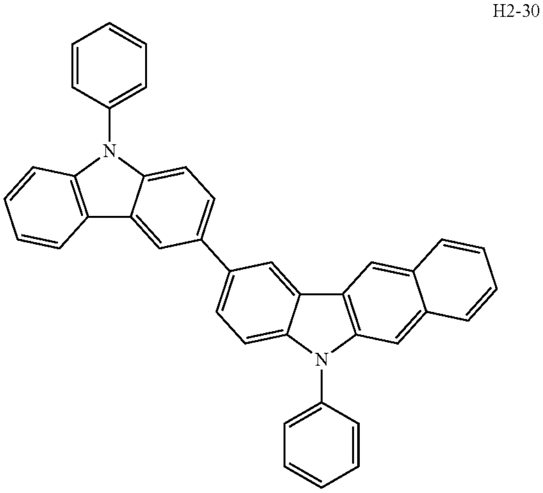
H2-31
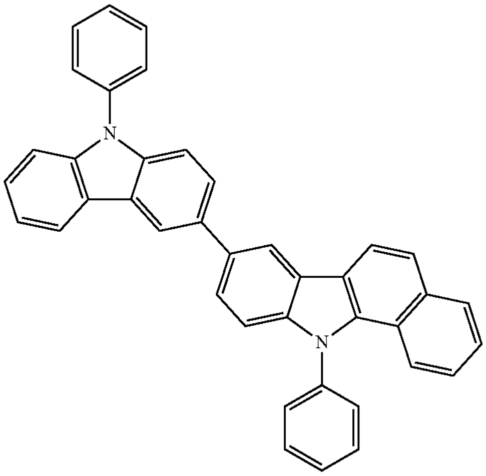

-continued
H2-32
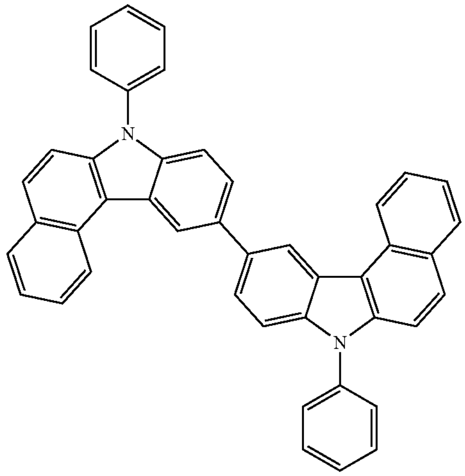
H2-33
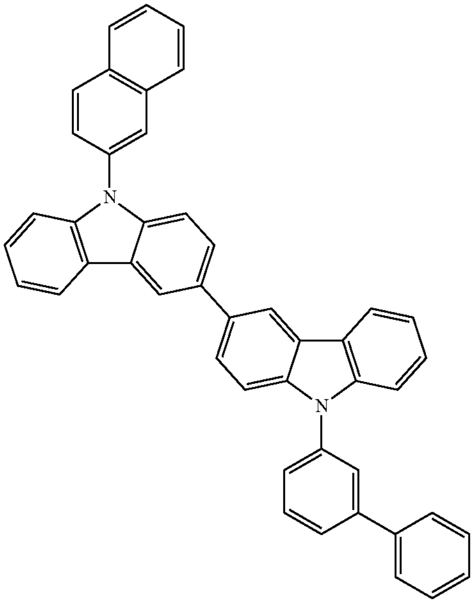
and
-continued
H2-34
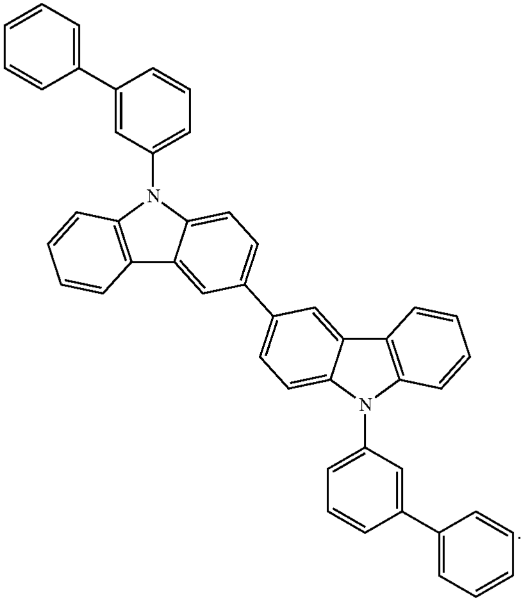
.
10. An organic electroluminescent device comprising the organic electroluminescent compound according to claim 1.
11. An organic electroluminescent device comprising the plurality of host materials according to claim 7.
* * * * *